US011638716B2

(12) United States Patent
Iyer et al.

(10) Patent No.: US 11,638,716 B2
(45) Date of Patent: May 2, 2023

(54) COMPOUNDS, COMPOSITIONS, AND METHODS FOR THE TREATMENT OF DISEASE

(71) Applicant: F-star Therapeutics, Inc., Cambridge (GB)

(72) Inventors: Radhakrishnan P. Iyer, Shrewsbury, MA (US); Anjaneyulu Sheri, Shrewsbury, MA (US); Geeta Meher, Hopkinton, MA (US); Sreerupa Challa, Shrewsbury, MA (US); Shenghua Zhou, Shrewsbury, MA (US)

(73) Assignee: F-star Therapeutics, Inc., Cambridge (GB)

( * ) Notice: Subject to any disclaimer, the term of this patent is extended or adjusted under 35 U.S.C. 154(b) by 365 days.

(21) Appl. No.: 16/643,393

(22) PCT Filed: Aug. 30, 2018

(86) PCT No.: PCT/US2018/048705
§ 371 (c)(1),
(2) Date: Feb. 28, 2020

(87) PCT Pub. No.: WO2019/046511
PCT Pub. Date: Mar. 7, 2019

(65) Prior Publication Data
US 2021/0205347 A1 Jul. 8, 2021

Related U.S. Application Data

(60) Provisional application No. 62/664,493, filed on Apr. 30, 2018, provisional application No. 62/552,473, filed on Aug. 31, 2017.

(51) Int. Cl.
C07H 19/213 (2006.01)
C07H 19/11 (2006.01)
A61P 35/00 (2006.01)
A61K 31/7084 (2006.01)
A61K 45/06 (2006.01)
C07C 69/92 (2006.01)
C07H 19/207 (2006.01)

(52) U.S. Cl.
CPC .......... A61K 31/7084 (2013.01); A61K 45/06 (2013.01); A61P 35/00 (2018.01); C07C 69/92 (2013.01); C07H 19/11 (2013.01); C07H 19/207 (2013.01); C07H 19/213 (2013.01)

(58) Field of Classification Search
None
See application file for complete search history.

(56) References Cited

U.S. PATENT DOCUMENTS

2017/0044206 A1* 2/2017 Altman ................. C07H 19/20
2017/0158724 A1 6/2017 Adams et al.

FOREIGN PATENT DOCUMENTS

| WO | WO-2013/185052 A1 | 12/2013 |
| WO | WO-2014/093936 A1 | 6/2014 |
| WO | WO-2014/127378 A2 | 8/2014 |
| WO | WO-2014/127378 A8 | 10/2014 |
| WO | WO-2014/189805 A1 | 11/2014 |
| WO | WO-2014/189806 A1 | 11/2014 |
| WO | WO-2015/077354 A1 | 5/2015 |
| WO | WO-2015/185565 A1 | 12/2015 |
| WO | WO-2016/096677 A1 | 6/2016 |
| WO | WO-2016/120305 A1 | 8/2016 |
| WO | WO-2016/145102 A1 | 9/2016 |
| WO | WO-2017/009829 A1 | 1/2017 |
| WO | WO-2017/027645 A1 | 2/2017 |
| WO | WO-2017/027646 A1 | 2/2017 |
| WO | WO-2017/075477 A1 | 5/2017 |
| WO | WO-2017/093933 A1 | 6/2017 |
| WO | WO-2017/096963 A1 | 6/2017 |
| WO | WO-2017/106740 A1 | 6/2017 |
| WO | WO-2017/123657 A1 | 7/2017 |
| WO | WO-2017/123669 A1 | 7/2017 |
| WO | WO-2017/151922 A1 | 9/2017 |
| WO | WO-2017/161349 A1 | 9/2017 |
| WO | WO-2017/186711 A1 | 11/2017 |
| WO | WO-2018/009466 A1 | 1/2018 |
| WO | WO-2018/045204 A1 | 3/2018 |
| WO | WO-2018/067423 A1 | 4/2018 |
| WO | WO-2018/100558 A2 | 6/2018 |
| WO | WO-2018/118664 A1 | 6/2018 |
| WO | WO-2018/118665 A1 | 6/2018 |
| WO | WO-2018/156625 A1 | 8/2018 |
| WO | WO-2018/198076 A1 | 11/2018 |
| WO | WO-2018/208667 A1 | 11/2018 |
| WO | WO-2018/231752 A1 | 12/2018 |
| WO | WO-2018/234805 A1 | 12/2018 |
| WO | WO-2018/234807 A1 | 12/2018 |
| WO | WO-2018/234808 A1 | 12/2018 |
| WO | WO-2019/027857 A1 | 2/2019 |
| WO | WO-2019/027858 A1 | 2/2019 |
| WO | WO-2019/035901 A1 | 2/2019 |
| WO | WO-2019/046511 A1 | 3/2019 |
| WO | WO-2019/067468 A1 | 4/2019 |
| WO | WO-2019/100061 A1 | 5/2019 |
| WO | WO-2019/104353 A1 | 5/2019 |
| WO | WO-2019/125974 A1 | 6/2019 |

(Continued)

OTHER PUBLICATIONS

International Search Report and Written Opinion for International Application No. PCT/US18/48705 dated Dec. 18, 2018.
Extended European Search Report for International Application No. PCT/US2018/048705 dated May 31, 2021.

Primary Examiner — Traviss C McIntosh, III
(74) Attorney, Agent, or Firm — Foley Hoag LLP; Dana M. Gordon; Alexander J. Chatterley

(57) ABSTRACT

Disclosed are compounds and compositions for the activation or induction of expression of a pattern recognition receptor (e.g., STING, RIG-I, MDA5), and methods of use thereof.

38 Claims, 40 Drawing Sheets

(56) References Cited

FOREIGN PATENT DOCUMENTS

| WO | WO-2019/147509 A1 | 8/2019 |
| WO | WO-2019/161171 A1 | 8/2019 |
| WO | WO-2019/165032 A1 | 8/2019 |
| WO | WO-2019/191070 A1 | 10/2019 |
| WO | WO-2019/195063 A1 | 10/2019 |
| WO | WO-2019/195124 A1 | 10/2019 |
| WO | WO-2019/234008 A1 | 12/2019 |
| WO | WO-2019/238786 A1 | 12/2019 |
| WO | WO-2019/242404 A1 | 12/2019 |
| WO | WO-2019/243823 A1 | 12/2019 |
| WO | WO-2019/243825 A1 | 12/2019 |
| WO | WO-2020/010092 A1 | 1/2020 |
| WO | WO-2020/010451 A1 | 1/2020 |
| WO | WO-2020/020155 A1 | 1/2020 |

* cited by examiner

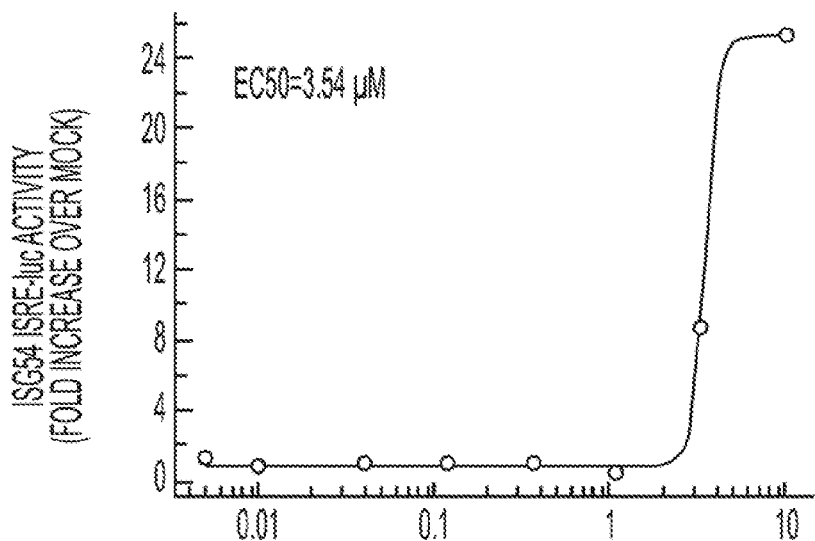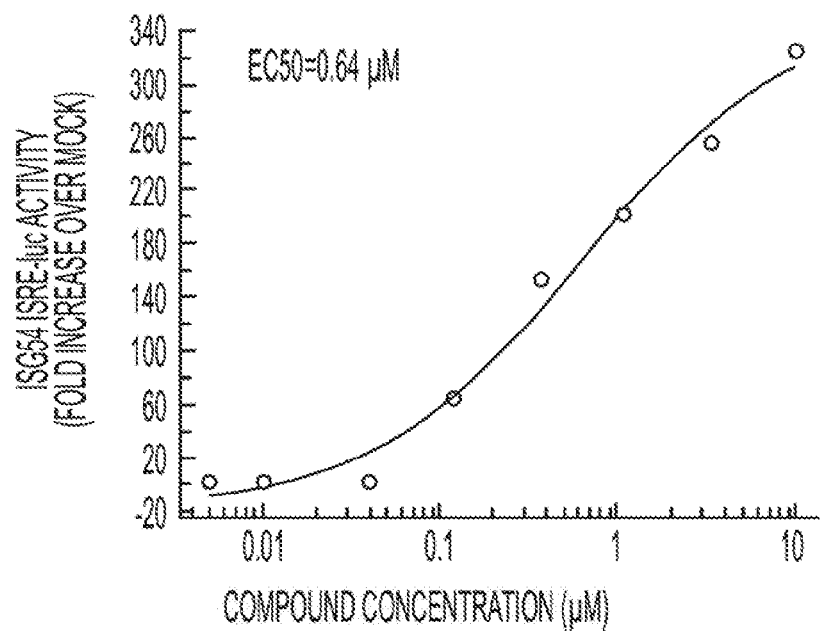
FIG. 1

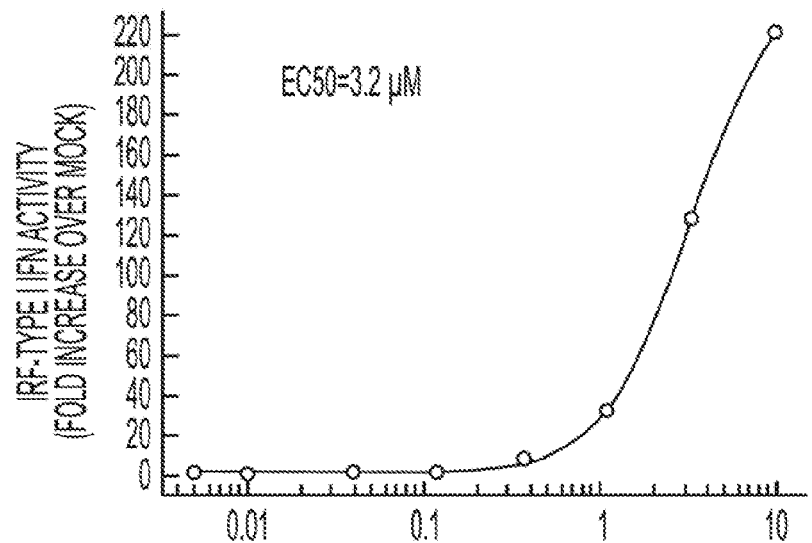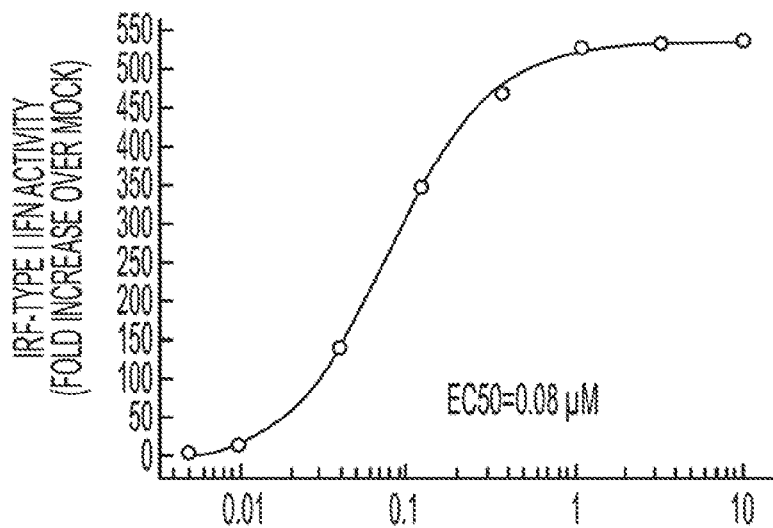
FIG. 4

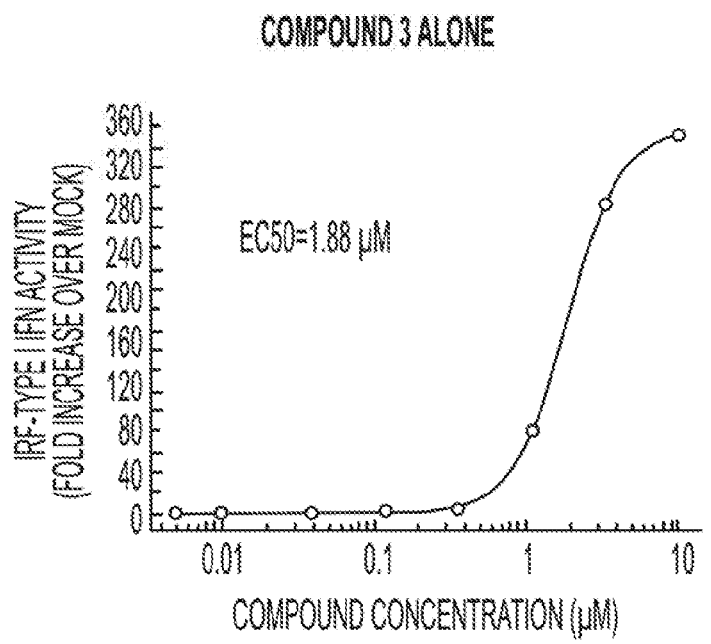
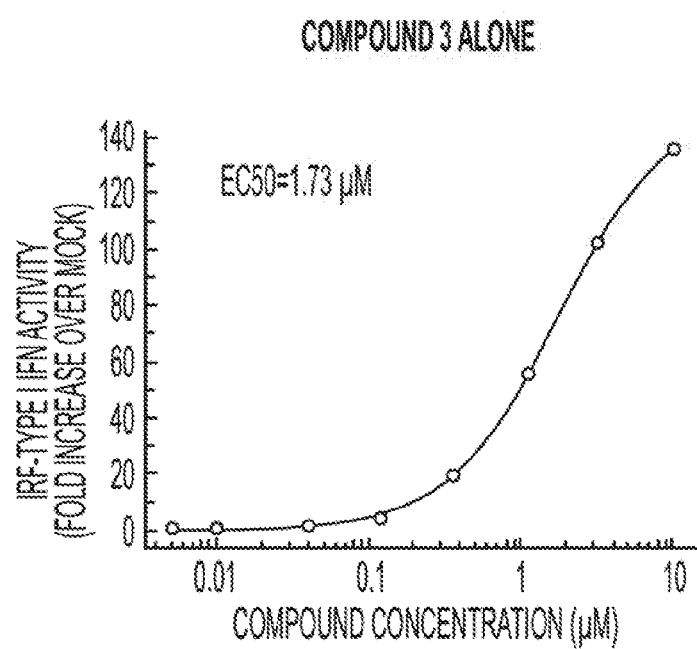
FIG. 9A

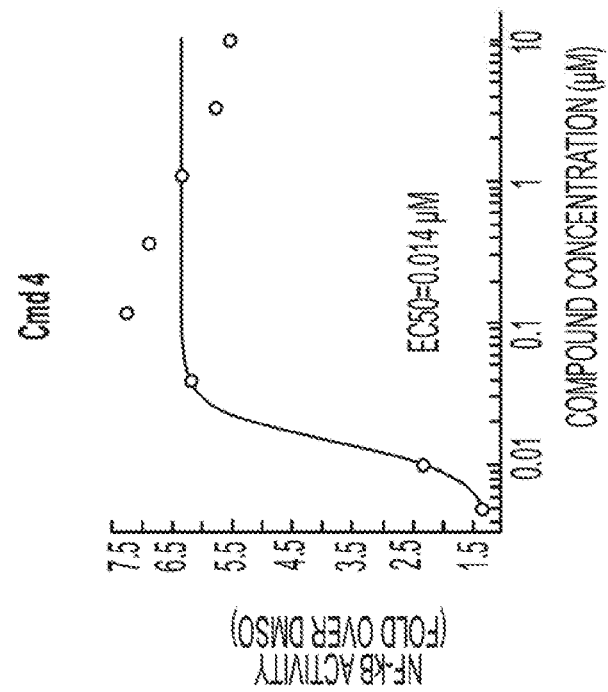
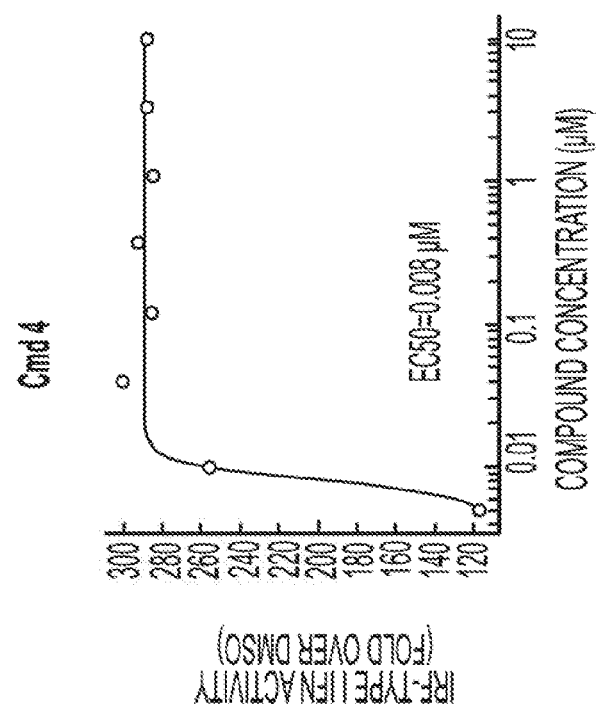
FIG. 12

RESPONSE SUMMARY THE STUDY TO DETERMINE THE EFFICACY OF COMPOUND 4 IN THE CT26 MURINE COLON CARCINOMA MODEL USING FEMALE BALB/C MICE

| GROUP | n | TREATMENT REGIMEN | | | | MEDIAN | | | STATISTICAL SIGNIFICANCE | | MTV (n) | REGRESSIONS | | | MEAN BW | DEATHS | |
|---|---|---|---|---|---|---|---|---|---|---|---|---|---|---|---|---|---|
| | | AGENT | mg/kg | ROUTE | SCHEDULE | TTE | T-C | %TGD | vs G1 | vs G3 | DAY 29 | PR | CR | TFS | NADIR | TR | NTR |
| 1 | 8 | VEHICLE | — | IV | DAYS 1,5,9,14 | 15.2 | — | — | — | *** | — | 0 | 0 | 0 | — | 0 | 0 |
| 2 | 8 | CMD 4 | 1 | IV | DAYS 1,5,9,14 | 25.6 | 10.4 | 68 | *** | * | 1372 (1) | 0 | 0 | 0 | -1.6% DAY 2 | 0 | 0 |
| 3 | 8 | CMD 4 | 3 | IV | DAYS 1,5,9,14 | 29.0 | 13.8 | 91 | *** | — | 257 (6) | 3 | 0 | 0 | -8.5% DAY 3 | 0 | 0 |

THIS TABLE DISPLAYS THE SCHEDULED TREATMENT REGIMEN AT COMPLETION OF THE STUDY.

VEHICLE = SALINE

STUDY ENDPOINT = 2000 mm$^3$; STUDY DURATION = 29 DAYS
n = NUMBER OF ANIMALS IN A GROUP NOT DEAD FROM ACCIDENTAL OR UNKNOWN CAUSES, OR EUTHANIZED FOR SAMPLING
TTE = TIME TO ENDPOINT; T-C = DIFFERENCE BETWEEN MEDIAN TTE (DAYS) OF TREATED VERSUS CONTROL GROUP; %TGD = [(T-C)/C] x 100 THE MAXIMUM T-C IN THIS STUDY IS 13.8 DAYS (91%), COMPARED TO GROUP
STATISTICAL SIGNIFICANCE (LOGRANK TEST): NE = NOT EVALUABLE, NS = NOT SIGNIFICANT, * = $p < 0.05$,  = $p < 0.01$, * = $p < 0.001$, COMPARED TO GROUP INDICATED
MTV (n) = MEDIAN TUMOR VOLUME (mm$^3$) FOR THE NUMBER OF ANIMALS ON THE DAY OF TGD ANALYSIS (EXCLUDES ANIMALS WITH TUMOR VOLUME AT ENDPOINT)
PR = PARTIAL REGRESSIONS; CR = TOTAL NUMBER COMPLETE REGRESSIONS; TFS = TUMOR FREE SURVIVORS, I.E., CRS AT END OF STUDY
MEAN BW NADIR = LOWEST GROUP MEAN BODY WEIGHT, AS % CHANGE FROM DAY 1; — INDICATES NO DECREASE IN MEAN BODY WEIGHT WAS OBSERVED
TR = TREATMENT-RELATED DEATH; NTR = NON-TREATMENT-RELATED DEATH

FIG. 15

TUMOR GROWTH INHIBITION THE STUDY TO DETERMINE THE EFFICACY OF COMPOUND 4 IN THE
CT26 MURINE COLON CARCINOMA MODEL USING FEMALE BALB/C MICE

| GROUP | n | TREATMENT REGIMEN ||||  MTV (N) DAY 18 | %TGI | STATISTICAL SIGNIFICANCE || REGRESSIONS || MEAN BW NADIR | DEATHS ||
|---|---|---|---|---|---|---|---|---|---|---|---|---|---|
| | | AGENT | mg/kg | ROUTE | SCHEDULE | | | vs G1 | vs G3 | PR | CR | | TR | NTR |
| 1 | 8 | VEHICLE | --- | IV | DAYS 1,5,9,14 | 3402 (8) | --- | | *** | 0 | 0 | --- | 0 | 0 |
| 2 | 8 | CMD 4 | 1 | IV | DAYS 1,5,9,14 | 363 (8) | 89 | *** | * | 0 | 0 | -1.6% DAY 2 | 0 | 0 |
| 3 | 8 | CMD 4 | 3 | IV | DAYS 1,5,9,14 | 79 (8) | 98 | *** | --- | 0 | 0 | -8.5% DAY 3 | 0 | 0 |

THIS TABLE DISPLAYS THE SCHEDULED TREATMENT REGIMEN AT COMPLETION OF THE STUDY

VEHICLE = SALINE

STUDY ENDPOINT = 2000 mm³; STUDY DURATION = 18 DAYS
n = NUMBER OF ANIMALS IN A GROUP NOT DEAD FROM ACCIDENTAL OR UNKNOWN CAUSES, OR EUTHANIZED FOR SAMPLING
%TGI = [(1-(MTV DRUG TREATED/MTV CONTROL)] x 100 = PERCENT TUMOR GROWTH INHIBITION, COMPARED TO GROUP INDICATED
STATISTICAL SIGNIFICANCE (MANN-WHITNEY U TEST): NE = NOT EVALUABLE, NS = NOT SIGNIFICANT,
* = $p < 0.05$,  = $p < 0.01$, * = $p < 0.001$, COMPARED TO GROUP INDICATED
MTV (n) = MEDIAN TUMOR VOLUME (mm³) FOR THE NUMBER OF ANIMALS ON THE DAY OF TGI ANALYSIS (INCLUDES ANIMALS WITH TUMOR VOLUME AT ENDPOINT)
PR = PARTIAL REGRESSION, CR = COMPLETE REGRESSION
MEAN BW NADIR = LOWEST GROUP MEAN BODY WEIGHT, AS % CHANGE FROM DAY 1; --- INDICATES NO DECREASE IN MEAN BODY WEIGHT WAS OBSERVED
TR = TREATMENT-RELATED DEATH; NTR = NON-TREATMENT-RELATED DEATH

FIG. 16

BalbC MICE (FEMALE, 10 WEEKS OF AGE) WERE INTRAVENOUSLY INJECTED VIA TAIL VEIN WITH SALINE CONTROL. CMD3 AT 9 mg/kg OF MOUSE BODY. SPLEEN SAMPLES WERE COLLECTED AT 24 HRS POST-TREATMENT. RNA WAS EXTRACTED AND THE EXPRESSION OF REPRESENTATIVE ISGs WAS QUANTIFIED USING Q-PCR. RESULTS ARE SHOWN AS FOLD INCREASE OVER HOUSEKEEPING GENE.

| SAMPLE | N(SITES) | Kd(μM) | ΔH1(cal/mlo) | ΔS(cal/mol·deg) |
|---|---|---|---|---|
| CMD 3-A | 0.350 | 0.7 | 3651 | 40.4 |
| CMD 3-B | 0.584 | 1.75 | 4124 | 40.2 |

FIG. 33
CONTINUED

COMPOUNDS, COMPOSITIONS, AND METHODS FOR THE TREATMENT OF DISEASE

RELATED APPLICATIONS

This application is a § 371(c) National Stage of PCT/US2018/048705, filed Aug. 30, 2018; which claims the benefit of priority to U.S. provisional patent application Nos. 62/664,493, filed Apr. 30, 2018; and 62/552,473, filed Aug. 31, 2017.

FIELD

Disclosed are compounds and compositions that activate in a host the innate immune defense system and induce expression of pattern recognition receptors, as well as methods of using them for the treatment of a microbial infection or a proliferative disease (e.g., cancer).

BACKGROUND

A key feature of the innate immune system is the recognition and elimination of foreign substances. Identification of these pathogenic invaders occurs through host recognition of evolutionarily conserved microbial structures known as pathogen-associated molecular patterns (PAMPs) (Jensen, S. and Thomsen, A. R. *J Virol* (2012) 86:2900-2910). These PAMPs include a wide array of molecular structures, such as nucleic acids, lipopolysaccharides, and glycoproteins that may be broadly shared by multiple microbial species and are critical to their survival and/or pathogenicity. Host recognition may occur by multiple pathways, such as activation of pattern recognition receptors (PRRs), which ultimately lead to downstream signaling events and culminate in the mounting of an immune response.

To date, several PRRs have been identified that serve as sensors of pathogenic infection. For example, the retinoic acid-inducible gene-I (RIG-I) protein is a RNA helicase that also functions as a sensor of microbial-derived RNA. RIG-I is important factor in host recognition of RNA viruses from a variety of different viral families, including Flaviviridae (e.g., West Nile virus, Hepatitis C virus, Japanese encephalitis virus, Dengue virus), Paramyxoviridae (e.g., Sendai virus, Newcastle disease virus, Respiratory syncytial virus, Measles virus), Rhabdoviridae (e.g., Rabies virus), Orthomyxoviridae (e.g., influenza A virus, influenza B virus), and Arenaviridae (e.g., Lassa virus). Stimulator of interferon genes (STING) is a cytoplasmic adaptor protein that activates the TBK1-IRF3 signaling complex, resulting in induction of type I interferons (IFN-β and IFN-α) and other immune pathway proteins. Other PRRs also play a role in sensing microbial-derived nucleic acids, including NOD2, LGP2, MDA5, and a number of Toll-like receptors (TLRs) that are expressed on the cell surface and within endosomal compartments.

A shortcoming of many current antiviral therapies relates to the emergence of drug resistant variants that occurs upon extended use. In addition, many available treatments require persistent and long-term therapy, which often results in unwanted side effects and the risk of relapse upon conclusion of treatment. Further, many viruses can be subdivided into different genotypes, and certain drugs developed against one genotype may not be active against other genotypes. In contrast, the use of small molecule mimics of viral-derived RNA capable of PRR induction provides an alternate approach to the treatment of viral infection, as these compounds may be agnostic to genotype, may possess both direct antiviral activity as well as the ability to activate the host immune response, and potentially limit the development of drug resistance and toxicity. As such, there exists a need for a new generation of therapies that induce expression of PRRs for use in the treatment of disease and as diagnostic tools.

In addition, RIG-I serves as a biomarker for the prediction of prognosis for certain types of cancer, such as hepatocellular carcinoma (Hou, J. et al, *Cancer Cell* (2014) 25:49-63). Recent publications have highlighted the importance of RIG-I and STING as mediators of innate and adaptive immunity, and RIG-I and STING agonists have been recognized as immuno-oncology agents in cancer therapy (Li, X. Y. et al, *Mol Cell Oncol* (2014) 1:e968016; Woo, S. R. *Trends in Immunol* (2015) 36:250-256). In particular, RIG-I is involved in the regulation of basic cellular processes such as hematopoietic proliferation and differentiation, maintenance of leukemic stemness, and tumorigenesis of hepatocellular carcinoma, indicating that RIG-I performs an essential function as a tumor suppressor. Importantly, the STING pathway of cytosolic DNA sensing has been shown to play an important mechanistic role in innate immune sensing, driving type I IFN production in cancer and in the context of immune-oncology applications, including therapeutics and diagnostics.

SUMMARY

Cyclic dinucleotide compounds, compositions comprising cyclic dinucleotide compounds, and related methods of use are described herein.

In one aspect, the disclosure features a compound of Formula (I):

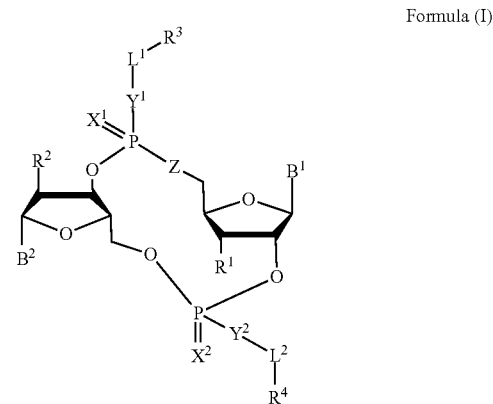

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) $OC_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more R⁸; R⁵ is hydrogen or $C_1$-$C_{20}$ alkyl (e.g., $C_1$-$C_6$ alkyl); R⁶ is halo, —CN, $C_1$-$C_{20}$ alkyl (e.g., $C_1$-$C_6$ alkyl), OR⁷, oxo, cycloalkyl, heterocyclyl, aryl, or heteroaryl, wherein each alkyl, cycloalkyl, heterocyclyl, aryl, and heteroaryl is optionally substituted with one or more R⁹; R⁷ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more R⁹; each R⁸ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N(R⁵)—$C_1$-$C_{20}$ alkyl (e.g., $C_1$-$C_6$ alkyl), N(R⁵)C(O)—$C_1$-$C_{20}$ alkyl (e.g., $C_1$-$C_6$ alkyl), OC(O)N(R⁵)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N(R⁵)-aryl, C(O)N(R⁵)-heteroaryl, N(R⁵)C(O)-aryl, N(R⁵)₂C(O)-aryl, or N(R⁵)C(O)-heteroaryl, S(O)₂N(R⁵)-aryl, wherein each alkyl, heteroalkyl, aryl, and heteroaryl is optionally substituted by one or more R⁹; and each R⁹ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the compound is a compound of Formula (I-a), (I-b), (I-c), or (I-d):

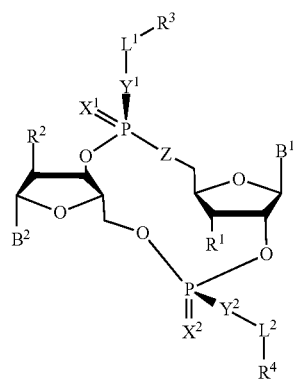

Formula (I-a)

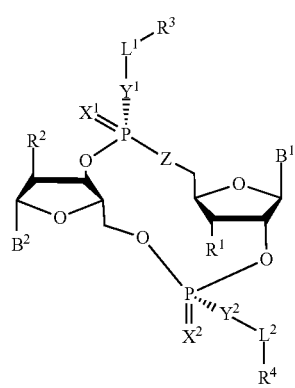

Formula (I-b)

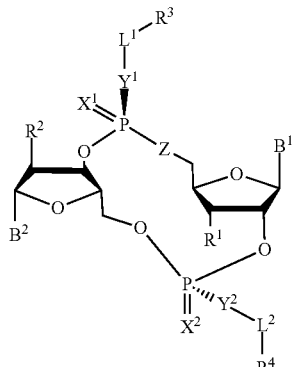

Formula (I-c)

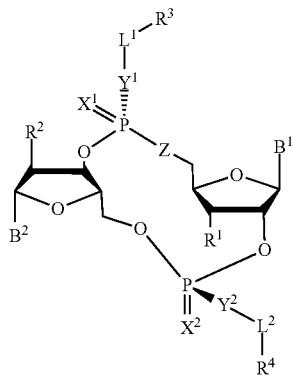

Formula (I-d)

or a pharmaceutically acceptable salt thereof, wherein each of Z, B¹, B², X¹, X², Y, Y², L¹, L², R¹, R², R³, R⁴, and subvariables thereof, are as previously described.

In one aspect, the present disclosure describes a method of inducing the expression of a pattern recognition receptor in a subject suffering from a microbial infection, comprising administering to the subject an effective amount of a compound of Formula (I),

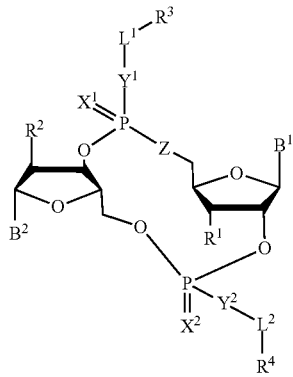

Formula (I)

or a pharmaceutically acceptable salt or stereoisomer thereof, wherein:

Z is either S or O each of B¹ and B² is independently a purinyl nucleobase or pyrimidinyl nucleobase;

each of X¹ and X² is independently O or S;

each of Y¹ and Y² is independently O, S, or NR⁵;

each of $L^1$ and $L^2$ is independently absent, $C_1$-$C_6$ alkyl or $C_1$-$C_6$ heteroalkyl, wherein each $C_1$-$C_6$ alkyl and $C_1$-$C_6$ heteroalkyl is optionally substituted with $R^6$;

each of $R^1$ and $R^2$ is independently hydrogen, halo, —CN, $C_1$-$C_{20}$ alkyl (e.g., $C_1$-$C_6$ alkyl), or $OR^7$;

each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), cycloalkyl, heterocyclyl, $OC(O)OC_1$-$C_{20}$ alkyl (e.g., $C_1$-$C_6$ alkyl), aryl, or heteroaryl, wherein each $C_1$-$C_{20}$ alkyl, $C_1$-$C_{20}$ heteroalkyl, cycloalkyl, heterocyclyl, aryl, $OC(O)O\ C_1$-$C_{20}$ alkyl (e.g., $C_1$-6 alkyl), and heteroaryl is optionally substituted with 1-5 $R^8$;

each $R^5$ is independently hydrogen or $C_1$-$C_{20}$ alkyl (e.g., $C_1$-$C_6$ alkyl);

$R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$;

$R^7$ is hydrogen, $C_1$-$C_{20}$ alkyl (e.g., $C_1$-$C_6$ alkyl), cycloalkyl, heterocyclyl, aryl, or heteroaryl, wherein each $C_1$-$C_{20}$ alkyl, cycloalkyl, heterocyclyl, aryl, or heteroaryl is optionally substituted with 1-5 $R^9$;

each $R^8$ is independently $C_1$-$C_{20}$ alkyl (e.g., $C_1$-$C_6$ alkyl), O-aryl, $OC(O)NR_5$—$C_1$-$C_{20}$ alkyl (e.g., $C_1$-$C_6$ alkyl), $S(O)_2NR_5$-aryl, $NR_5C(O)$-aryl, $NR_5R_5C(O)$-aryl, $C(O)$-aryl, $C(O)$-heteroaryl, $OC(O)$-aryl, or $OC(O)$-heteroaryl, $OC(O)$—$C_1$-$C_{20}$ alkyl (e.g., $C_1$-$C_6$), $OC(O)O$—$C_1$-$C_{20}$ alkyl (e.g., $C_1$-$C_6$), wherein each $C_1$-$C_{20}$ alkyl, O-aryl, $OC(O)NR_5$—$C_1$-$C_{20}$ alkyl, $S(O)_2NR_5$-aryl, $NR_5C(O)$-aryl, $CH_2NR_5C(O)$-aryl, $C(O)$-aryl, $C(O)$-heteroaryl, $OC(O)$-aryl, or $OC(O)$-heteroaryl, $OC(O)$—$C_1$-$C_{20}$ alkyl (e.g., $C_1$-$C_6$), $OC(O)O$—$C_1$-$C_{20}$ alkyl (e.g., $C_1$-$C_6$), is optionally substituted by 1-5 $R^9$; and each $R^9$ is independently $C_1$-$C_{20}$ alkyl (e.g., $C_1$-$C_6$ alkyl), halo, —CN, OH, O—$C_1$-$C_{20}$ alkyl, O—$C_1$-$C_{20}$ heteroalkyl, O-aryl, O-heteroaryl.

In another aspect, the disclosure features a method of treating cancer in a subject, the method comprising administering to the subject a therapeutically effective amount of a compound of Formula (I),

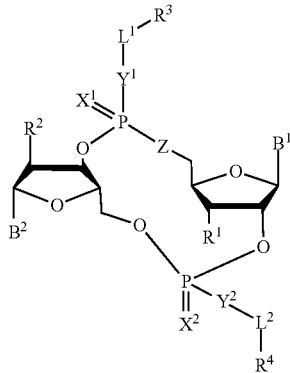

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), $OC(O)OC_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, $C(O)$—$C_1$-$C_{20}$ alkyl, $OC(O)$—$C_1$-$C_{20}$ alkyl (e.g., $C_1$-$C_6$ alkyl), $C(O)O$—$C_1$-$C_{20}$ alkyl (e.g., $C_1$-$C_6$ alkyl), $OC(O)O$—$C_1$-$C_{20}$ alkyl (e.g., $C_1$-$C_6$ alkyl), $C(O)N(R^5)$—$C_1$-$C_{20}$ alkyl (e.g., $C_1$-$C_6$ alkyl), $N(R^5)C(O)$—$C_1$-$C_{20}$ alkyl (e.g., $C_1$-$C_6$ alkyl), $OC(O)N(R^5)$—$C_1$-$C_{20}$ alkyl (e.g., $C_1$-$C_6$ alkyl), O-aryl, O-heteroaryl, $C(O)$-aryl, $C(O)$-heteroaryl, $OC(O)$-aryl, $C(O)O$-aryl, $OC(O)$-heteroaryl, $C(O)O$-heteroaryl, $C(O)O$-aryl, $C(O)O$-heteroaryl, $C(O)N(R^5)$-aryl, $C(O)N(R^5)$-heteroaryl, $N(R^5)C(O)$-aryl, $N(R^5)_2C(O)$-aryl, or $N(R^5)C(O)$-heteroaryl, $S(O)_2N(R^5)$-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In another aspect, the disclosure features a composition, comprising a vaccine, and a vaccine adjuvant comprising a compound of Formula (I),

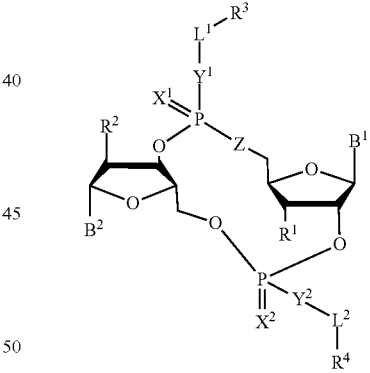

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), $OC(O)OC_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In another aspect, the disclosure features a method of inducing the expression of a pattern recognition receptors (PRR) for immune-modulation in a subject, the method comprising administering to the subject an effective amount of a compound of Formula (I),

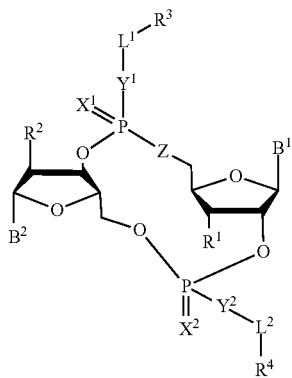

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) OC$_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In another aspect, the disclosure features a method of inducing the expression of a pattern recognition receptor (PRR) for immunomodulation and inducing a therapeutic response in a subject having cancer, the method comprising administering to the subject an effective amount of a compound of Formula (I),

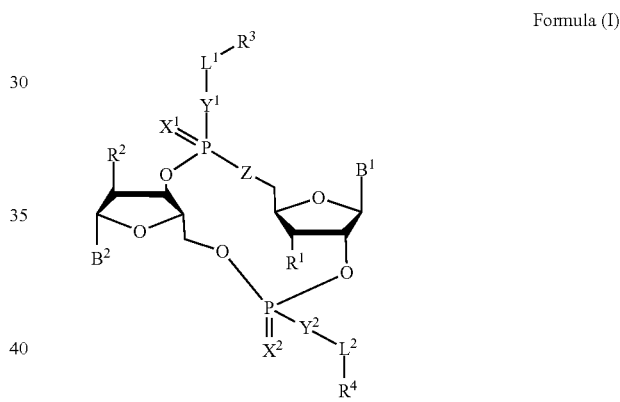

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) OC$_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, O—$C_1$-$C_{20}$—NR$^{10}$R$^{10}$, halo, —CN, OH, oxo, aryl, heteroaryl, O-aryl, or O-heteroaryl.

In another aspect, the present disclosure features a method of inducing an immune response in a subject, the method comprising administering to the subject a therapeutically effective amount of a compound of Formula (I),

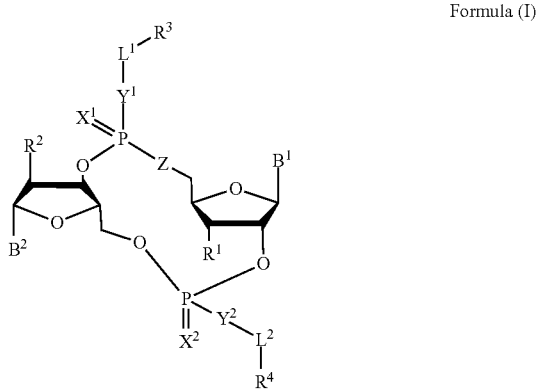

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or NR$^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or OR$^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O)OC$_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), OR$^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)—$C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments, the immune response comprises antitumoral immunity. In some embodiments, the immune response comprises induction of a PRR (e.g., STING, RIG-I, MDA5).

BRIEF DESCRIPTION OF THE DRAWINGS

FIG. 1 depicts SZ14 cells treated with either compound 2 or compound 4 and digitonin for 5.5 hours. ISG54 ISRE-luciferase activity was determined and normalized to DMSO treated cells (mean±standard deviation of triplicate wells per stimulant).

FIG. 4 depicts RAW-Lucia-ISG-WT and RAW-Lucia-ISG-STING KO cells were stimulated with compound 2 or compound 4, alone for 19 hours. Activity of secreted luciferase (IRF-type I IFN activity) in cell culture supernatant was measured using Invivogen's Quanti-luc. Data is shown as fold induction over DMSO treated cells (mean±standard deviation of triplicate wells per stimulant). $EC_{50}$ values were calculated using XLfit. Neither compound induced IRF activity in STING KO cells.

FIG. 9A THP1-Dual (WT) cells were stimulated with compound 3 alone (top panel) or compound/lipo mixture (bottom panel) for 20 hours. Activities of secreted luciferase (IRF-type I IFN activity) in cell culture supernatant were measured using Invivogen's Quanti-luc and Quanti-blue, respectively. Data are shown as fold induction over DMSO treated cells (mean±standard deviation of triplicate wells per stimulant). $EC_{50}$ values were calculated using XLfit.

FIG. 12 depicts THP1-Dual-WT cells in a 96-well plate that were stimulated in triplicate with 8 concentrations of compound 4 for 20 hours. Activities of IRF-driven secreted luciferase and NF-κB-driven SEAP in cell culture supernatant were measured using Invivogen's Quanti-luc and Quanti-blue, respectively. Data is shown as fold increase over DMSO treated cells (mean±standard deviation of triplicate wells per stimulant). Compound 4 did not induced IRF activity in THP1-STING KO cells.

FIG. 15 depicts the response summary in the study to determine the efficacy of compound 4 in a CT26 murine colon carcinoma model using female balb/c mice. Mice in the treatment groups took at least 10 days longer to reach the endpoint when compared to the vehicle group.

FIG. 16 depicts tumor growth inhibition in the study to determine the efficacy of compound 4 in a CT26 murine colon carcinoma model using female balb/c mice. Mice in the treatment groups displayed at least 89% increase tumor growth inhibition when compared to the vehicle group.

DETAILED DESCRIPTION

Figure 2:
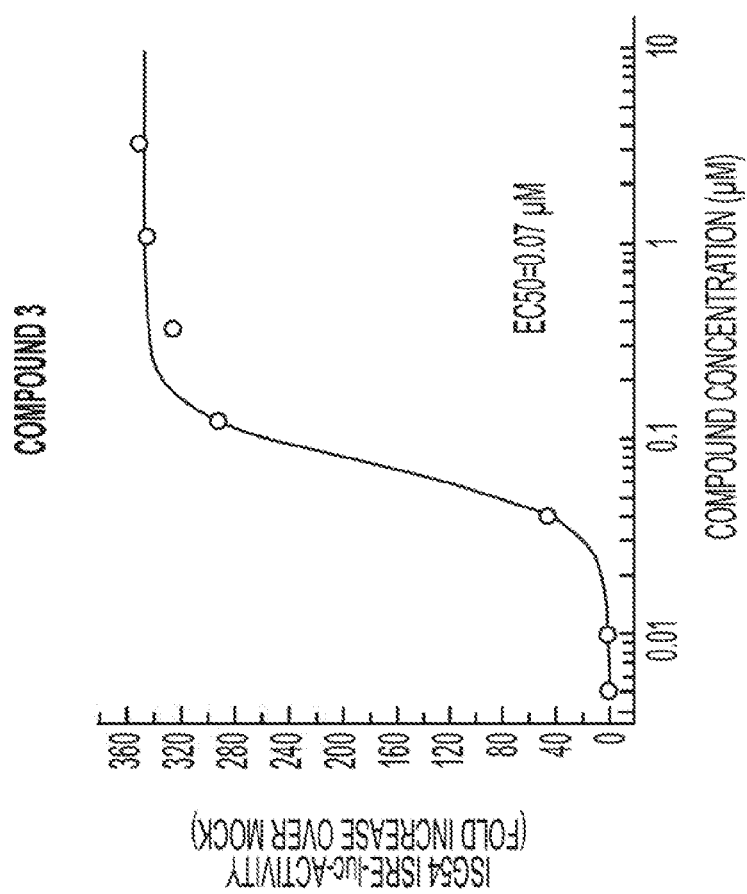
FIG. 2 depicts SZ14 cells treated with compound 3 and digitonin for 6 hours. ISG54 ISRE-luciferase activity was determined and normalized to DMSO treated cells (mean±standard deviation of triplicate wells per stimulant).
Figure 3A:
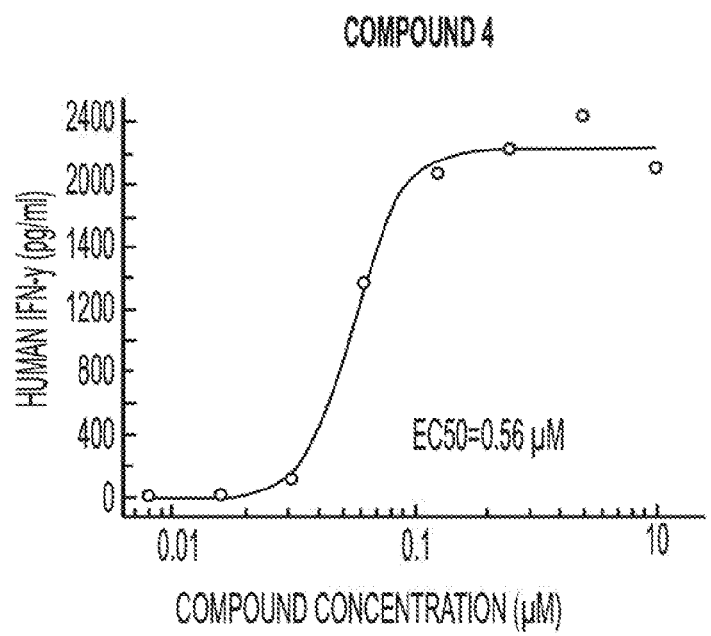
FIG. 3A depicts NK-92 cells were stimulated with compound 4 alone in the absence of IL-2 for 23 hours. Levels of IFN-γ in culture supernatants were quantified using ELISA, and results were shown as pg/mL. Cells were also treated with control DMSO as well as cultured with medium in presence/absence of IL-2
Figure 3B:
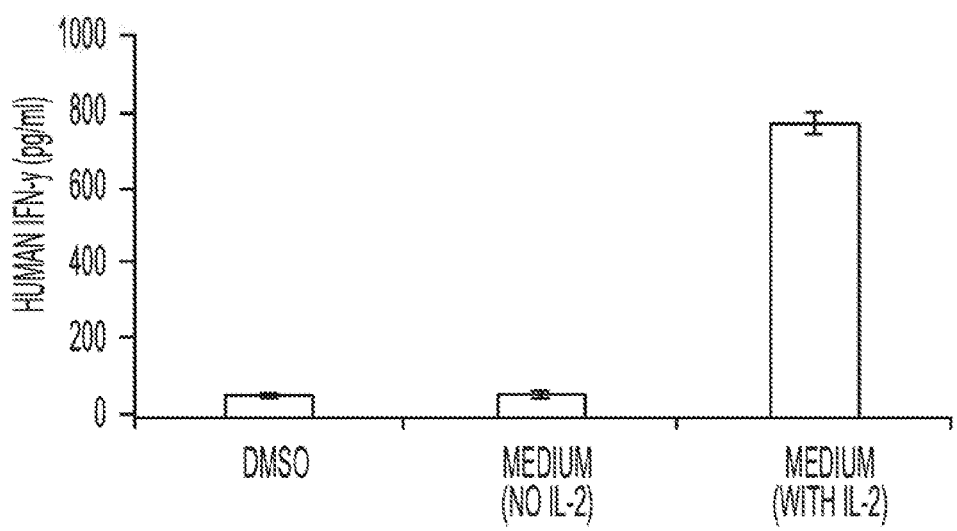
FIG. 3B depicts that the growth of NK-92 cells is IL-2 dependent. The presence of IL-2 is able to induce the production of IFN-γ.
Figure 5:
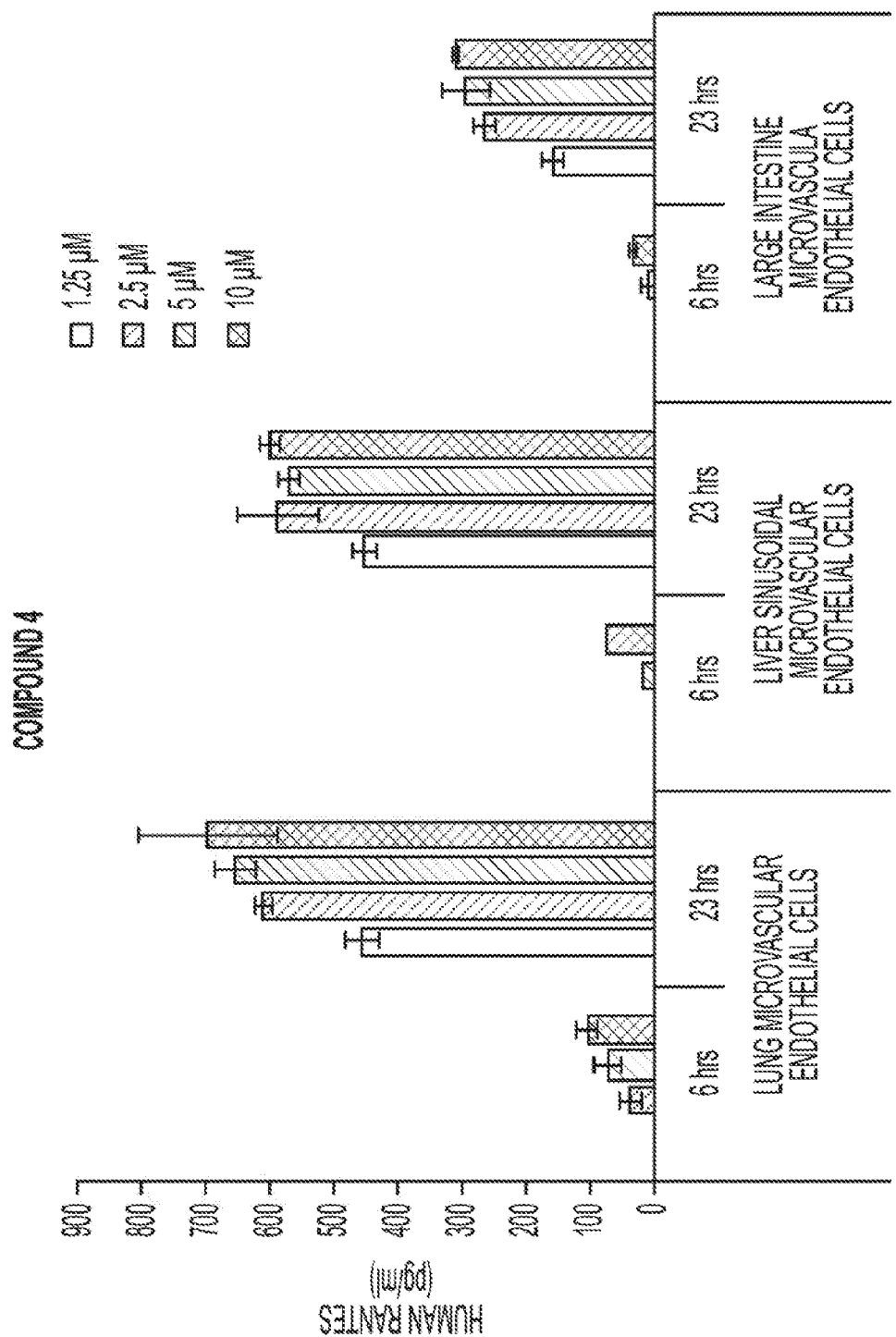
FIG. 5 depicts human endothelial cells isolated from lung microvascular, liver sinusoidal microvascular, and large intestine microvascular were plated into 96-well plate and stimulated with compound 4 alone. Cell culture supernatants were collected at 6 and 23 hours post-treatment. Levels of RANTES in culture supernatants were quantified using ELISA and results were shown as pg/mL. Concentrations (1.25, 2.5, 5, and 10 micromolar) increase from left to right within each of the six bar graphs.
Figure 6A:
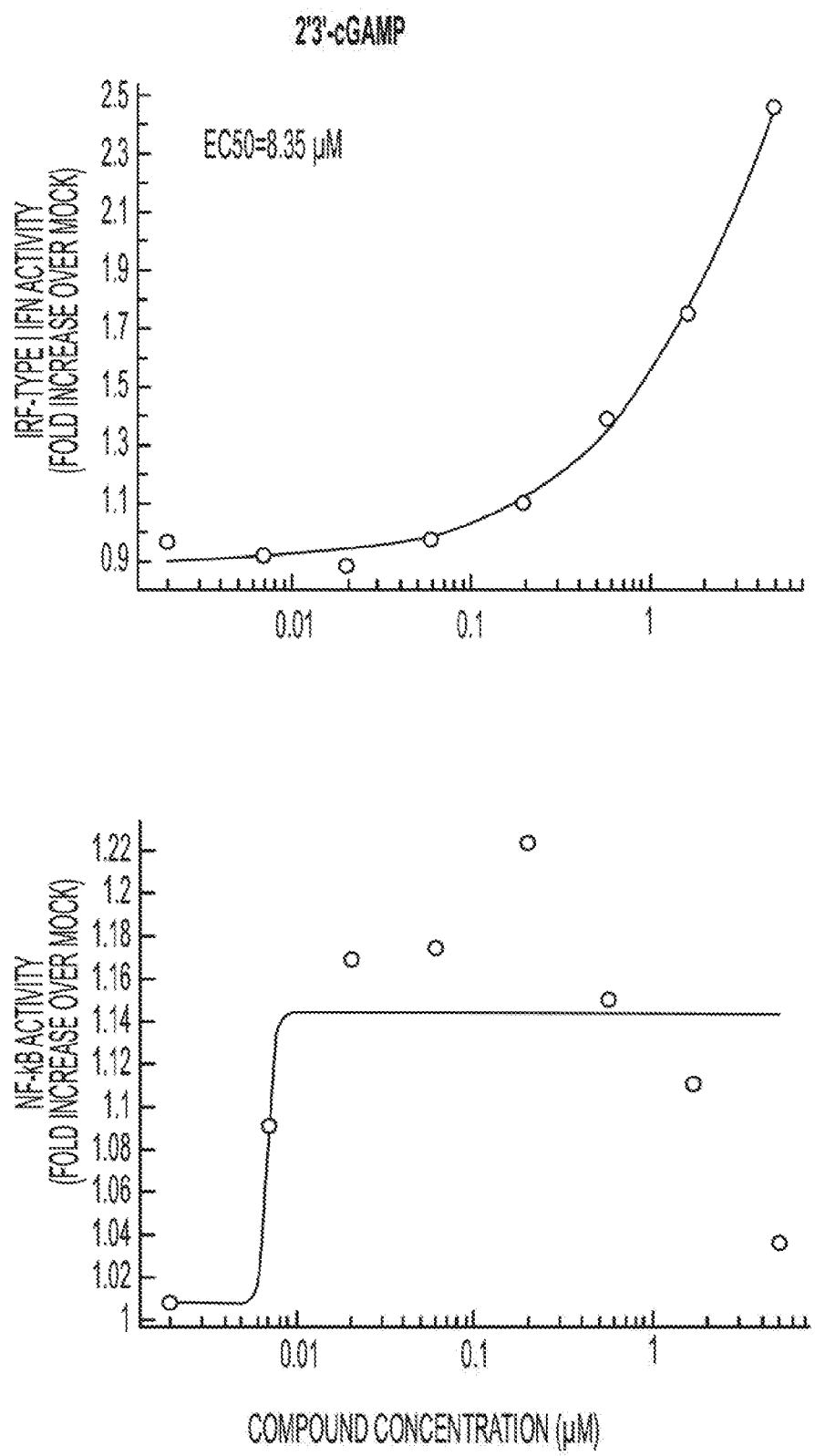
FIG. 6 depicts THP1-Dual-KI-STING-R232 cells stimulated with compound alone for 20 hours. Activities of secreted luciferase (IRF-type I IFN activity) (top panels) and NF-κB (bottom panels) in cell culture supernatant were measured using Invivogen's Quanti-luc and Quanti-blue, respectively. Data are shown as fold induction over DMSO treated cells (mean±standard deviation of triplicate wells per stimulant). $EC_{50}$ values were calculated using XLfit. THP1-Dual-KI-STING-R232 reporter cell line was generated from THP-Dual-STING KO cells by inserting STING-R232 (STING-WT) to rescue the STING signaling pathway. Compound did not induce IRF activity in STING KO cells.
Figure 6B:
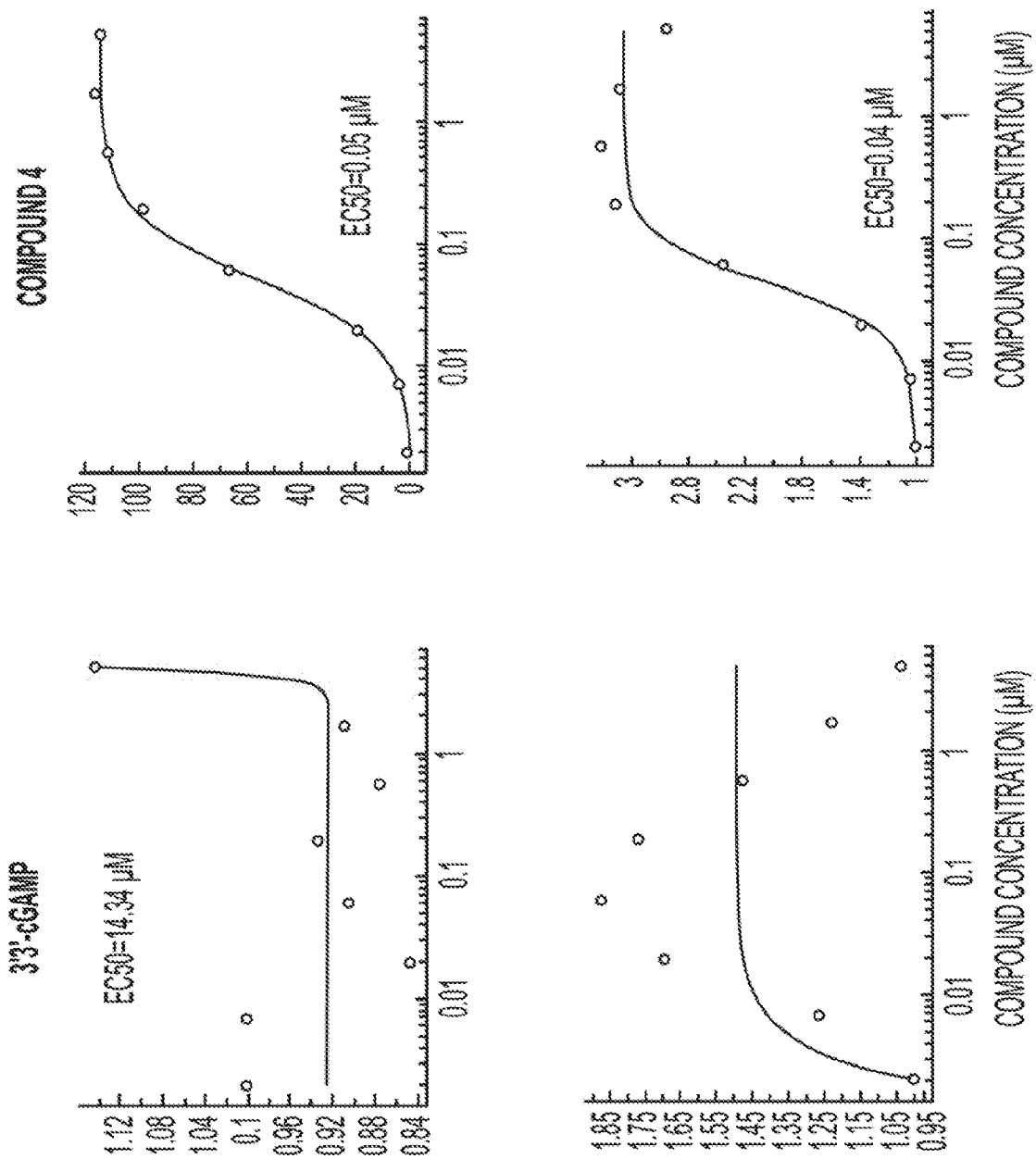
Figure 7A:
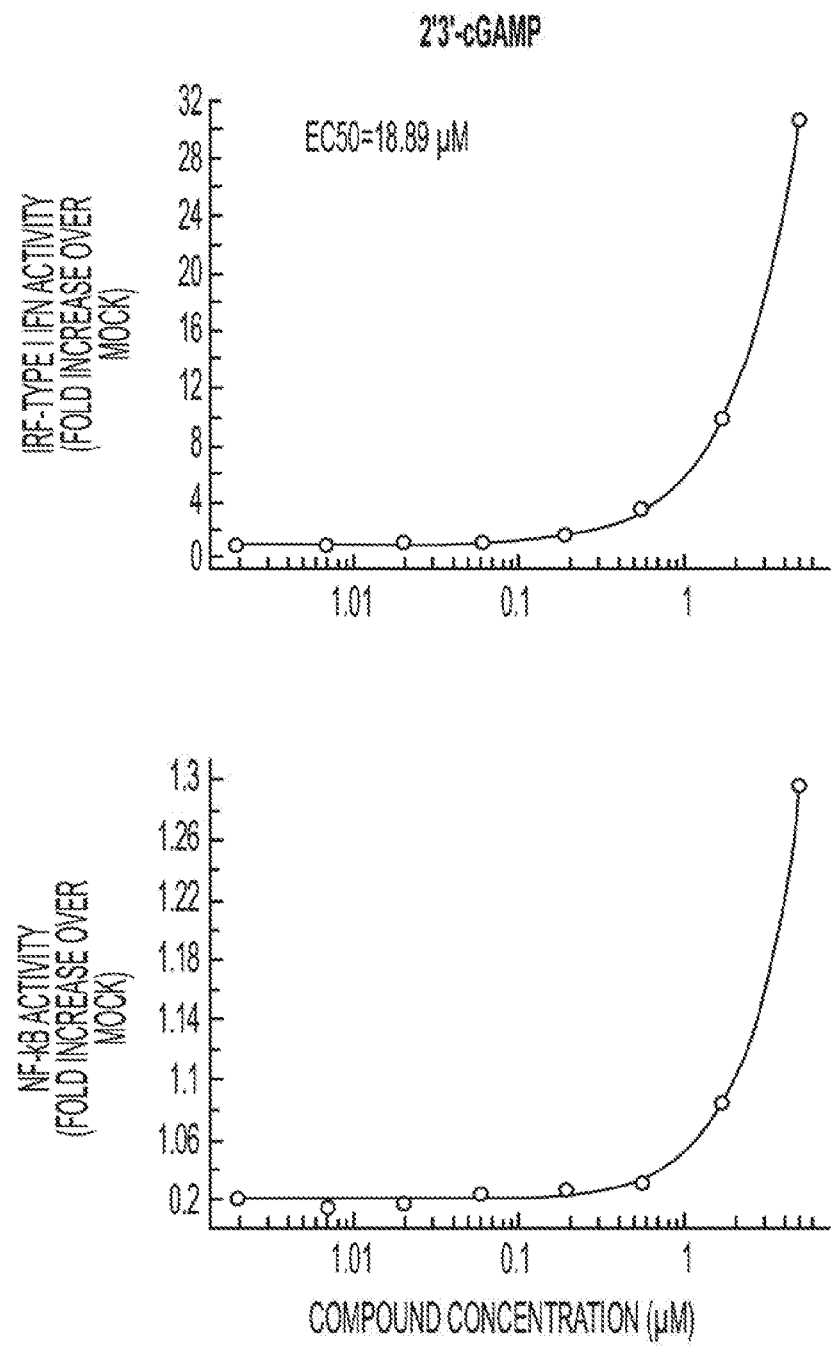
FIG. 7 depicts THP1-Dual-WT cells stimulated with compound alone for 20 hrs. Activities of secreted luciferase (IRF-type I IFN activity) (top panels) and NF-κB (bottom panels) in cell culture supernatant were measured using Invivogen's Quanti-luc and Quanti-blue, respectively. Data are shown as fold induction over DMSO treated cells (mean±standard deviation of triplicate wells per stimulant). $EC_{50}$ values were calculated using XLfit. THP1-Dual-WT cells express STING-HAQ variant. Compound did not induce IRF activity in STING KO cells.
Figure 7B:
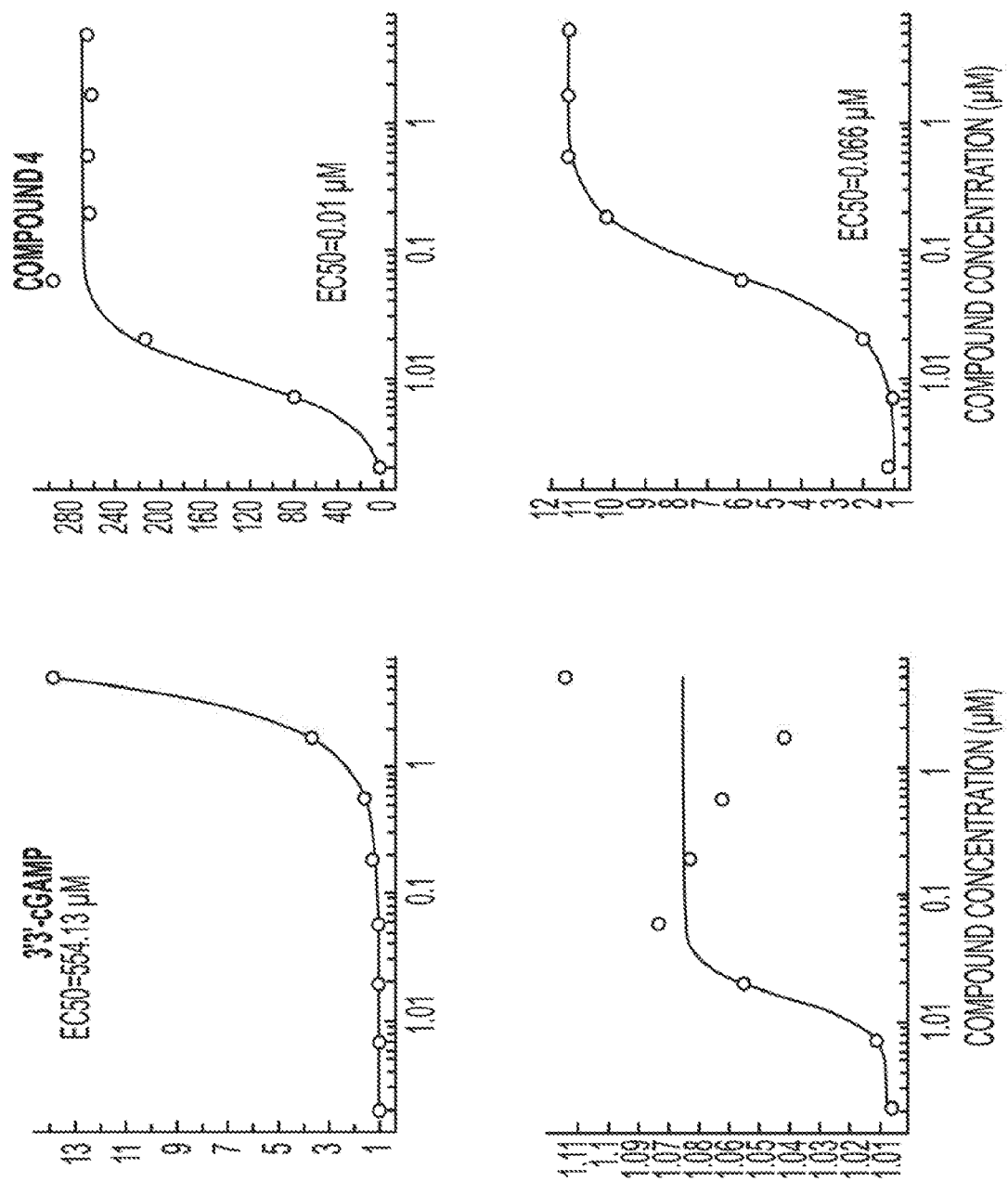
Figure 8A:
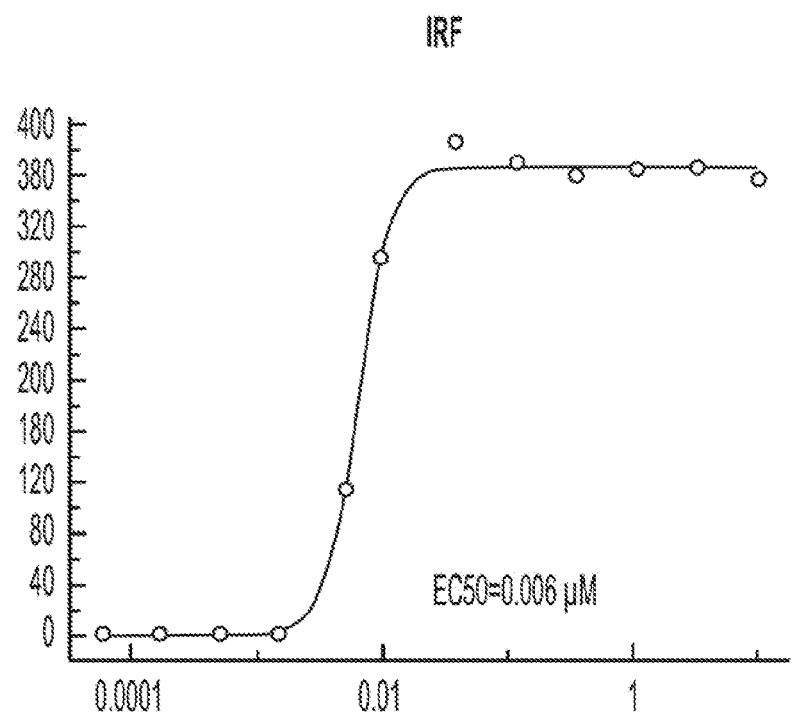
FIG. 8A depicts THP1-Dual-WT cell stimulated in triplicate with compound 4 alone for 20 hours. Activities of IRF-driven secreted luciferase in cell culture supernatant were measured using Invivogen's Quanti-luc and Quanti-blue, respectively. Data are shown as fold increase over DMSO treated cells (mean±standard deviation of triplicate wells per stimulant).
Figure 8B:
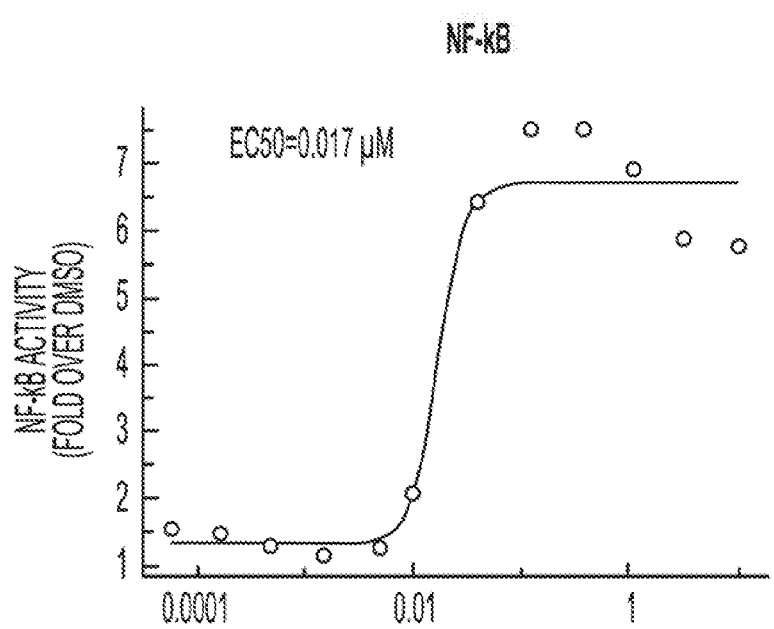
FIG. 8B depicts THP1-Dual-WT cell stimulated in triplicate with compound 4 alone for 20 hours. Activities of NF-κB in cell culture supernatant were measured using Invivogen's Quanti-luc and Quanti-blue, respectively. Data are shown as fold increase over DMSO treated cells (mean±standard deviation of triplicate wells per stimulant).
Figure 8C:
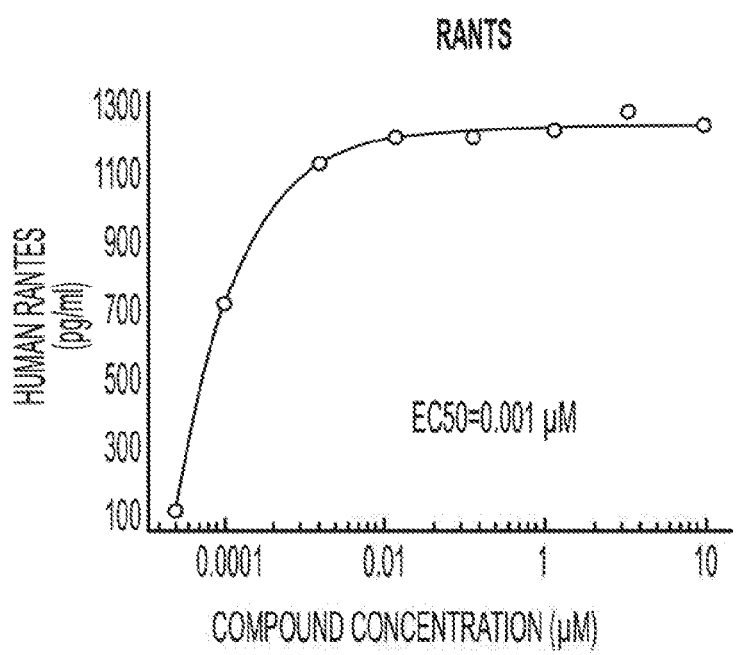
FIG. 8C depicts THP1-Dual-WT cell stimulated in triplicate with compound 4 alone for 20 hours. Levels of RANTES in culture supernatants were quantified using ELISA and results were shown as pg/mL.
Figure 8D:
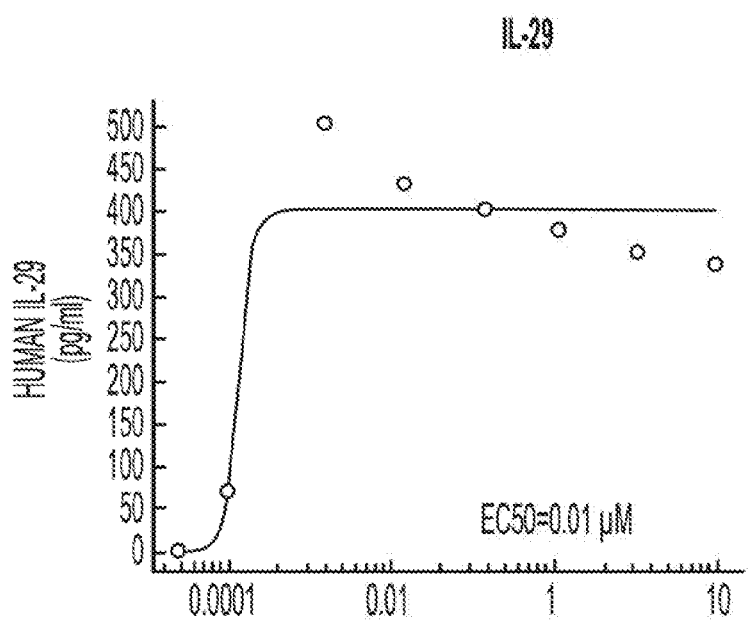
FIG. 8D depicts THP1-Dual-WT cell stimulated in triplicate with compound 4 alone for 20 hours. Levels of IL-29 in culture supernatants were quantified using ELISA and results were shown as pg/mL.
Figure 9B:
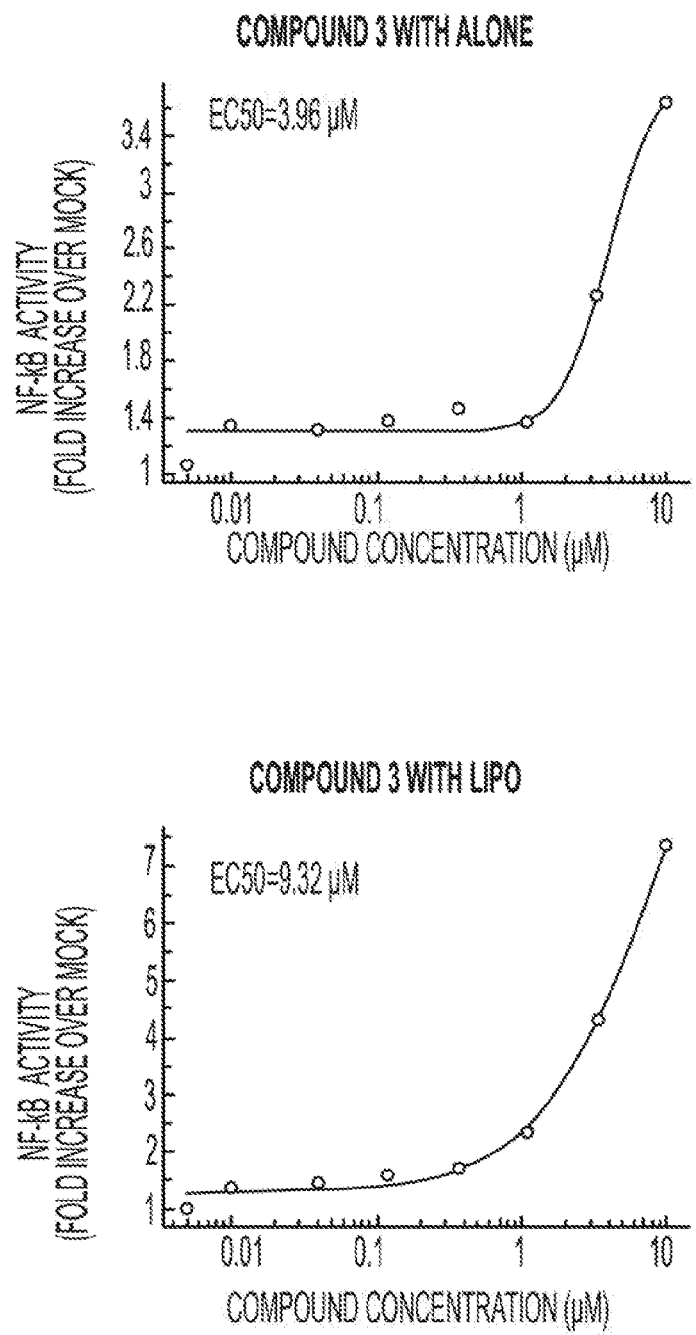
FIG. 9B depicts THP1-Dual (WT) cells were stimulated with compound 3 alone (top panel) or compound/lipo mixture (bottom panel) for 20 hours. Activities of sNF-κB in cell culture supernatant were measured using Invivogen's Quanti-luc and Quanti-blue, respectively. Data are shown as fold induction over DMSO treated cells (mean±standard deviation of triplicate wells per stimulant). $EC_{50}$ values were calculated using XLfit.
Figure 10:
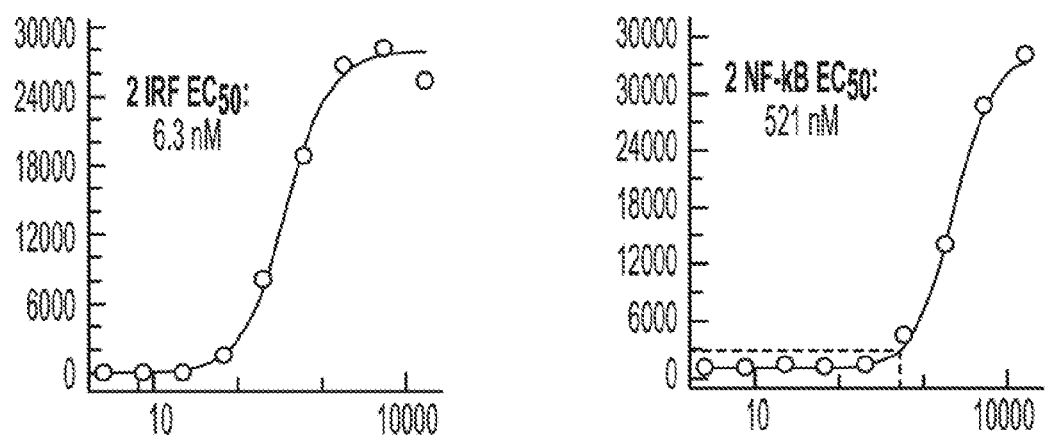
FIG. 10 depicts THP1 dual & STING KO THP1 dual cells grown in complete media were treated with various concentrations of compound 2 or DMSO control with Lipofectamine LTX. Dual cells carry both secreted embryonic alkaline phosphatase (SEAP) reporter gene under the control of an IFN-b minimal promoter fused to five copies of the NF-kB consensus transcriptional response element to measure NF-kB activity and Lucia reporter gene under the control of an ISG54 minimal promoter to measure IRF activity. After 20 hours incubation, IRF activity was assessed using QUANTI-luc to measure levels of Lucia and NF-kB activity was determined by measure SEAP levels at 620-655 nm. % induction was calculated from fold change in luminescence/absorbance compared to DMSO treated sample.
Figure 11:
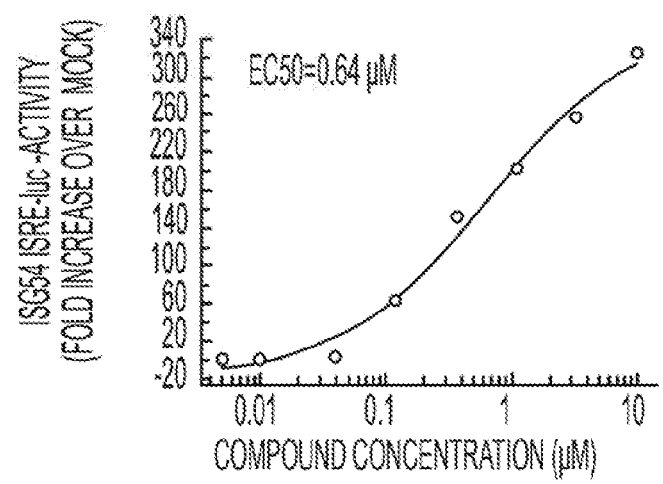
FIG. 11 depicts SZ14 reporter cells (a HEK293-derived type I IFN inducible reporter cell line) that were treated with compound and digitonin. ISG54 ISRE-luciferase activity was determined and normalized to DMSO treated cells (mean±standard deviation of triplicate wells per stimulant).
Figure 13:
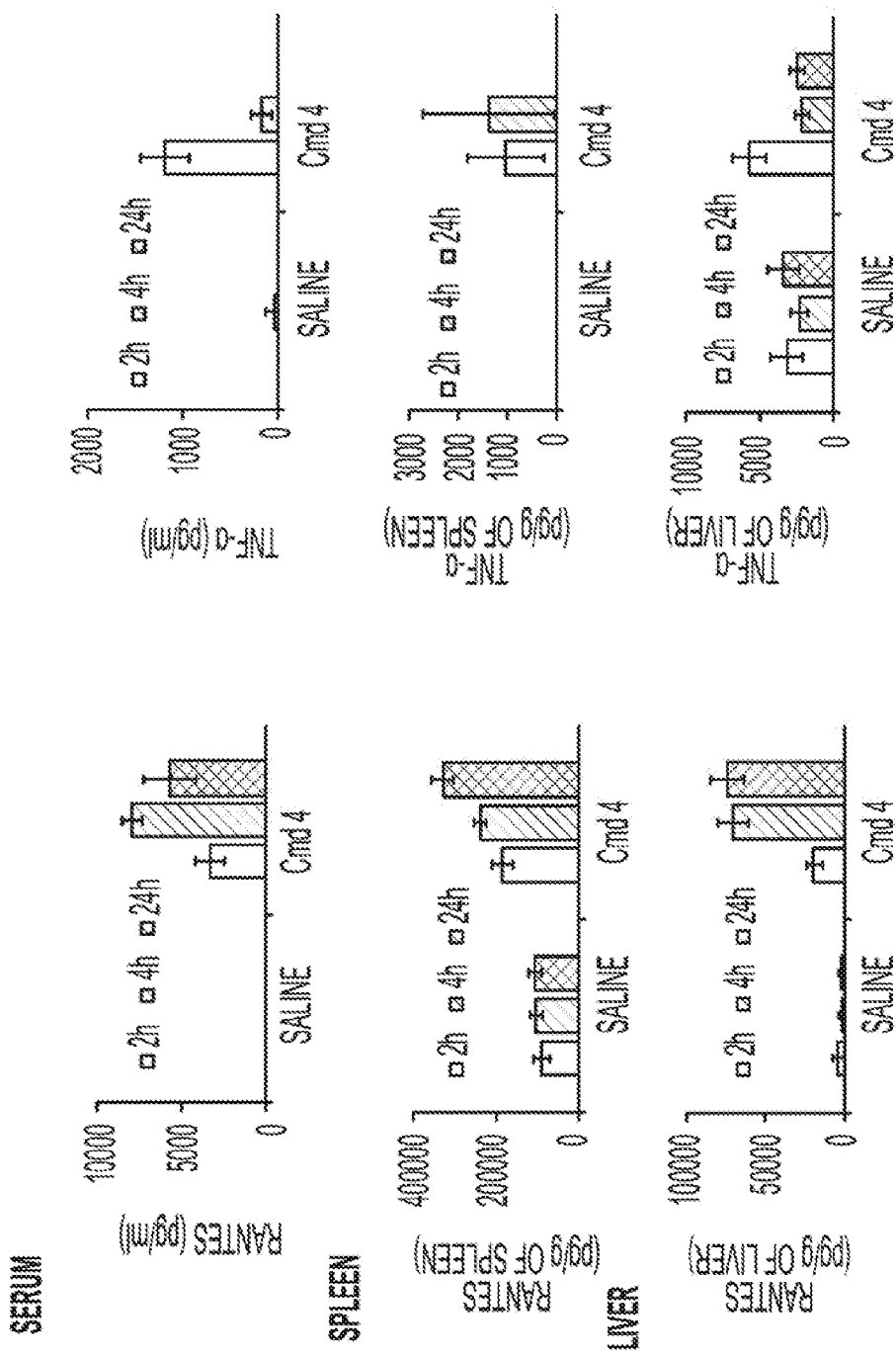
FIG. 13 depicts the treatment of groups of 5 Balb/C mice (female, 8 weeks of age) which were intravenously injected via tail vein with saline control or compound 4 at 9 mg/kg. Serum, spleen, and liver samples were collected at 2, 4, and 24 hours post-treatment. Levels of RANTES (A, C, E) and TNF-α (B, D, F) were measured using ELISA. Results are displayed as pg/mL for serum samples and pg/g of tissue for spleen and liver samples.
Figure 14:
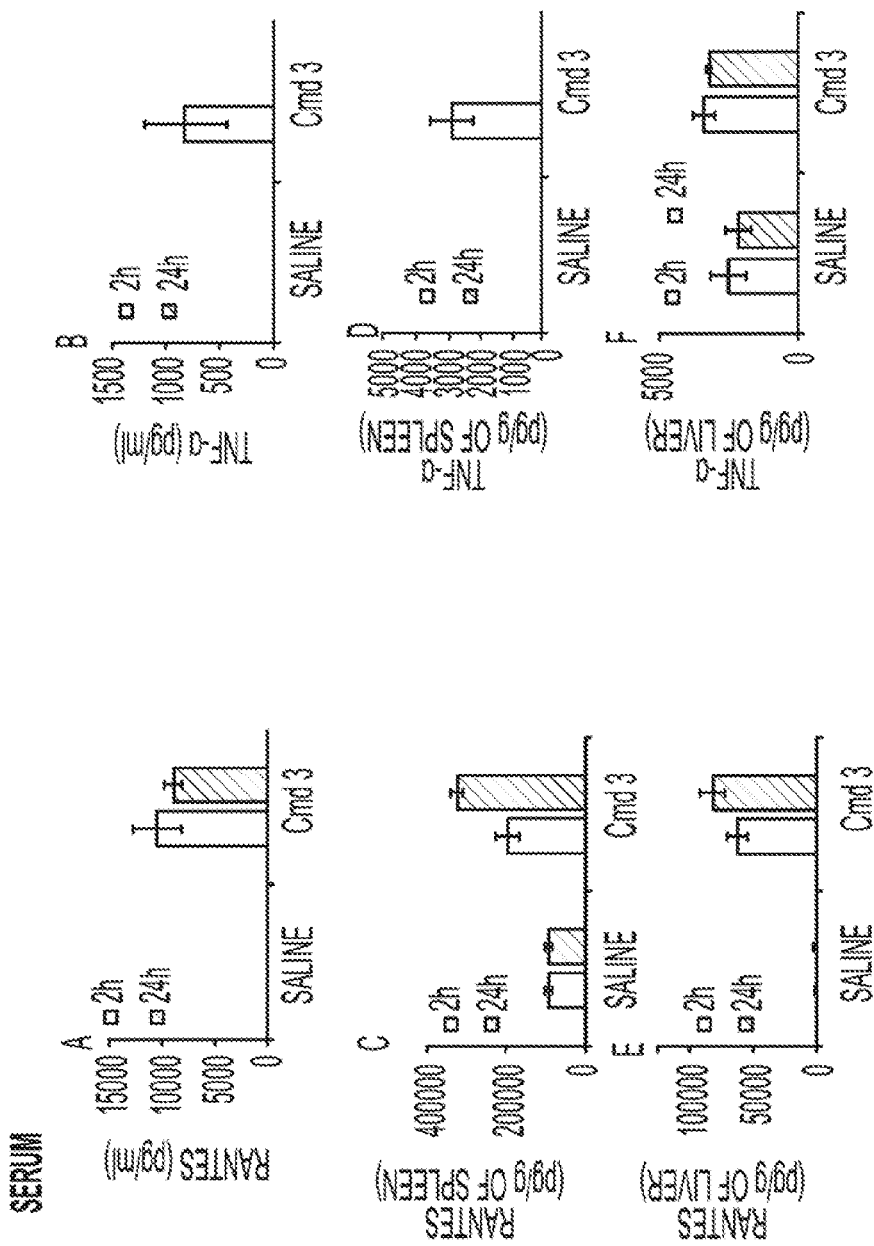
FIG. 14 depicts the treatment groups of 5 Balb/C mice (female, 10 weeks of age) which were intravenously injected via tail vein with saline control or compound 3 at 9 mg/kg. Serum, spleen, and liver samples were collected at 2 and 24 hrs post-treatment. Levels of RANTES and TNF-α were measured using ELISA and results are shown as pg/mL for serum samples and pg/g of tissue for spleen and liver samples.
Figure 17:
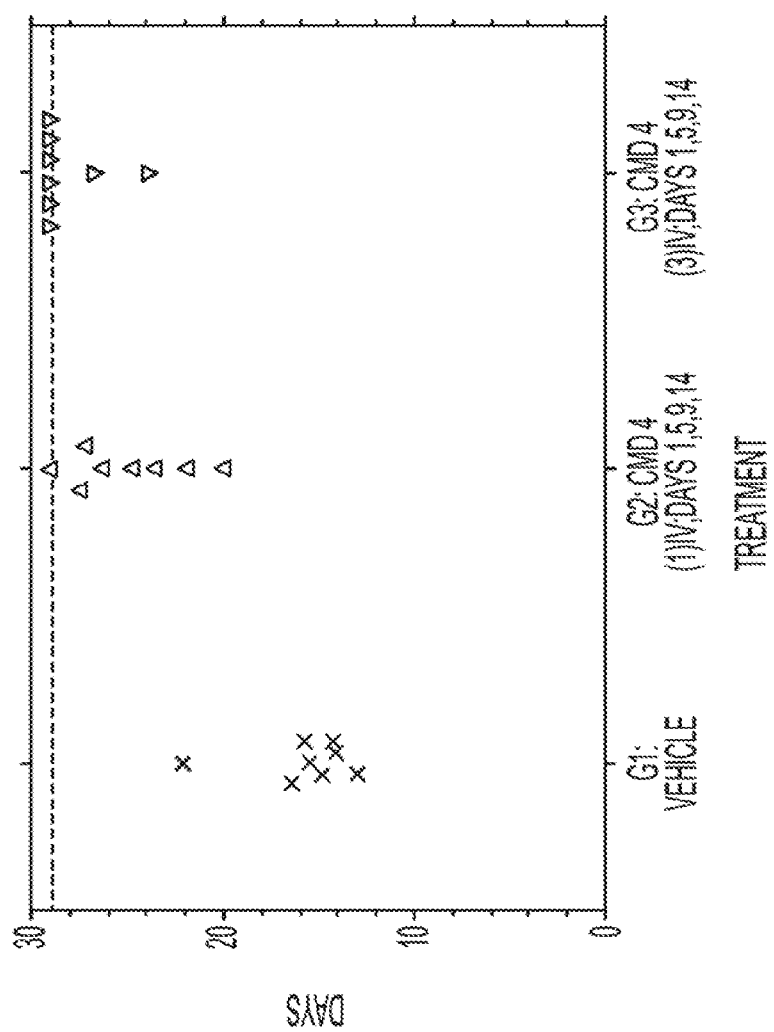
FIG. 17 depicts the individual times to endpoint for mice in the study to determine the efficacy of compound 4 in a CT26 murine colon carcinoma model using female balb/c mice. Mice in the treatment groups took longer to reach the endpoint when compared to the vehicle group.
Figure 18:
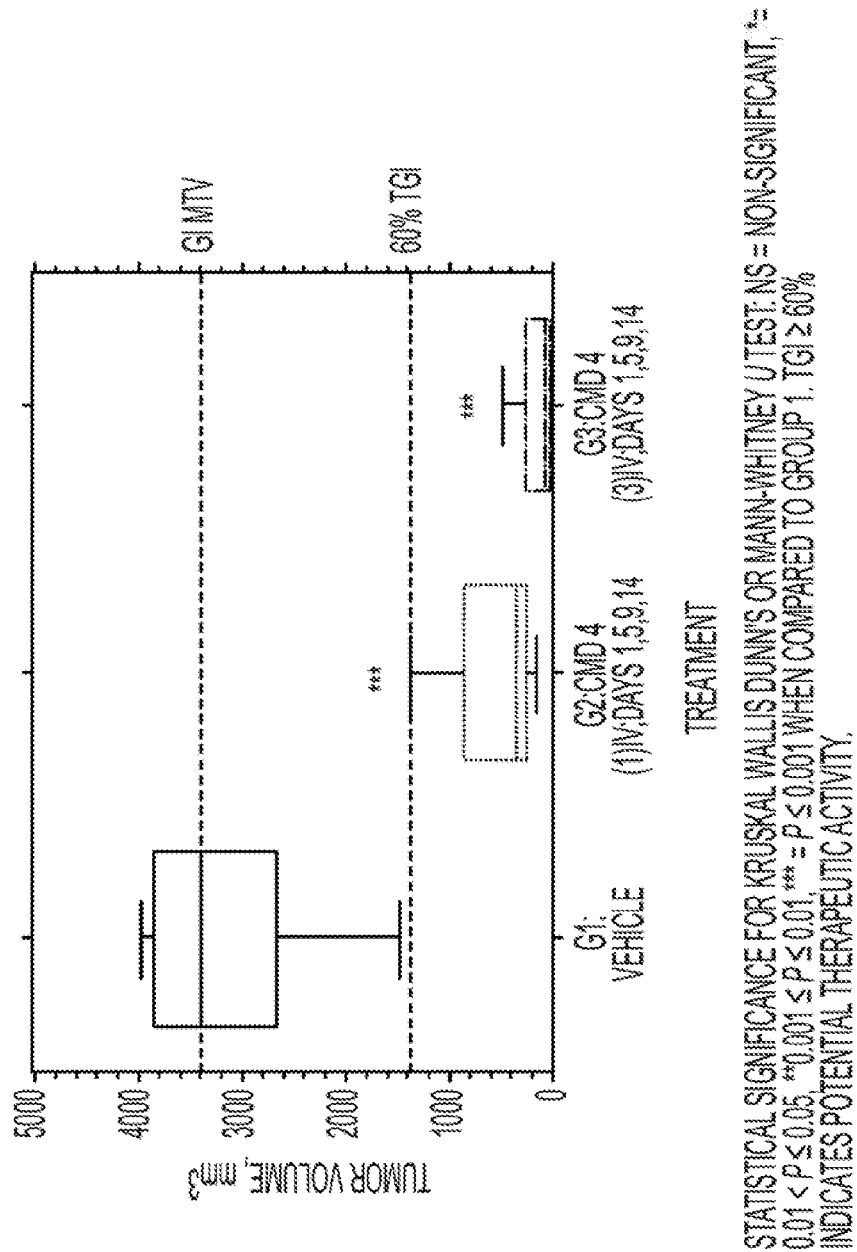
FIG. 18 depicts the tumor volume distribution on day 18 in the study to determine the efficacy of compound 4 in a CT26 murine colon carcinoma model using female balb/c mice. Mice in the treatment groups possessed significantly smaller tumor volumes when compared to the vehicle group.
Figure 19:
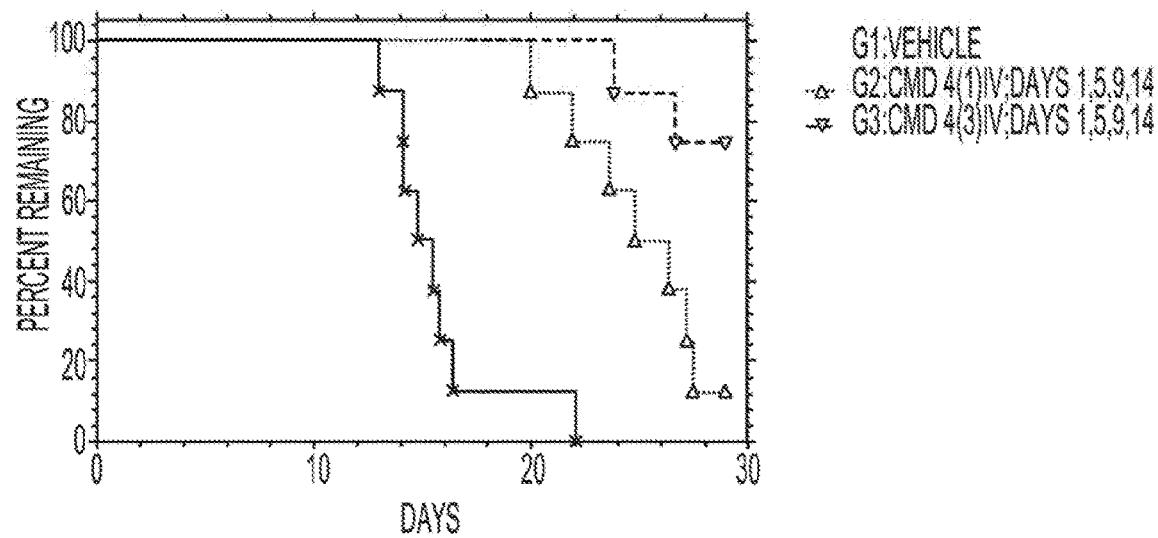
FIG. 19 depicts the Kaplan-Meier plot for the study to determine the efficacy of compound 4 in a CT26 murine colon carcinoma model using female balb/c mice. The treatment groups had a greater percent of mice remaining at day 21 than the vehicle group.

The present disclosure relates to methods of activating and/or inducing the expression of PRRs (e.g., STING) in a subject, in particular for the treatment of a microbial infection or a proliferative disease (e.g., cancer). In some embodiments, the method comprises administration of a compound of Formula (I) or pharmaceutically acceptable salt thereof. It is to be noted that induction of any PRR with these compounds can stimulate interferon and/or NF-кB production which can induce the expression of a variety of PRRs which are inducible genes by feedback mechanism.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the term "acquire" or "acquiring" as the terms are used herein, refer to obtaining possession of a physical entity (e.g., a sample, e.g., blood sample or liver biopsy specimen), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g., LC-MS.

As used herein, the terms "induce" or "induction of" refer to the increase or enhancement of a function, e.g., the increase or enhancement of the expression of a pattern recognition receptor (e.g, STING). In some embodiments, "induction of PRR expression" refers to induction of transcription of PRR RNA, e.g., STING RNA (e.g., mRNA, e.g., an increase or enhancement of), or the translation of a PRR protein, e.g., the STING protein (e.g., an increase or enhancement of). In some embodiments, induction of PRR expression (e.g., STING expression) refers to the increase or enhancement of the concentration of a PRR RNA, e.g., or STING RNA (e.g., mRNA) or the STING protein, e.g., in a cell. In some embodiments, induction of PRR expression (e.g., STING expression) refers to the increase of the number of copies of PRR RNA, e.g., STING RNA (e.g., mRNA) or PRR protein, e.g., the STING protein, e.g., in a cell. In some embodiments, to induce expression of a PRR (e.g., STING) may refer to the initiation of PRR RNA (e.g., STING RNA (e.g., mRNA)) or transcription or PRR protein (e.g., STING protein) translation. In some embodiments, to induce expression of a PRR (e.g., STING) may refer to an increase in the rate of PRR RNA (e.g., STING RNA (e.g., mRNA)) transcription or an increase in the rate of PRR protein (e.g., STING protein) expression.

As used herein, the terms "activate" or "activation" refer to the stimulation or triggering of a function, e.g., of a downstream pathway, e.g., a downstream signaling pathway. In some embodiments, activation of a pattern recognition receptor (PRR) (e.g., STING) refers to the stimulation of a specific protein or pathway, e.g., through interaction with a downstream signaling partner (e.g., IFN-β promoter stimulator 1 (IPS-1), IRF3, IRF7, NF-кB, interferons (e.g., IFN-α or IFN-β) and/or cytokines). In some embodiments, activation is distinct from the induction of expression of a PRR. In some embodiments, a PRR may be activated without resulting in an induction of PRR expression (e.g., expression of STING). In some embodiments, activation may include induction of expression of a PRR (e.g., STING). In some embodiments, activation of a PRR may trigger the induction of expression of a PRR (e.g., STING) by about 0.1%, about 0.5%, about 1%, about 5%, about 10%, about 15%, about 20%, about 25%, about 30%, about 40%, about 50%, about 60%, about 70%, about 80%, about 90%, about 95%, or more compared to a reference standard (e.g., basal expression levels of a PRR (e.g., STING)).

As used herein, an amount of a compound, conjugate, or substance effective to treat a disorder (e.g., a disorder described herein), "therapeutically effective amount," "effective amount" or "effective course" refers to an amount of the compound, substance, or composition which is effective, upon single or multiple dose administration(s) to a subject, in treating a subject, or in curing, alleviating, relieving or improving a subject with a disorder (e.g., a microbial infection) beyond that expected in the absence of such treatment.

As used herein, the terms "prevent" or "preventing" as used in the context of a disorder or disease, refer to administration of an agent to a subject, e.g., the administration of a compound of the present disclosure (e.g., compound of Formula (I)) to a subject, such that the onset of at least one symptom of the disorder or disease is delayed as compared to what would be seen in the absence of administration of said agent.

As used herein, the terms "reference treatment" or "reference standard" refer to a standardized level or standardized treatment that is used as basis for comparison. In some embodiments, the reference standard or reference treatment is an accepted, well known, or well characterized standard or treatment in the art. In some embodiments, the reference standard describes an outcome of a method described herein. In some embodiments, the reference standard describes a level of a marker (e.g., a level of induction of a PRR, e.g., STING) in a subject or a sample, e.g., prior to initiation of treatment, e.g., with a compound or composition described herein. In some embodiments, the reference standard describes a measure of the presence of, progression of, or severity of a disease or the symptoms thereof, e.g., prior to initiation of treatment, e.g., with a compound or composition described herein.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dogs, cats, cows, pigs. In exemplary embodiments of the disclosure, the subject is a woodchuck (e.g., an Eastern woodchuck (*Marmota monax*)).

As used herein, the terms "treat" or "treating" a subject having a disorder or disease refer to subjecting the subject to a regimen, e.g., the administration of a compound of Formula (I) or pharmaceutically acceptable salt thereof, or a composition comprising Formula (I) or pharmaceutically acceptable salt thereof, such that at least one symptom of the disorder or disease is cured, healed, alleviated, relieved, altered, remedied, ameliorated, or improved. Treating includes administering an amount effective to alleviate, relieve, alter, remedy, ameliorate, improve or affect the disorder or disease, or the symptoms of the disorder or disease. The treatment may inhibit deterioration or worsening of a symptom of a disorder or disease.

As used herein, the term "Cmd" refers to the word "compound" or "Compound", and all of the terms are used interchangeably.

Numerous ranges, e.g., ranges for the amount of a drug administered per day, are provided herein. In some embodiments, the range includes both endpoints. In other embodiments, the range excludes one or both endpoints. By way of example, the range can exclude the lower endpoint. Thus, in such an embodiment, a range of 250 to 400 mg/day, excluding the lower endpoint, would cover an amount greater than 250 that is less than or equal to 400 mg/day.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH₂ and —CH₂CH=CH₂.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH₂— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroalkyl" refers to an "alkyl" moiety wherein at least one of the carbone molecules has been replaced with a heteroatom such as O, S, or N.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

The term "nucleobase" as used herein, is a nitrogen-containing biological compound found linked to a sugar within a nucleoside—the basic building blocks of deoxyribonucleic acid (DNA) and ribonucleic acid (RNA). The primary, or naturally occurring, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Adenine and guanine belong to the double-ringed class of molecules called purines (abbreviated as R). Cytosine, thymine, and uracil are all pyrimidines. Other nucleobases that do not function as normal parts of the genetic code are termed non-naturally occurring.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Pattern Recognition Receptors

The disclosure presented herein features methods for the activation and induction of PRR expression (e.g., STING expression) in a subject, e.g., a subject with a microbial infection (e.g., a viral infection, bacterial infection, fungal infection, or parasitic infection) or a proliferative disease (e.g., cancer).

Pattern recognition receptors (PRRs) are a broad class of proteins which recognize pathogen-associated molecular patterns (PAMPs) conserved within pathogenic invaders. PAMPs are typically products of biosynthetic pathways that are essential to the survival and/or infectivity of the pathogen, e.g., lipopolysaccharides, glycoproteins, and nucleic acids. Recognition of PAMPs by their cognate PRRs activates signaling pathways that result in the production of immune defense factors such as pro-inflammatory and anti-inflammatory cytokines, type I interferons (IFN-$\alpha$, IFN-$\beta$), and/or interferon stimulated genes (ISGs). It is well known that induction of innate immune signaling also results in the activation of T cell responses as well as the induction of adaptive immunity. These downstream immune effects are essential for clearance of the virus through apoptosis and killing of infected cells through cytotoxic T lymphocytes and other defense mechanisms. It is also well known that interferons act on ISRE (interferon response elements) that can trigger the production of ISGs, which play an important role in antiviral cellular defense.

The stimulator of interferon genes (STING) is a cytosolic microbial-derived DNA sensor that has been shown to be particularly sensitive to double-stranded DNA and cyclic dinucleotides (e.g., cyclic di-GMP) (Burdette, D. L. and Vance, R. E. (2013) *Nat Immunol* 14:19-26). Two molecules of STING form a homodimer mediated by an $\alpha$-helix present in the C-terminal dimerization domain, and molecular binding studies have revealed that each STING dimer binds one molecule of microbial nucleic acids, e.g., DNA or a cyclic dinucleotide. Upon ligand binding, STING activates the innate immune response through interaction with RIG-I and IPS-1, resulting in interferon production (e.g., IFN-$\alpha$ and IFN-$\beta$) and other downstream signaling events. Since its discovery, STING has been shown to function as a critical sensor of viruses (e.g., adenovirus, herpes simplex virus, hepatitis B virus, vesicular stomatitis virus, hepatitis C virus), bacteria (e.g., *Listeria monocytogenes, Legionella pneumopholia, Mycobacterium tuberculosis*) and protozoa (*Plasmodium falciparum, Plasmodium berghei*). In addition, STING has been shown to play a major role in the innate immune response against tumor antigens, driving dendritic cell activation and subsequent T cell priming in several cancers (Woo, S. R. et al. *Trends in Immunol* (2015) 36:250-256).

Another class of PRRs includes RIG-I, which is the founding member of a family of PRRs termed RIG-I-like receptors (RLRs) that primarily detect RNA derived from foreign sources. It is a critical sensor of microbial infection (e.g., viral infection) in most cells and is constitutively expressed at low levels in the cytosol. After ligand binding, the expression of RIG-I is rapidly enhanced, leading to increased RIG-I concentrations in the cell (Jensen, S. and Thomsen, A. R. *J Virol* (2012) 86:2900-2910; Yoneyama M. et al. *Nat Immunol* (2004) 5:730-737). RIG-I is an ATPdependent helicase containing a central DExD/H box ATPase domain and tandem N-terminal caspase-recruiting domains (CARDs) that mediate downstream signaling. The C-terminus of RIG-I comprises an ssRNA/dsRNA-binding domain that when unbound acts to silence CARD function at the N-terminus. Without wishing to be bound by theory, it is believed that upon recognition of target RNA structures, two N-terminal CARDs are exposed, allowing for interaction with the CARD of a downstream binding partner, IFN-3 promoter stimulator 1 (IPS-1), also known as mitochondrial antiviral signaling molecule (MAVS) and CARDIF. This interaction in turn triggers further downstream signaling, such as induction of IRF3, IRF7, NF-κB, IFNs, and cytokine production that results in the initiation of the host immune response.

Other RLRs are homologous to RIG-I and function in a similar manner, including MDA5, LGP2, and RNase L. MDA5 is highly homologous to RIG-I, and has been shown to be crucial for triggering a cytokine response upon infection with picornaviruses (e.g., encephalomyocarditis virus (EMCV), Theiler's virus, and Mengo virus), Sendai virus, rabies virus, West Nile virus, rabies virus, rotavirus, murine hepatitis virus, and murine norovirus. LPG2 lacks a CARD domain found in RIG-I and MDA5, which is responsible for direct interaction with IPS-1 to initiate downstream signaling. As such, LPG2 is believed to behave as a modulator of the innate immune response in conjunction with other CARD-bearing RLRs such as RIG-I and MDA5.

Another class of PRRs encompasses the nucleotide-binding and oligomerization domain (NOD)-like receptors, or NLR family (Caruso, R. et al, Immunity (2014) 41:898-908), which includes the microbial sensor NOD2. NOD2 is composed of an N-terminal CARD, a centrally-located nucleotide-binding oligomerization domain, and a C-terminal leucine rich repeat domain that is responsible for binding microbial PAMPs, such as bacterial peptidoglycan fragments and microbial nucleic acids. Ligand binding activates NOD2 and is believed to drive interaction with the CARD-containing kinase RIPK2, which in turn activates a number of downstream proteins including NF-κB, MAPK, IRF7, and IRF3, the latter of which results in the induction of type 1 interferons. NOD2 is expressed in a diverse set of cell types, including macrophages, dendritic cells, paneth cells, epithelial cells (e.g., lung epithelial cells, intestinal epithelia), and osteoblasts. NOD2 has been established as a sensor of infection by variety of pathogenic invaders, such as protozoa (e.g., *Toxoplasma gondii* and *Plasmodium berghei*), bacteria (e.g., *Bacillus anthracis, Borrelia burgdorferi, Burkholderia pseudomallei, Helicobacter hepaticus, Legionella pneumophilia, Mycobacterium tuberculosis, Propionibacterium acne, Porphyromonas gingivalis, Salmonella enterica*, and *Streptococcus pneumonia*), and viruses (e.g., respiratory syncytial virus and murine norovirus-1) (Moreira, L. O. and Zamboni, D. S. *Front Immunol* (2012) 3:1-12). Recent work has shown that mutation of NOD2 may contribute to inflammatory diseases such as Crohn's disease, resulting in an aberrant inflammatory response upon stimulation.

Representative Compounds

The present disclosure features compounds and methods for the induction of PRR expression (e.g., STING expression) in a subject (e.g., a subject with a microbial infection (e.g., a viral infection, bacterial infection, fungal infection, or parasitic infection) or a proliferative disease (e.g., cancer)), comprising administration of an effective amount of a compound of Formula (I) or a pharmaceutically acceptable salt or stereoisomer thereof.

In some embodiments, the present disclosure features a compound of Formula (I) in which the 3'-OH end of a first nucleoside is joined to the 5'-OH of a second nucleoside through a linkage; and the 2'-OH end of the second nucleoside is joined to the 5'-OH of the first nucleoside through a linkage.

In some embodiments, the compound is a compound of Formula (I):

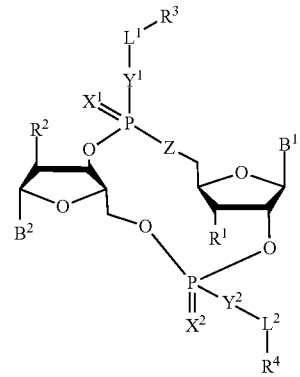

Formula (I)

or a pharmaceutically acceptable salt or stereoisomer thereof, wherein: Z is either S or O; each of $B^1$ and $B^2$ is independently a purinyl nucleobase or pyrimidinyl nucleobase; each of $X^1$ and $X^2$ is independently O or S; each of $Y^1$ and $Y^2$ is independently O, S, or $NR^5$; each of $L^1$ and $L^2$ is independently absent, $C_1$-$C_6$ alkyl or $C_1$-$C_6$ heteroalkyl, wherein each alkyl and heteroalkyl is optionally substituted with $R^6$; each of $R^1$ and $R^2$ is independently hydrogen, halo, —CN, $C_1$-$C_{20}$ alkyl (e.g., $C_1$-$C_6$ alkyl), or $OR^7$; each of $R^3$ and $R^4$ is independently hydrogen, $C_1$-$C_{20}$ alkyl (e.g., $C_1$-$C_6$ alkyl), $C_1$-$C_{20}$ heteroalkyl (e.g., $C_1$-$C_6$ heteroalkyl), OC(O) $OC_1$-$C_{20}$ alkyl (e.g., $C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$; $R^5$ is hydrogen or $C_1$-$C_{20}$ alkyl (e.g., $C_1$-$C_6$ alkyl); $R^6$ is halo, —CN, $C_1$-$C_{20}$ alkyl (e.g., $C_1$-$C_6$ alkyl), $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$; $R^7$ is hydrogen, $C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$; each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl (e.g., $C_1$-$C_6$ alkyl), C(O)O—$C_1$-$C_{20}$ alkyl (e.g., $C_1$-$C_6$ alkyl), OC(O)O—$C_1$-$C_{20}$ alkyl (e.g., $C_1$-$C_6$ alkyl), C(O)N($R^5$)— $C_1$-$C_{20}$ alkyl (e.g., $C_1$-$C_6$ alkyl), N($R^5$)C(O)—$C_1$-$C_{20}$ alkyl (e.g., $C_1$-$C_6$ alkyl), OC(O)N($R^5$)—$C_1$-$C_{20}$ alkyl (e.g., $C_1$-$C_6$ alkyl), O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, C(O)N($R^5$)-aryl, C(O)N($R^5$)-heteroaryl, N($R^5$)C(O)-aryl, N($R^5$)$_2$C(O)-aryl, or N($R^5$)C(O)-heteroaryl, S(O)$_2$N($R^5$)-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

In some embodiments Z is S. In some embodiments Z is O. In some embodiments, at least one of $B^1$ or $B^2$ is a purinyl nucleobase. In some embodiments, each of $B^1$ or $B^2$ is independently a purinyl nucleobase. In some embodiments, $B^1$ is a purinyl nucleobase. In some embodiments, $B^2$ is a pyrimidinyl nucleobase. In some embodiments, $B^1$ is a purinyl nucleobase and $B^2$ is a pyrimidinyl nucleobase.

In some embodiments Z is S. In some embodiments Z is O.

In some embodiments, at least one of $B^1$ or $B^2$ is a purinyl nucleobase. In some embodiments, each of $B^1$ or $B^2$ is independently a purinyl nucleobase. In some embodiments, $B^1$ is a purinyl nucleobase. In some embodiments, $B^2$ is a pyrimidinyl nucleobase. In some embodiments, $B^1$ is a purinyl nucleobase and $B^2$ is a pyrimidinyl nucleobase. In some embodiments, $B^1$ is a pyrimidinyl nucleobase. In some embodiments, $B^2$ is a purinyl nucleobase. In some embodiments, $B^1$ is a pyrimidinyl nucleobase and $B^2$ is a purinyl nucleobase.

In some embodiments, each of $B^1$ or $B^2$ is selected from a naturally occurring nucleobase or a modified nucleobase. In some embodiments, each of $B^1$ or $B^2$ is selected from adenosinyl, guanosinyl, cytosinyl, thyminyl, uracilyl, 5'-methylcytosinyl, 5'-fluorouracilyl, 5'-propynyluracilyl, and 7-deazaadenosinyl. In some embodiments, each of $B^1$ or $B^2$ is selected from:

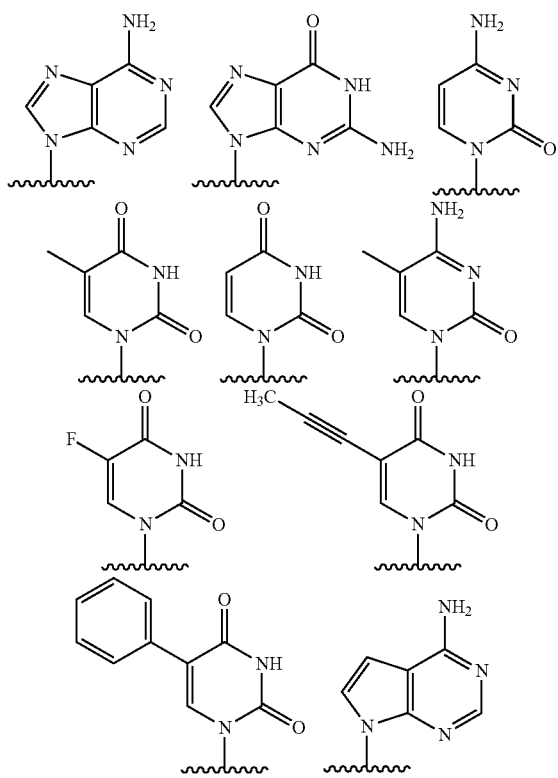

wherein " ⁓⁓⁓ " indicates the linkage of the nucleobase to the ribose ring.

In some embodiments, one of $B^1$ or $B^2$ is selected from a naturally occurring nucleobase and the other of $B^1$ or $B^2$ is a modified nucleobase. In some embodiments, one of $B^1$ or $B^2$ is adenosinyl, guanosinyl, thyminyl, cytosinyl, or uracilyl, and the other of $B^1$ or $B^2$ is 5'-methylcytosinyl, 5'-fluorouracilyl, 5'-propynyluracilyl, or 7-deazaadenosinyl.

In some embodiments, $B^1$ is adenosinyl or guanosinyl. In some embodiments, $B^2$ is cytosinyl, thyminyl, or uracilyl. In some embodiments, $B^1$ is adenosinyl or guanosinyl and $B^2$ is cytosinyl, thyminyl, or uracilyl. In some embodiments, $B^2$ is adenosinyl or guanosinyl. In some embodiments, $B^1$ is cytosinyl, thyminyl, or uracilyl. In some embodiments, $B^2$ is adenosinyl or guanosinyl and $B^1$ is cytosinyl, thyminyl, or uracilyl.

In some embodiments, each of $B^1$ and $B^2$ is independently uracilyl. In some embodiments, each of $B^1$ and $B^2$ is independently adenosinyl.

In some embodiments, each of $R^1$ and $R^2$ is independently hydrogen, halo, or $OR^7$. In some embodiments, each of $R^1$ and $R^2$ is independently halo (e.g., fluoro). In some embodiments, each of $R^1$ and $R^2$ is not hydrogen or $OR^7$.

In some embodiments, $X^1$ is O. In some embodiments, $X^2$ is O. In some embodiments, each of $X^1$ and $X^2$ is independently O.

In some embodiments, $Y^1$ is O or S. In some embodiments, $Y^2$ is O or S. In some embodiments, each of $Y^1$ and $Y^2$ is independently O or S. In some embodiments, one of $Y^1$ or $Y^2$ is O and the other of $Y^1$ or $Y^2$ is S. In some embodiments, each of $Y^1$ or $Y^2$ is independently S. In some embodiments, each of $Y^1$ or $Y^2$ is independently O.

In some embodiments, $L^1$ is $C_1$-$C_6$ alkyl (e.g., $CH_2$). In some embodiments, $L^2$ is $C_1$-$C_6$ alkyl (e.g., $CH_2$). In some embodiments, each of $L^1$ and $L^2$ is independently $C_1$-$C_6$ alkyl (e.g., $CH_2$).

In some embodiments, $R^3$ is hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$. In some embodiments, $R^3$ is phenyl substituted with 1 $R^8$.

In some embodiments, $R^4$ is independently hydrogen, aryl, or heteroaryl, wherein aryl and heteroaryl is optionally substituted with 1-5 $R^8$. In some embodiments, $R^4$ is aryl or heteroaryl, each of which is optionally substituted with 1-5 $R^8$. In some embodiments, $R^4$ is phenyl substituted with 1 $R^8$.

In some embodiments, each of $R^3$ and $R^4$ is independently hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$, and $R^4$ is hydrogen. In some embodiments, $R^3$ is phenyl substituted with 1 $R^8$ and $R^4$ is hydrogen. In some embodiments, each of $R^3$ and $R^4$ is independently phenyl substituted with 1 $R^8$.

In some embodiments, each of $Y^1$ and $Y^2$ is O and each of $R^3$ and $R^4$ is independently hydrogen. In some embodiments, $Y^2$ is O and $R^4$ is hydrogen. In some embodiments, each of $Y^1$ and $Y^2$ is independently S and each of $R^3$ and $R^4$ is independently substituted with 1 $R^8$. In some embodiments, $Y^1$ is S and $R^3$ is substituted with 1 $R^8$.

In some embodiments, each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, OC(O)O—$C_1$-$C_{20}$ alkyl, OC(O)N($R^5$)—$C_1$-$C_{20}$ alkyl, O-aryl, C(O)-aryl, OC(O)-aryl, or C(O)N($R^5$)-aryl, wherein each alkyl, heteroalkyl, aryl, and heteroaryl is optionally substituted by one or more $R^9$.

In some embodiments, $R^8$ is C(O)-aryl optionally substituted by 1-5 $R^9$ (e.g., 1 $R^9$). In some embodiments, $R^8$ is OC(O)-aryl optionally substituted by 1-5 $R^9$ (e.g., 1 $R^9$).

In some embodiments, $R^9$ is O—$C_1$-$C_{12}$ alkyl (e.g., O—$CH_2(CH_2)CH_3$). In some embodiments, $R^9$ is O—$C_1$-$C_{10}$ alkyl (e.g., O—$CH_2(CH_2)CH_3$). In some embodiments, $R^9$ is O—$C_1$-$C_8$ alkyl (e.g., O—$CH_2(CH_2)_6CH_3$). In some embodiments, $R^9$ is O—$C_1$-$C_6$ alkyl (e.g., O—$CH_2(CH_2)_4CH_3$).

substituted by 1-5 $R^9$; and each $R^9$ is independently $O-C_1-C_{20}$ alkyl.

In some embodiments, the compound of Formula (I) is selected from those depicted in Table 1.

TABLE 1

(Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 1 | 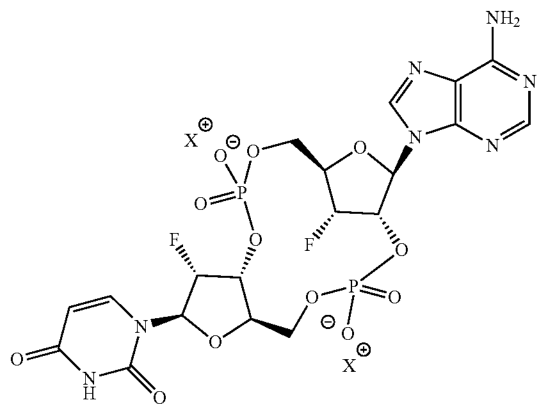 |
| 2 | 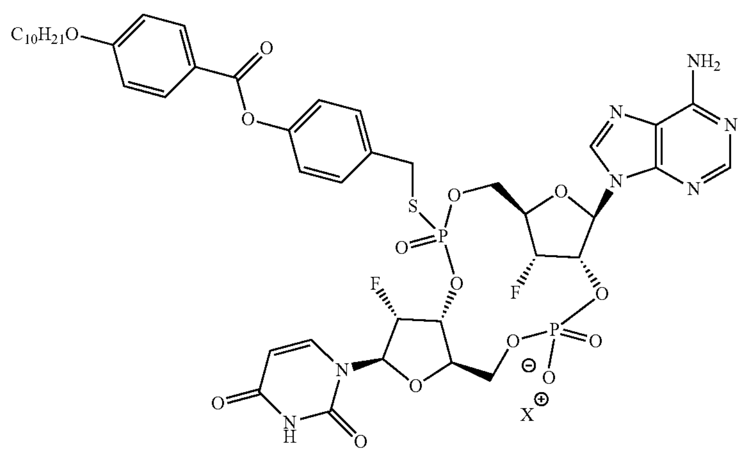 |
| 3 | 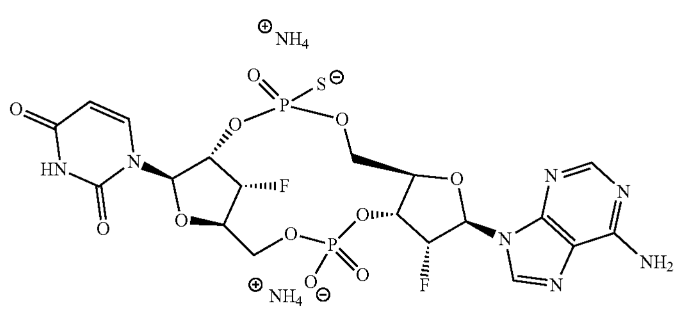 [SMILES: [NH4+] ; Nc1ncnc2c1ncn2[C@@H]1O[C@@H]2COP(=O)([S-])O[C@@H]3[C@H](F)[C@@H](COP(=O)([O-])O[C@H]2[C@H]1F)O[C@H]3n1ccc(=O)[nH]c1=O ; [NH4+]] |

US 11,638,716 B2
TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 4 | 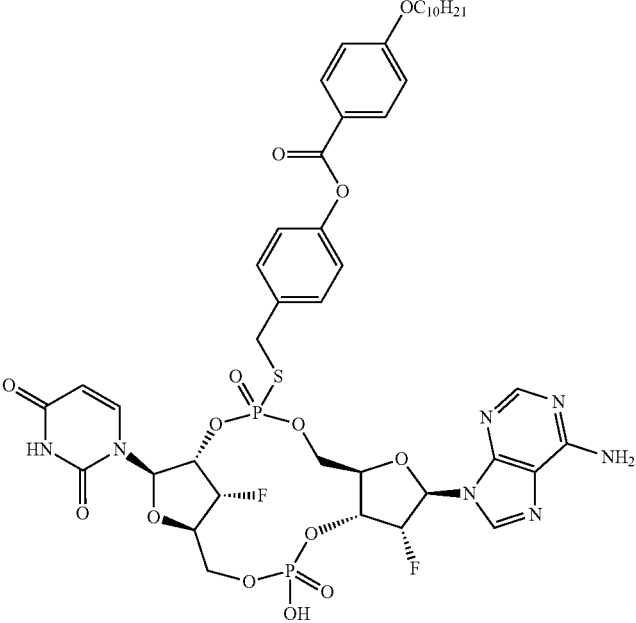 |
| 5 | 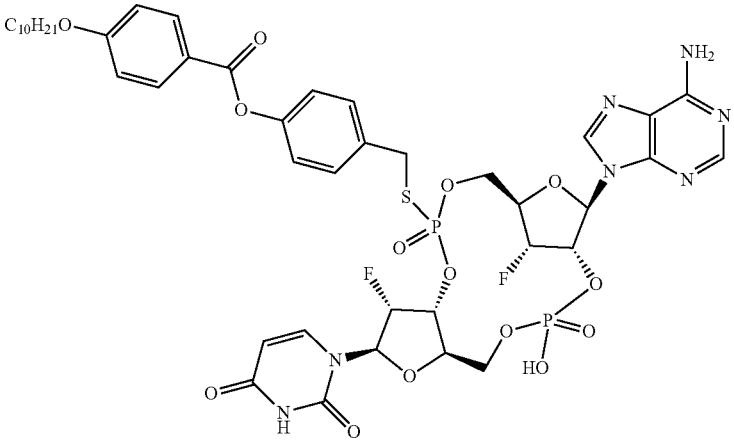 |
| 6 | 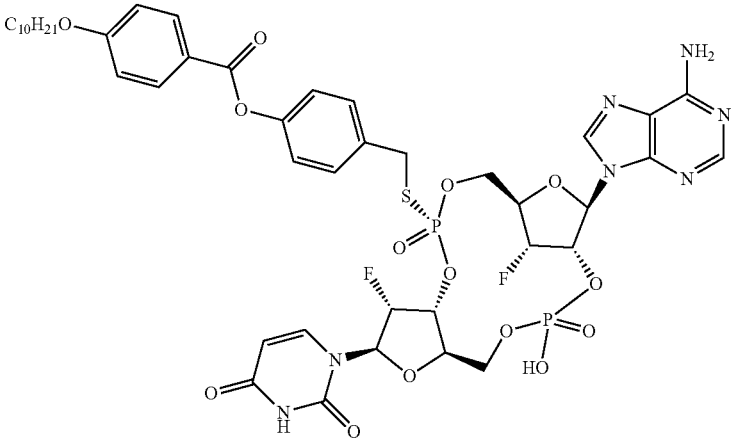 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 7 | 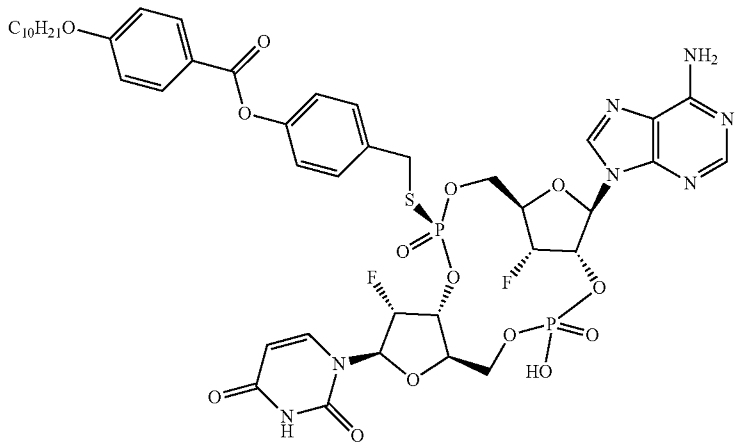 |
| 8 | 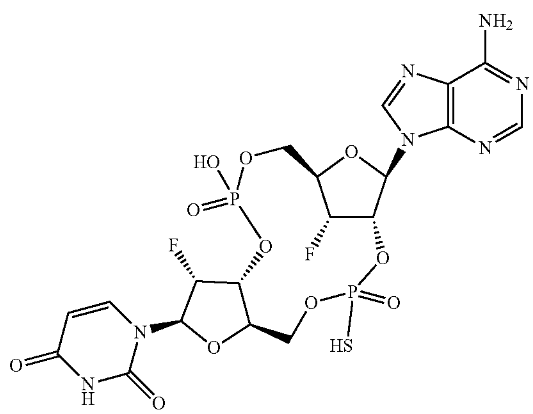 [SMILES: Nc1ncnc2c1ncn2[C@@H]1O[C@@H]2COP(=O)(S)O[C@H]3[C@@H](F)[C@H](n4ccc(=O)[nH]c4=O)O[C@@H]3COP(=O)(O)O[C@@H]1[C@@H]2F] |
| 9 | 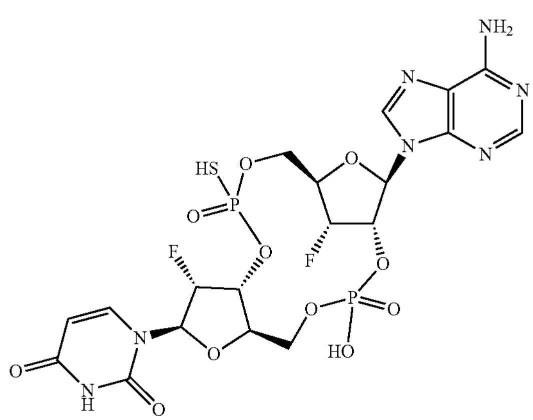 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 10 | 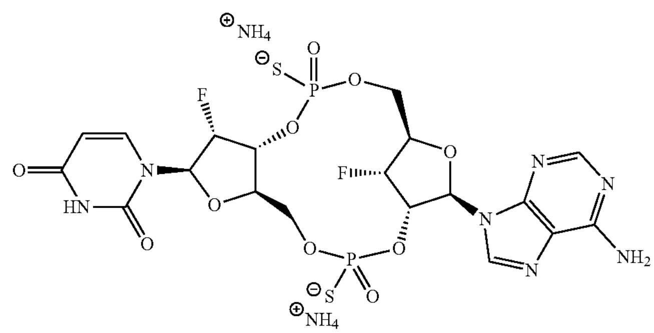 [SMILES: [NH4+] ; Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([S-])O[C@@H]1[C@@H]2F ; [NH4+]] |
| 11 | 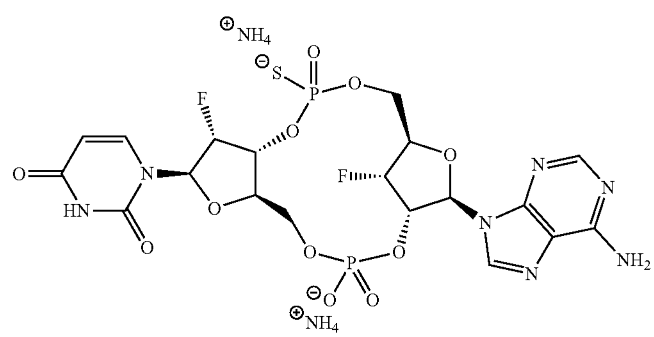 [SMILES: [NH4+] ; Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([O-])O[C@@H]1[C@@H]2F ; [NH4+]] |
| 12 | 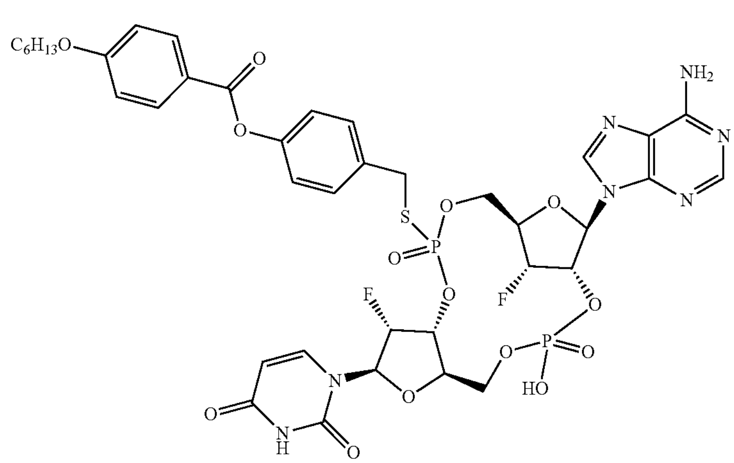 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
| --- | --- |
| 13 | 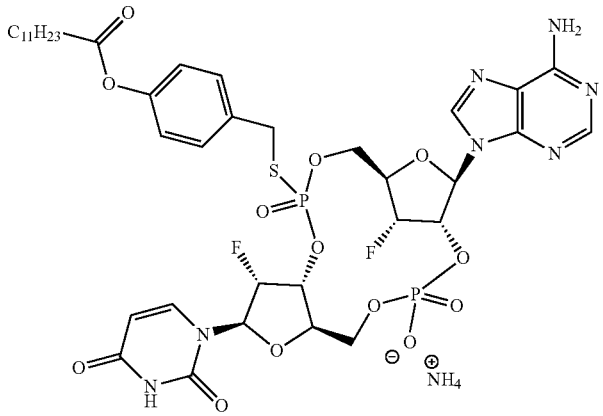 |
| 14 | 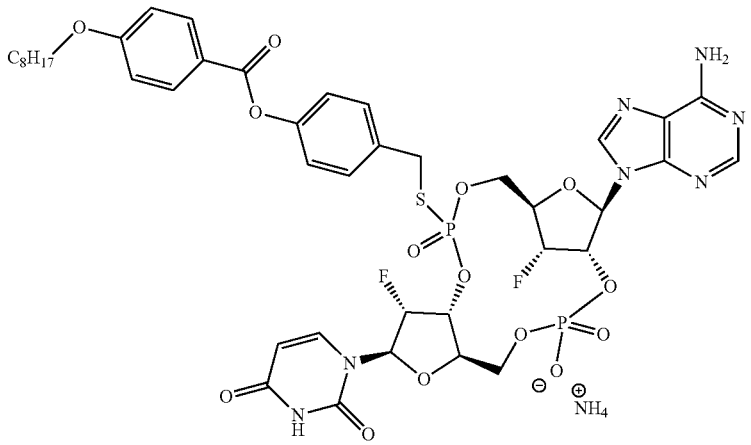 |
| 15 | 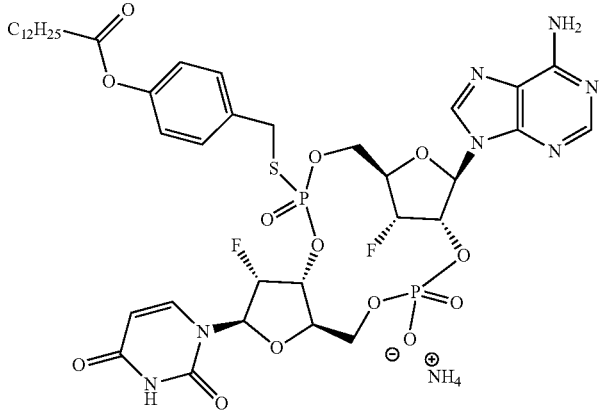 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 16 | 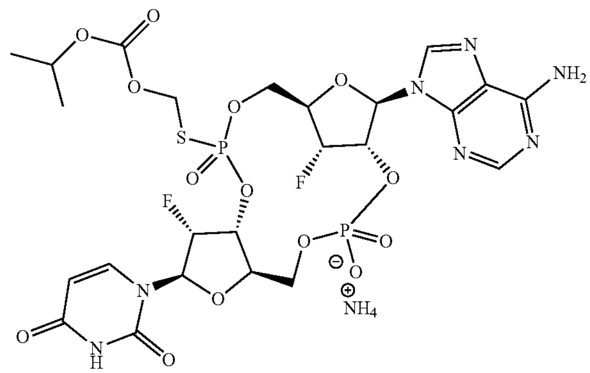 [SMILES: CC(C)OC(=O)OCSP1(=O)OC[C@H]2O[C@@H](n3cnc4c(N)ncnc43)[C@H](OP(=O)([O-])OC[C@H]3O[C@@H](n4ccc(=O)[nH]c4=O)[C@H](F)[C@@H]3O1)[C@@H]2F ; [NH4+]] |
| 17 | 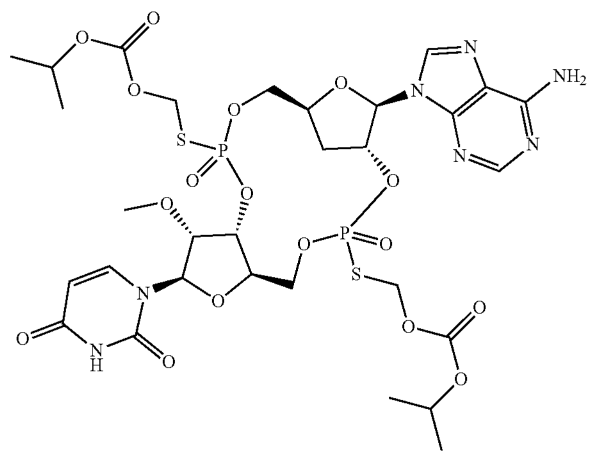 [SMILES: CO[C@@H]1[C@@H]2OP(=O)(SCOC(=O)OC(C)C)OC[C@@H]3C[C@@H](OP(=O)(SCOC(=O)OC(C)C)OC[C@H]2O[C@H]1n1ccc(=O)[nH]c1=O)[C@H](n1cnc2c(N)ncnc21)O3] |
| 18 | 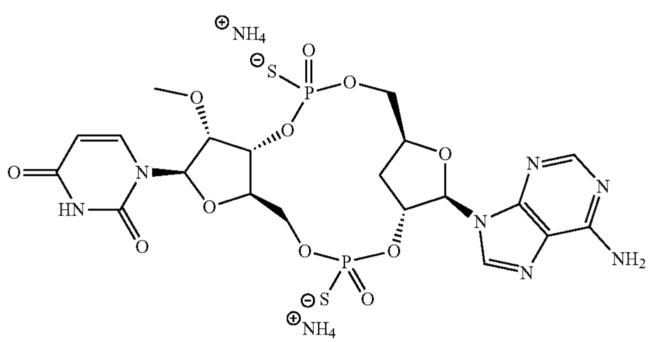 [SMILES: [NH4+] ; CO[C@@H]1[C@@H]2OP(=O)([S-])OC[C@@H]3C[C@@H](OP(=O)([S-])OC[C@H]2O[C@H]1n1ccc(=O)[nH]c1=O)[C@H](n1cnc2c(N)ncnc21)O3 ; [NH4+]] |
| 19 | 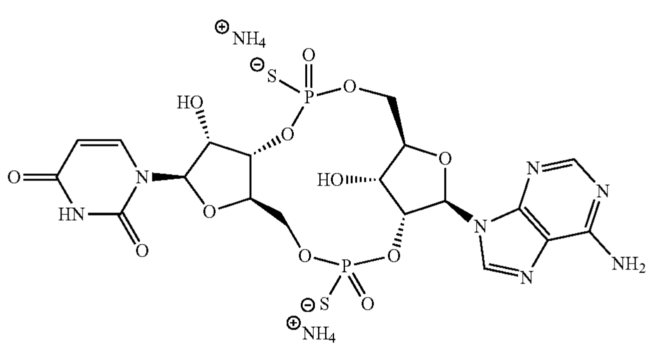 [SMILES: [NH4+] ; Nc1ncnc2c1ncn2[C@@H]1O[C@@H]2COP(=O)([S-])O[C@H]3[C@@H](O)[C@H](n4ccc(=O)[nH]c4=O)O[C@@H]3COP(=O)([S-])O[C@@H]1[C@@H]2O ; [NH4+]] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 20 | 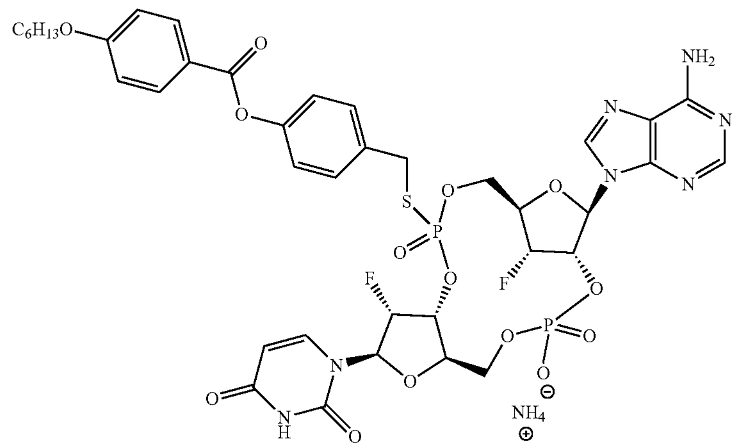 |
| 21 | 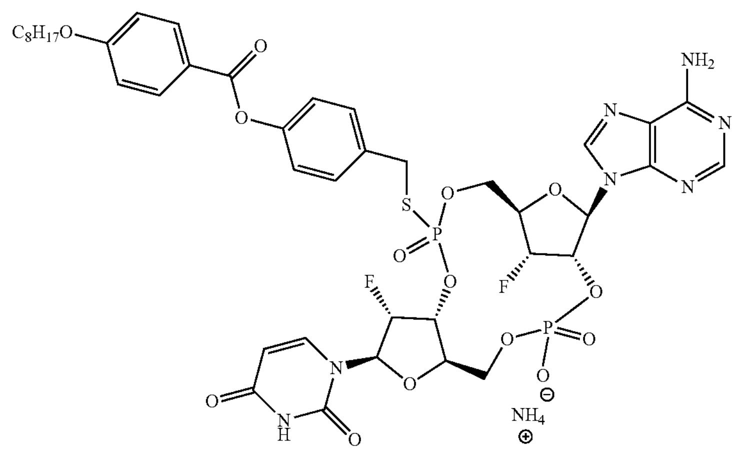 |
| 22 | 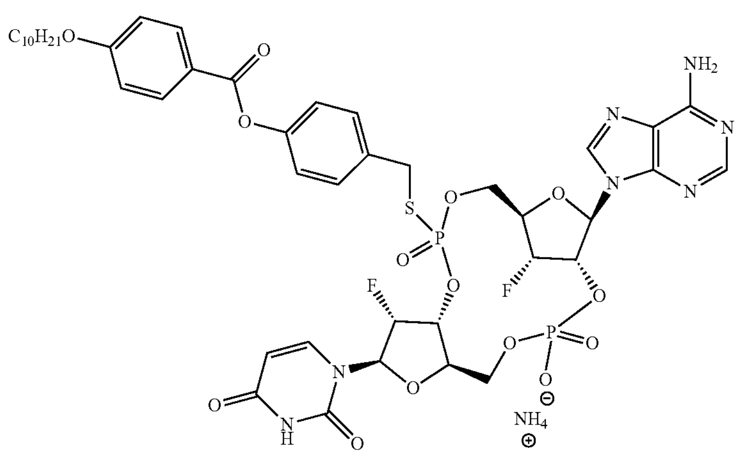 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 23 | 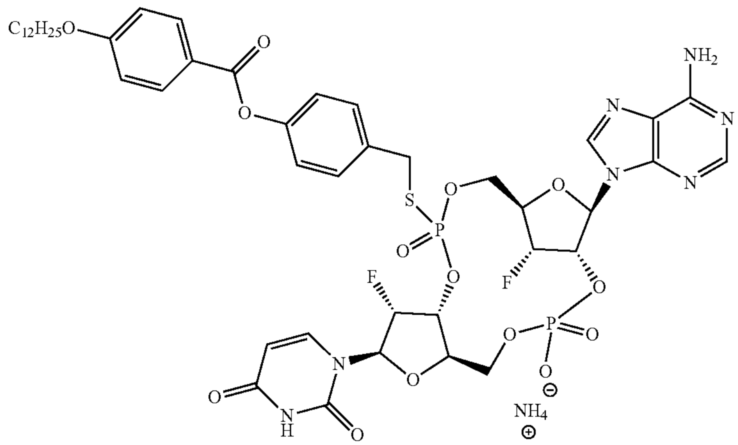 |
| 24 | 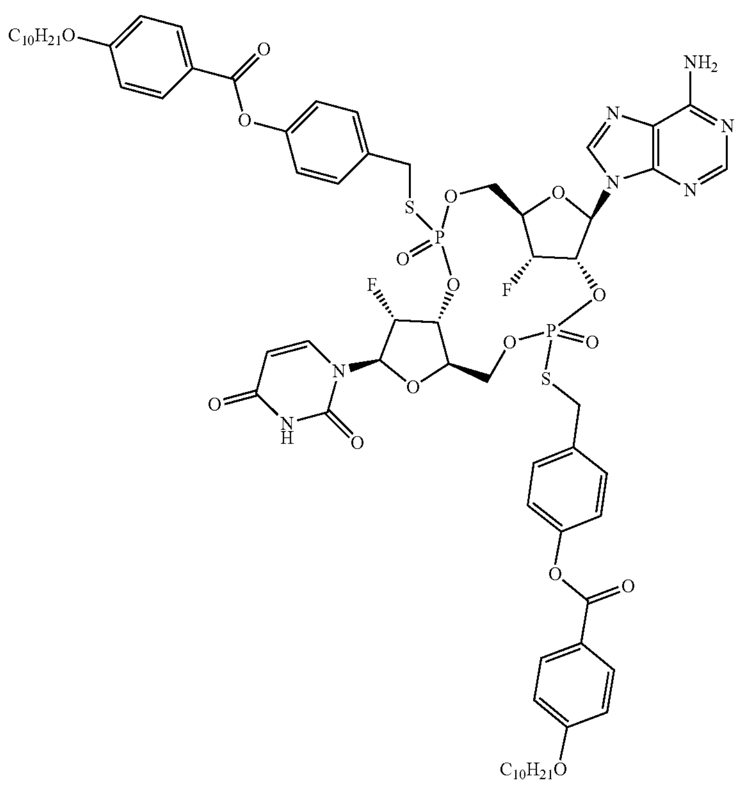 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 25 | 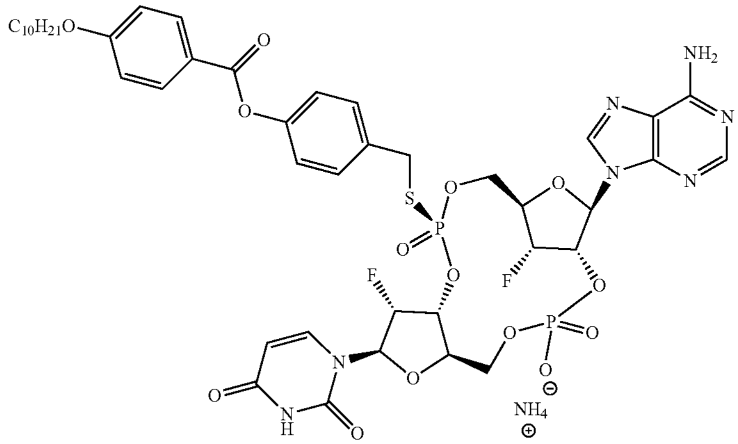 |
| 26 | 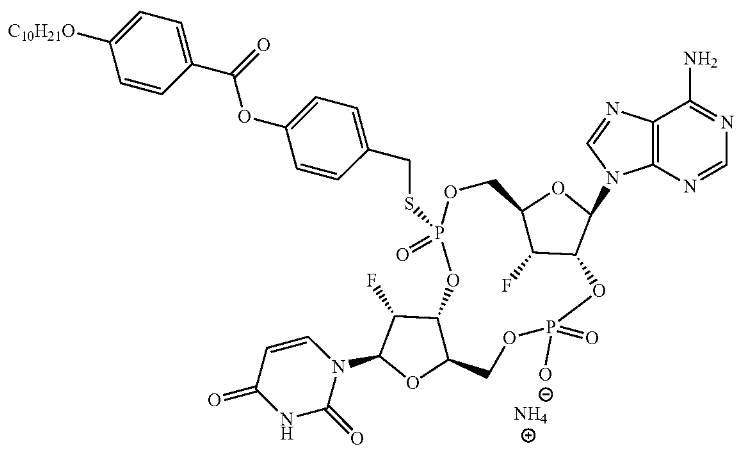 |
| 27 | 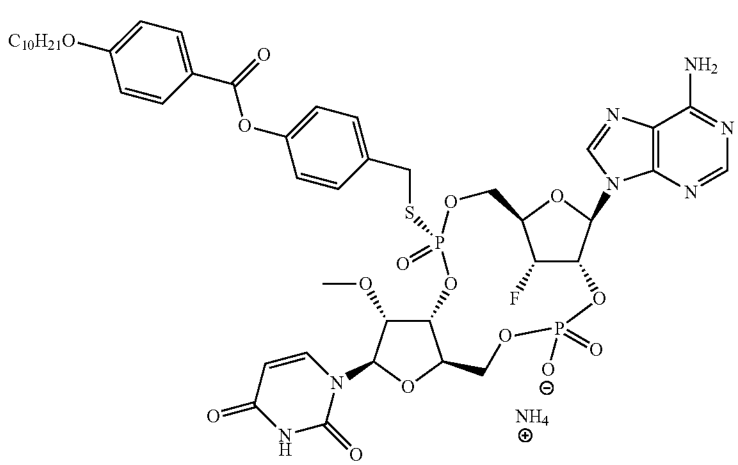 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 28 | 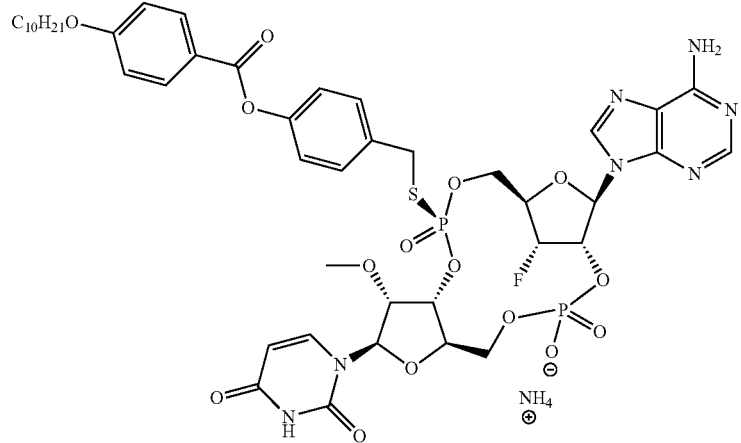 |
| 29 | 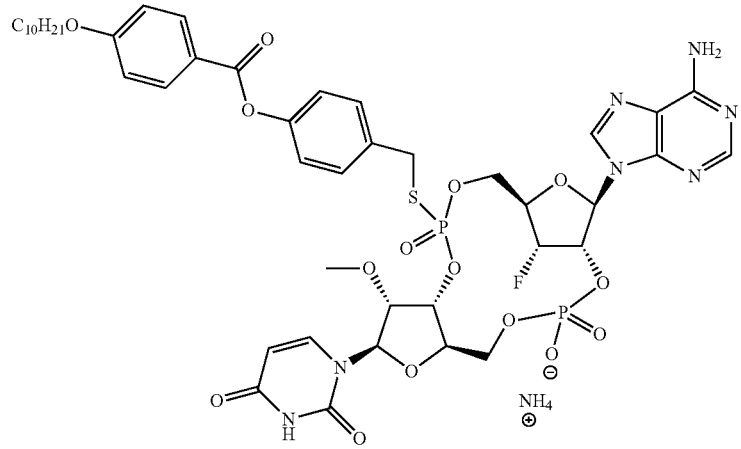 |
| 30 | 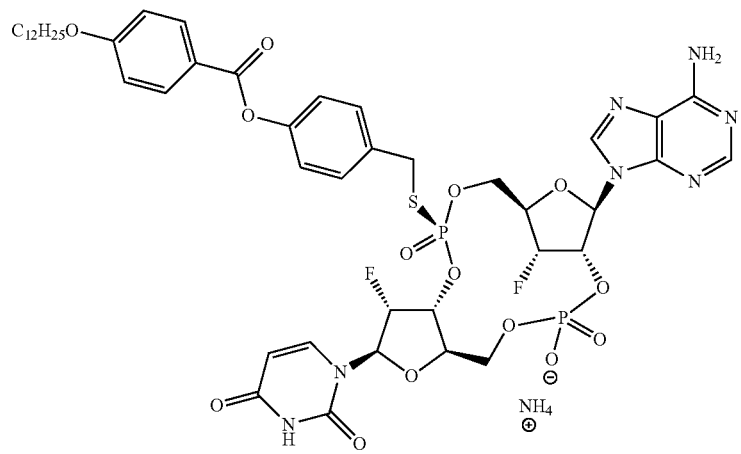 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 31 | 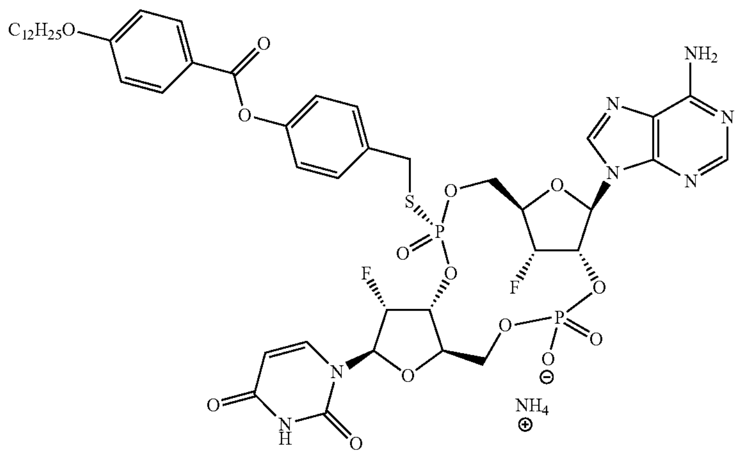 |
| 32 | 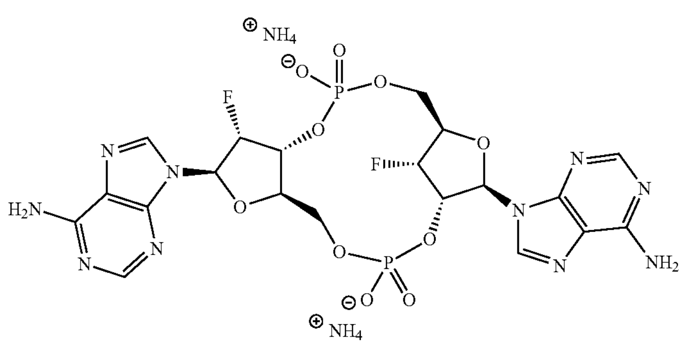 [SMILES: [NH4+] ; Nc1ncnc2c1ncn2[C@@H]1O[C@@H]2COP(=O)([O-])O[C@@H]3[C@H](F)[C@@H](COP(=O)([O-])O[C@H]2[C@H]1F)O[C@H]3n1cnc2c(N)ncnc21 ; [NH4+]] |
| 33 | 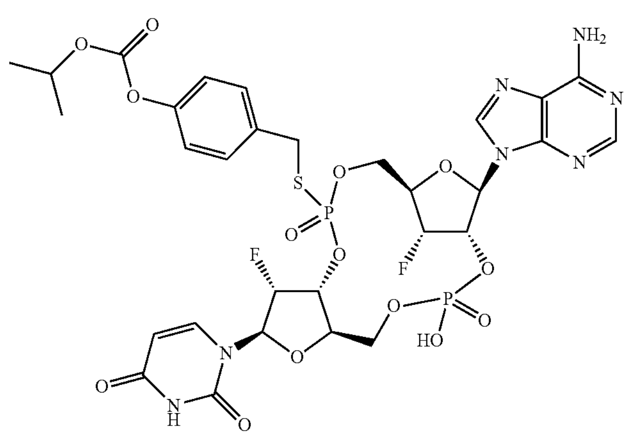 [SMILES: CC(C)OC(=O)Oc1ccc(CSP2(=O)OC[C@H]3O[C@@H](n4cnc5c(N)ncnc54)[C@H](OP(=O)(O)OC[C@H]4O[C@@H](n5ccc(=O)[nH]c5=O)[C@H](F)[C@@H]4O2)[C@@H]3F)cc1] |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 34 | 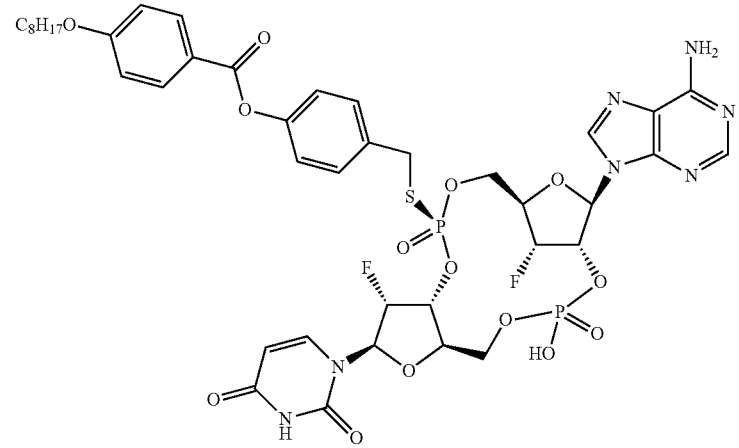 |
| 35 | 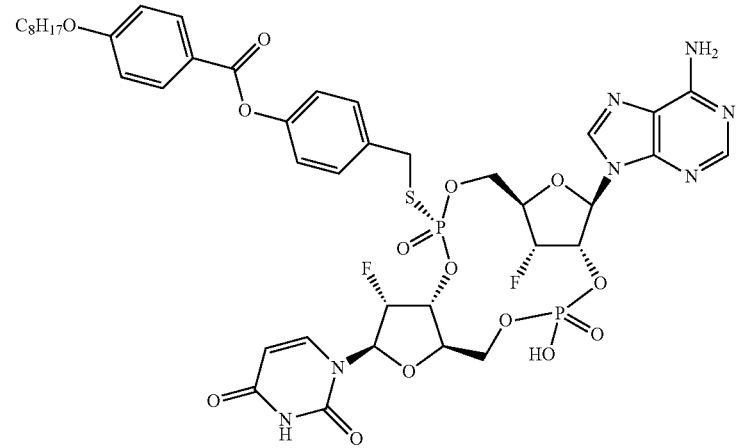 |
| 36 | 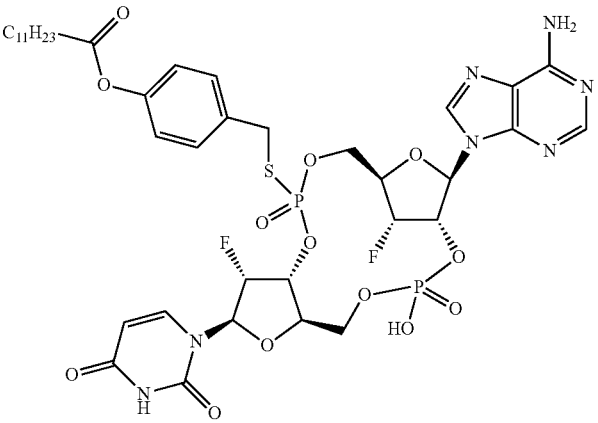 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 37 | 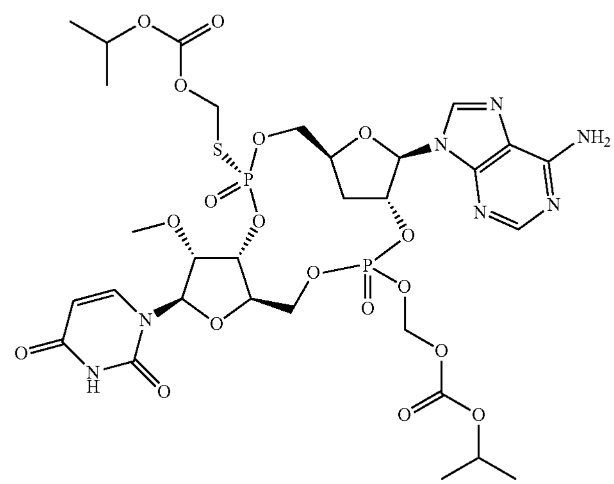 [SMILES: CO[C@@H]1[C@@H]2O[P@](=O)(SCOC(=O)OC(C)C)OC[C@@H]3C[C@@H](OP(=O)(OCOC(=O)OC(C)C)OC[C@H]2O[C@H]1n1ccc(=O)[nH]c1=O)[C@H](n1cnc2c(N)ncnc21)O3] |
| 38 | 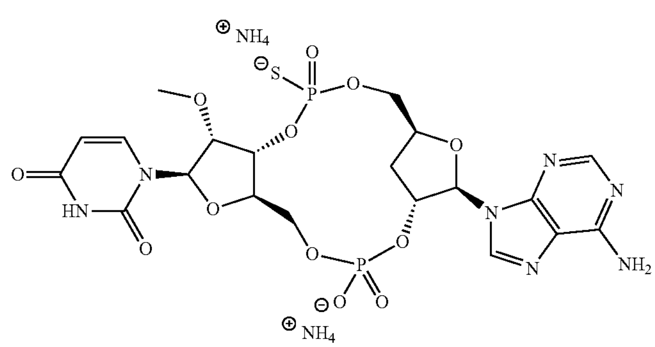 [SMILES: [NH4+] ; CO[C@@H]1[C@@H]2OP(=O)([S-])OC[C@@H]3C[C@@H](OP(=O)([O-])OC[C@H]2O[C@H]1n1ccc(=O)[nH]c1=O)[C@H](n1cnc2c(N)ncnc21)O3 ; [NH4+]] |
| 39 | 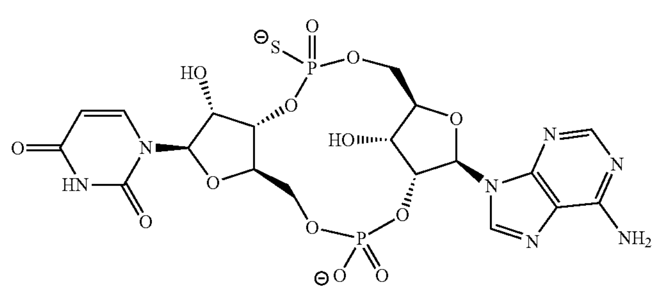 [SMILES: Nc1ncnc2c1ncn2[C@@H]1O[C@@H]2COP(=O)([S-])O[C@H]3[C@@H](O)[C@H](n4ccc(=O)[nH]c4=O)O[C@@H]3COP(=O)([O-])O[C@@H]1[C@@H]2O] |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 40 | 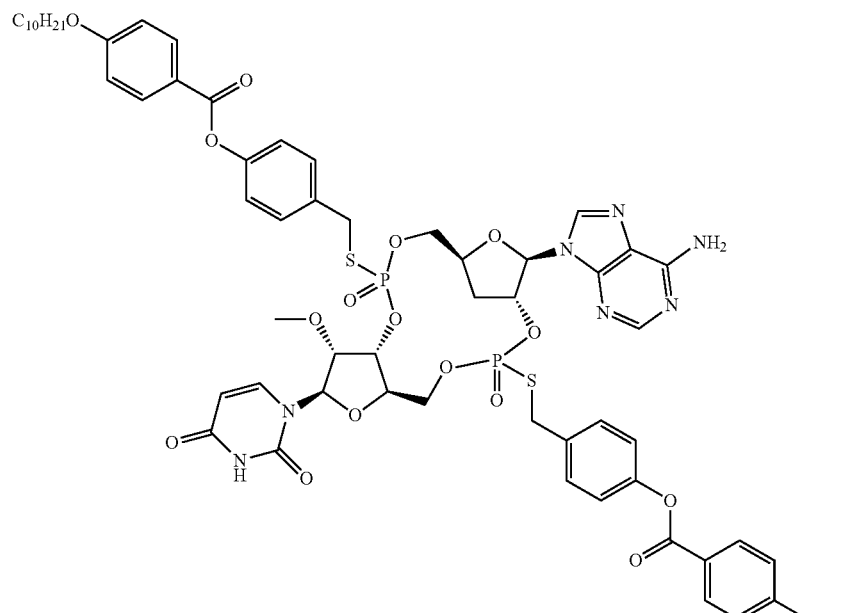 |
| 41 | 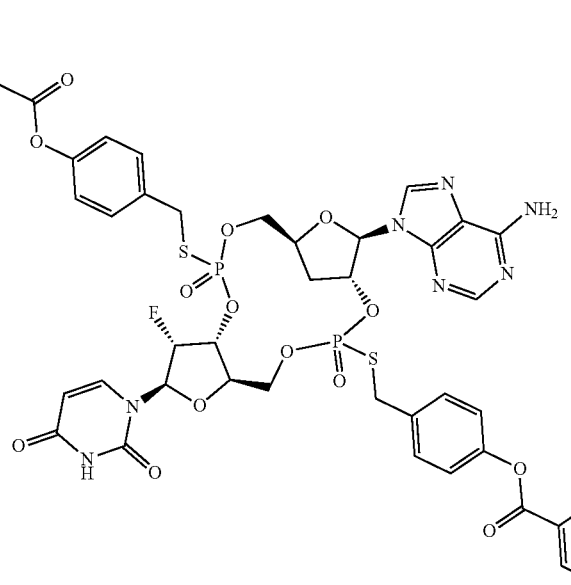 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 42 | 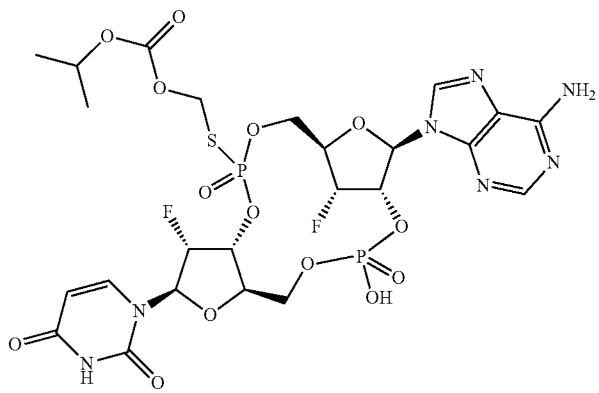 [SMILES: CC(C)OC(=O)OCSP1(=O)OC[C@H]2O[C@@H](n3cnc4c(N)ncnc43)[C@H](OP(=O)(O)OC[C@H]3O[C@@H](n4ccc(=O)[nH]c4=O)[C@H](F)[C@@H]3O1)[C@@H]2F] |
| 43 | 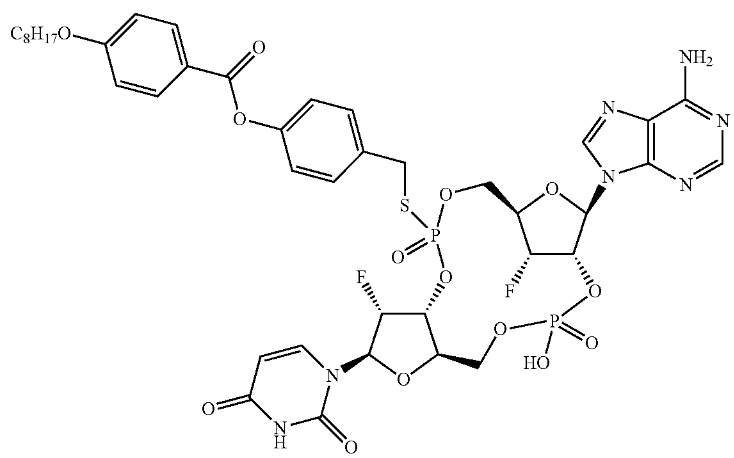 |
| 44 | 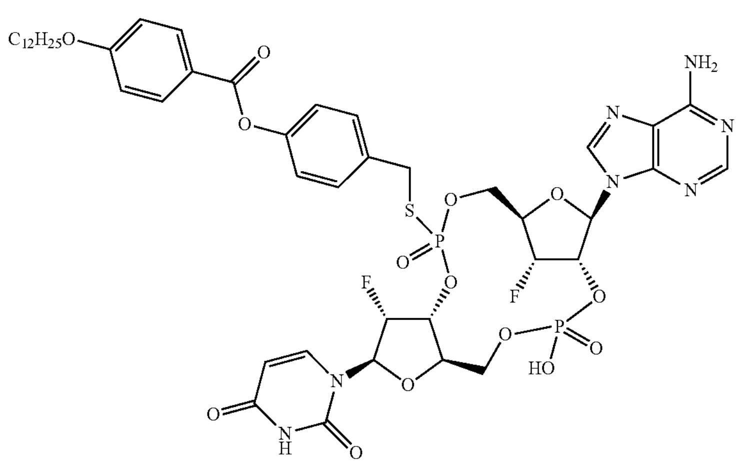 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
| --- | --- |
| 45 | 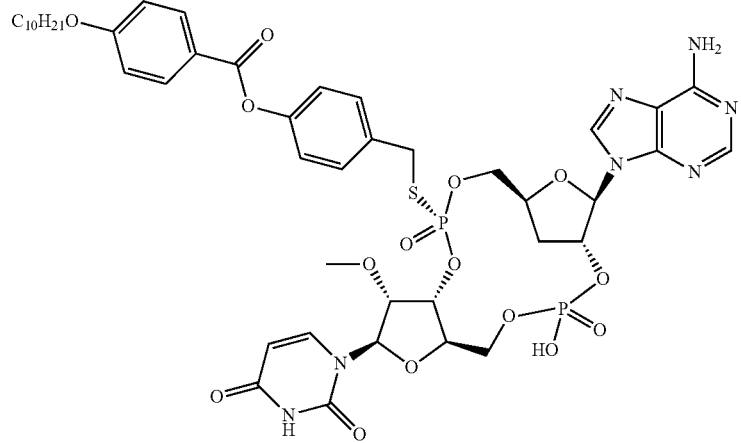 |
| 46 | 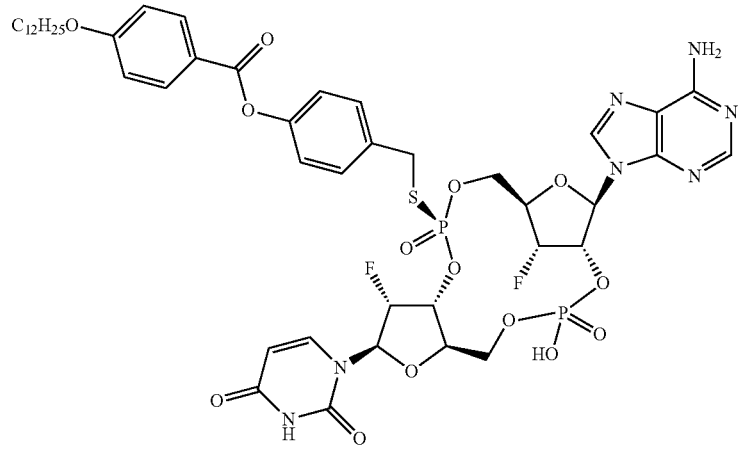 |
| 47 | 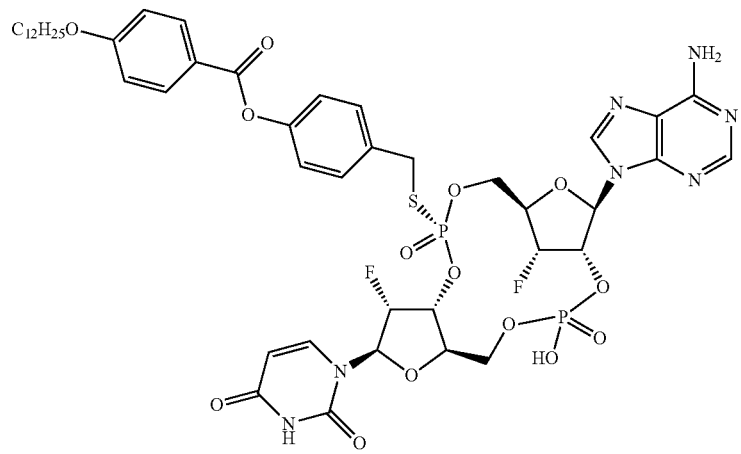 |

US 11,638,716 B2
TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 48 | 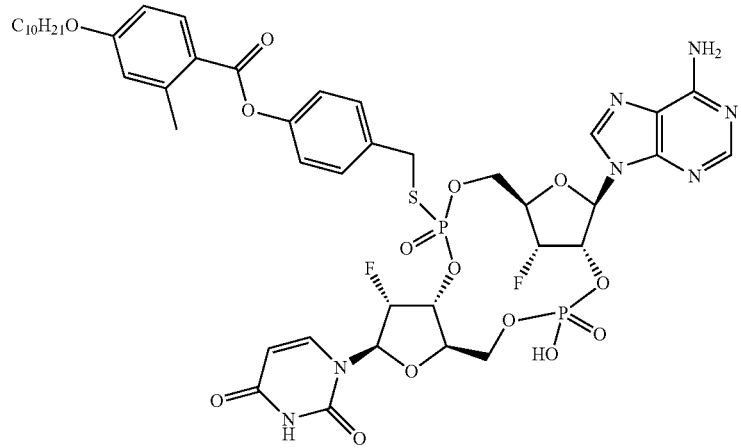 |
| 49 | 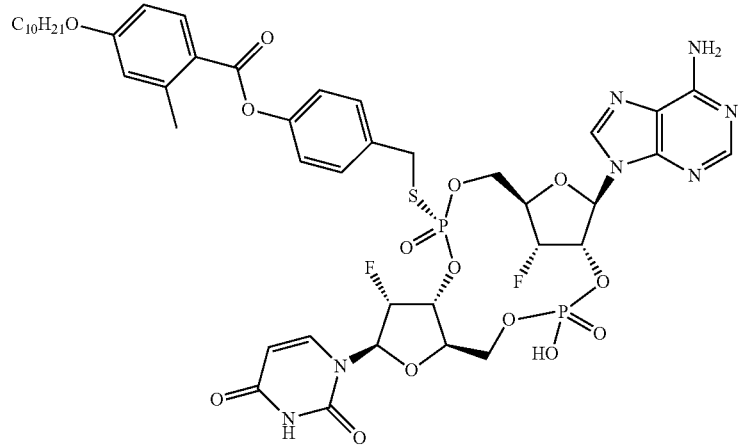 |
| 50 | 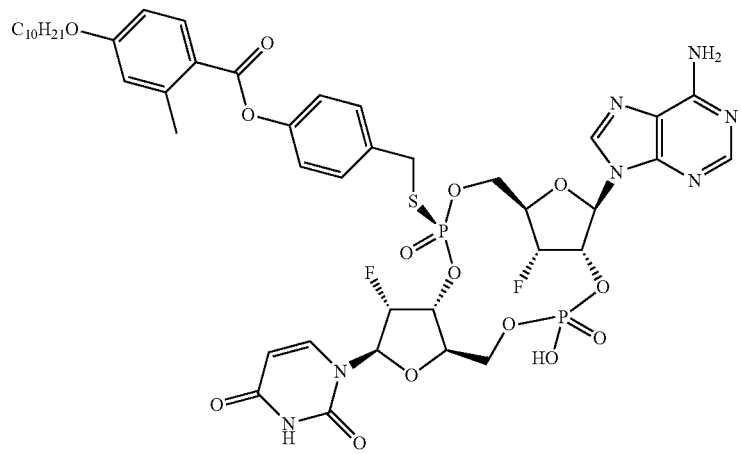 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 51 | 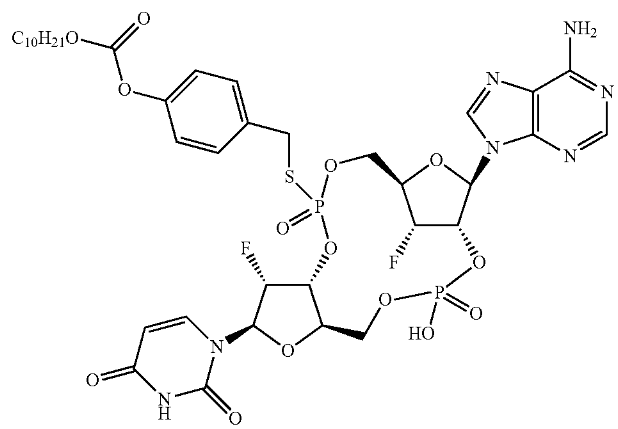 |
| 52 | 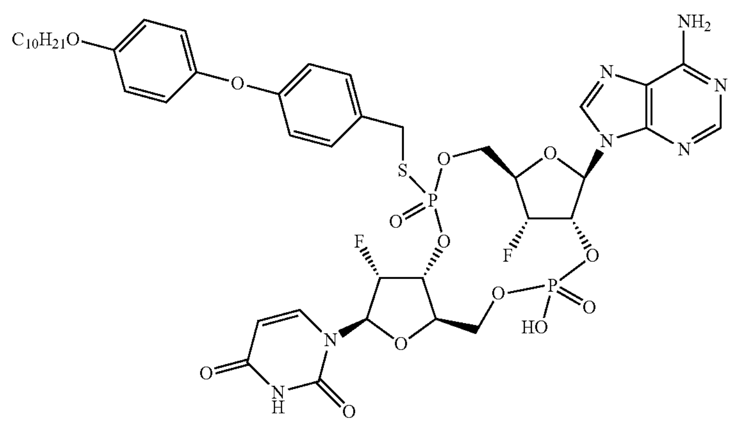 |
| 53 | 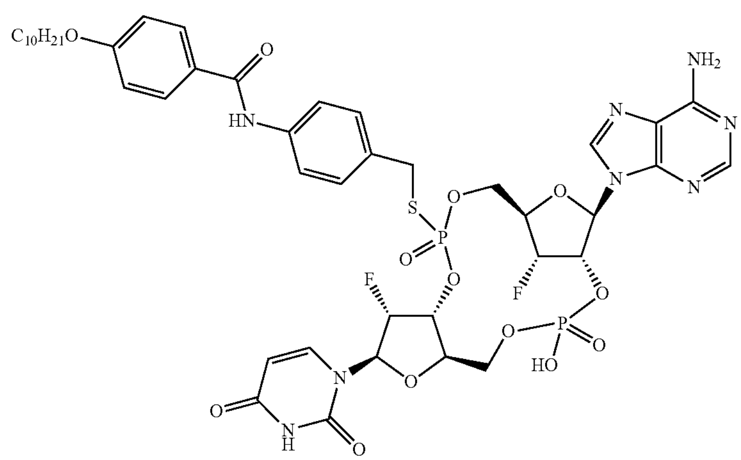 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 54 | 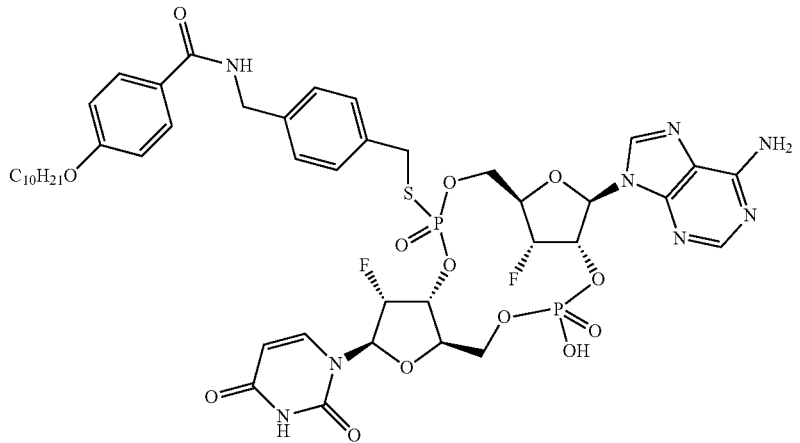 |
| 55 | 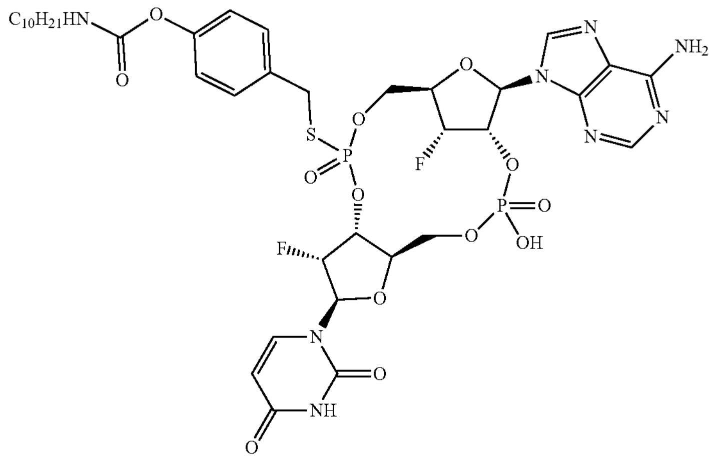 |
| 56 | 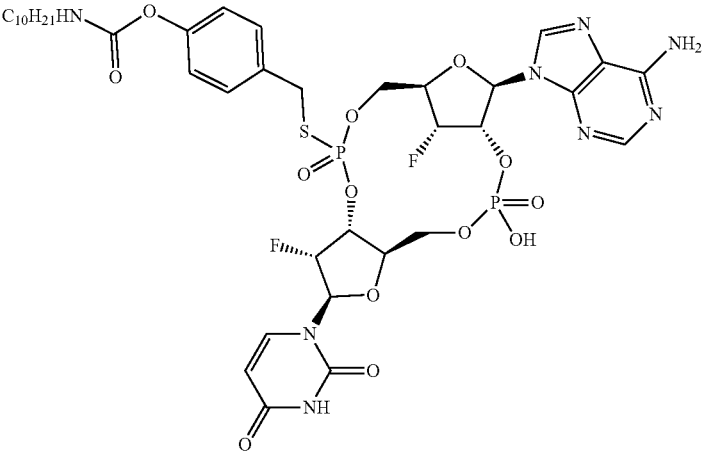 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 57 | 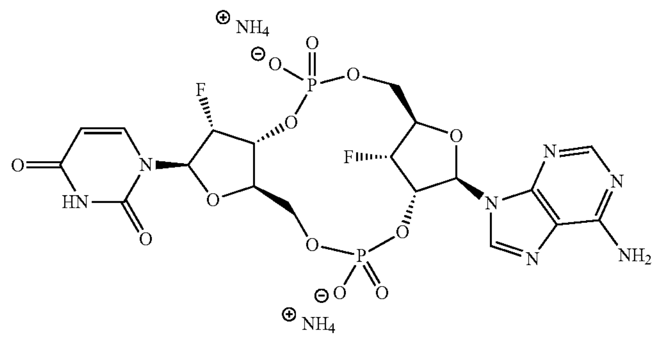 [SMILES: [NH4+] ; Nc1ncnc2c1ncn2[C@@H]1O[C@@H]2COP(=O)([O-])O[C@H]3[C@@H](F)[C@H](n4ccc(=O)[nH]c4=O)O[C@@H]3COP(=O)([O-])O[C@@H]1[C@@H]2F ; [NH4+]] |
| 58 | 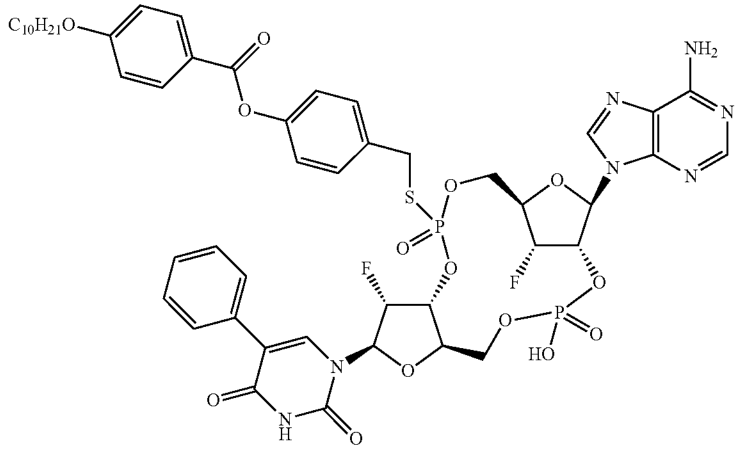 |
| 59 | 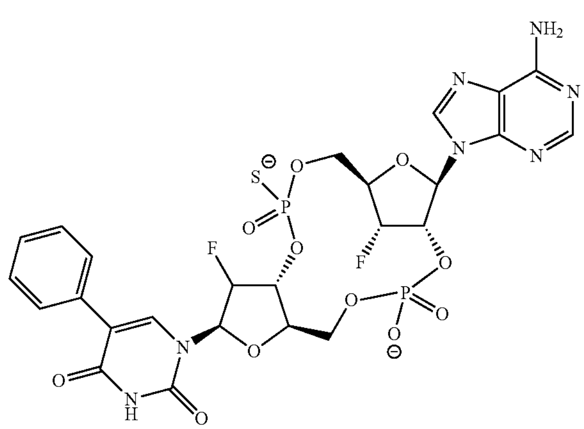 [SMILES: Nc1ncnc2c1ncn2[C@@H]1O[C@@H]2COP(=O)([S-])O[C@H]3C(F)[C@H](n4cc(-c5ccccc5)c(=O)[nH]c4=O)O[C@@H]3COP(=O)([O-])O[C@@H]1[C@@H]2F] |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 60 | 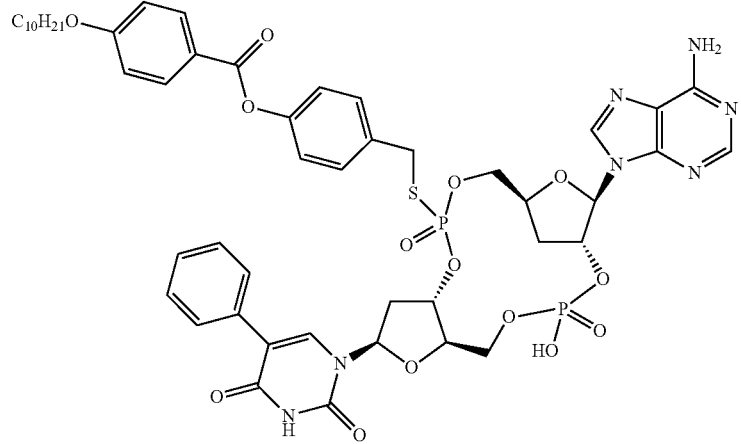 |
| 61 | 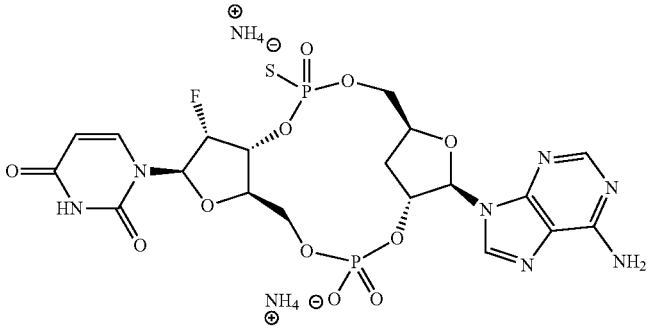 |
| 62 | 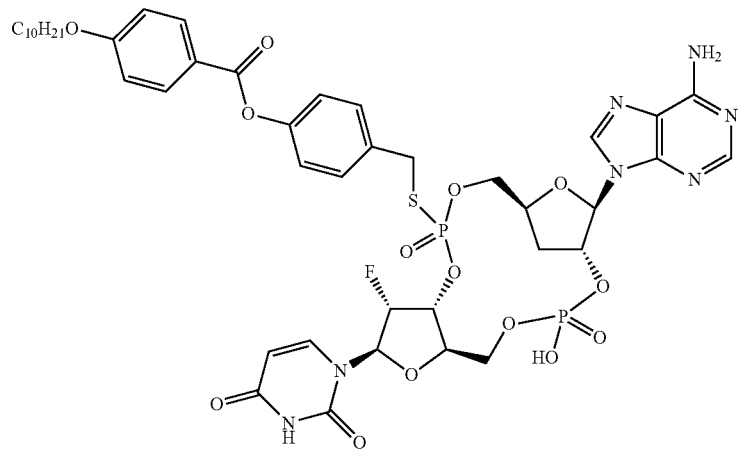 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 63 | 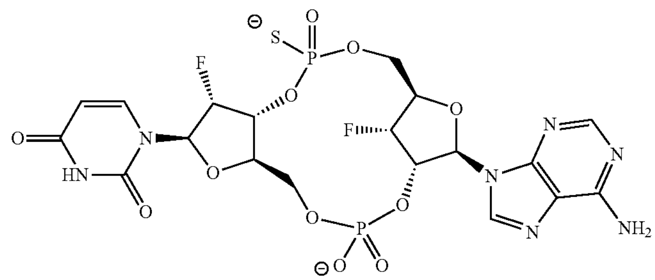 [SMILES: Nc1ncnc2c1ncn2[C@@H]1O[C@@H]2COP(=O)(S)O[C@H]3[C@@H](F)[C@H](n4ccc(=O)[nH]c4=O)O[C@@H]3COP(=O)([O-])O[C@@H]1[C@@H]2F] |
| 64 | 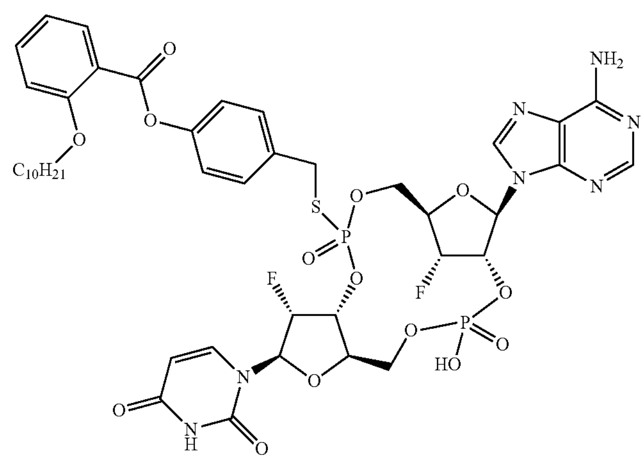 |
| 65 | 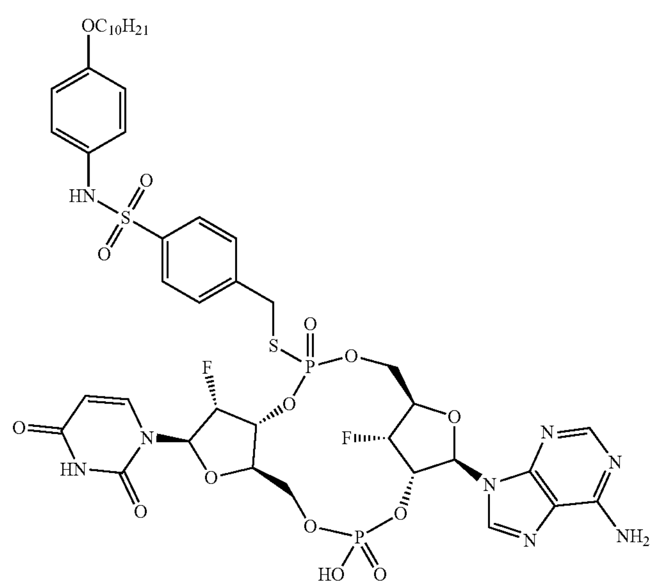 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 66 | 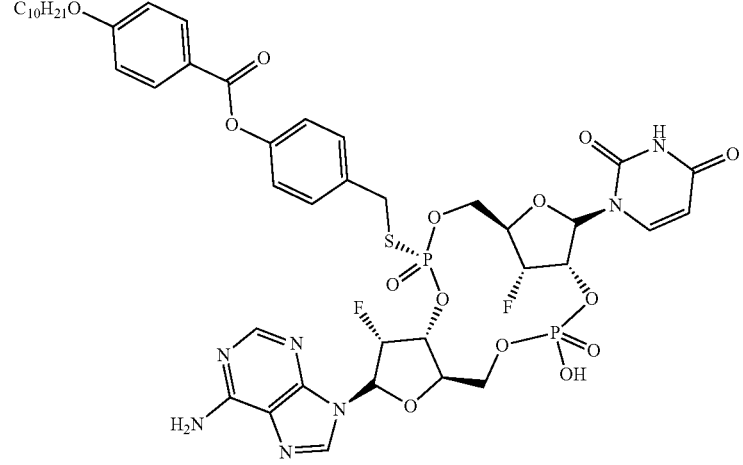 |
| 67 | 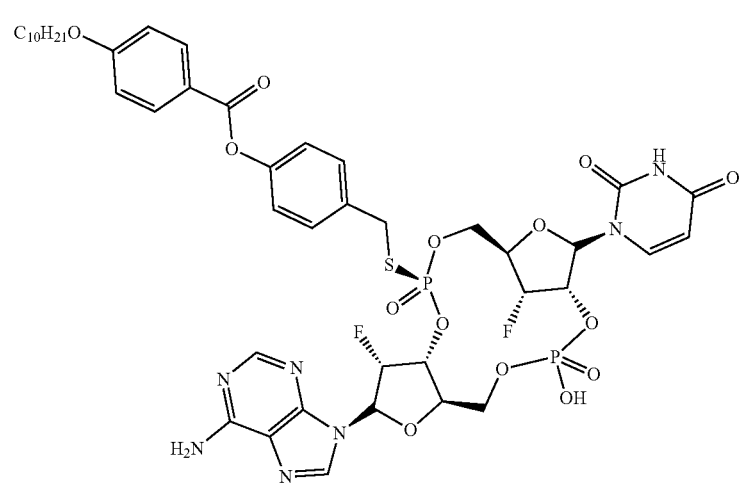 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 68 | 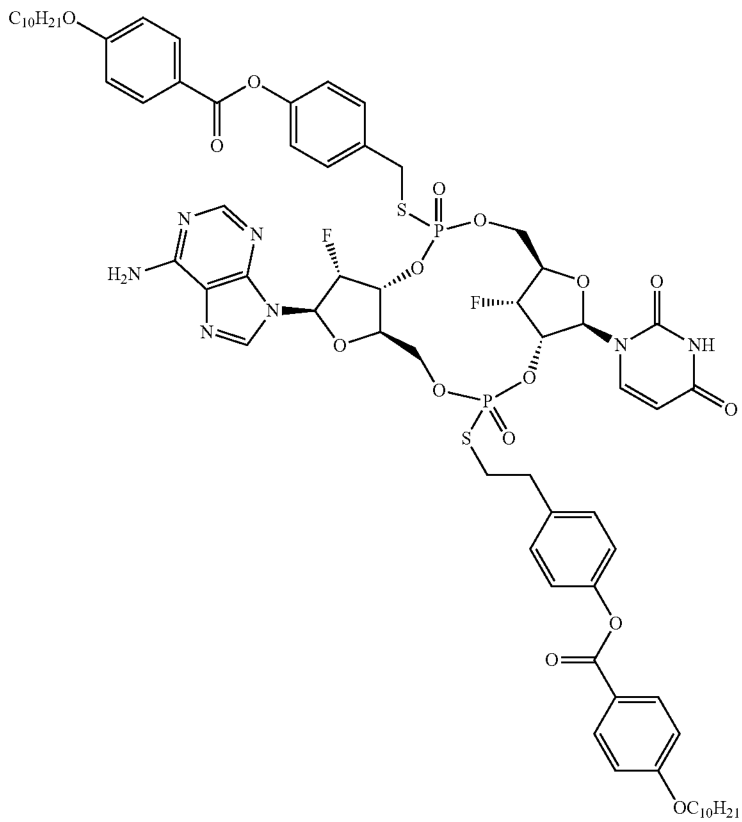 |
| 69 | 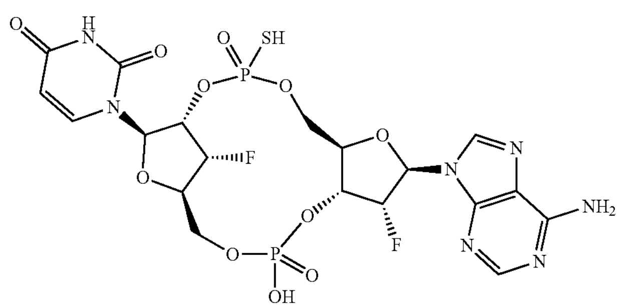 [SMILES: Nc1ncnc2c1ncn2[C@@H]1O[C@@H]2COP(=O)(S)O[C@@H]3[C@H](F)[C@@H](COP(=O)(O)O[C@H]2[C@H]1F)O[C@H]3n1ccc(=O)[nH]c1=O] |
| 70 | 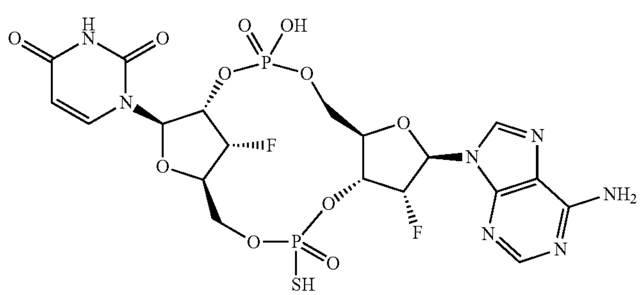 [SMILES: Nc1ncnc2c1ncn2[C@@H]1O[C@@H]2COP(=O)(O)O[C@@H]3[C@H](F)[C@@H](COP(=O)(S)O[C@H]2[C@H]1F)O[C@H]3n1ccc(=O)[nH]c1=O] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 71 | 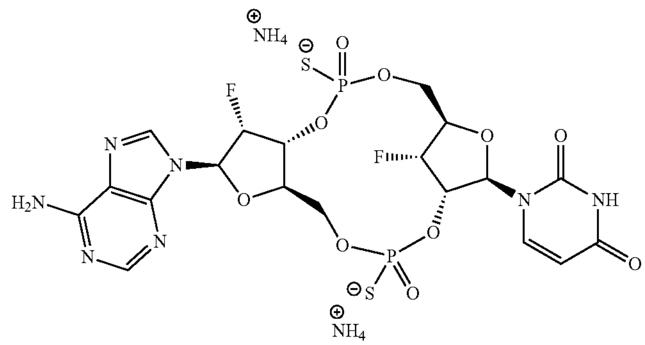 [SMILES: [NH4+] ; Nc1ncnc2c1ncn2[C@@H]1O[C@@H]2COP(=O)([S-])O[C@@H]3[C@H](F)[C@@H](COP(=O)([S-])O[C@H]2[C@H]1F)O[C@H]3n1ccc(=O)[nH]c1=O ; [NH4+]] |
| 72 | 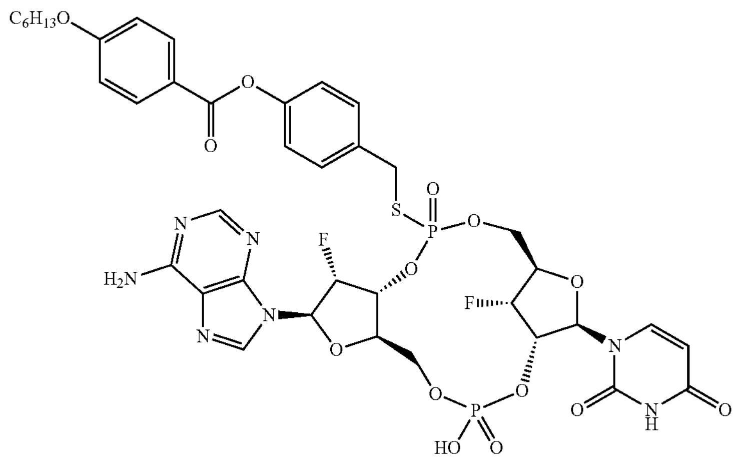 |
| 73 | 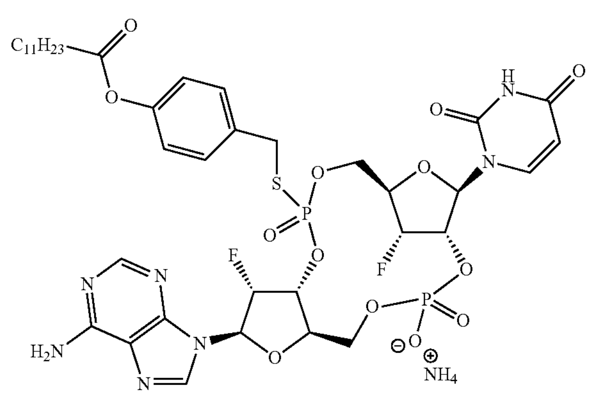 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 74 | 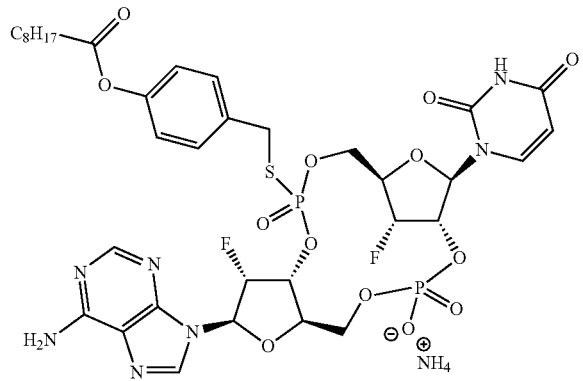 |
| 75 | 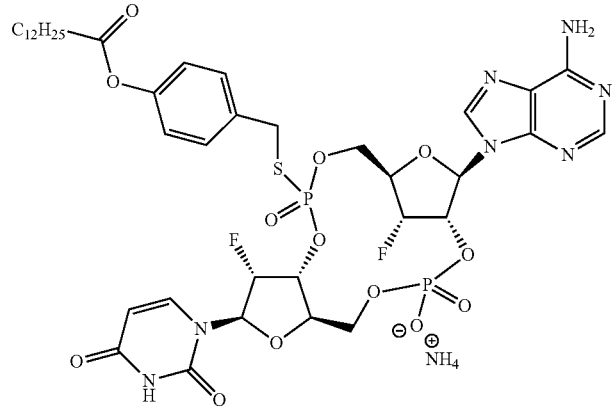 |
| 76 | 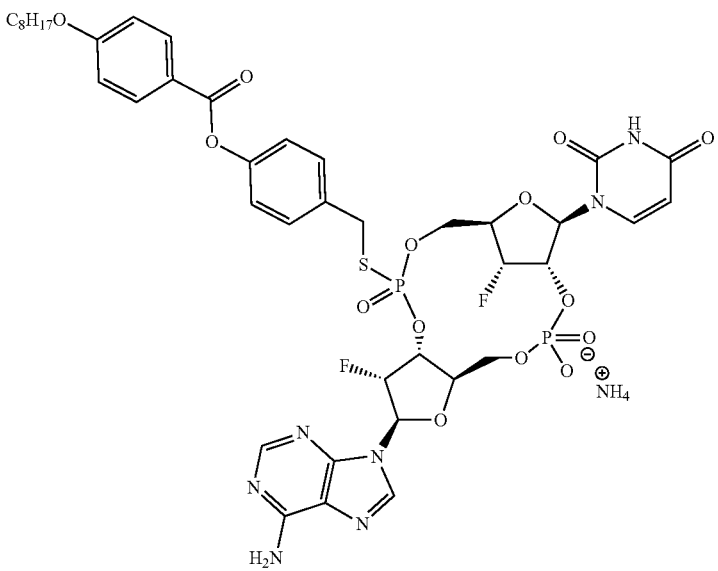 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 77 | 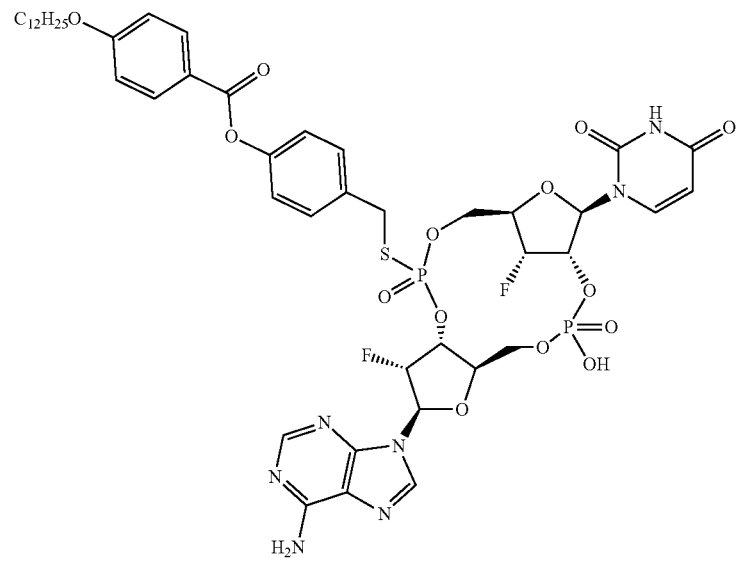 |
| 78 | 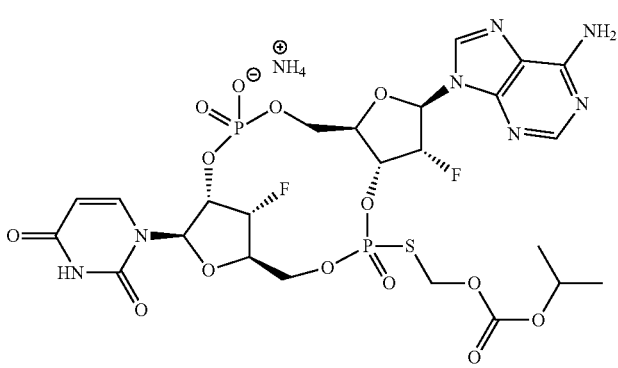 [SMILES: CC(C)OC(=O)OCSP1(=O)OC[C@H]2O[C@@H](n3ccc(=O)[nH]c3=O)[C@H](OP(=O)([O-])OC[C@H]3O[C@@H](n4cnc5c(N)ncnc54)[C@H](F)[C@@H]3O1)[C@@H]2F ; [NH4+]] |
| 79 | 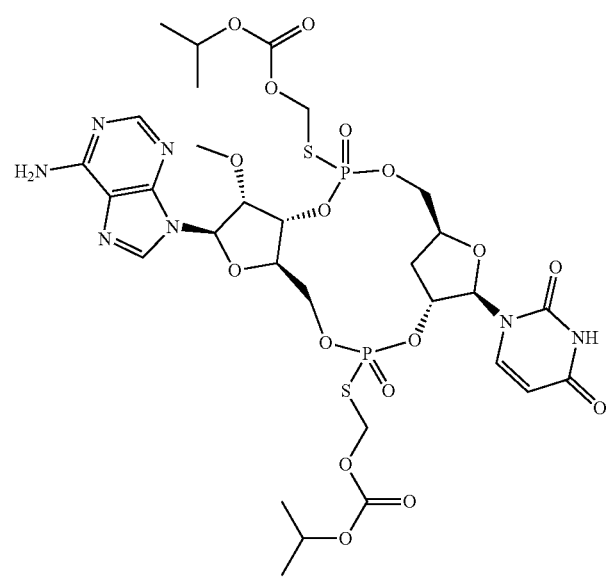 [SMILES: CO[C@@H]1[C@@H]2OP(=O)(SCOC(=O)OC(C)C)OC[C@@H]3C[C@@H](OP(=O)(SCOC(=O)OC(C)C)OC[C@H]2O[C@H]1n1cnc2c(N)ncnc21)[C@H](n1ccc(=O)[nH]c1=O)O3] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 80 | 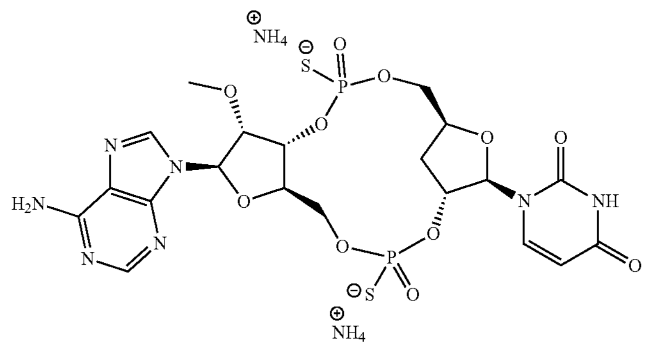 [SMILES: [NH4+] ; CO[C@@H]1[C@@H]2OP(=O)([S-])OC[C@@H]3C[C@@H](OP(=O)([S-])OC[C@H]2O[C@H]1n1cnc2c(N)ncnc21)[C@H](n1ccc(=O)[nH]c1=O)O3 ; [NH4+]] |
| 81 | 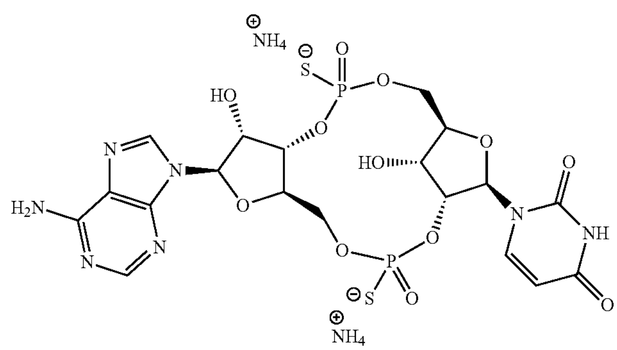 [SMILES: [NH4+] ; Nc1ncnc2c1ncn2[C@@H]1O[C@@H]2COP(=O)([S-])O[C@@H]3[C@H](O)[C@@H](COP(=O)([S-])O[C@H]2[C@H]1O)O[C@H]3n1ccc(=O)[nH]c1=O ; [NH4+]] |
| 82 | 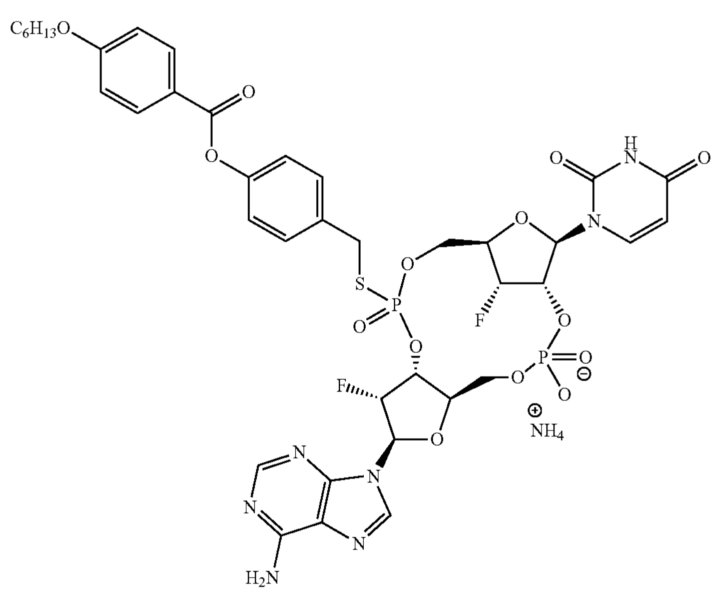 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 83 | 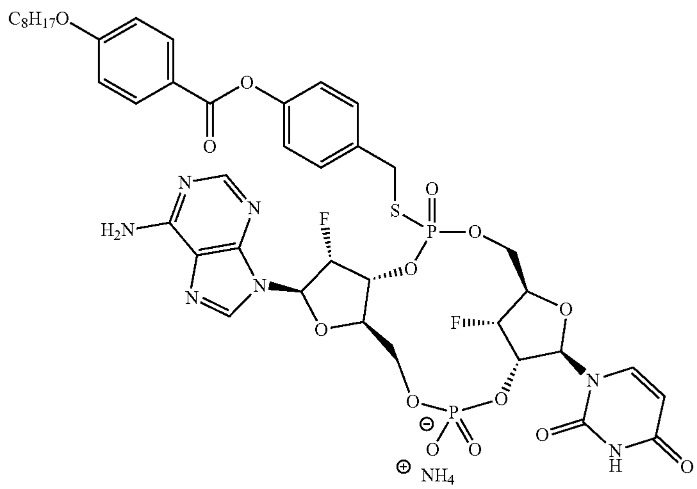 |
| 84 | 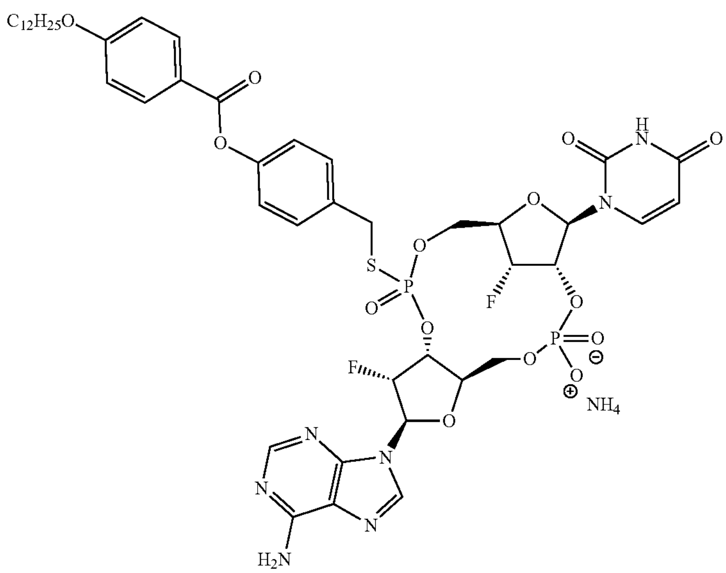 |
| 85 | 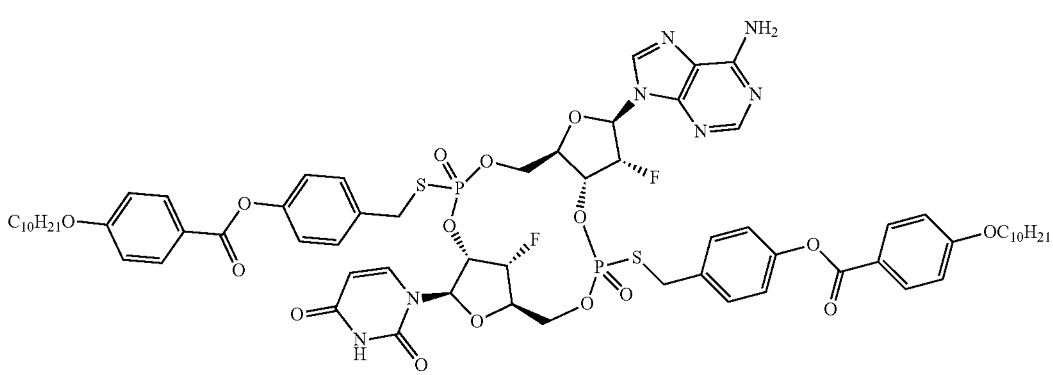 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 86 | 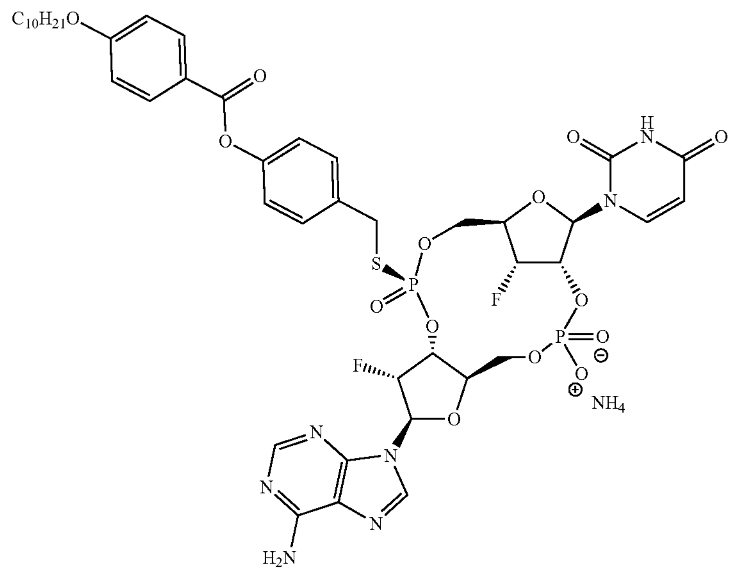 |
| 87 | 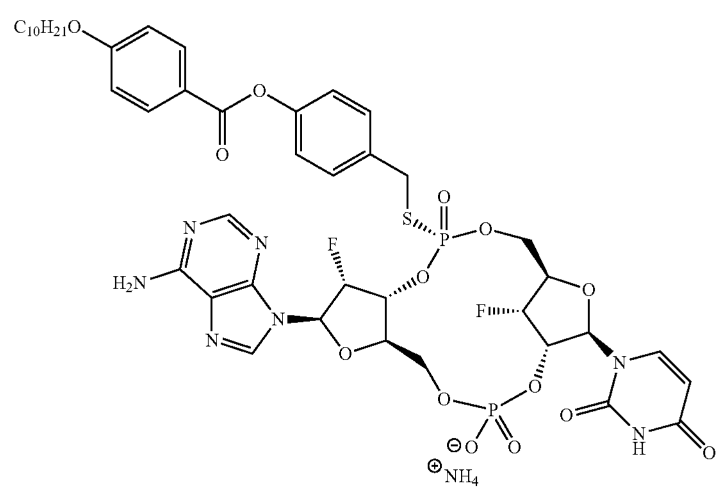 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 88 | 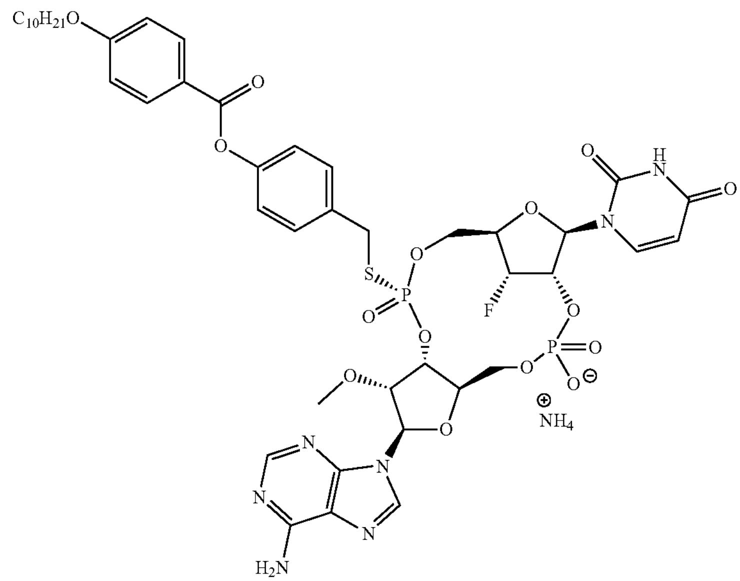 |
| 89 | 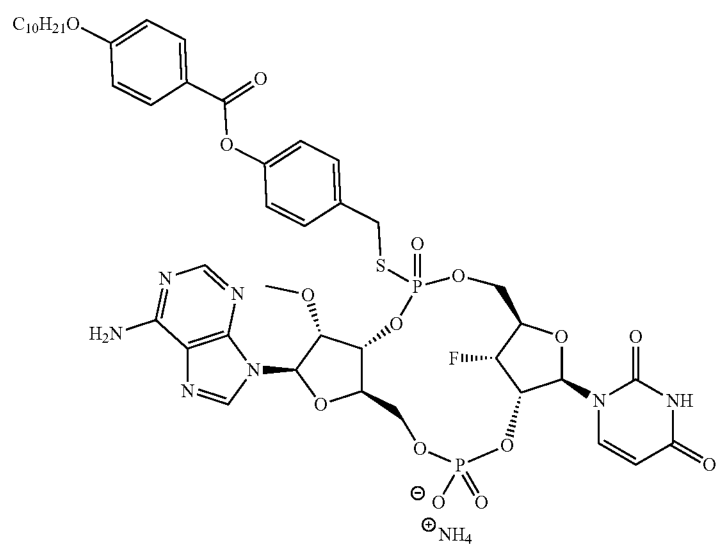 |
| 90 | 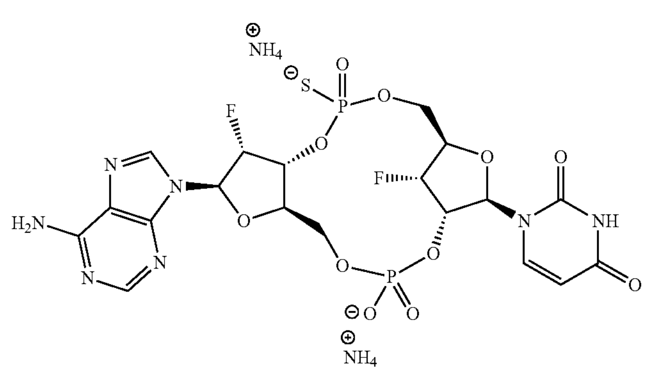 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 91 | 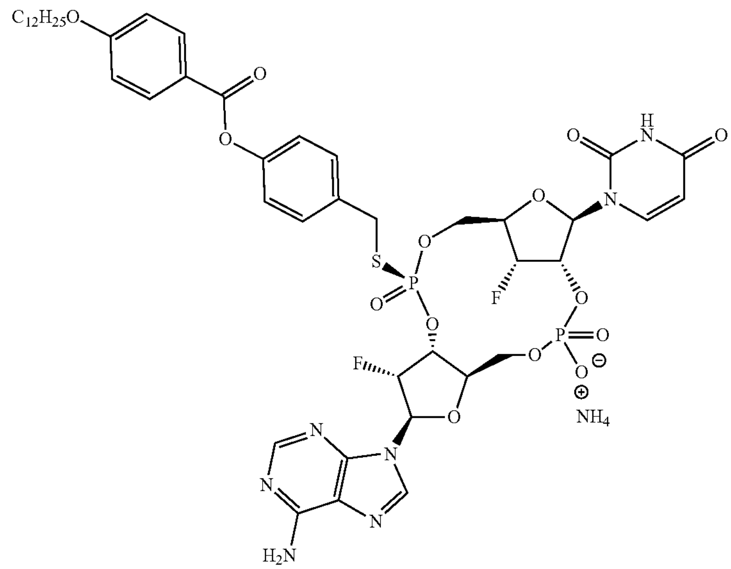 |
| 92 | 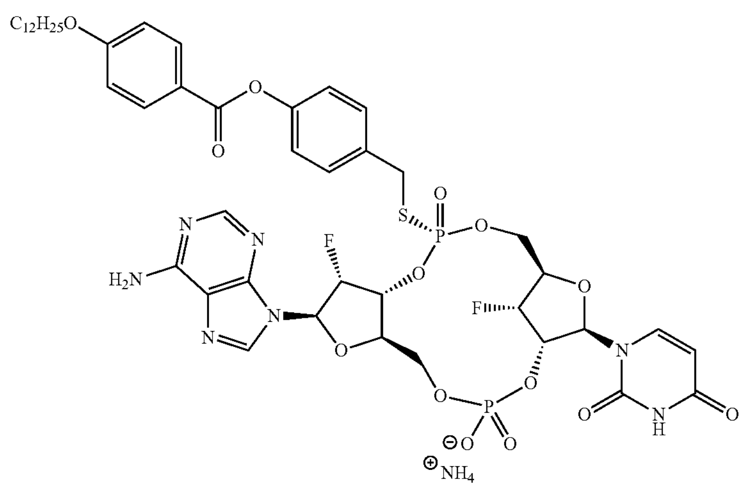 |
| 93 | 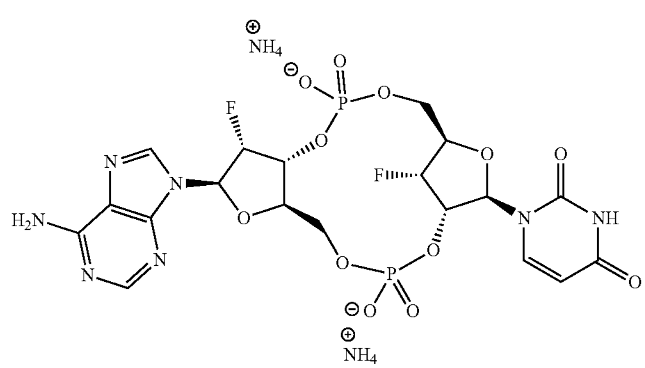 [SMILES: [NH4+] ; Nc1ncnc2c1ncn2[C@@H]1O[C@@H]2COP(=O)([O-])O[C@@H]3[C@H](F)[C@@H](COP(=O)([O-])O[C@H]2[C@H]1F)O[C@H]3n1ccc(=O)[nH]c1=O ; [NH4+]] |

US 11,638,716 B2
TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 94 | 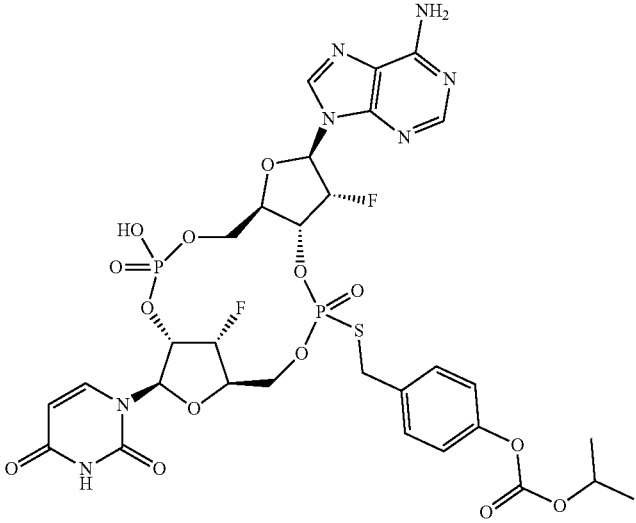 [SMILES: CC(C)OC(=O)Oc1ccc(CSP2(=O)OC[C@H]3O[C@@H](n4ccc(=O)[nH]c4=O)[C@H](OP(=O)(O)OC[C@H]4O[C@@H](n5cnc6c(N)ncnc65)[C@H](F)[C@@H]4O2)[C@@H]3F)cc1] |
| 95 | 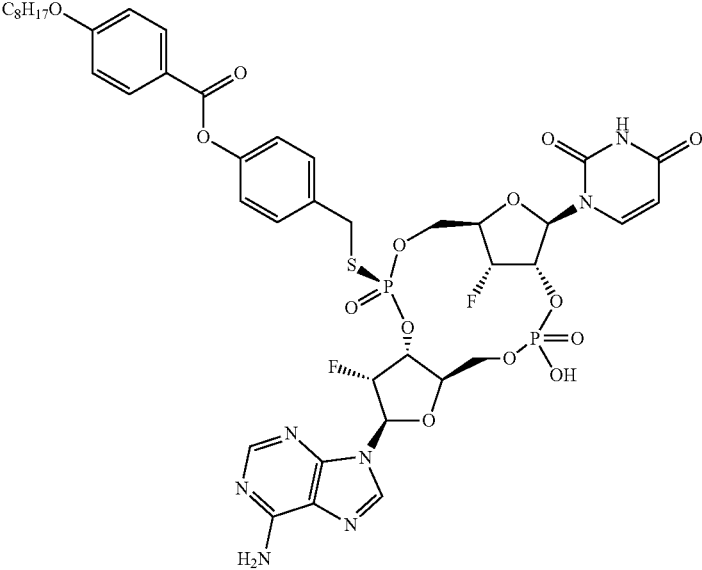 |
| 96 | 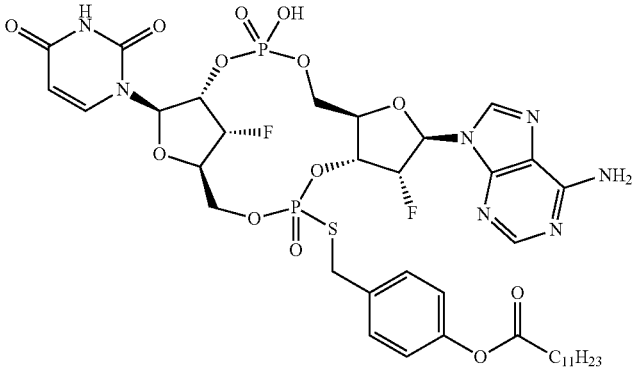 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 97 | 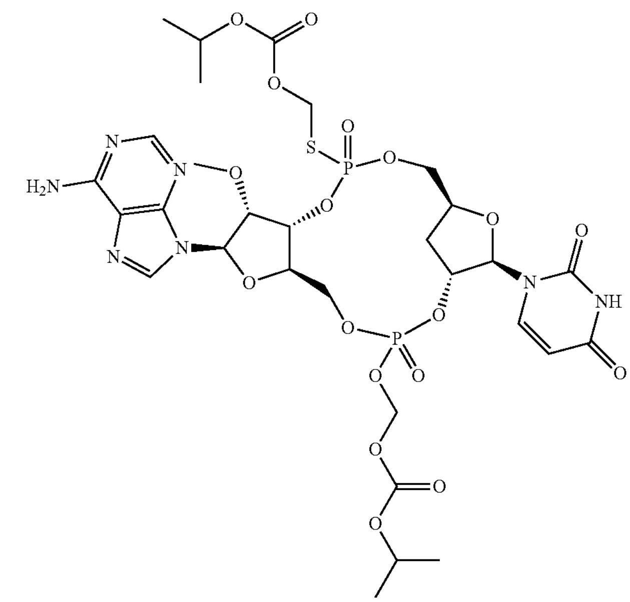 [SMILES: CO[C@@H]1[C@@H]2OP(=O)(SCOC(=O)OC(C)C)OC[C@@H]3C[C@@H](OP(=O)(OCOC(=O)OC(C)C)OC[C@H]2O[C@H]1n1cnc2c(N)ncnc21)[C@H](n1ccc(=O)[nH]c1=O)O3] |
| 98 | 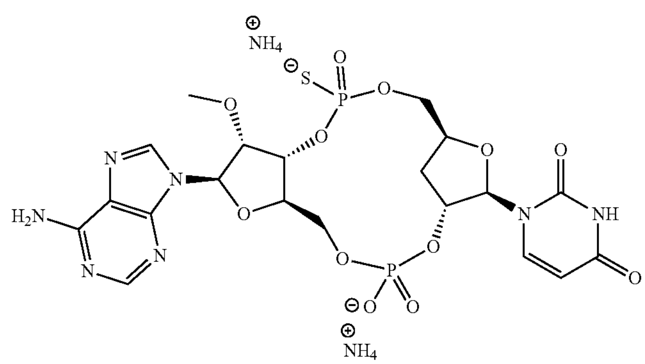 [SMILES: [NH4+] ; CO[C@@H]1[C@@H]2OP(=O)([S-])OC[C@@H]3C[C@@H](OP(=O)([O-])OC[C@H]2O[C@H]1n1cnc2c(N)ncnc21)[C@H](n1ccc(=O)[nH]c1=O)O3 ; [NH4+]] |
| 99 | 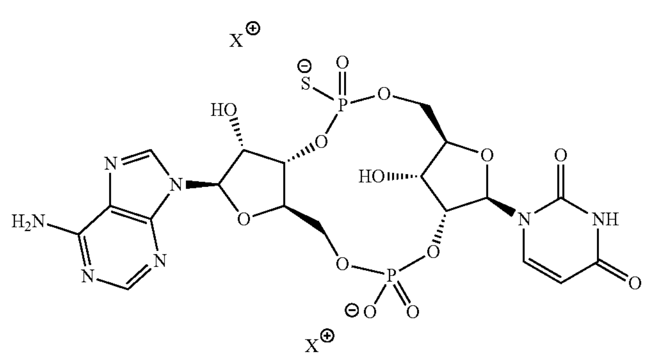 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 100 | 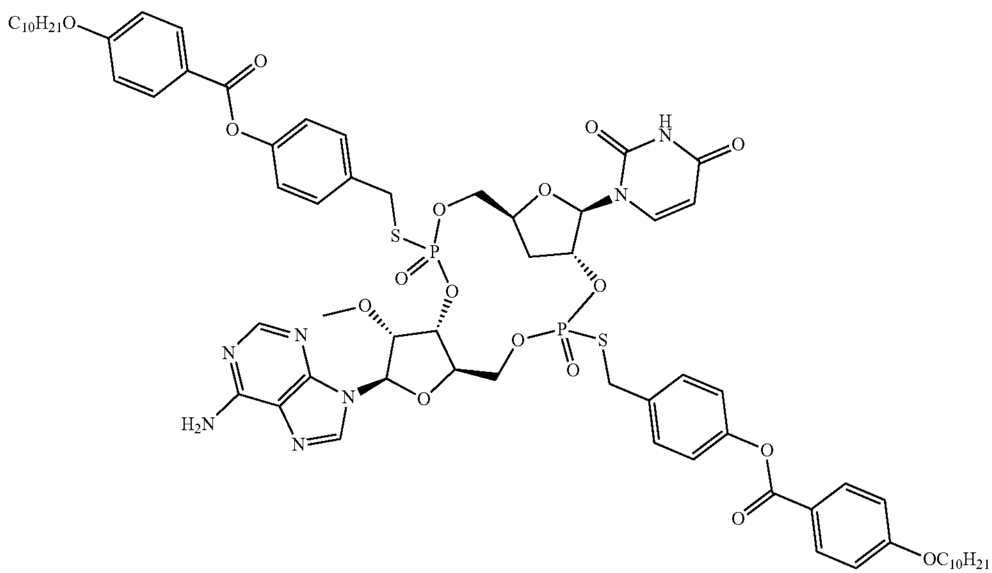 |
| 101 | 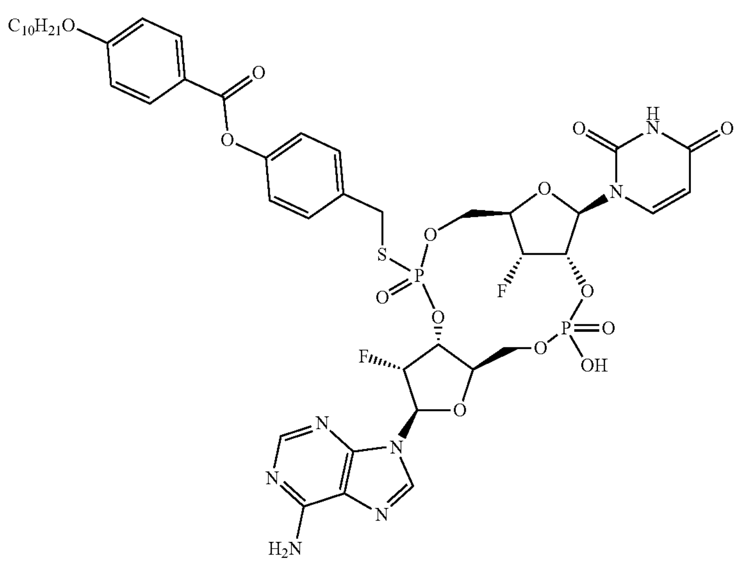 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 102 | 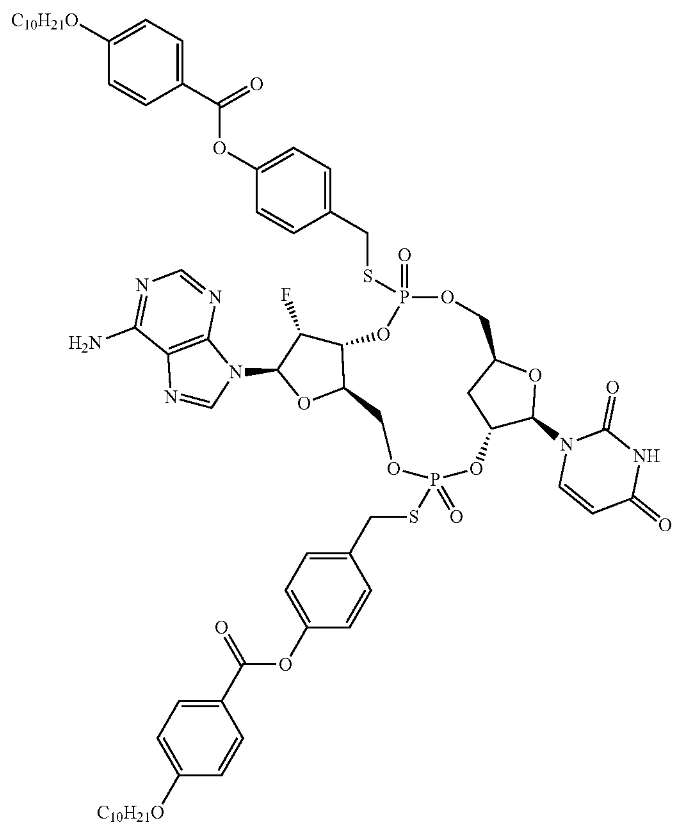 |
| 103 | 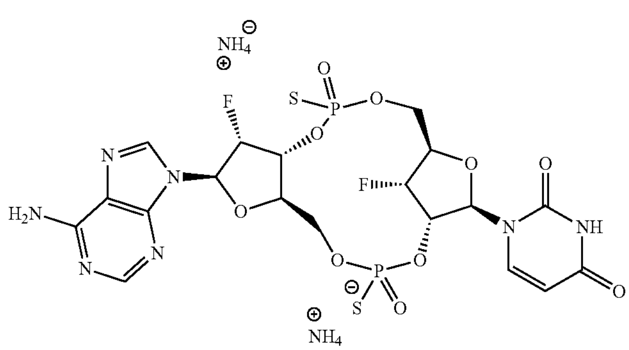 |

US 11,638,716 B2
97                                                                                                 98
TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 104 | 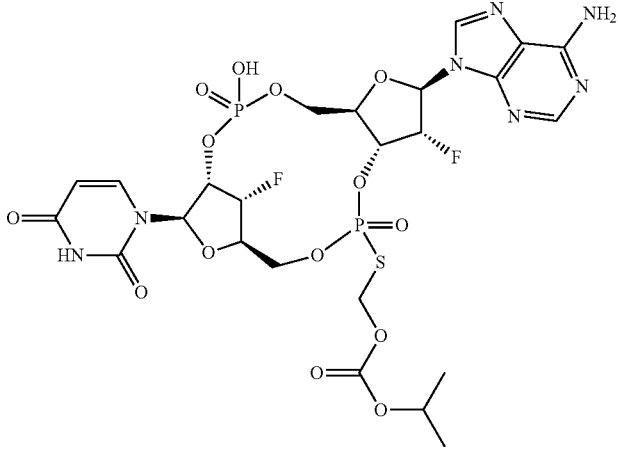 [SMILES: CC(C)OC(=O)OCSP1(=O)OC[C@H]2O[C@@H](n3ccc(=O)[nH]c3=O)[C@H](OP(=O)(O)OC[C@H]3O[C@@H](n4cnc5c(N)ncnc54)[C@H](F)[C@@H]3O1)[C@@H]2F] |
| 105 | 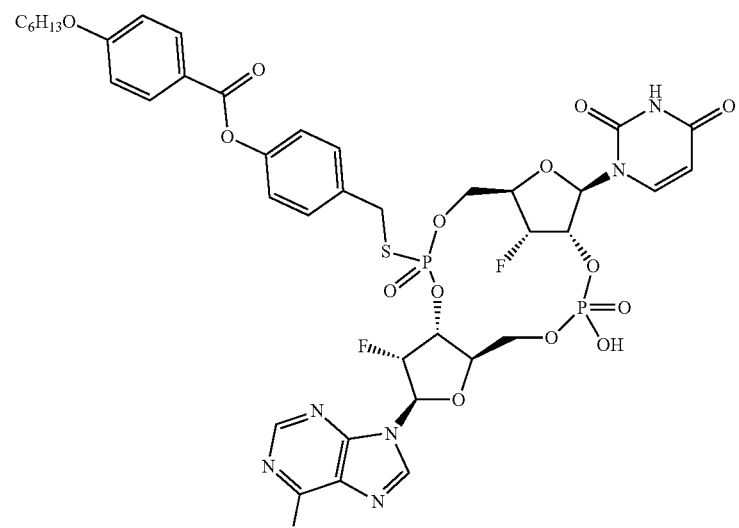 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 106 | 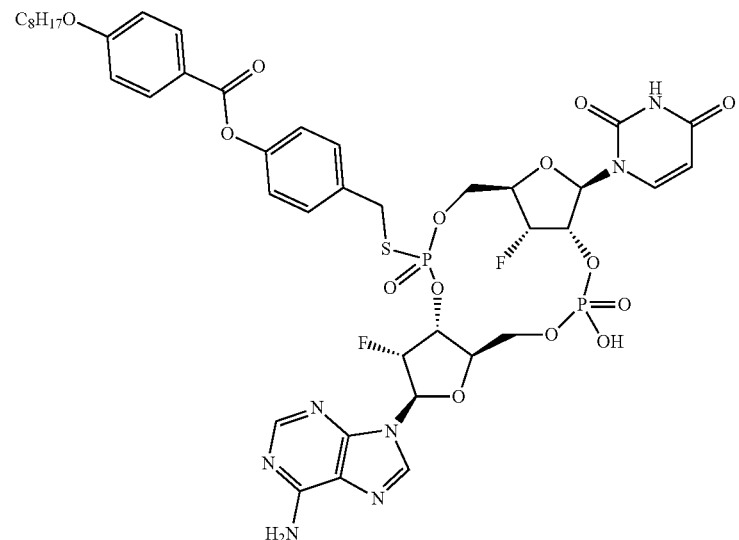 |
| 107 | 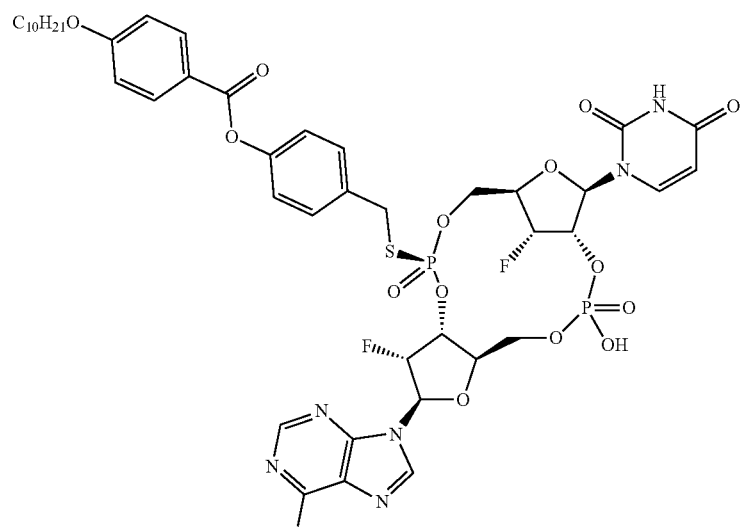 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 108 | 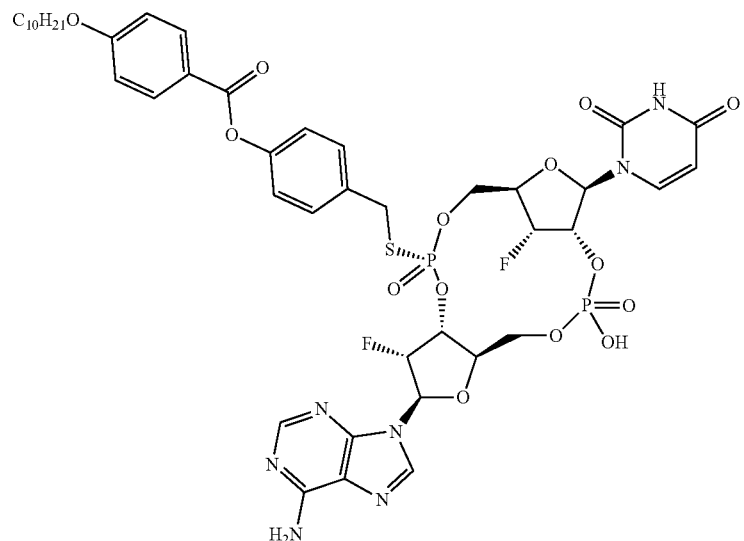 |
| 109 | 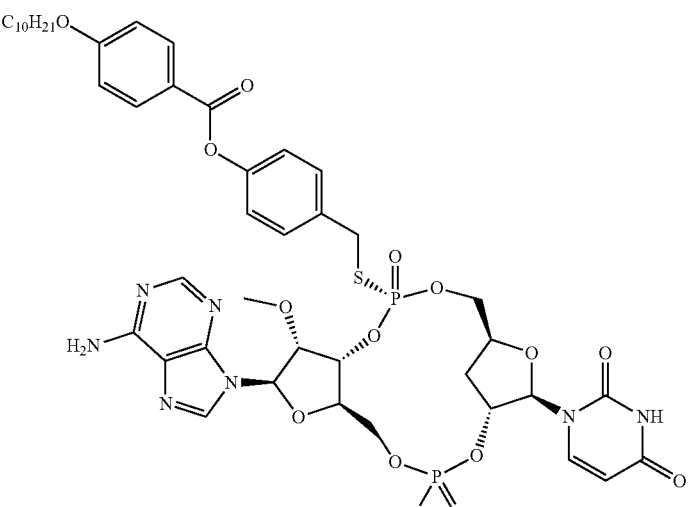 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 110 | 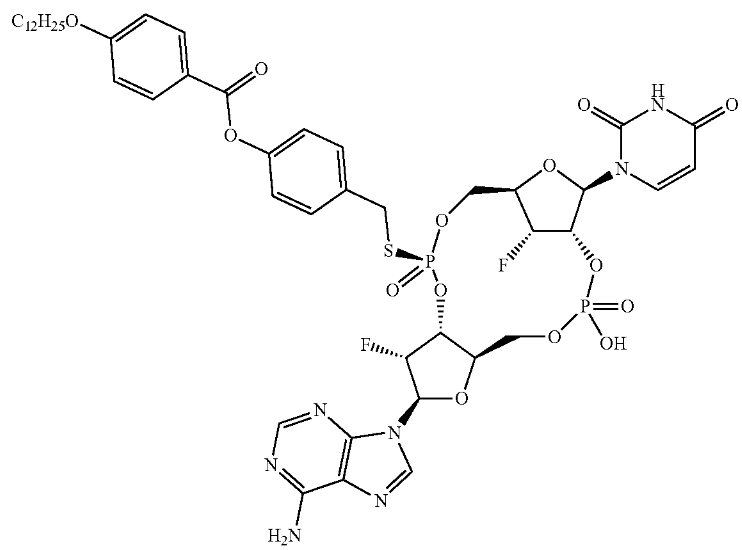 |
| 111 | 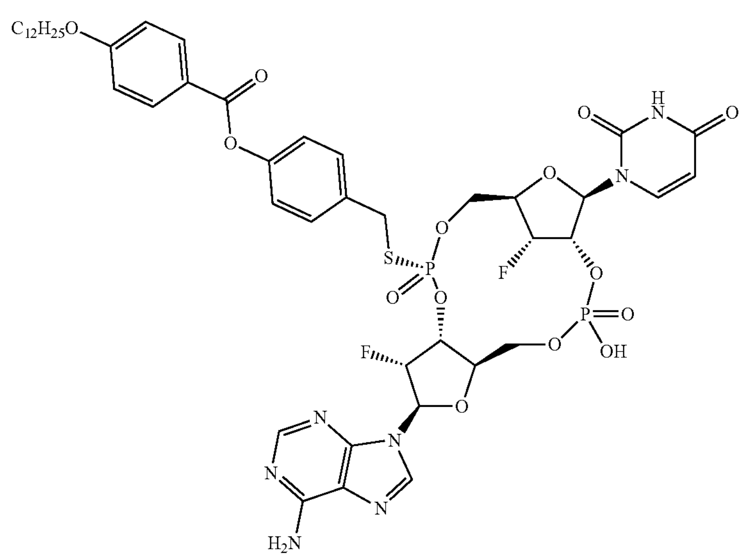 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 112 | 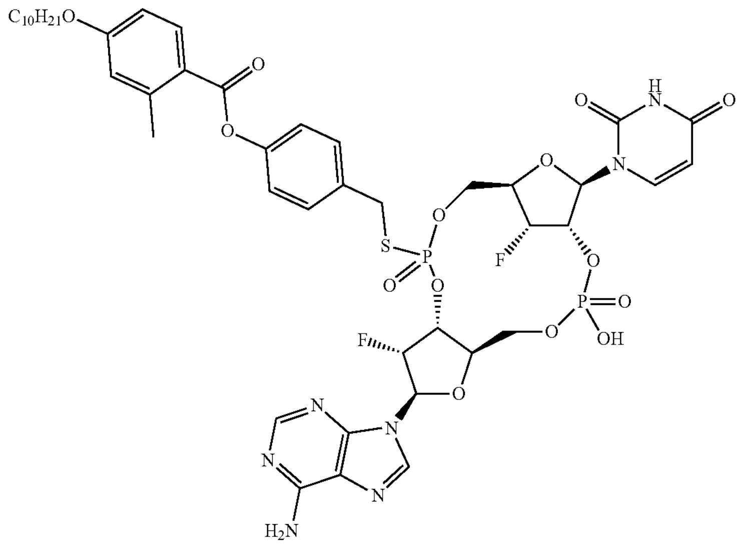 |
| 113 | 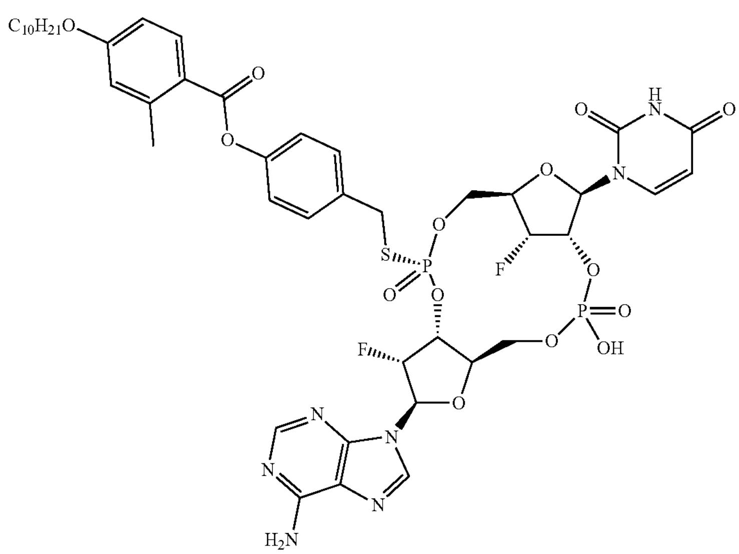 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 114 | 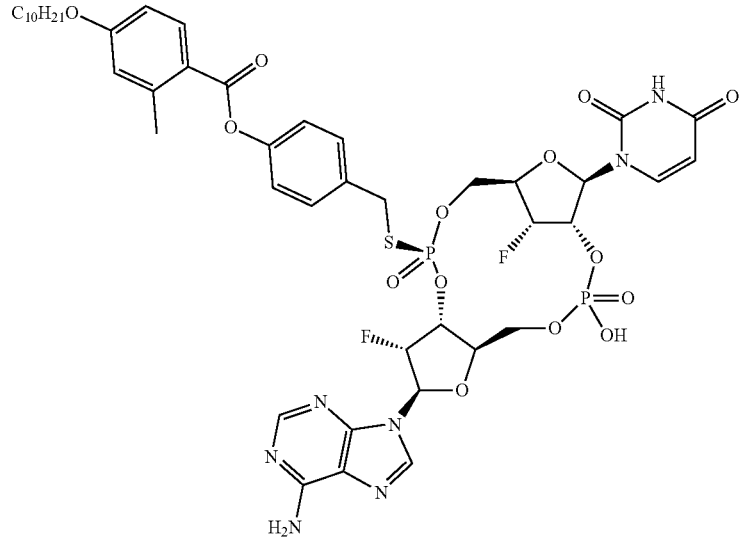 |
| 115 | 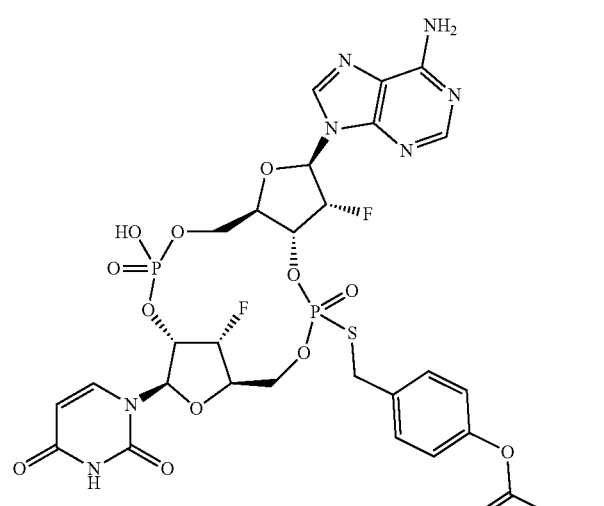 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 116 | 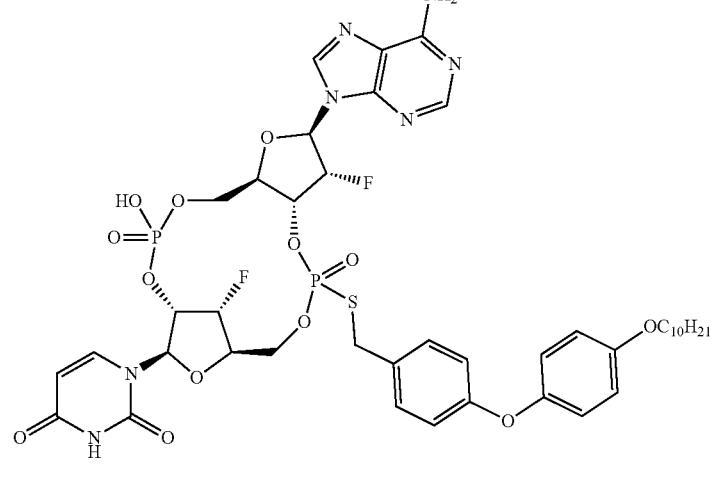 |
| 117 | 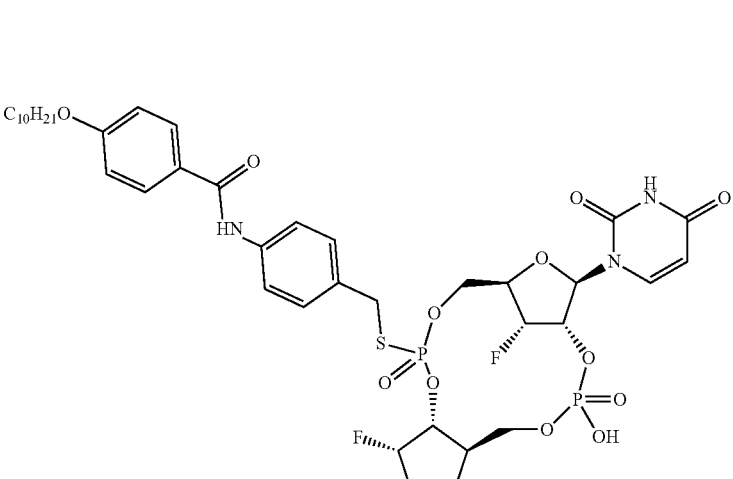 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 118 | 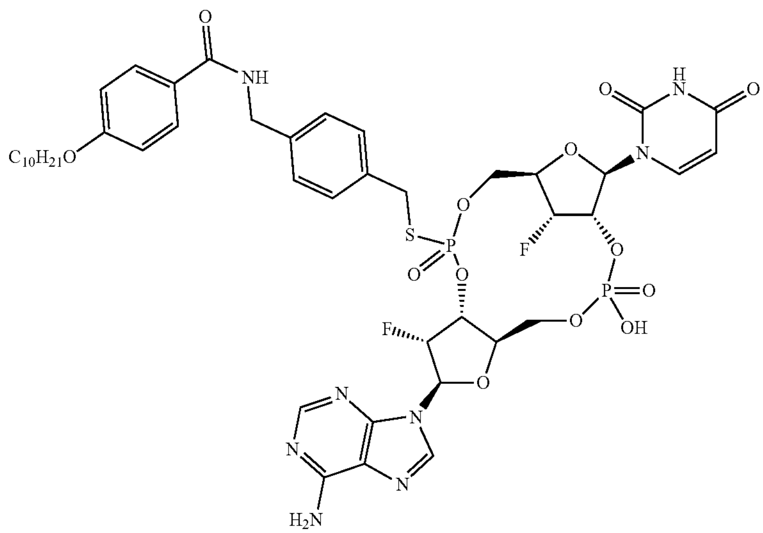 |
| 119 | 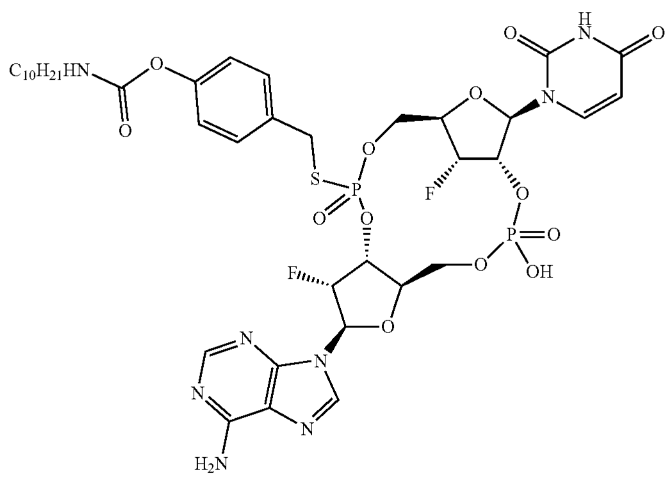 |
| 120 | 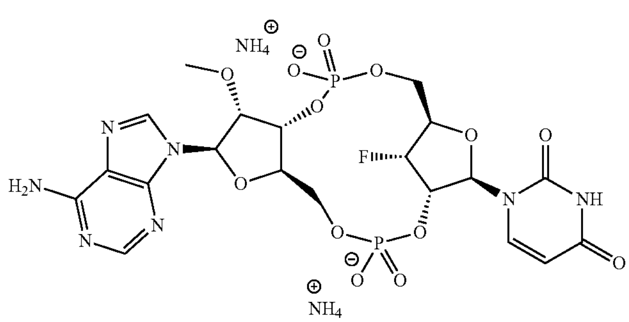 [SMILES: CO[C@@H]1[C@@H]2OP(=O)([O-])OC[C@H]3O[C@@H](n4ccc(=O)[nH]c4=O)[C@H](OP(=O)([O-])OC[C@H]2O[C@H]1n1cnc2c(N)ncnc21)[C@@H]3F ; [NH4+] ; [NH4+]] |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 121 | 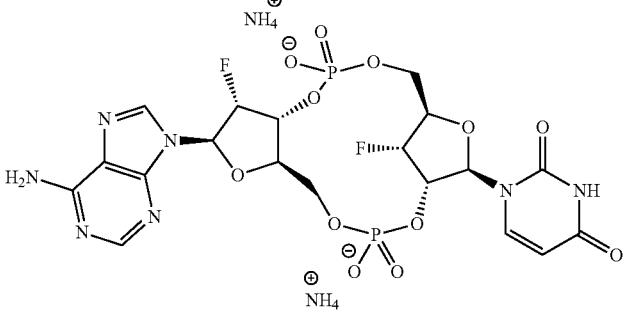 |
| 122 | 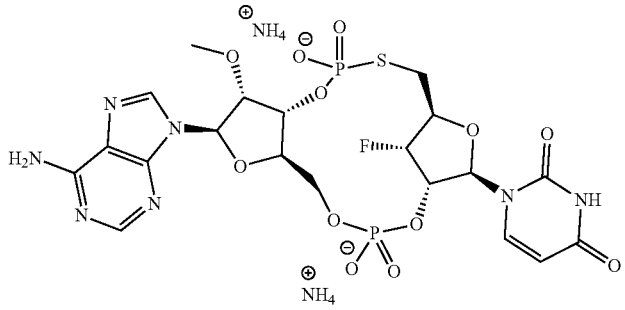 [SMILES: CO[C@@H]1[C@@H]2OP(=O)([O-])SC[C@H]3O[C@@H](n4ccc(=O)[nH]c4=O)[C@H](OP(=O)([O-])OC[C@H]2O[C@H]1n1cnc2c(N)ncnc21)[C@@H]3F ; [NH4+] ; [NH4+]] |
| 123 | 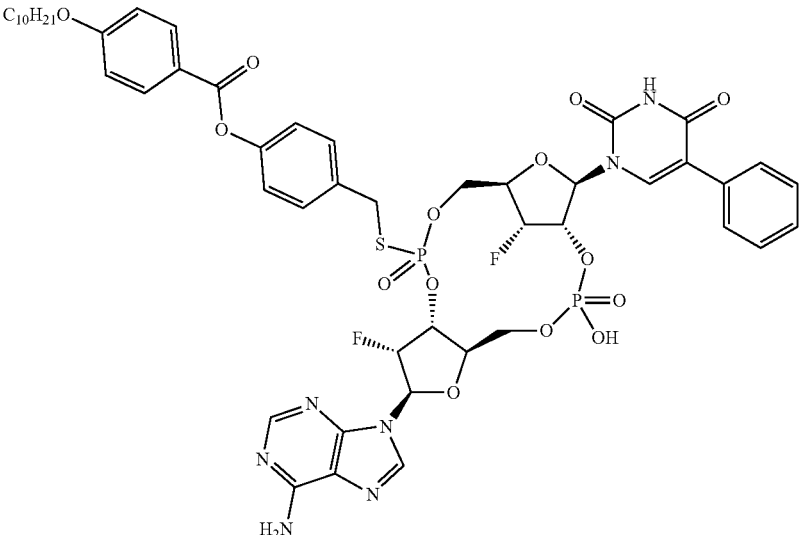 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 124 | 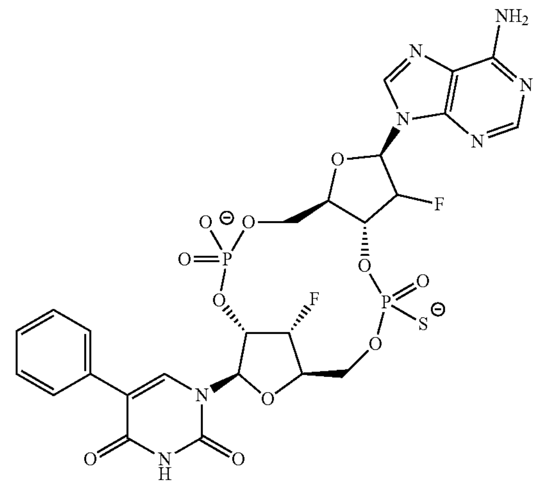 [SMILES: Nc1ncnc2c1ncn2[C@@H]1O[C@@H]2COP(=O)([O-])O[C@@H]3[C@H](F)[C@@H](COP(=O)([S-])O[C@H]2C1F)O[C@H]3n1cc(-c2ccccc2)c(=O)[nH]c1=O] |
| 125 | 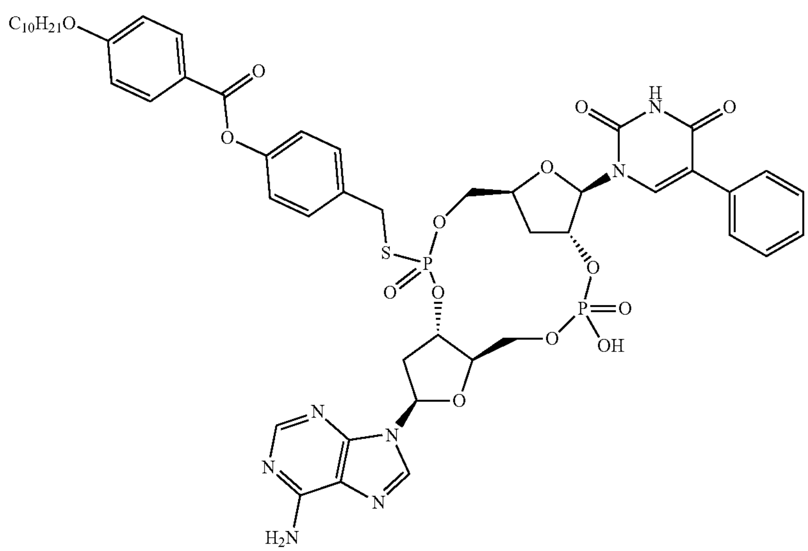 |
| 126 | 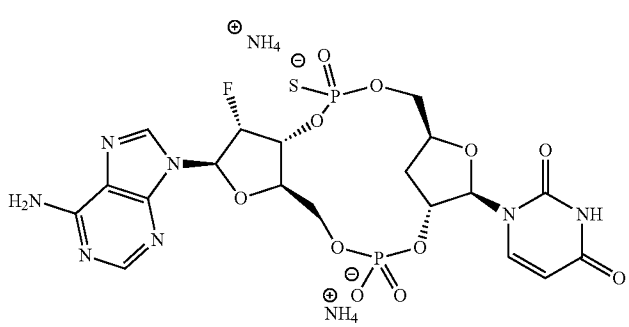 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 127 | 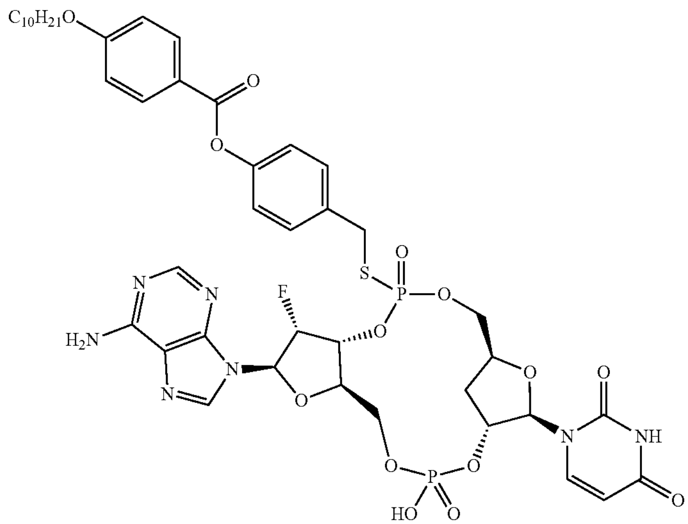 |
| 128 | 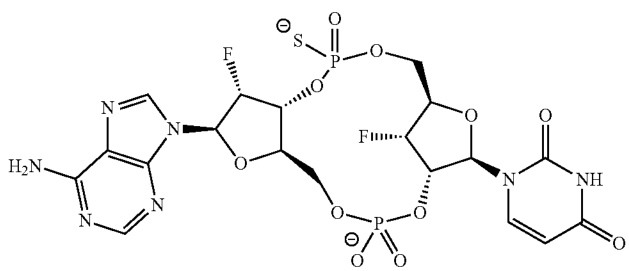 [SMILES: Nc1ncnc2c1ncn2[C@@H]1O[C@@H]2COP(=O)([O-])O[C@@H]3[C@H](F)[C@@H](COP(=O)([S-])O[C@H]2[C@H]1F)O[C@H]3n1ccc(=O)[nH]c1=O] |
| 129 | 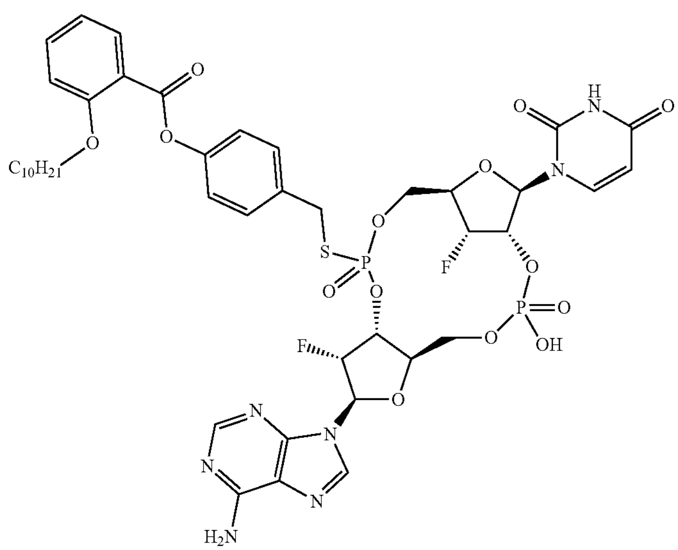 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 130 | 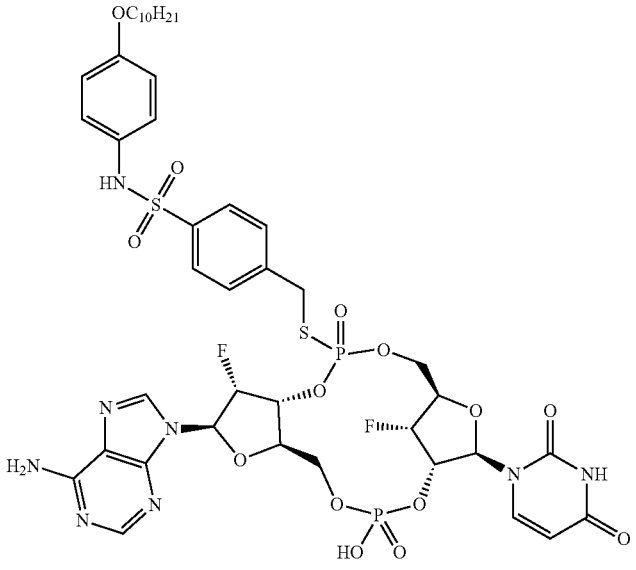 |
| 131 | 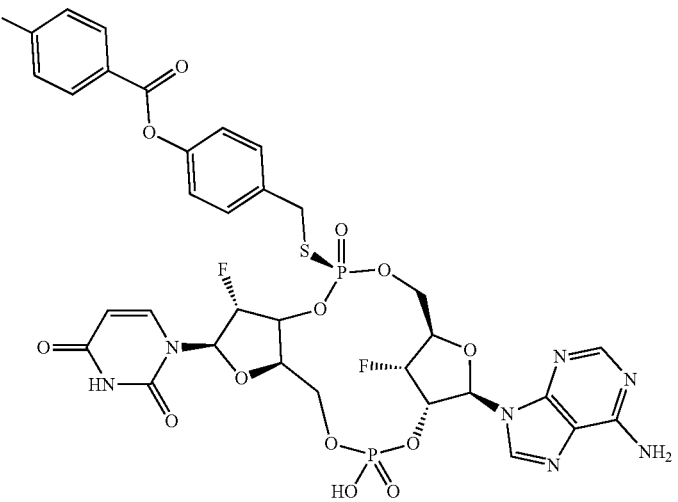 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 132 | 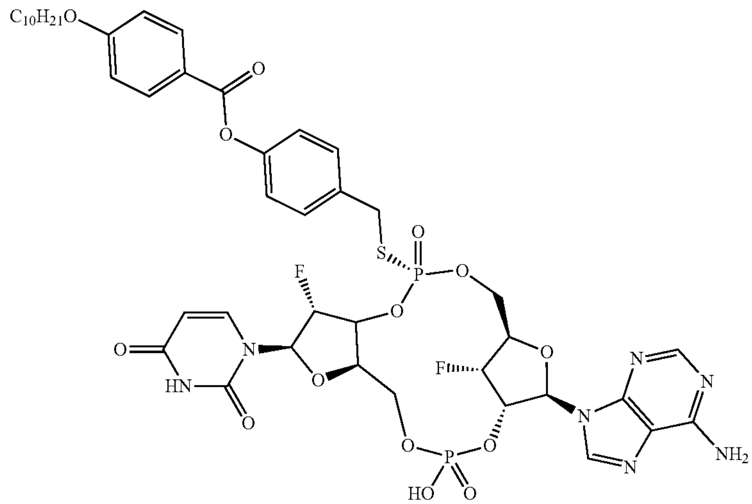 |
| 133 | 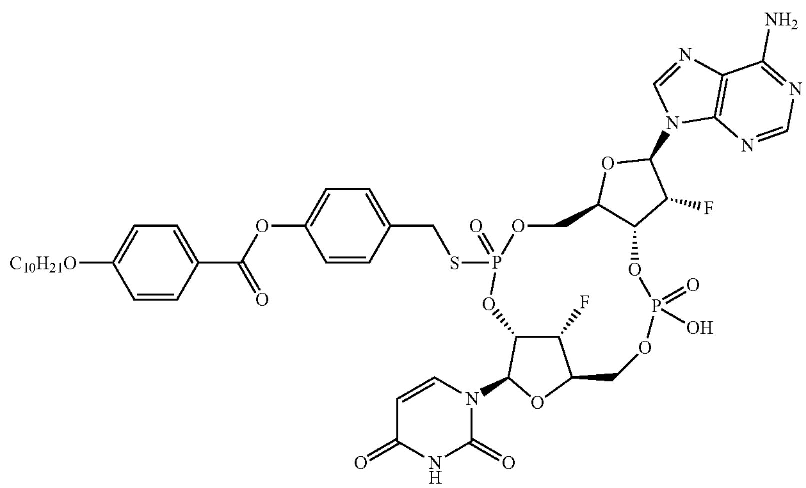 |
| 134 | 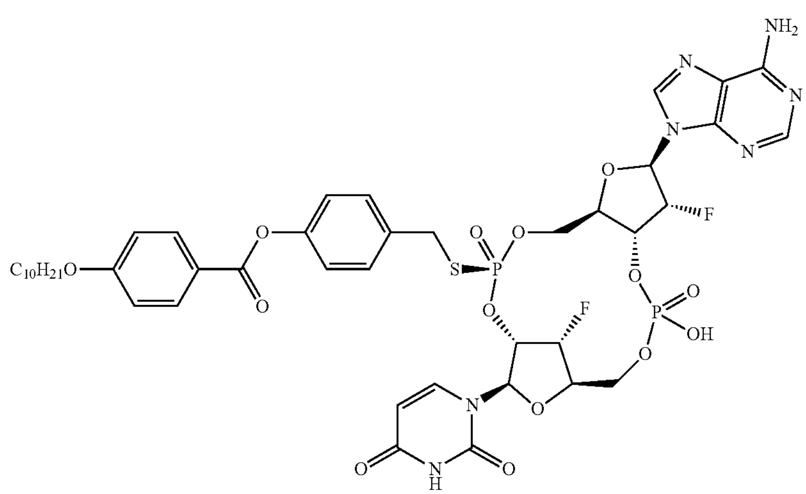 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 135 | 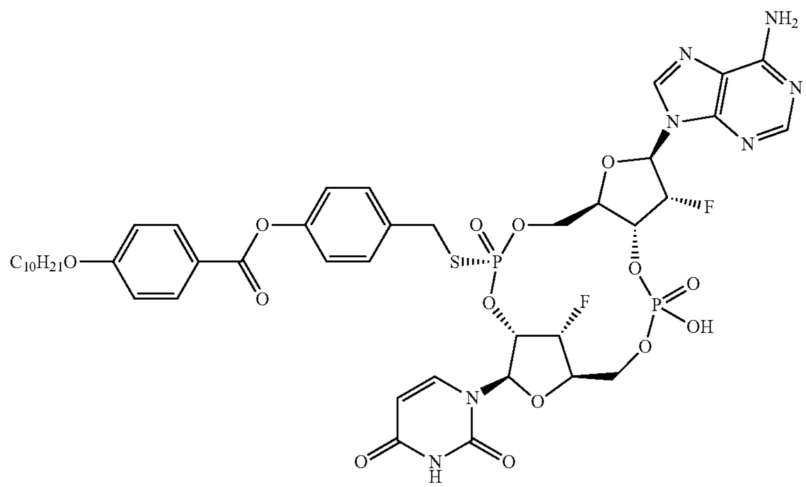 |
| 136 | 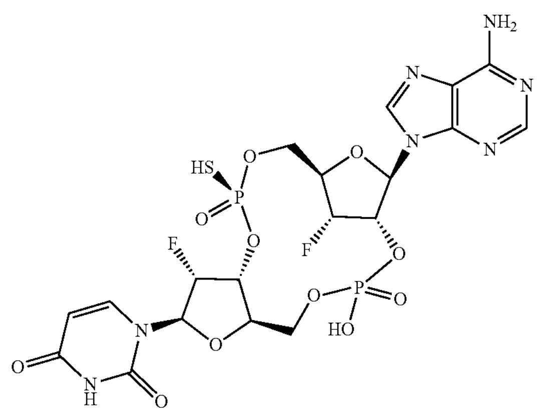 [SMILES: Nc1ncnc2c1ncn2[C@@H]1O[C@@H]2CO[P@](=O)(S)O[C@H]3[C@@H](F)[C@H](n4ccc(=O)[nH]c4=O)O[C@@H]3COP(=O)(O)O[C@@H]1[C@@H]2F] |
| 137 | 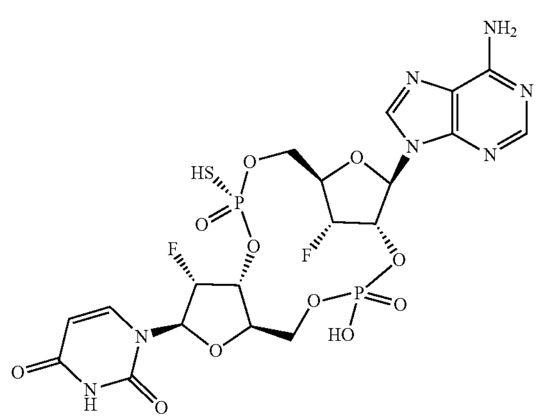 [SMILES: Nc1ncnc2c1ncn2[C@@H]1O[C@@H]2CO[P@@](=O)(S)O[C@H]3[C@@H](F)[C@H](n4ccc(=O)[nH]c4=O)O[C@@H]3COP(=O)(O)O[C@@H]1[C@@H]2F] |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 138 | 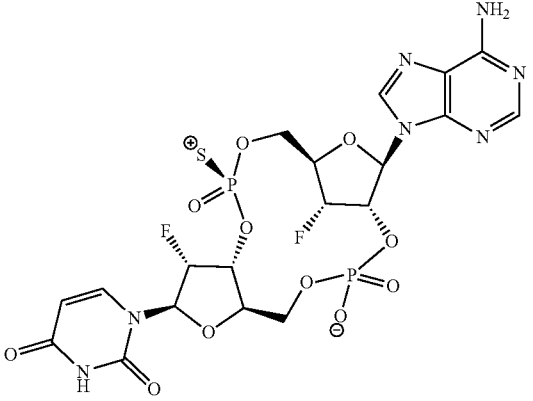 |
| 139 | 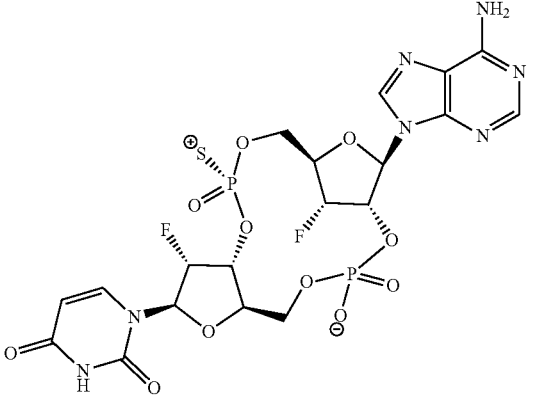 |
| 140 | 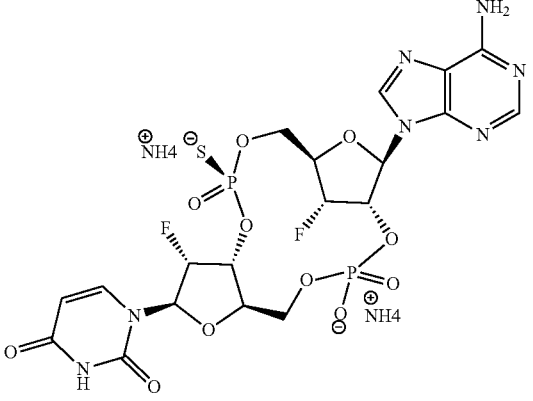 [SMILES: Nc1ncnc2c1ncn2[C@@H]1O[C@@H]2CO[P@](=O)([S-])O[C@H]3[C@@H](F)[C@H](n4ccc(=O)[nH]c4=O)O[C@@H]3COP(=O)([O-])O[C@@H]1[C@@H]2F ; [NH4+] ; [NH4+]] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 141 | 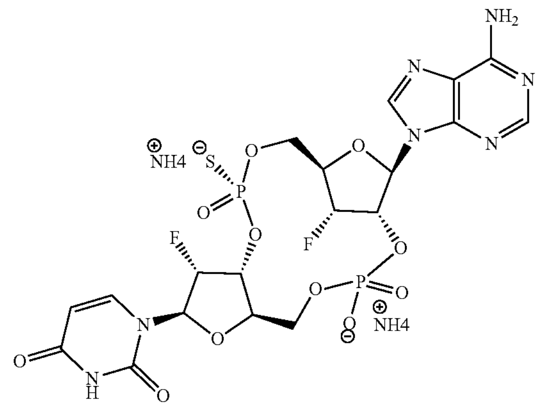 [SMILES: Nc1ncnc2c1ncn2[C@@H]1O[C@@H]2CO[P@@](=O)([S-])O[C@H]3[C@@H](F)[C@H](n4ccc(=O)[nH]c4=O)O[C@@H]3COP(=O)([O-])O[C@@H]1[C@@H]2F ; [NH4+] ; [NH4+]] |
| 142 | 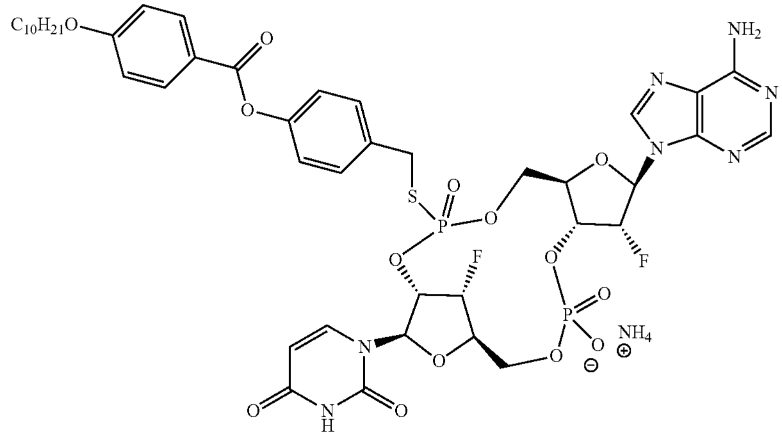 |
| 143 | 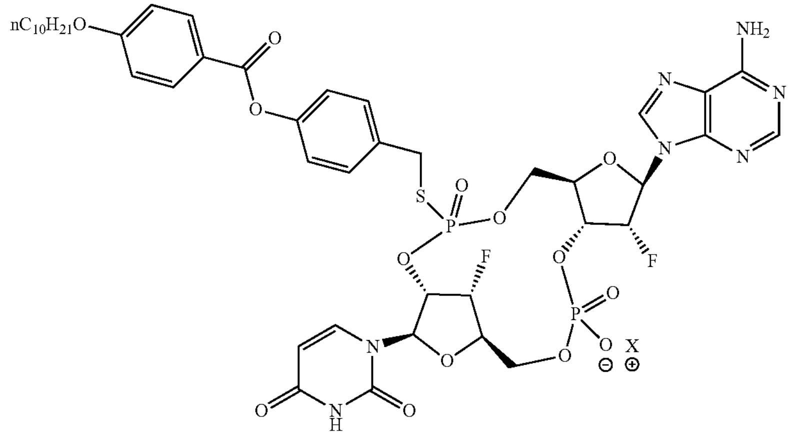 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 144 | 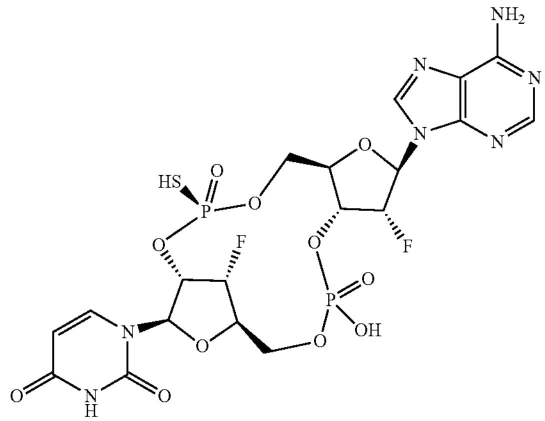 [SMILES: Nc1ncnc2c1ncn2[C@@H]1O[C@@H]2CO[P@](=O)(S)O[C@@H]3[C@H](F)[C@@H](COP(=O)(O)O[C@H]2[C@H]1F)O[C@H]3n1ccc(=O)[nH]c1=O] |
| 145 | 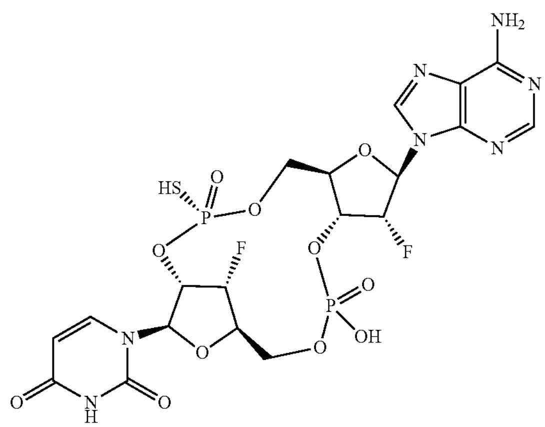 [SMILES: Nc1ncnc2c1ncn2[C@@H]1O[C@@H]2CO[P@@](=O)(S)O[C@@H]3[C@H](F)[C@@H](COP(=O)(O)O[C@H]2[C@H]1F)O[C@H]3n1ccc(=O)[nH]c1=O] |
| 146 | 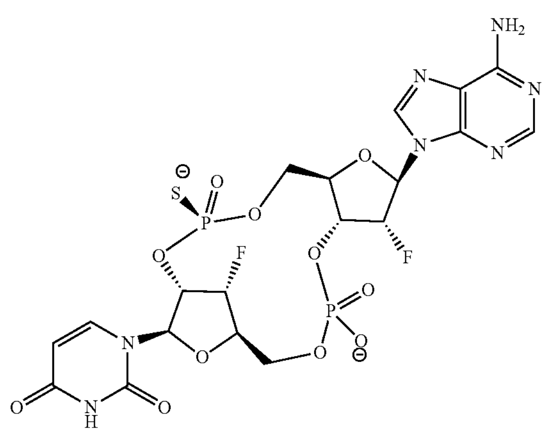 [SMILES: Nc1ncnc2c1ncn2[C@@H]1O[C@@H]2CO[P@](=O)([S-])O[C@@H]3[C@H](F)[C@@H](COP(=O)([O-])O[C@H]2[C@H]1F)O[C@H]3n1ccc(=O)[nH]c1=O] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 147 | 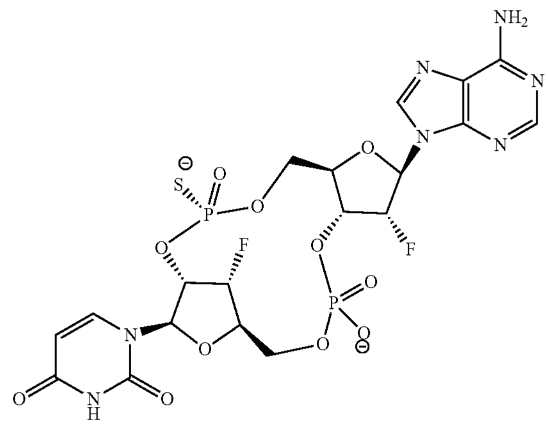 [SMILES: Nc1ncnc2c1ncn2[C@@H]1O[C@@H]2CO[P@@](=O)([S-])O[C@@H]3[C@H](F)[C@@H](COP(=O)([O-])O[C@H]2[C@H]1F)O[C@H]3n1ccc(=O)[nH]c1=O] |
| 148 | 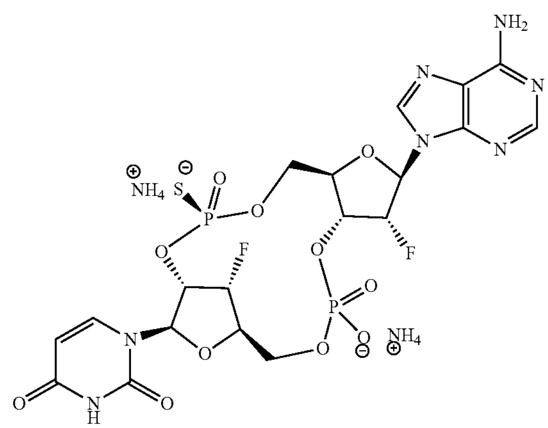 [SMILES: Nc1ncnc2c1ncn2[C@@H]1O[C@@H]2CO[P@](=O)([S-])O[C@@H]3[C@H](F)[C@@H](COP(=O)([O-])O[C@H]2[C@H]1F)O[C@H]3n1ccc(=O)[nH]c1=O ; [NH4+] ; [NH4+]] |
| 149 | 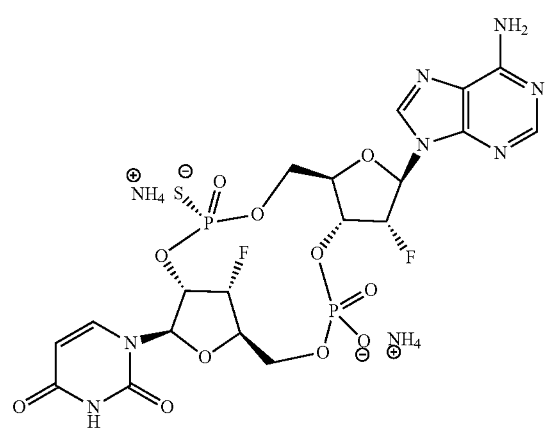 [SMILES: Nc1ncnc2c1ncn2[C@@H]1O[C@@H]2CO[P@@](=O)([S-])O[C@@H]3[C@H](F)[C@@H](COP(=O)([O-])O[C@H]2[C@H]1F)O[C@H]3n1ccc(=O)[nH]c1=O ; [NH4+] ; [NH4+]] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 150 | 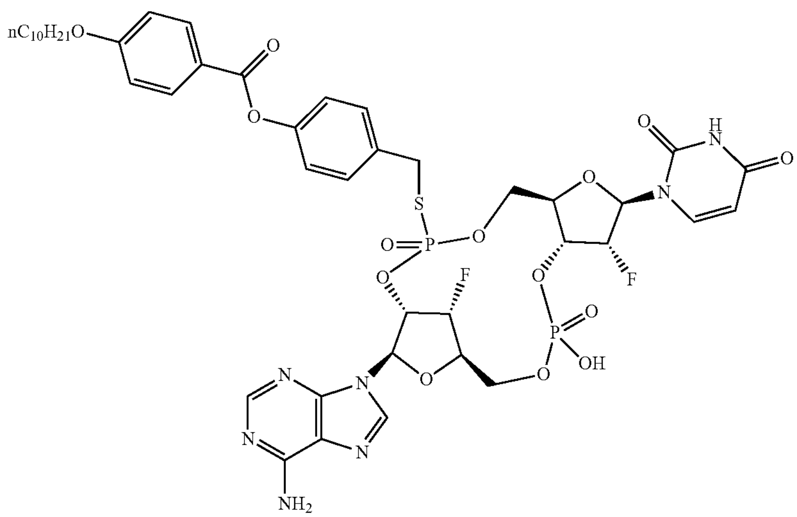 |
| 151 | 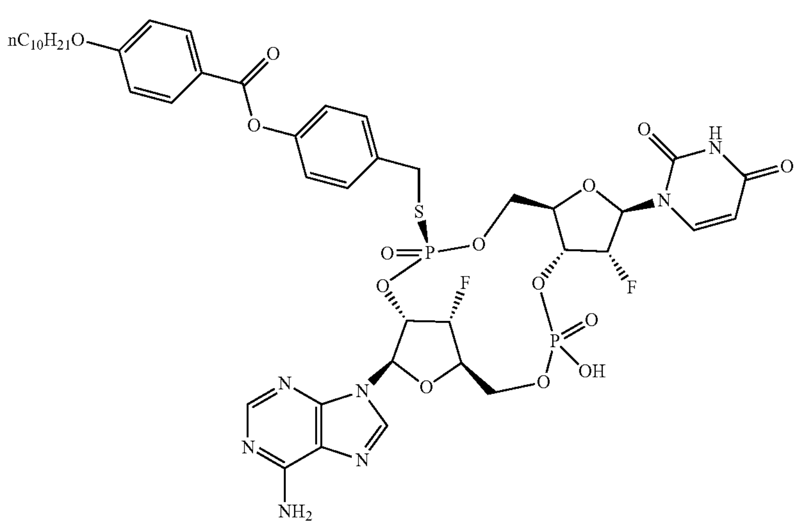 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 152 | 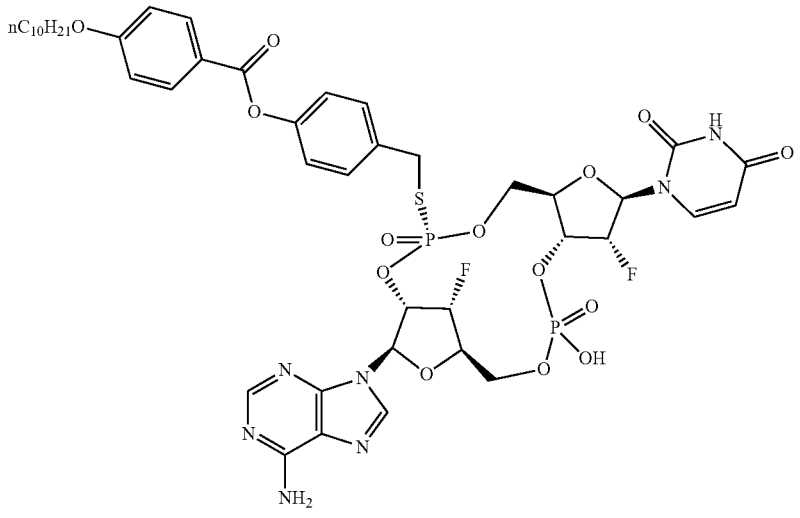 |
| 153 | 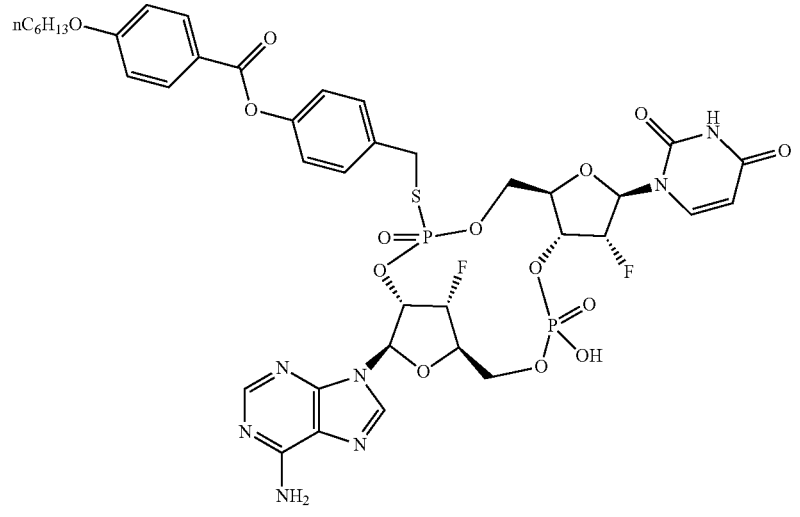 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 154 | 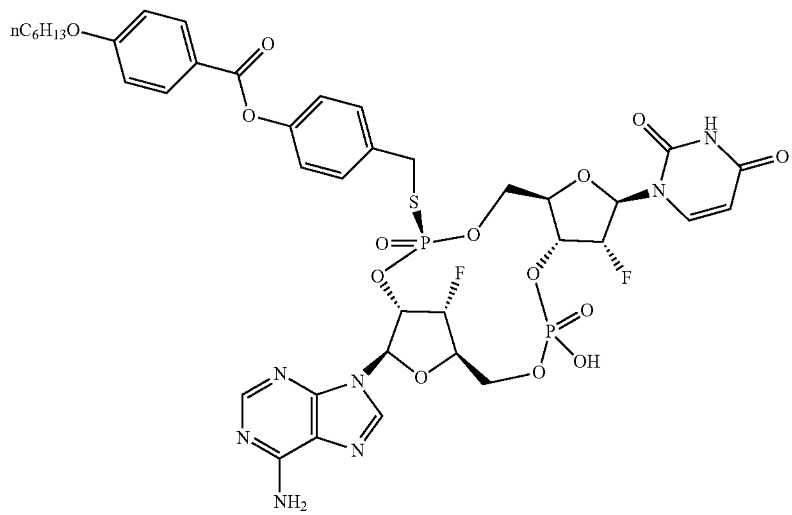 |
| 155 | 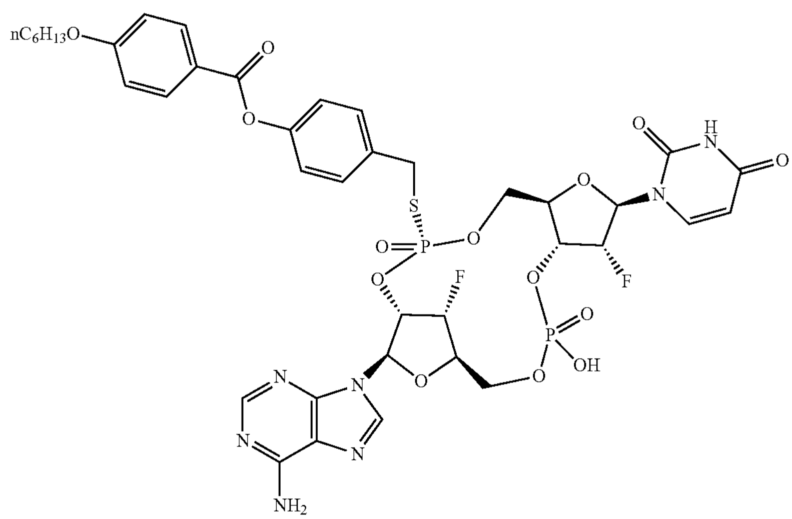 |
| 156 | 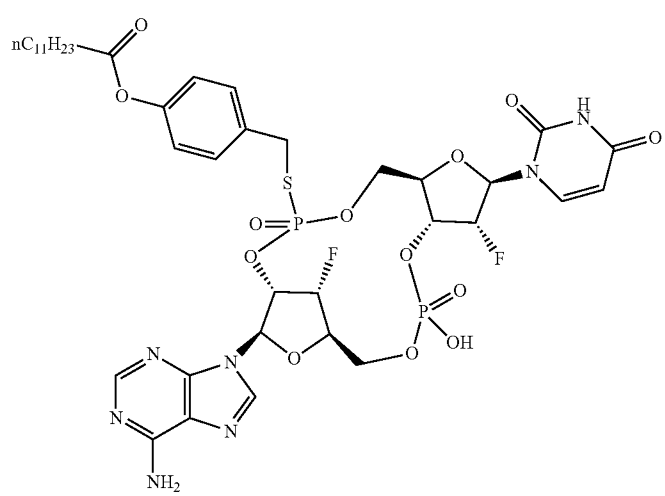 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 157 | 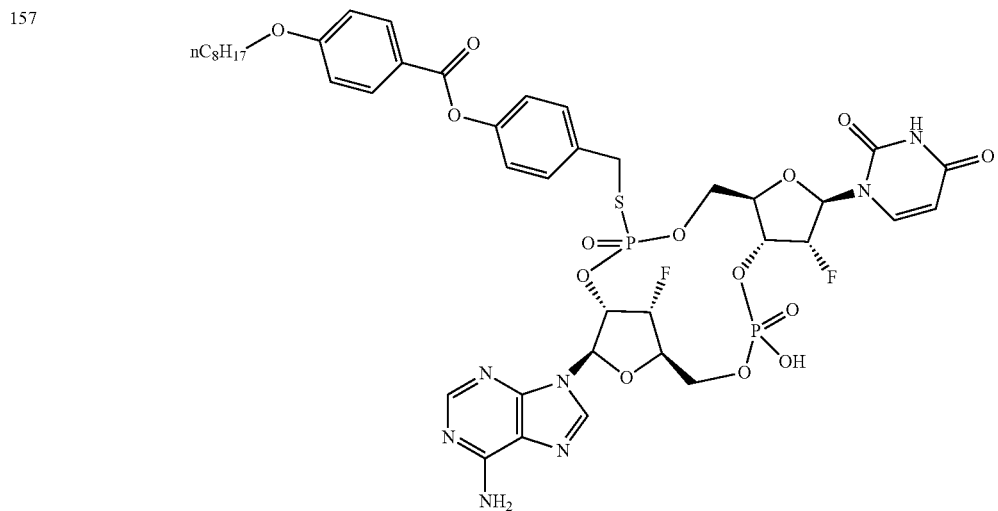 |
| 158 | 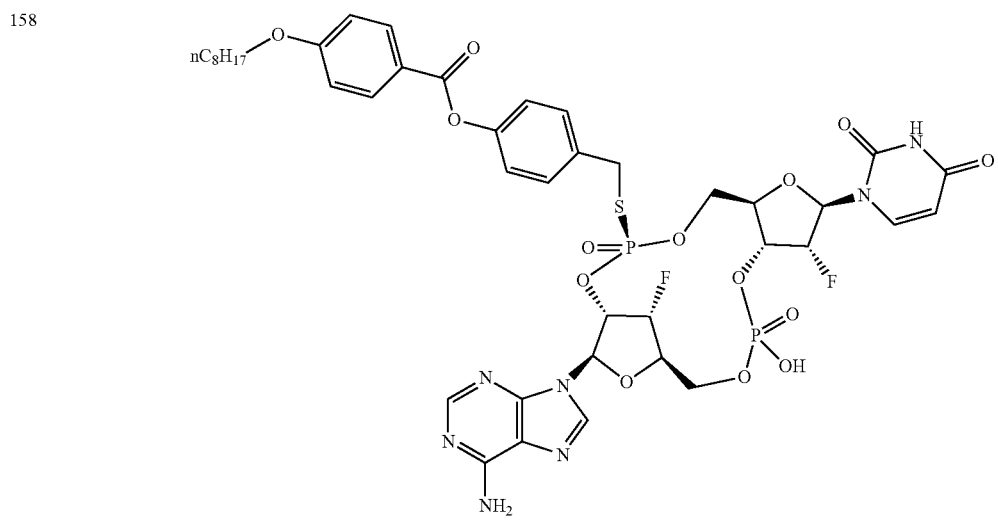 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 159 | 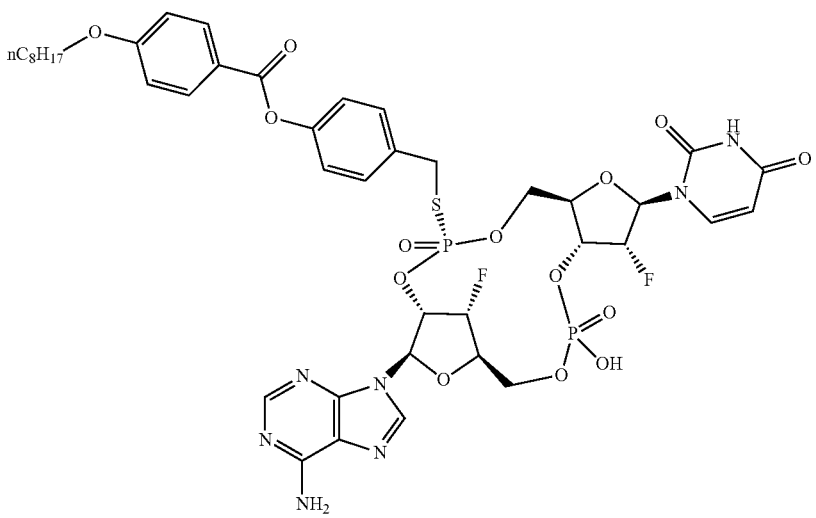 |
| 160 | 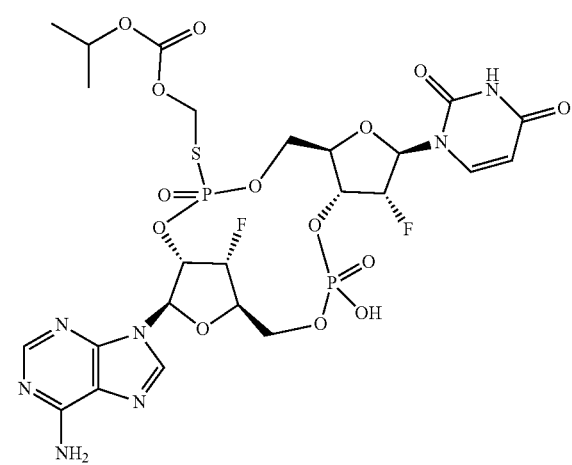 [SMILES: CC(C)OC(=O)OCSP1(=O)OC[C@H]2O[C@@H](n3ccc(=O)[nH]c3=O)[C@H](F)[C@@H]2OP(=O)(O)OC[C@H]2O[C@@H](n3cnc4c(N)ncnc43)[C@H](O1)[C@@H]2F] |
| 161 | 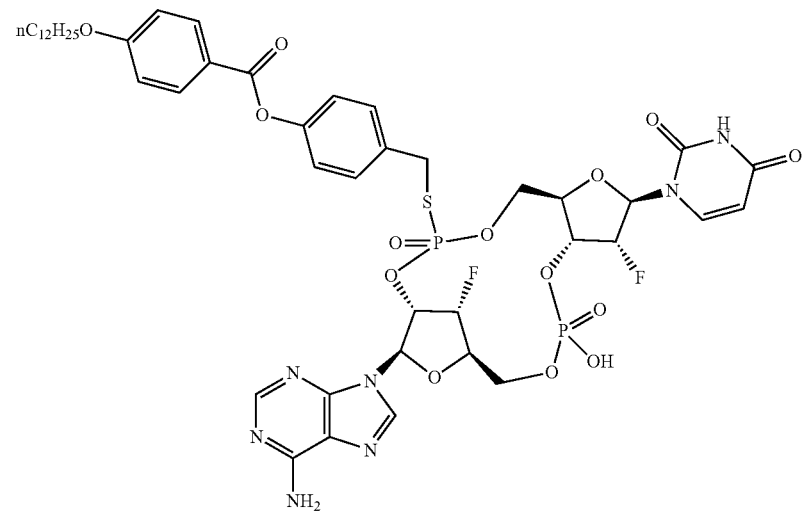 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 162 | 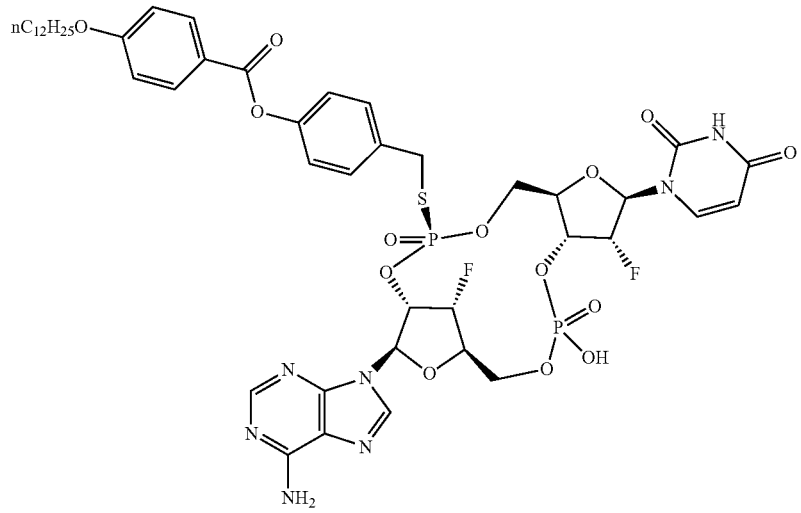 |
| 163 | 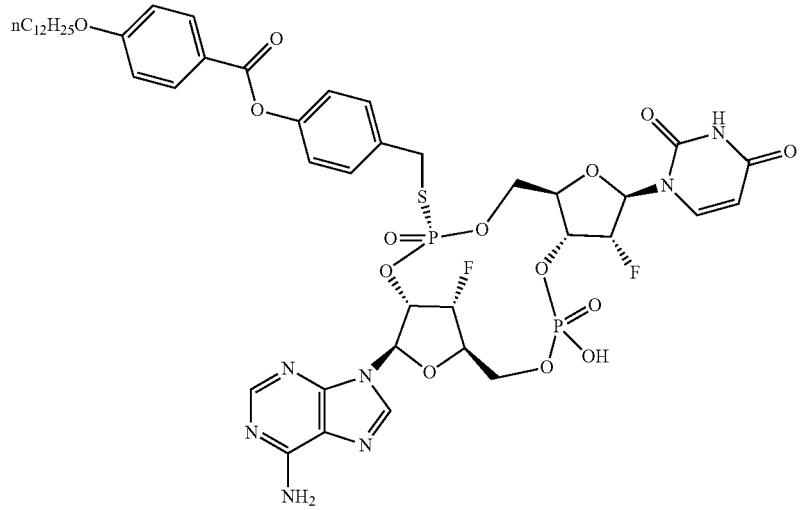 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 164 | 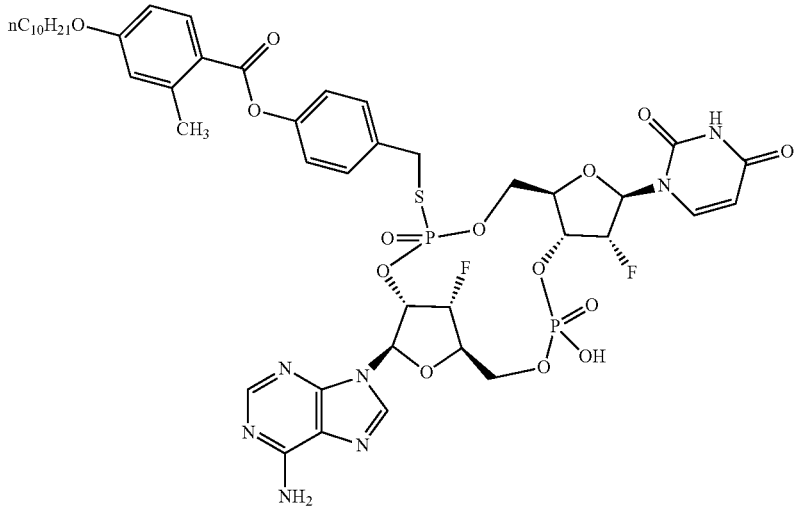 |
| 165 | 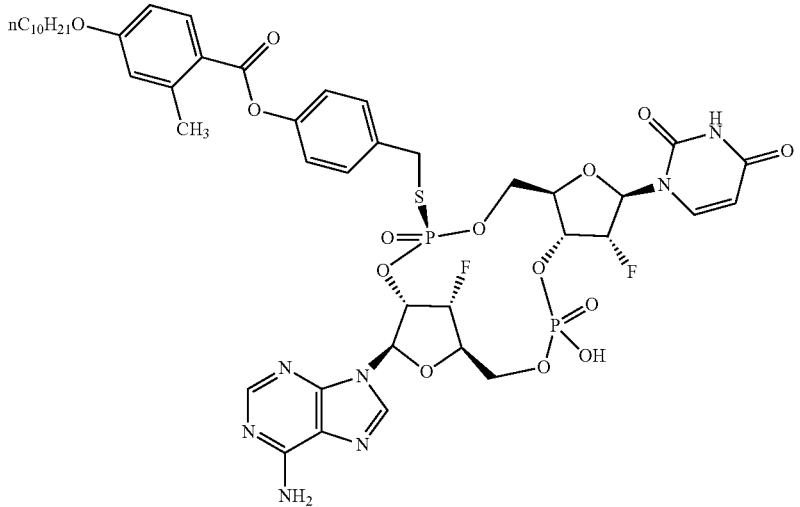 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 166 | 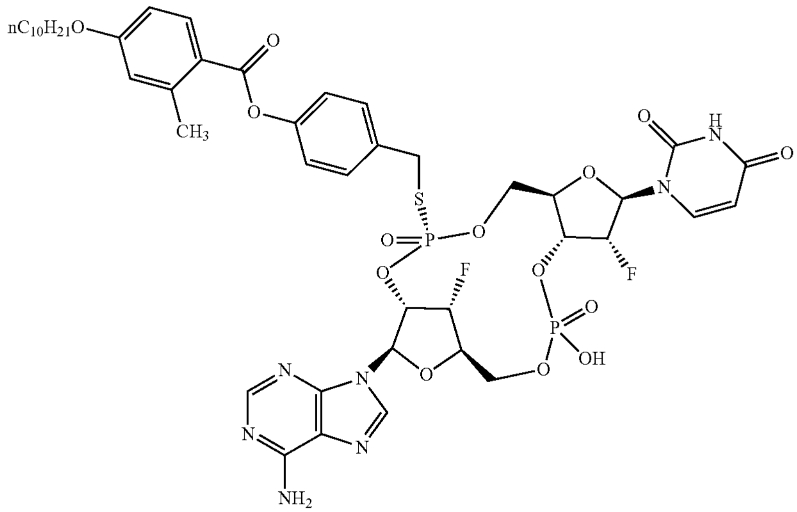 |
| 167 | 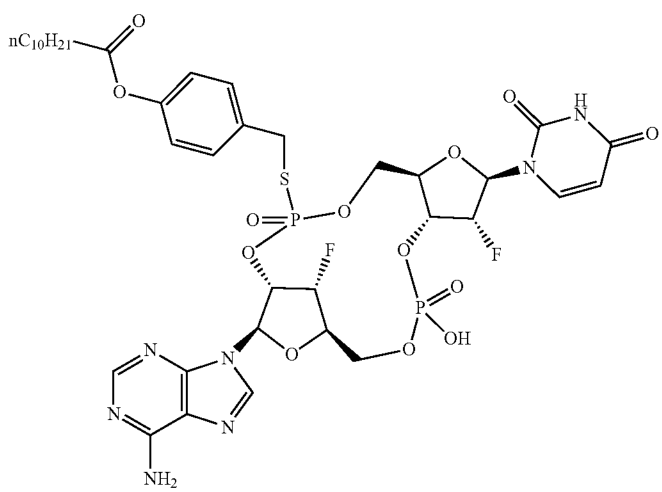 |
| 168 | 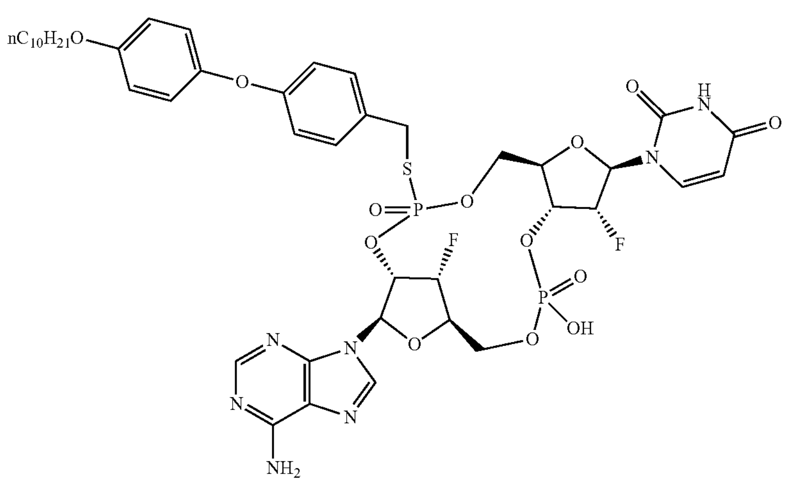 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 169 | 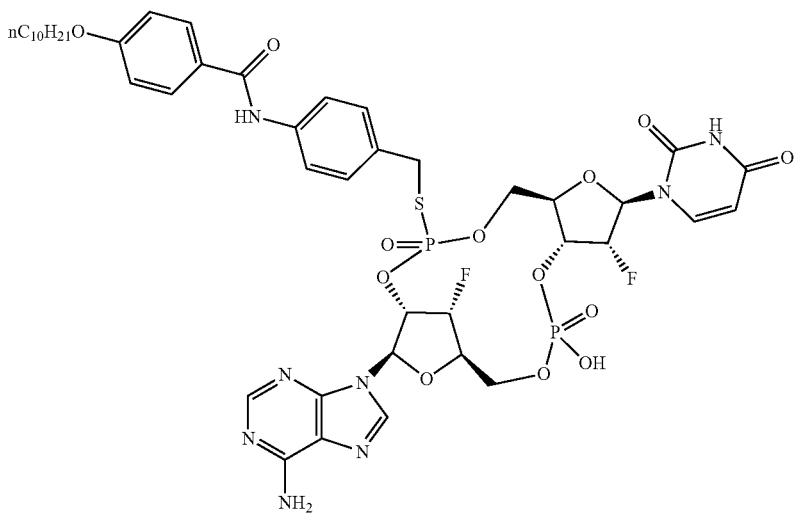 |
| 170 | 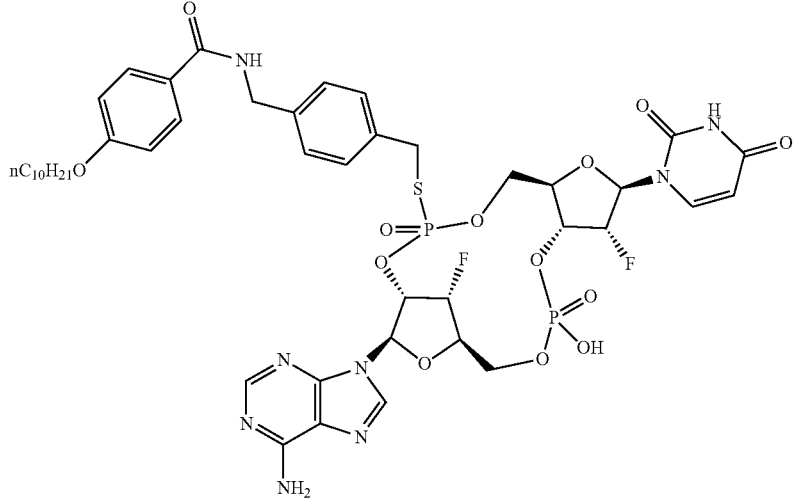 |
| 171 | 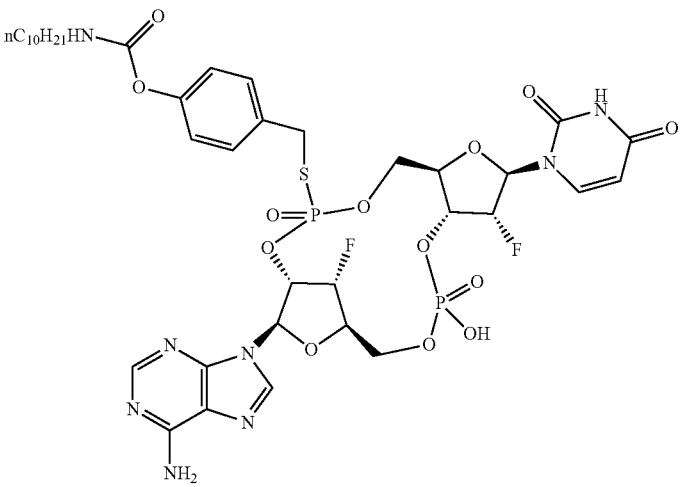 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 172 | 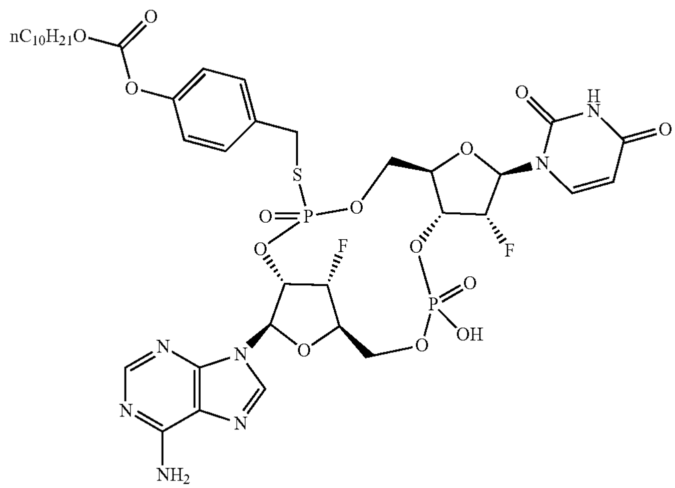 |
| 173 | 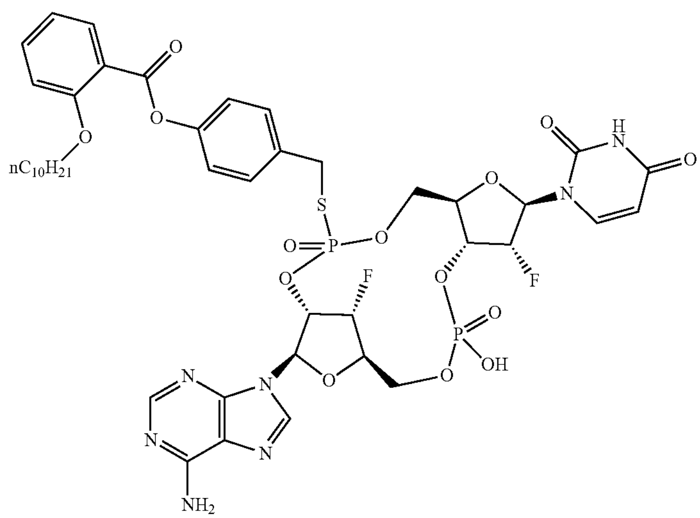 |
| 174 | 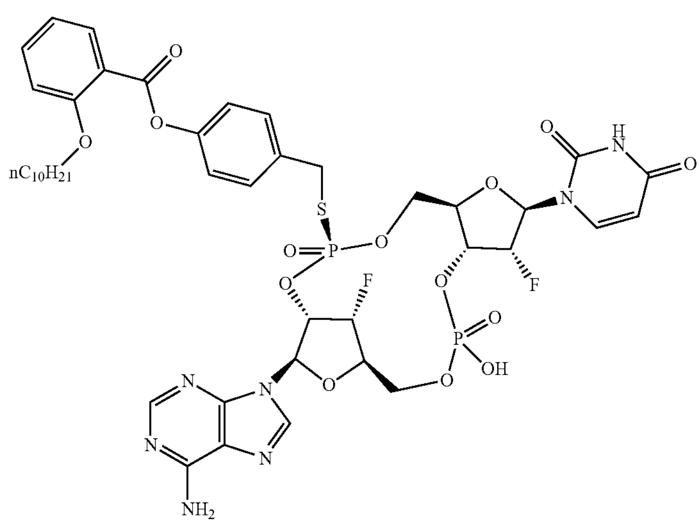 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 175 | 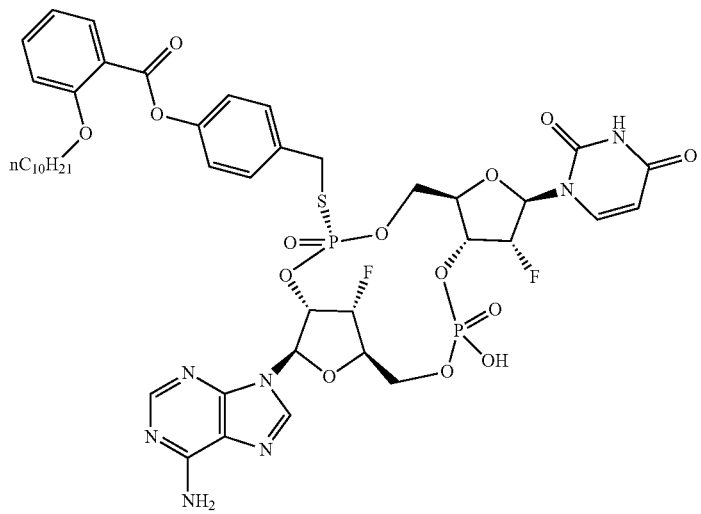 |
| 176 | 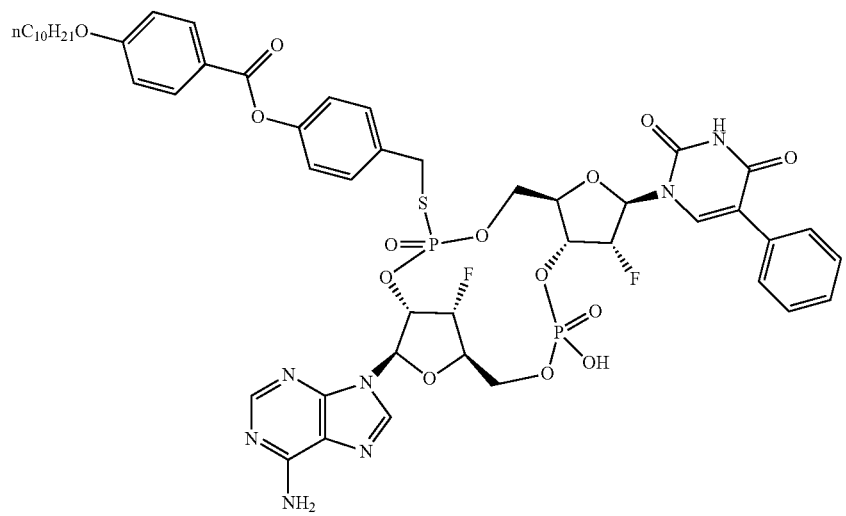 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 177 | 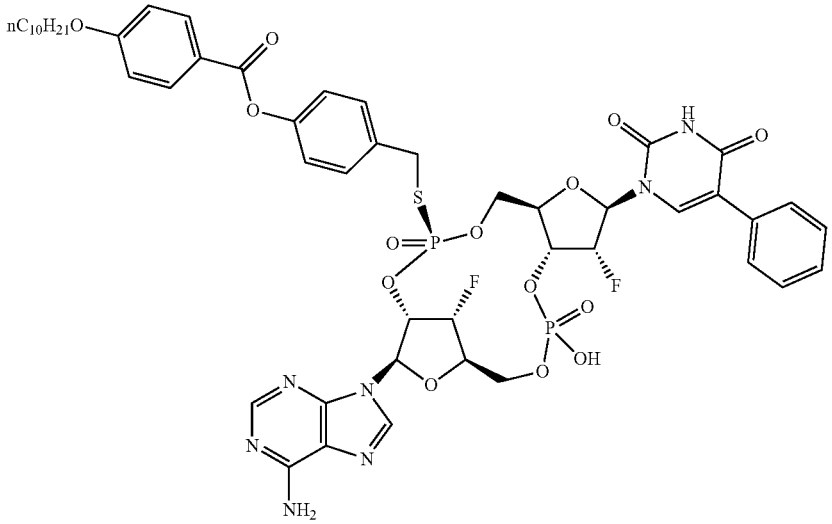 |
| 178 | 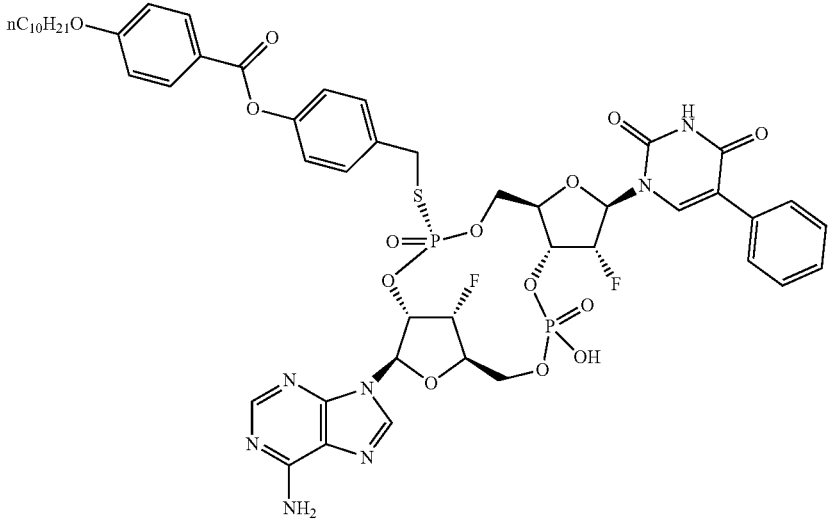 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 179 | *(structure)* |
| 180 | *(structure)* |
| 181 | *(structure)* |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
| --- | --- |
| 182 | 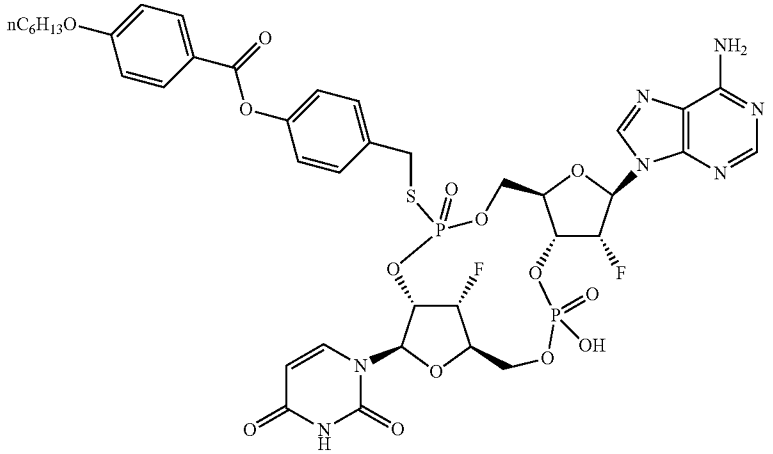 |
| 183 | 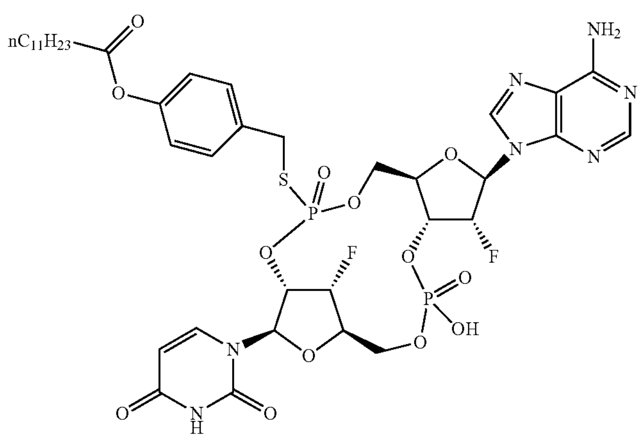 |
| 184 | 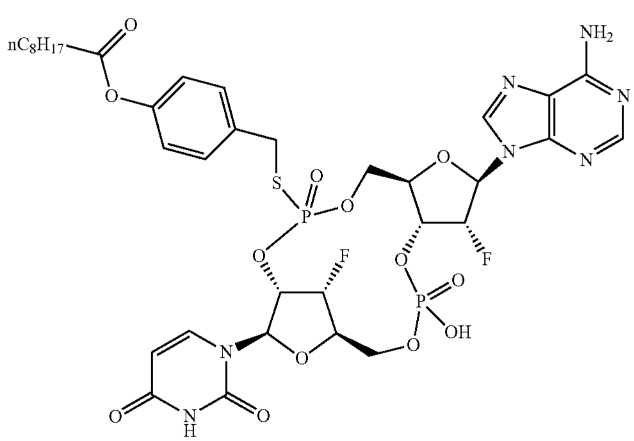 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 185 | 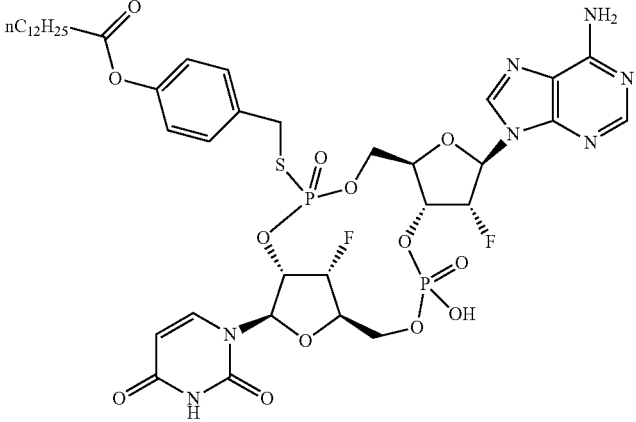 |
| 186 | 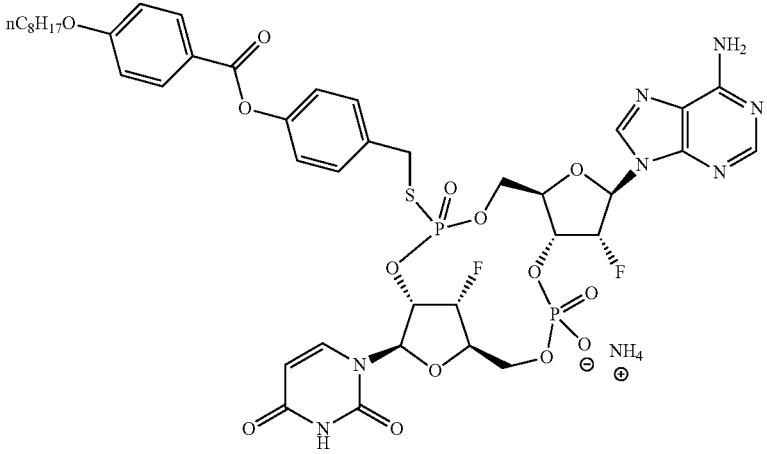 |
| 187 | 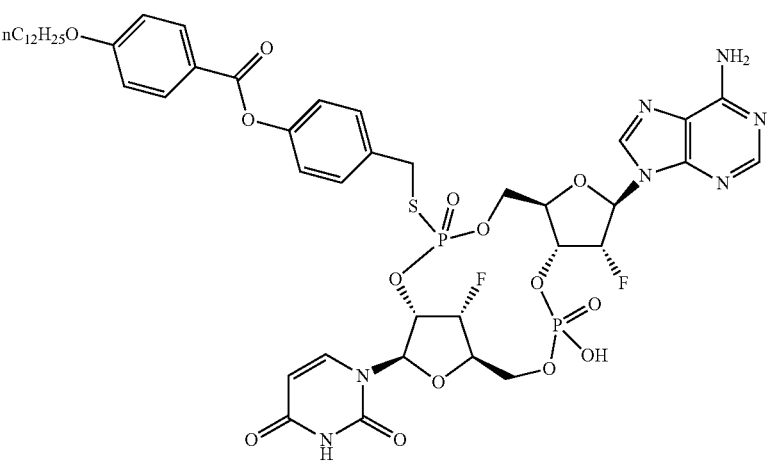 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 188 | 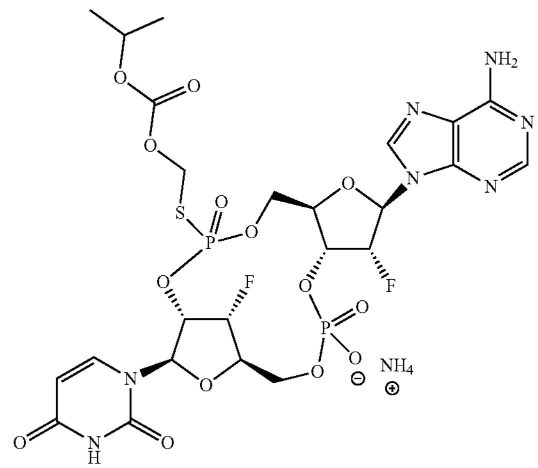 [SMILES: CC(C)OC(=O)OCSP1(=O)OC[C@H]2O[C@@H](n3cnc4c(N)ncnc43)[C@H](F)[C@@H]2OP(=O)([O-])OC[C@H]2O[C@@H](n3ccc(=O)[nH]c3=O)[C@H](O1)[C@@H]2F ; [NH4+]] |
| 189 | 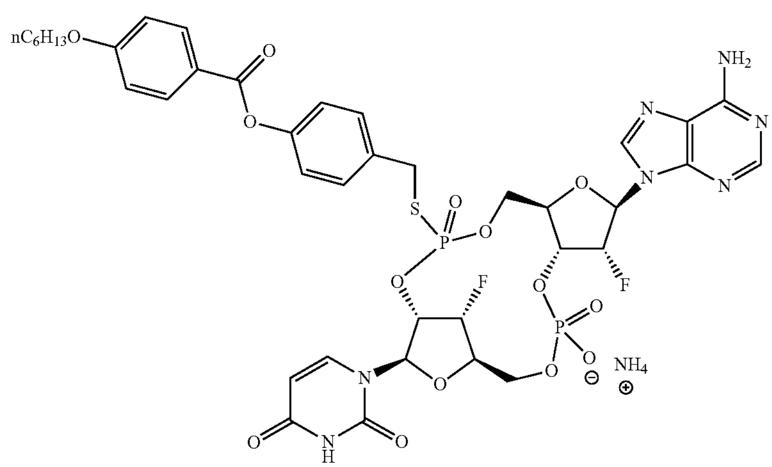 |
| 190 | 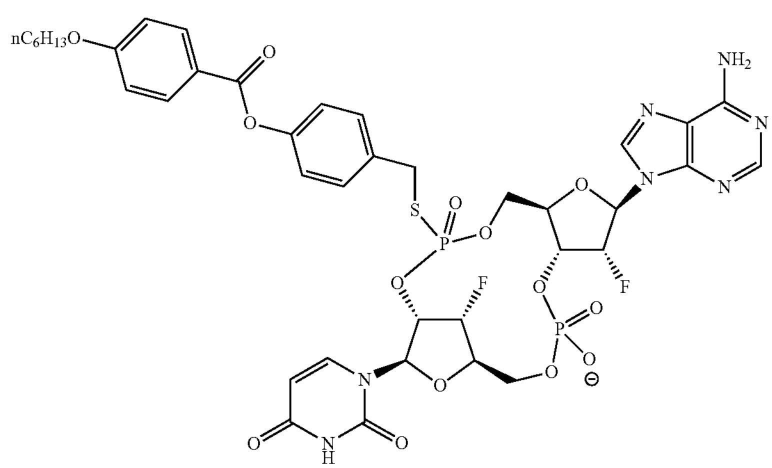 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 191 | 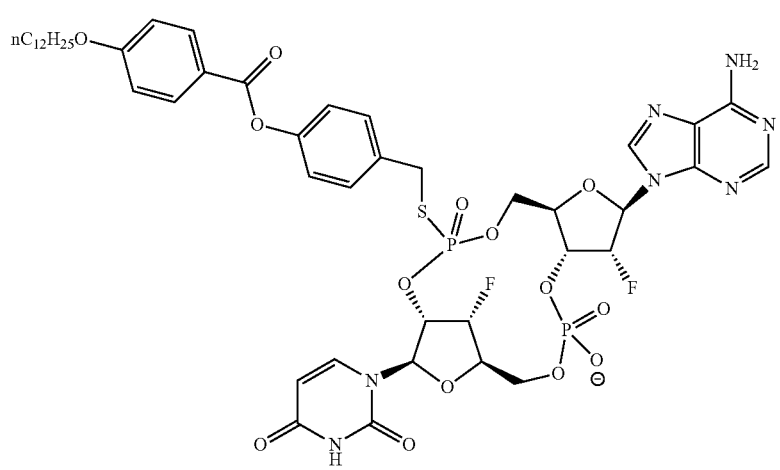 |
| 192 | 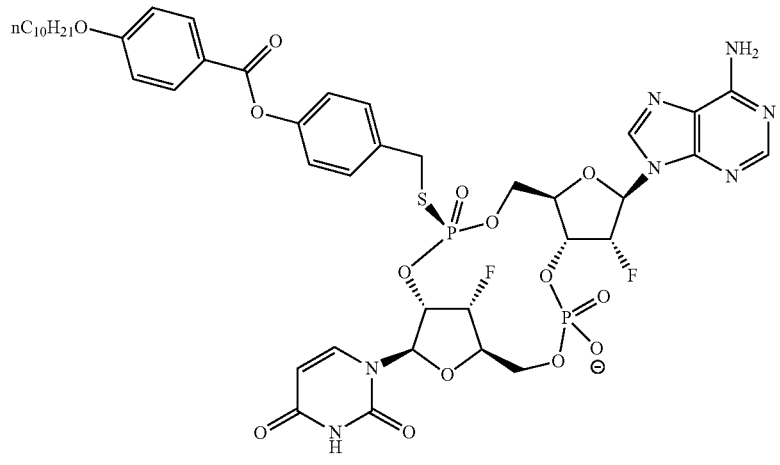 |
| 193 | 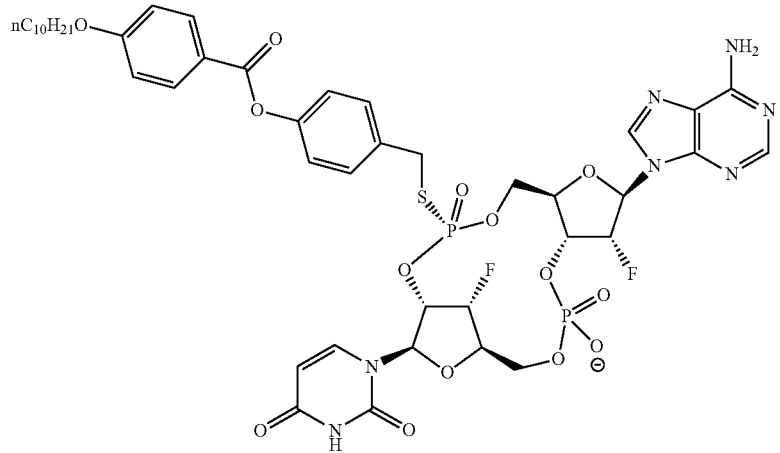 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 194 | 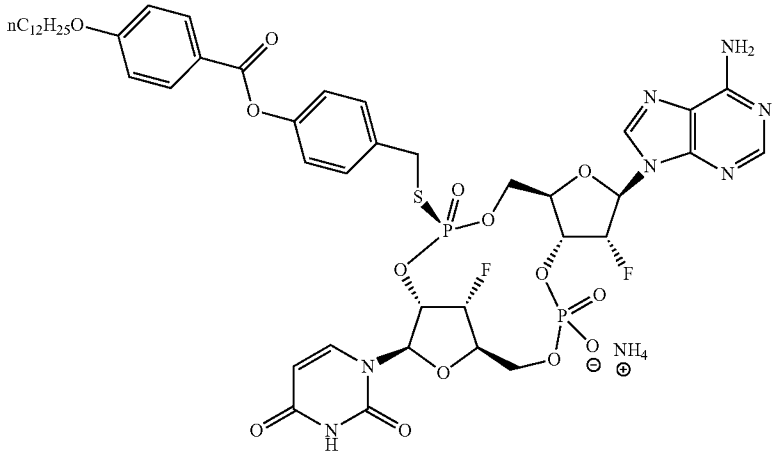 |
| 195 | 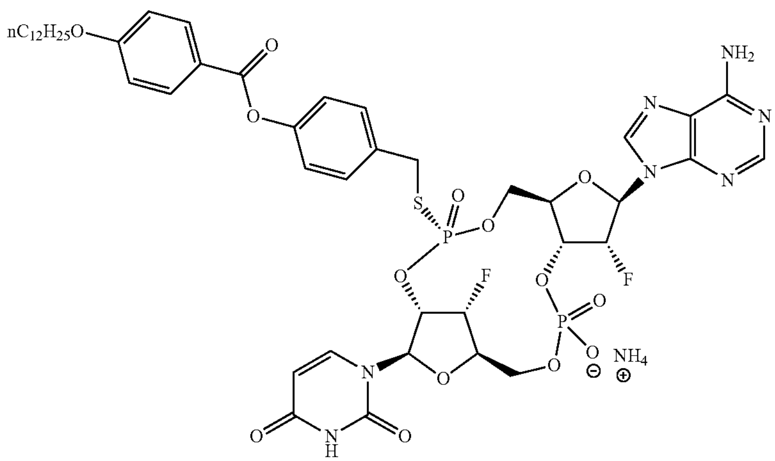 |
| 196 | 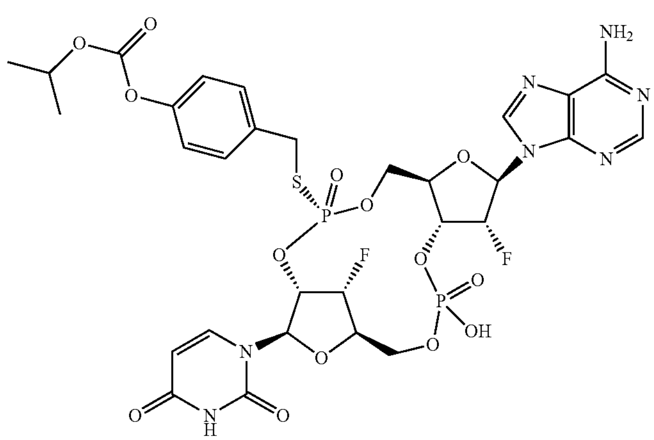 [SMILES: CC(C)OC(=O)Oc1ccc(CS[P@]2(=O)OC[C@H]3O[C@@H](n4cnc5c(N)ncnc54)[C@H](F)[C@@H]3OP(=O)(O)OC[C@H]3O[C@@H](n4ccc(=O)[nH]c4=O)[C@H](O2)[C@@H]3F)cc1] |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 197 | 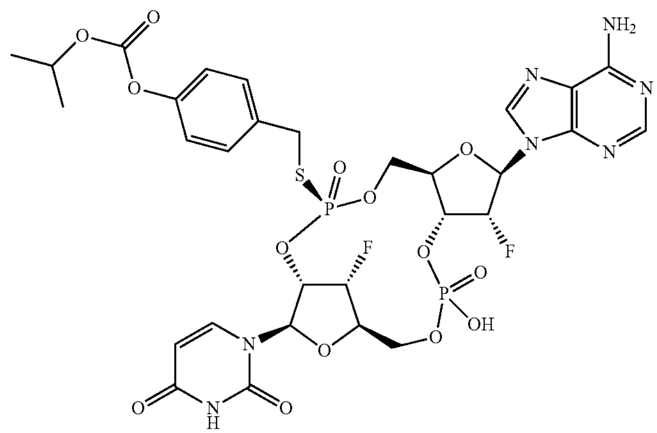 [SMILES: CC(C)OC(=O)Oc1ccc(CS[P@@]2(=O)OC[C@H]3O[C@@H](n4cnc5c(N)ncnc54)[C@H](F)[C@@H]3OP(=O)(O)OC[C@H]3O[C@@H](n4ccc(=O)[nH]c4=O)[C@H](O2)[C@@H]3F)cc1] |
| 198 | 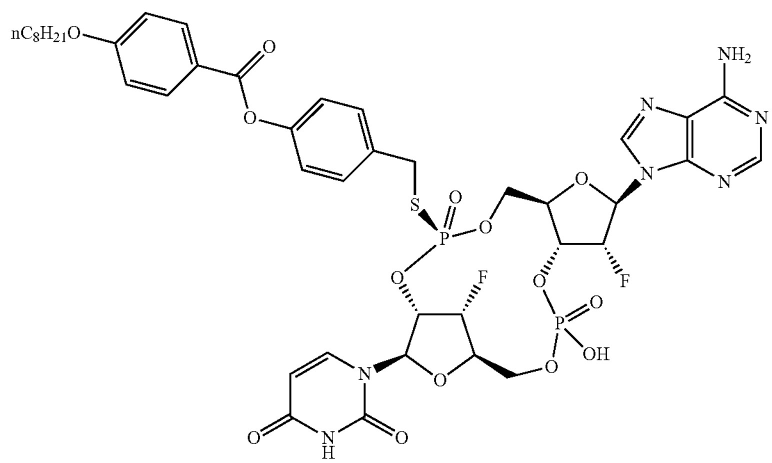 |
| 199 | 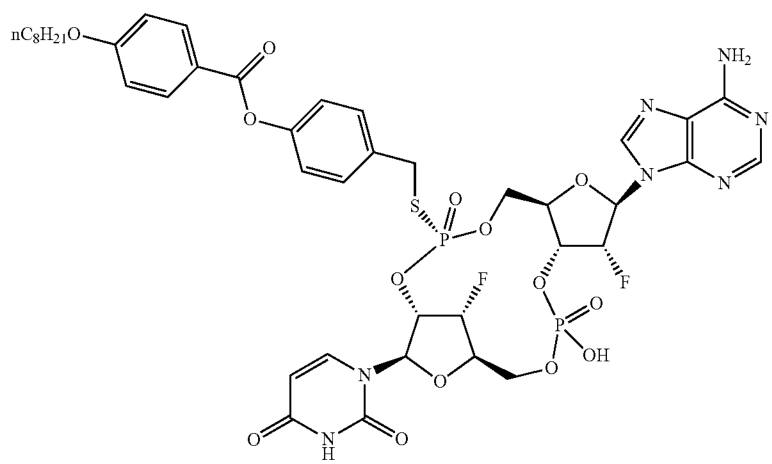 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 200 | 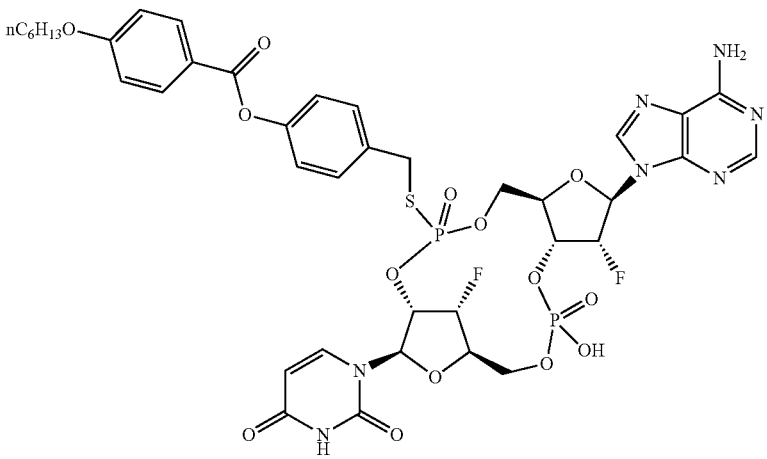 |
| 201 | 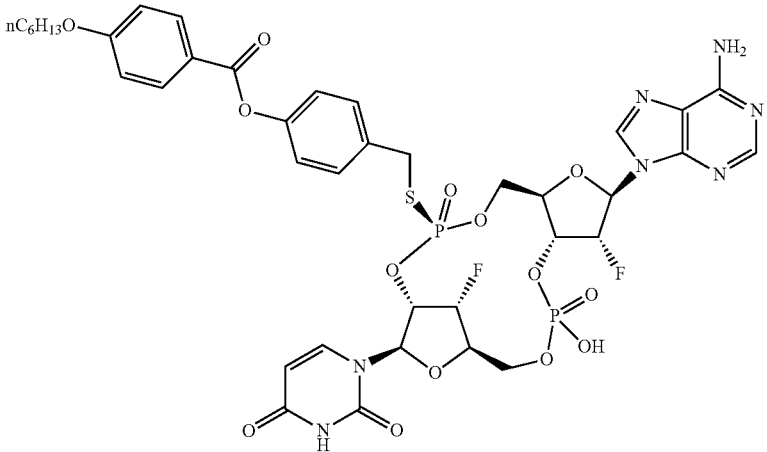 |
| 202 | 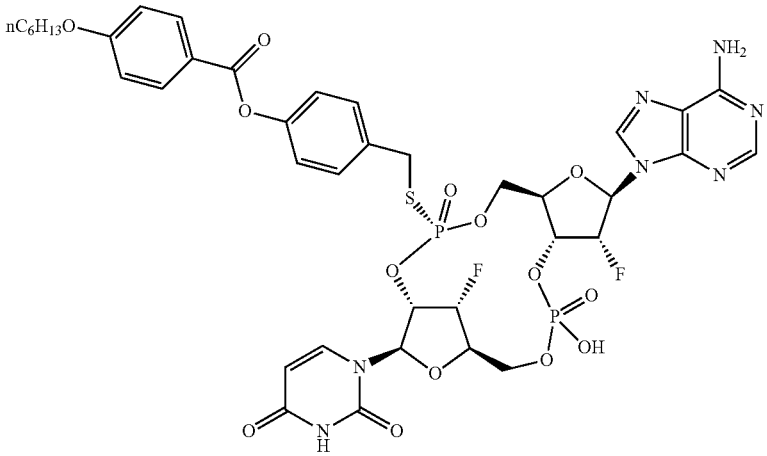 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 203 | 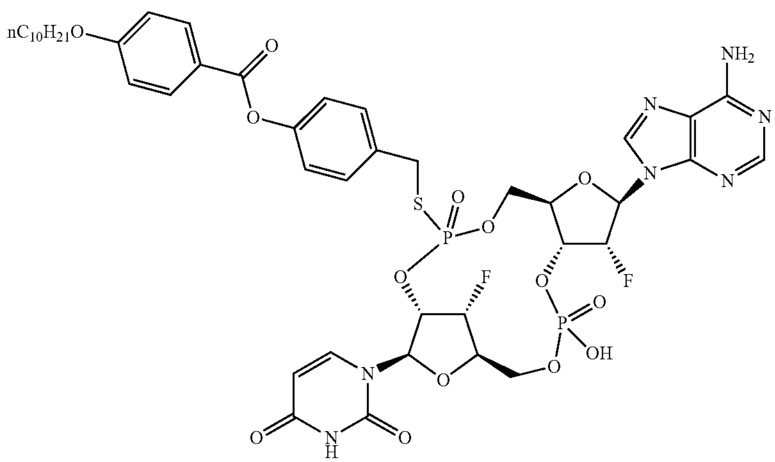 |
| 204 | 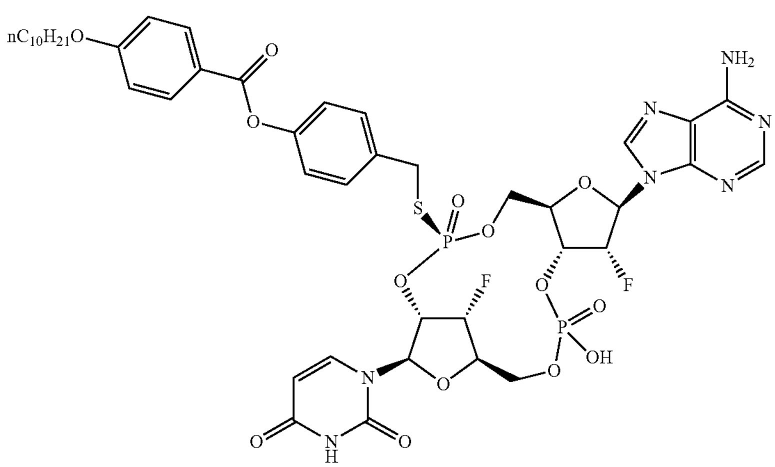 |
| 205 | 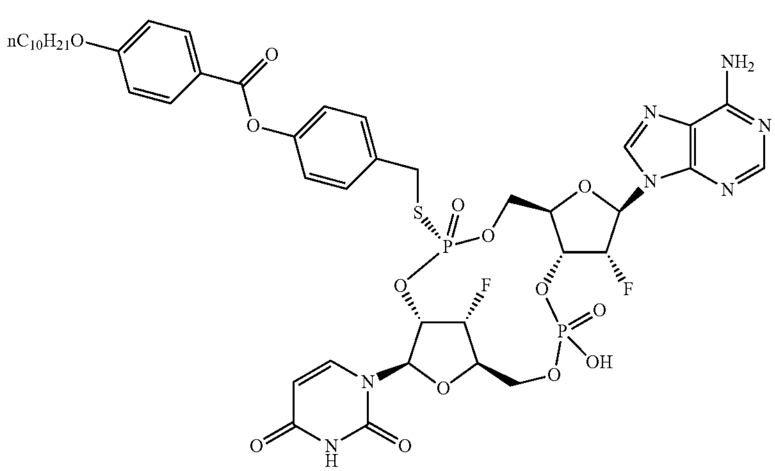 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 206 | 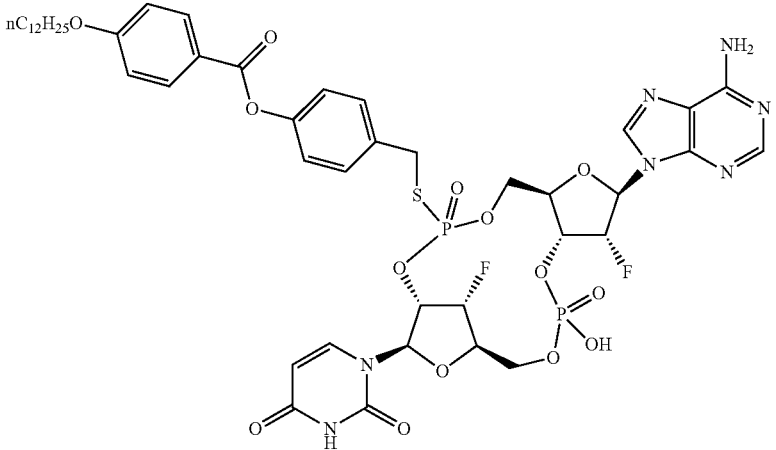 |
| 207 | 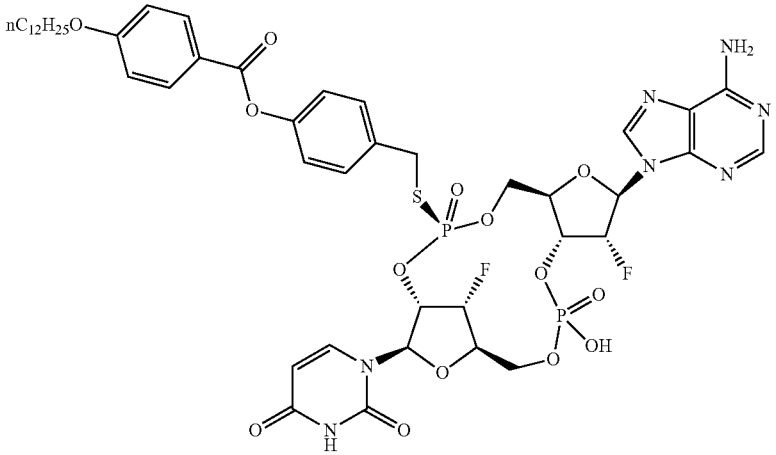 |
| 208 | 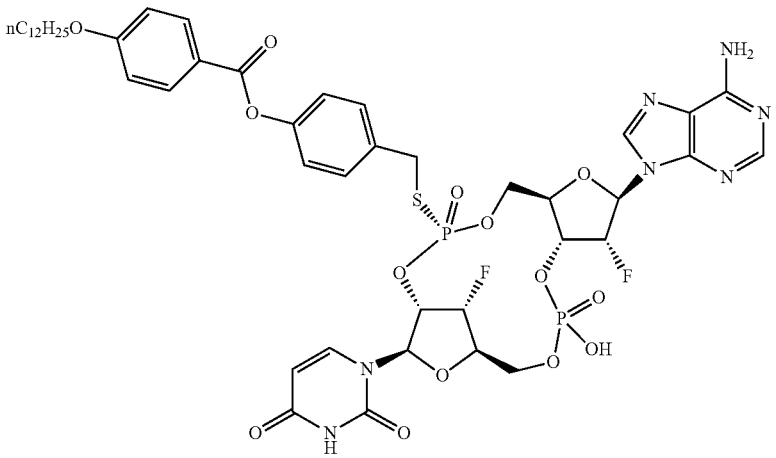 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 209 | 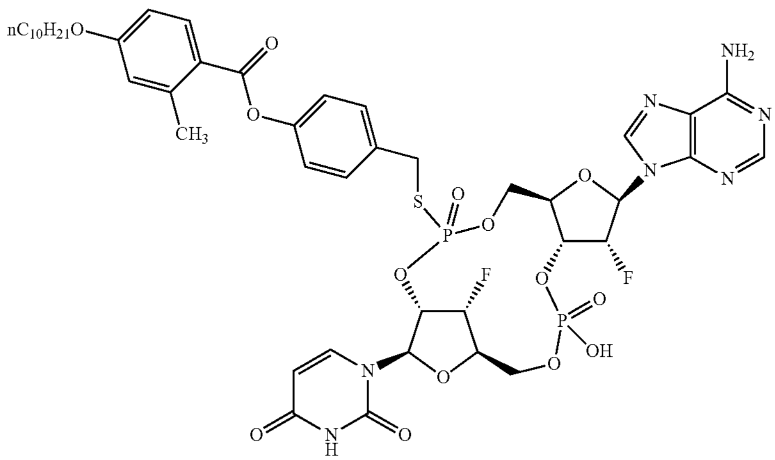 |
| 210 | 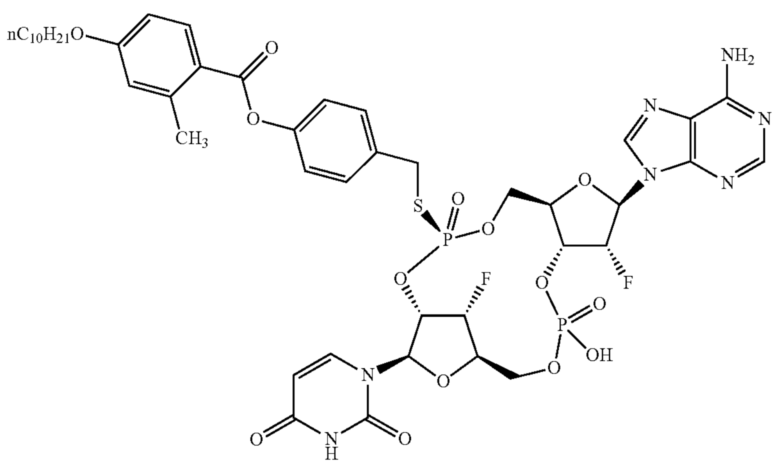 |
| 211 | 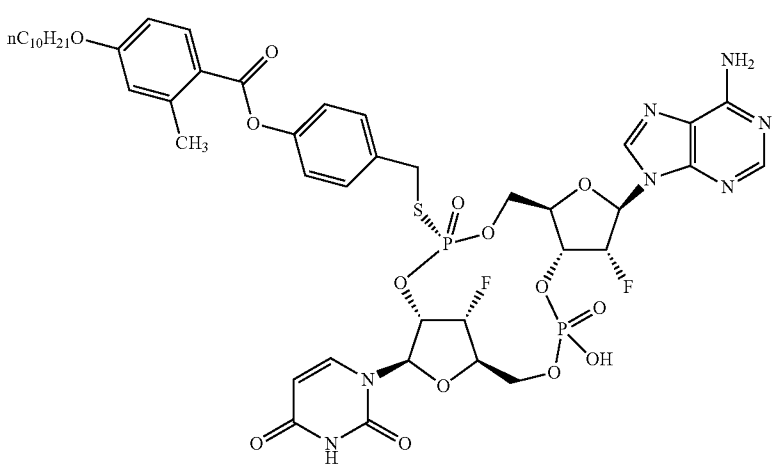 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 212 | 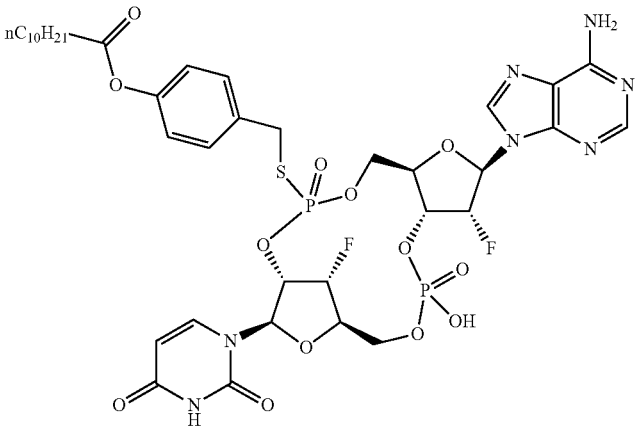 |
| 213 | 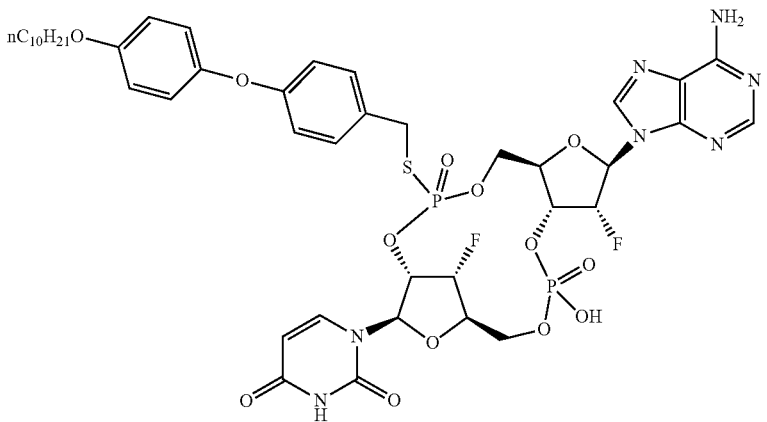 |
| 214 | 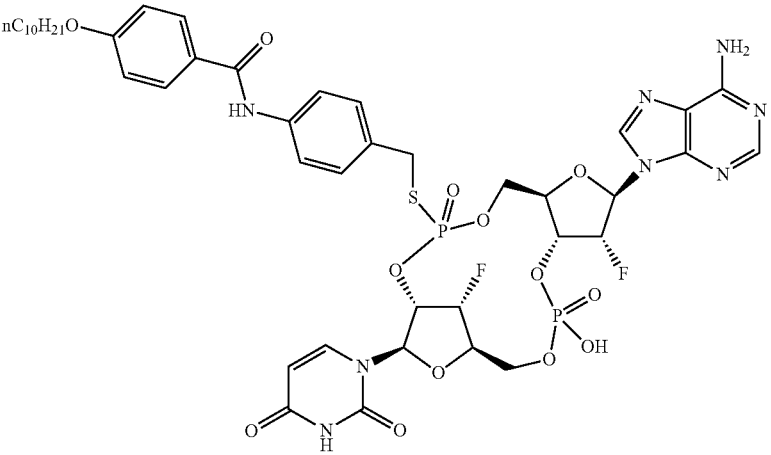 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 215 | 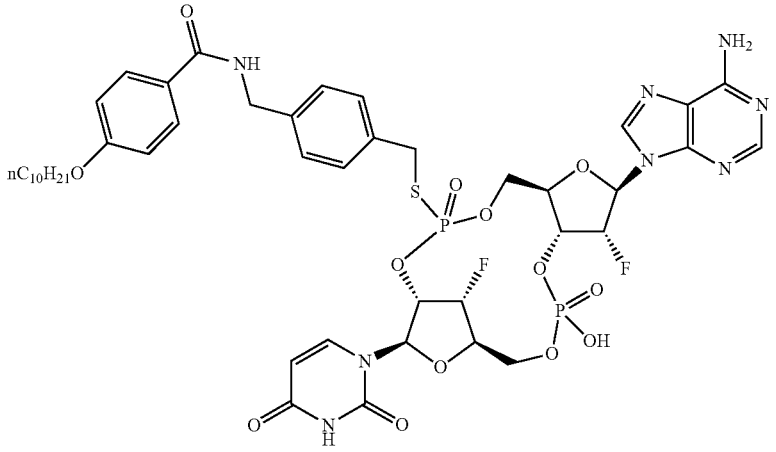 |
| 216 | 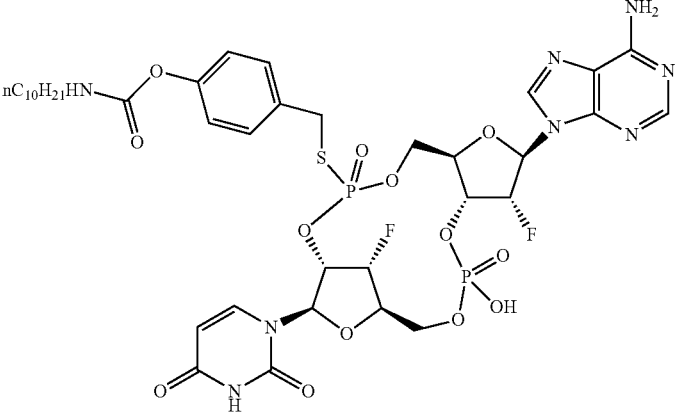 |
| 217 | 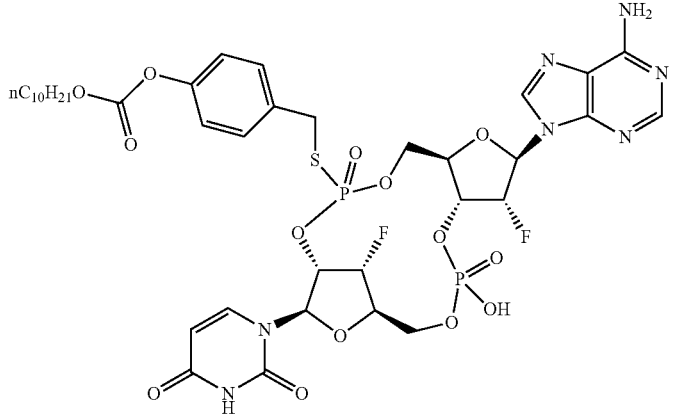 |

(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 218 | 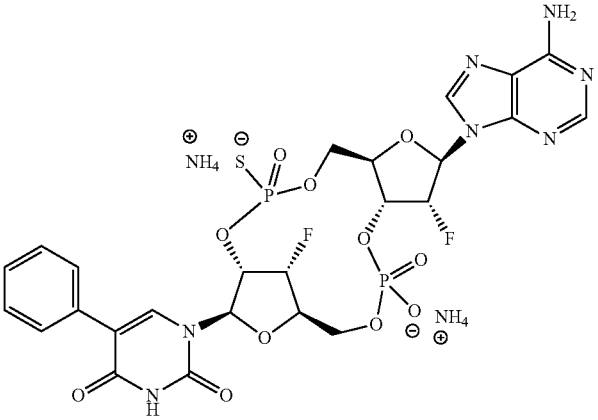 [SMILES: Nc1ncnc2c1ncn2[C@@H]1O[C@@H]2COP(=O)([S-])O[C@@H]3[C@H](F)[C@@H](COP(=O)([O-])O[C@H]2[C@H]1F)O[C@H]3n1cc(-c2ccccc2)c(=O)[nH]c1=O ; [NH4+] ; [NH4+]] |
| 219 | 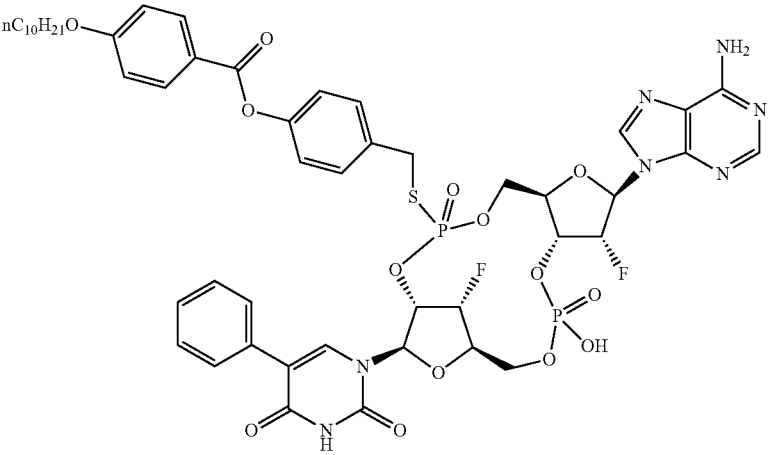 |
| 220 | 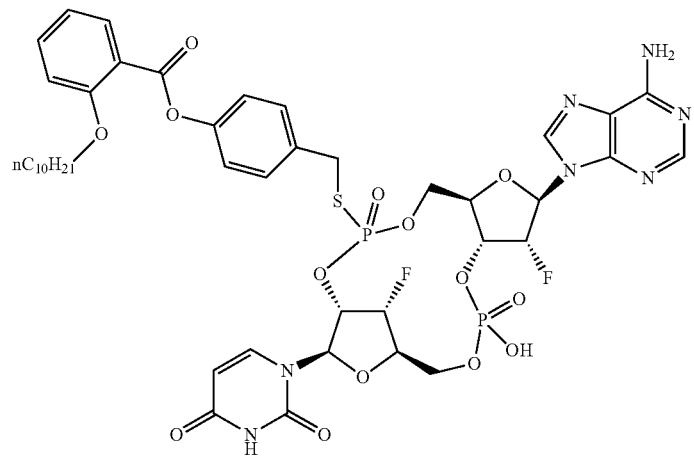 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 221 | 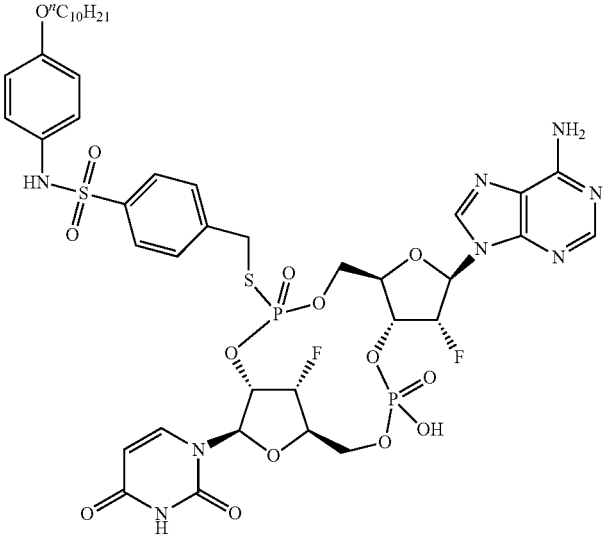 |
| 222 | 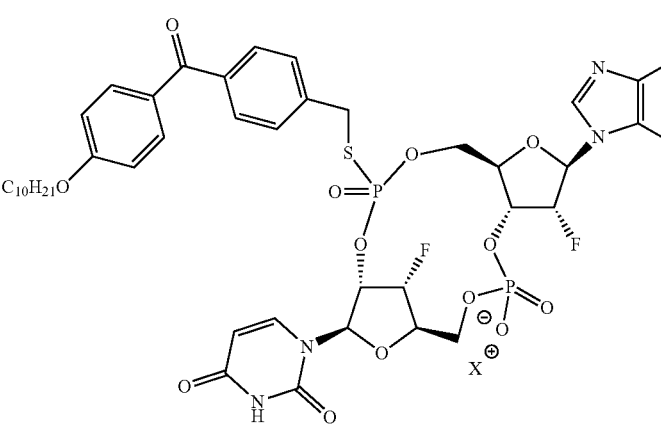 |
| 223 | 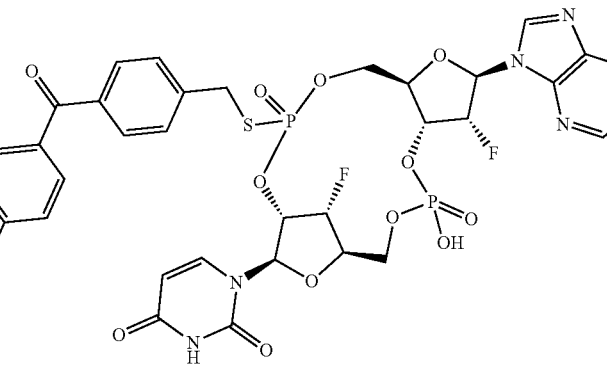 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 224 | *(structure)* |
| 225 | *(structure)* |
| 226 | *(structure)* |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 227 | 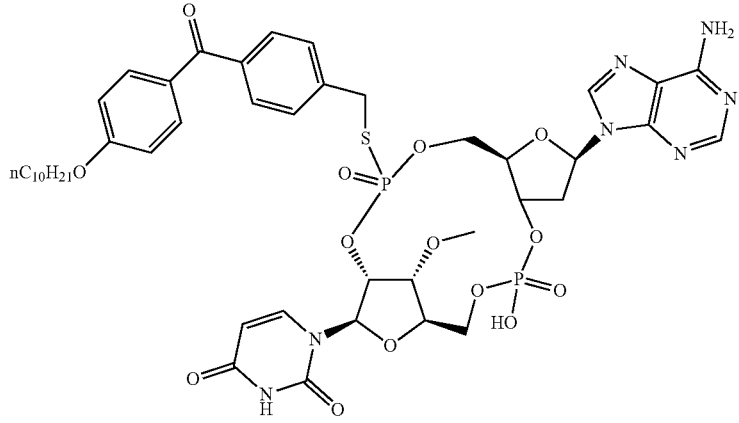 |
| 228 | 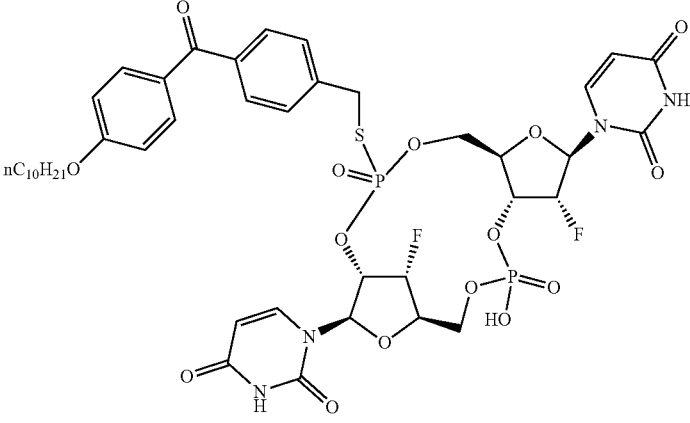 |
| 229 | 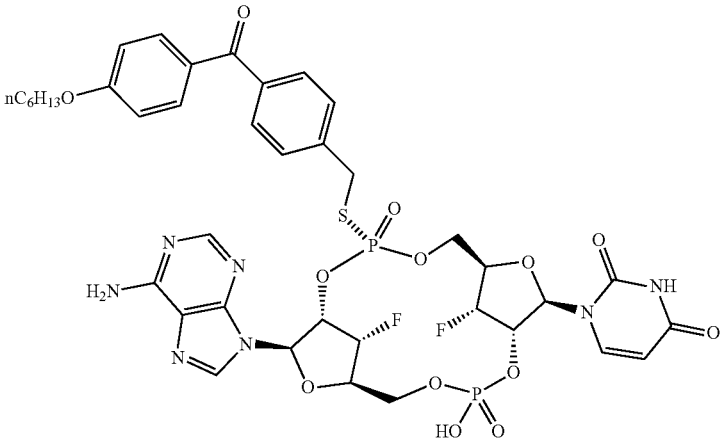 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 230 | *(structure shown)* |
| 231 | *(structure shown)* |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 232 | 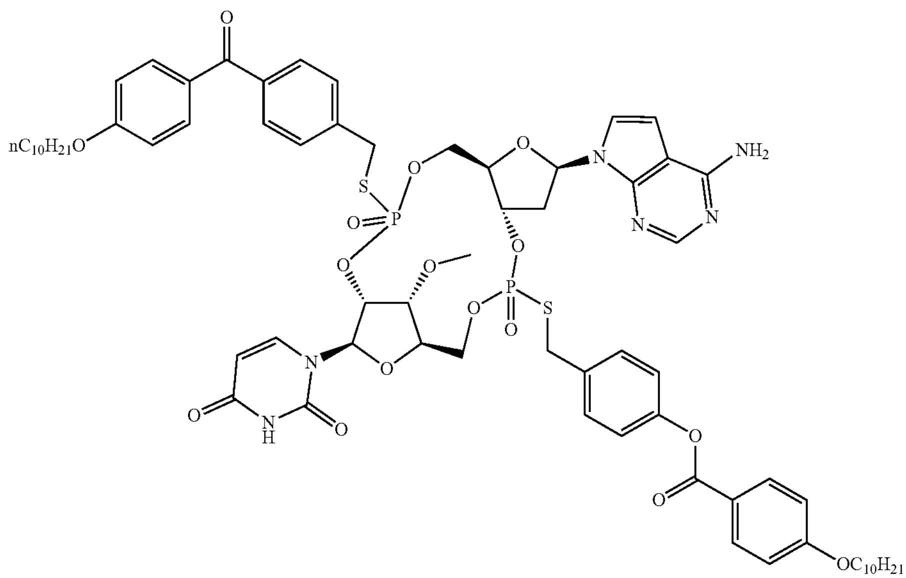 |
| 233 | 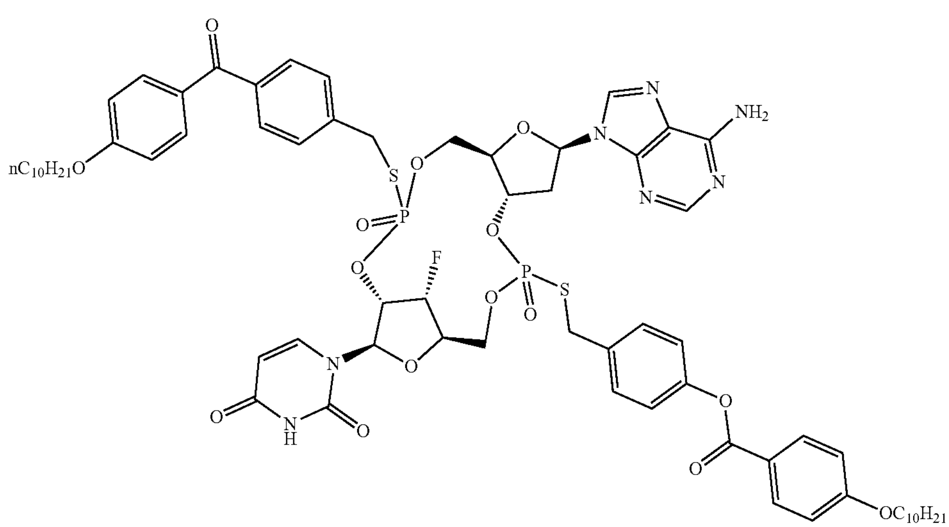 |

US 11,638,716 B2
195                                                                                                 196
TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 234 | 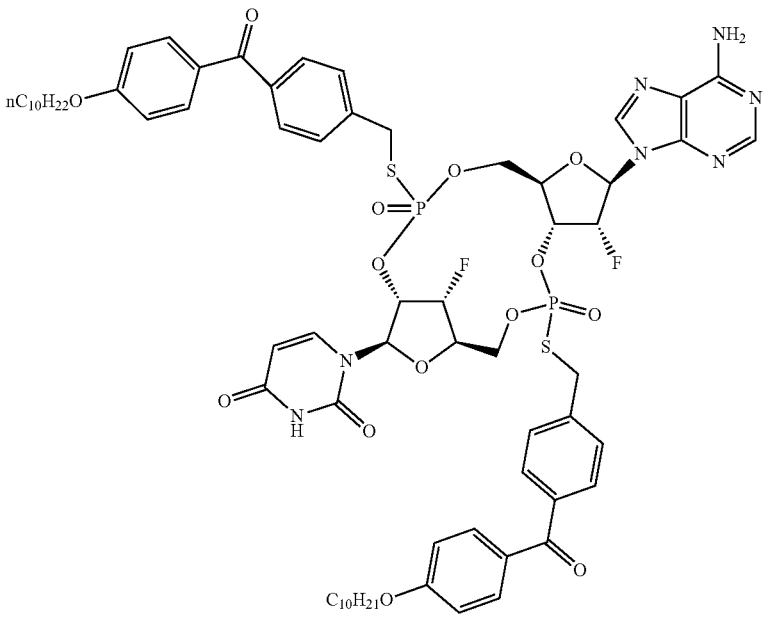 |
| 235 | 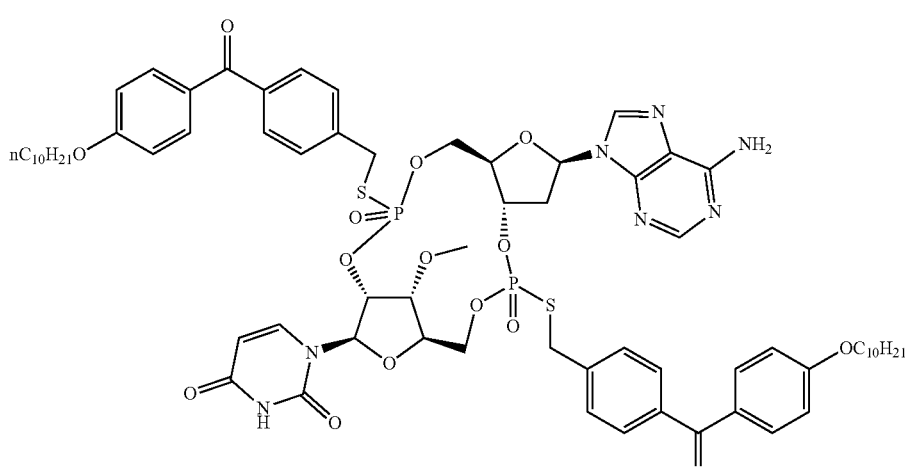 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 236 | 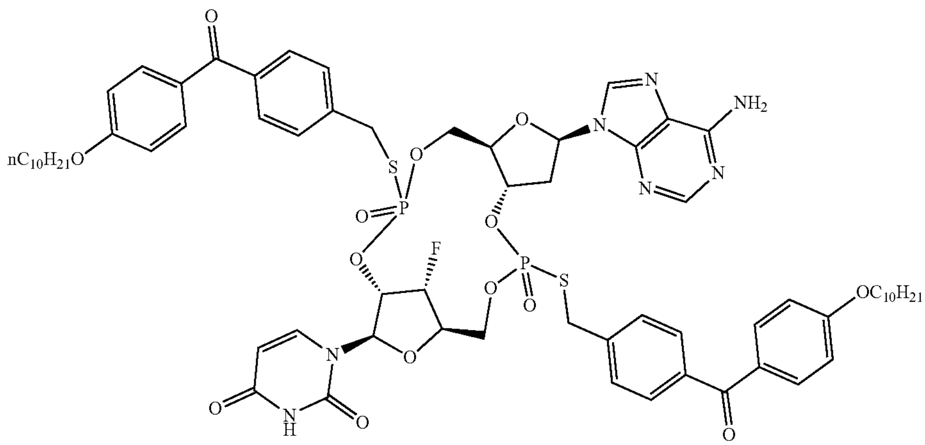 |
| 237 | 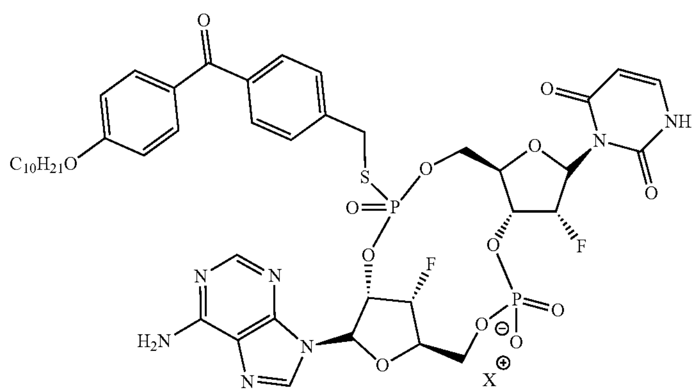 |
| 238 | 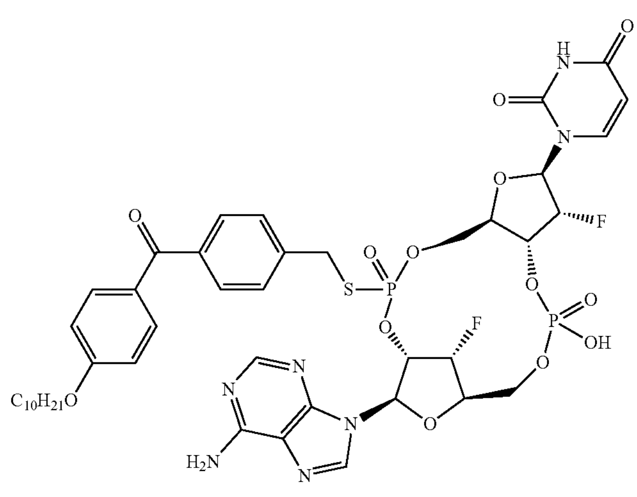 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 239 | 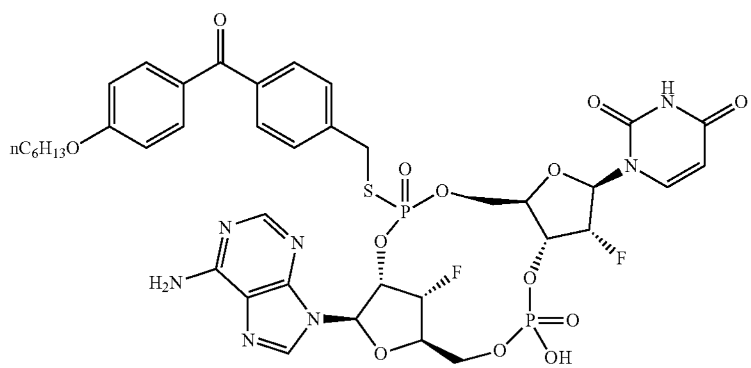 |
| 240 | 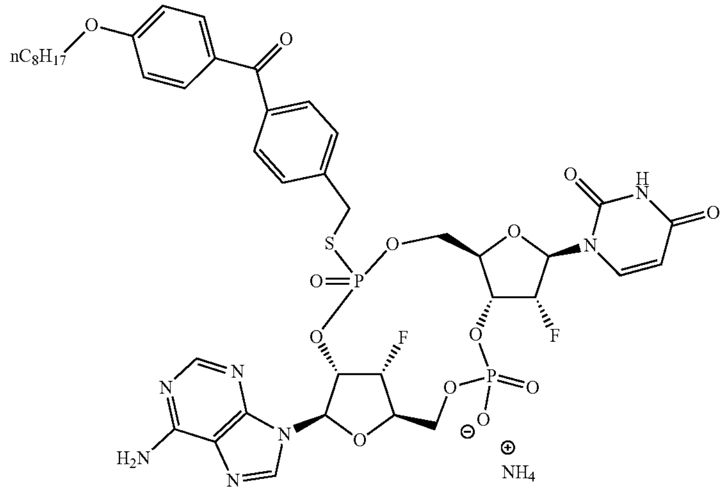 |
| 241 | 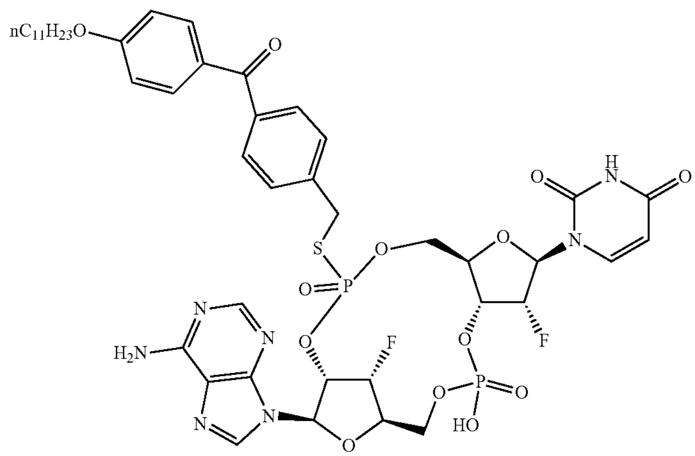 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 242 | *(chemical structure)* |
| 243 | *(chemical structure)* |
| 244 | *(chemical structure)* |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 245 | 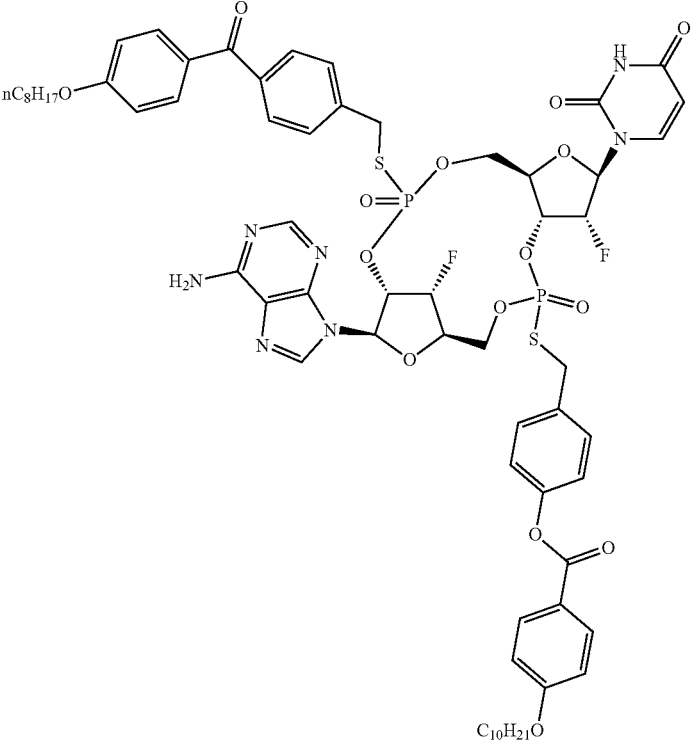 |
| 246 | 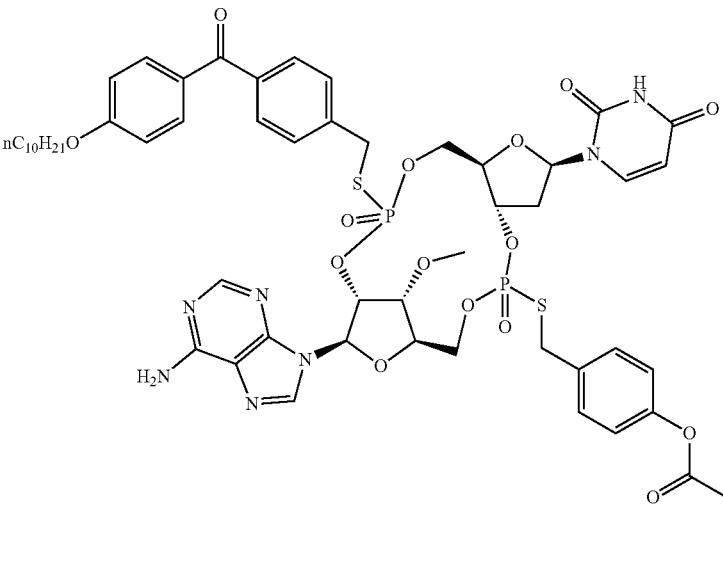 |

TABLE 1-continued
(Unless otherwise indicated in the table, a formula $C_nH_{(2n+1)}$ refers to an n-alkyl group. For example, $C_{10}H_{21}$ refers to n-decyl unless otherwise indicated.).
| Compound No. | Structure |
|---|---|
| 247 | 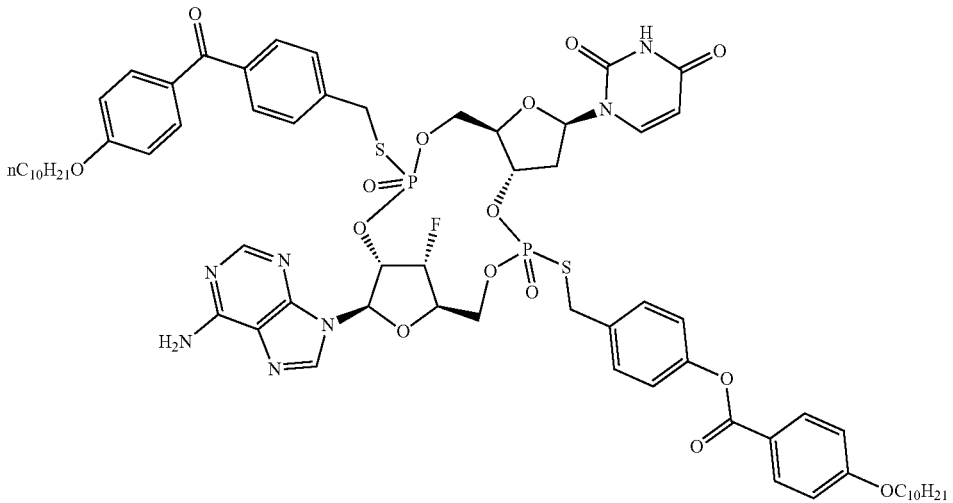 |
| 248 | 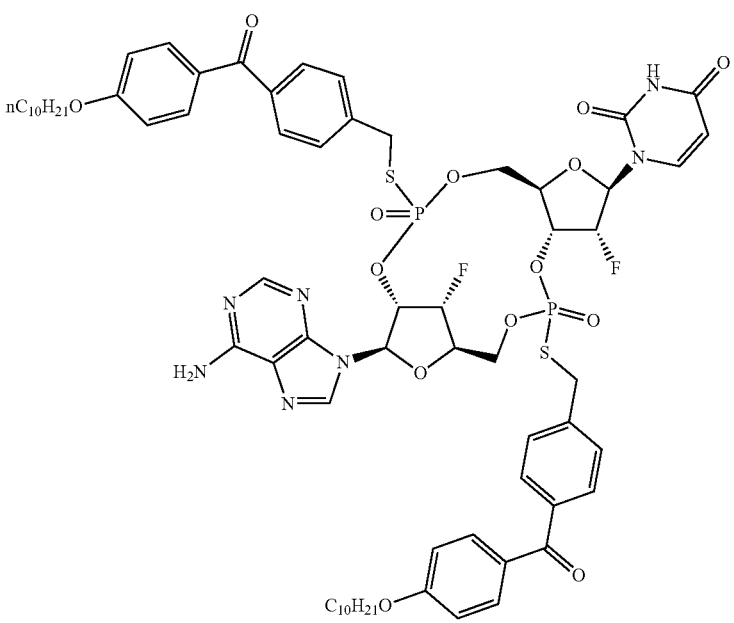 |

TABLE 1-continued (Unless otherwise indicated in the table, a formula $C_nH_{(2n+1)}$ refers to an n-alkyl group. For example, $C_{10}H_{21}$ refers to n-decyl unless otherwise indicated.).

| Compound No. | Structure |
|---|---|
| 249 | 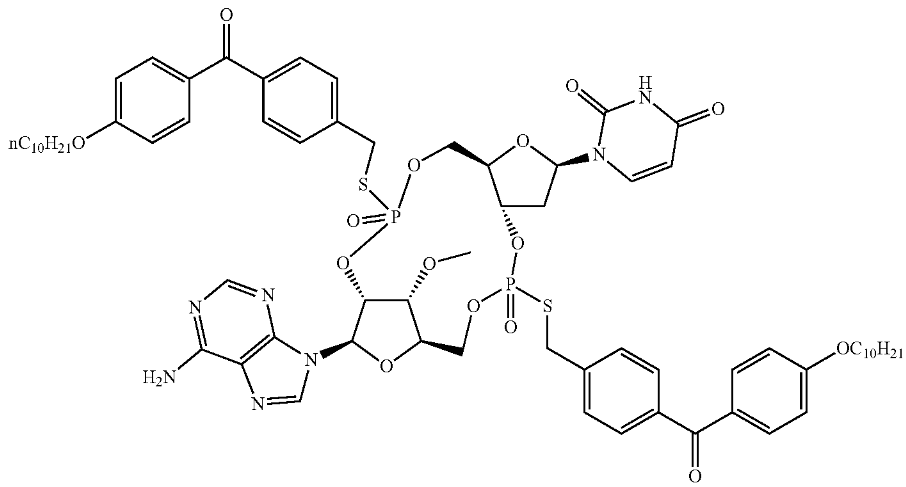 |
| 250 | 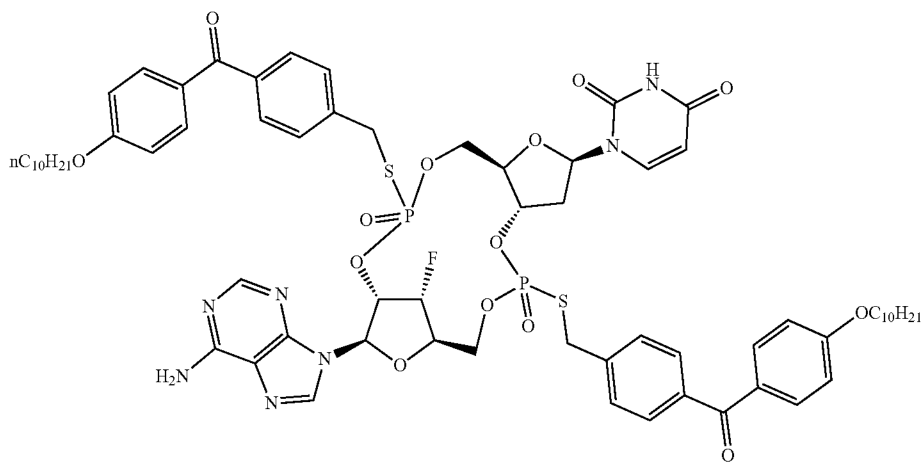 |
| 251 | | wherein X is any pharmaceutically acceptable counterion, e.g., lithium, sodium, potassium, calcium, magnesium, aluminum, ammonium, ethylamine, diethylamine, ethylenediamine, ethanolamine, diethanolamine, piperazine and the like (see, for example, Berge et al., supra); and the label "n" indicates that the associated alkyl chain is "normal" (i.e., unbranched). In some embodiments, the compound of Table 1 is not a salt (i.e., it's a free acid or free base).

In an embodiment, a compound described herein is in the form of a pharmaceutically acceptable salt. Exemplary salts are described herein, such as ammonium salts. In some embodiments, the compound is a mono-salt. In some embodiments, the compound is a di-salt. In some embodiments, a compound described herein (e.g., a compound in Table 1) is not a salt (e.g., is a free acid or free base).

Without wishing to be bound by theory, a compound of Formula (I) is a small molecule nucleic acid hybrid (cyclic dinucleotide) compound that combines both antiviral and immune modulating activities. The latter activity mediates, for example, controlled apoptosis of virus-infected hepatocytes via stimulation of the innate immune response, similar to what is also achieved by IFN-α therapy in patients suffering from a viral infection. The mechanism of action of a compound of Formula (I) entails its host immune stimulating activity, which may induce endogenous IFNs via the activation of a PRR, e.g., RIG-I, NOD2, and STING. Activation may occur by binding of a compound of Formula (I) to the nucleotide binding domain of a PRR (e.g., STING), as described previously, and may further result in the induction of PRR expression (e.g., STING expression).

The compounds provided herein may contain one or more asymmetric centers and thus occur as racemates and racemic mixtures, single enantiomers, individual diastereomers, and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds, phosphorus-oxygen bonds, or phosphorus-sulfur bonds) or substituents that can restrict bond rotation, e.g., restriction resulting from the presence of a ring or double bond. In some embodiments, the compound of Formula (I) comprises an isomer (e.g., an Rp-isomer or Sp isomer) or a mixture of isomers (e.g., Rp-isomers or Sp isomers) of a compound of Formula (I).

Exemplary Methods of Use

The present disclosure relates to methods for inducing the expression of a PRR (e.g., STING) in a subject through administration of an effective amount of a compound of Formula (I) or a pharmaceutically acceptable salt or stereoisomer thereof. In some embodiments, the subject may be suffering from a condition described below, e.g., a viral infection (e.g., viral latency), a bacterial infection, a cancer (e.g., a proliferative disease).

Treatment of Viral Infections

Pattern recognition receptors such as STING, RIG-I, and NOD2, have been shown to be an important factor in host recognition of a large number of RNA viruses from a variety of different viral families. In some embodiments, the methods of inducing expression of PRRs (e.g., STING) disclosed herein comprise administration of an effective amount of a compound of Formula (I) or a pharmaceutically acceptable salt or stereoisomer thereof to a subject infected with a microbial infection. In some embodiments, the microbial infection is a virus. In some embodiments, the virus is a RNA virus (e.g., a double-stranded RNA (dsRNA) virus, a single-stranded RNA (ssRNA) virus (e.g., a positive-strand (sense) ssRNA virus or a negative-strand (antisense) ssRNA virus), or a ssRNA retrovirus) or a DNA virus (e.g., a dsDNA virus, ssDNA virus, or a dsDNA retrovirus). In some embodiments, the virus may be a Group I, Group II, Group III, Group IV, Group V, Group VI, or Group VII class of virus, e.g., according to the Baltimore classification system.

In some embodiments, the virus is dsRNA virus, e.g., a Group III virus. In some embodiments, expression of a PRR (e.g., STING) is induced through host-produced or viral-derived RNA. In some embodiments, the virus is a dsRNA virus, and is a member of the Birnaviridae, Chrysoviridae, Cystoviridae, Endornaviridae, Hypoviridae, Megabirnaviridae, Partitiviridae, Picobirnaviridae, Reoviridae, or Totiviridae families, or other family of dsRNA virus. Exemplary dsRNA viruses and virus genera include, but are not limited to, Picobirnavirus, Rotavirus, Seadornavirus, Coltivirus, Orbivirus, and Orthoreovirus, or a subtype, species, or variant thereof.

In some embodiments, the virus is ssRNA virus, e.g., a positive-strand (sense) ssRNA virus, e.g., a Group IV virus. In some embodiments, expression of a PRR (e.g., STING) is induced through host-produced or viral-derived RNA. In some embodiments, the virus is a positive-strand (sense) ssRNA virus, and is a member of the Arteriviridae, Coronaviridae, Mesoniviridae, Roniviridae, Dicistroviridae, Iflaviridae, Marnaviridae, Picornaviridae, Secoviridae, Alphaflexiviridae, Betaflexiviridae, Gammaflexiviridae, Tymoviridae, Alphatetraviridae, Alvernaviridae, Astroviridae, Barnaviridae, Bromoviridae, Caliciviridae, Carmotetraviridae, Closteroviridae, Flaviviridae, Leviviridae, Luteoviridae, Narnaviridae, Nodaviridae, Permutotetraviridae, Potyviridae, Togaviridae, or Virgaviridae families, or other family of positive-strand (sense) ssRNA virus. Exemplary positive-strand (sense) ssRNA viruses and virus genera include, but are not limited to, Yellow fever virus, West Nile virus, Hepatitis C virus, Dengue fever virus, Rubella virus, Ross River virus, Sindbis virus, Chikungya virus, Norwalk virus, Japanese encephalitis virus, Tick-borne encephalitis virus, St. Louis encephalitis virus, Murray Valley encephalitis virus, Kyasanur Forest disease virus (e.g., Monkey disease virus), Western Equine encephalitis virus, Eastern Equine encephalitis virus, Venezuelan Equine encephalitis virus, Sapporo virus, Norovirus, Sapovirus, Calicivirus, Parechovirus, Hepatitis A virus, Rhinovirus (e.g., Rhinovirus A, Rhinovirus B, and Rhinovirus C), Enterovirus (e.g., Enterovirus A, Enterovirus B, Enterovirus C (e.g., poliovirus), Enterovirus D, Enterovirus E, Enterovirus F, Enterovirus G, or Enterovirus H), Apthovirus (e.g., Foot and mouth disease virus), Nidovirales (e.g., Cavally virus, Nam Dinh virus, Middle East respiratory syndrome coronavirus (MERS-CoV), Coronavirus HKU1, Coronavirus NL63, SARS-CoV, Coronavirus OC43, and Coronavirus 229E), Benyvirus, Blunevirus, Cilevirus, Hepevirus (e.g., Hepatitis E virus), Higrevirus, Idaeovirus, Negevirus, Ourmiavirus, Polemovirus, Sobemovirus, or Umbravirus, or a subtype, species, or variant thereof.

In some embodiments, the virus is a member of the genus Norovirus, or a subtype, species, or variant thereof. In some embodiments, the virus is the Norwalk virus, Hawaii virus, Snow Mountain virus, Mexico virus, Desert Shield virus, Southampton virus, Lordsdale virus, or Wilkinson virus, or a subtype or variant thereof. In some embodiments, the virus is a member of the genus Norovirus and can be classified as genogroup GI, genogroup GII, genogroup GIII, genogroup GIV, or genogroup GV.

In some embodiments, the virus is ssRNA virus, e.g., a negative-strand (antisense) ssRNA virus, e.g., a Group V virus. In some embodiments, expression of a PRR (e.g., STING) is induced through host-produced or viral-derived RNA. In some embodiments, the virus is a negative-strand (antisense) ssRNA virus, and is a member of the Bornaviridae, Filoviridae, Paramyxoviridae, Rhabdoviridae, Nyamiviridae, Arenaviridae, Bunyaviridae, Ophioviridae, or Orthomyxoviridae families, or other family of negative-strand (antisense) ssRNA virus. Exemplary negative-strand (antisense) ssRNA viruses and virus genera include, but are not limited to, Brona disease virus, Ebola virus, Marburg virus, Measles virus, Mumps virus, Nipah virus, Hendra virus, Respiratory syncytial virus, Influenza and Parainfluenza viruses, Metapneumovirus, Newcastle disease virus, Deltavirus (e.g., Hepatitis D virus), Dichohavirus, Emaravirus, Nyavirus, Tenuivirus, Varicosavirus, or a subtype, species, or variant thereof.

In some embodiments, the virus is an ssRNA retrovirus (ssRNA RT virus), e.g., a Group VI virus. In some embodiments, expression of a PRR (e.g., STING) is induced through host-produced or viral-derived RNA. In some embodiments, the virus is an ssRNA RT virus and is a member of the Metaviridae, Pseudoviridae, or Retroviridae families, or other family of ssRNA RT virus. Exemplary ssRNA RT viruses and virus genera include, but are not limited to, Metavirus, Errantivirus, Alpharetrovirus (e.g., Avian leukosis virus, Rous sarcoma virus), Betaretrovirus (e.g., Mouse mammary tumor virus), Gammaretrovirus (e.g., Murine leukemia virus, Feline leukemia virus), Deltaretrovirus (e.g., human T-lymphotropic virus), Epsilonretrovirus (e.g., Walleye dermal sarcoma virus), Lentivirus (e.g., Human immunodeficiency virus 1 (HIV)), or a subtype, species, or variant thereof.

In some embodiments, the virus is a DNA virus, e.g., a dsDNA virus or an ssDNA virus. In some embodiments, the virus is a dsDNA virus, e.g., a Group I virus, and expression of a PRR (e.g., STING) is induced through host-produced or viral-derived RNA. In some embodiments, the virus is a dsDNA virus and is a member of the Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Nimaviridae, Pandoraviridae, Papillomaviridae, Phycodnaviridae, Polydnaviruses, Polymaviridae, Poxviridae, Sphaerolipoviridae, Tectiviridae, or Turriviridae families, or other family of dsDNA virus. Exemplary dsDNA viruses and virus genera include, but are not limited to, Dinodnavirus, Nudivirus, smallpox, human herpes virus, Varicella Zoster virus, polyomavirus 6, polyomavirus 7, polyomavirus 9, polyomavirus 10, JC virus, BK virus, KI virus, WU virus, Merkel cell polyomavirus, Trichodysplasia spinulosa-associated polyomavirus, MX polyomavirus, Simian virus 40, or a subtype, species, or variant thereof.

In some embodiments, the virus is an ssDNA virus, e.g., a Group II virus, and expression of a PRR (e.g., STING) is induced through host-produced or viral-derived RNA. In some embodiments, the virus is an ssDNA virus and is a member of the Anelloviridae, Bacillariodnaviridiae, Bidnaviridae, Circoviridae, Geminiviridae, Inoviridae, Microviridae, Nanoviridae, Parvoviridae, or Spiraviridae families, or other family of ssDNA virus. Exemplary ssDNA viruses and virus genera include, but are not limited to, Torque teno virus, Torque teno midi virus, Torque teno mini virus, Gyrovirus, Circovirus, Parvovirus B19, Bocaparvovirus, Dependoparvovirus, Erythroparvovirus, Protoparvovirus, Tetraparvovirus, *Bombyx mori* densovirus type 2, lymphoidal parvo-like virus, Hepatopancreatic parvo-like virus, or a subtype, species, or variant thereof.

In some embodiments, the virus is a dsDNA reverse transcriptase (RT) virus, e.g., a Group VII virus, and expression of a PRR (e.g., STING) is induced through host-produced or viral-derived RNA. In some embodiments, the virus is a dsDNA RT virus and is a member of the Hepadnaviridae, or Caulimoviridae families, or other family of dsDNA RT virus. Exemplary dsDNA RT viruses and virus genera include, but are not limited to, Hepatitis B virus, or a subtype, species, or variant thereof.

In some embodiments, the virus (e.g., a virus described herein) is latent, e.g., within a cell. In some embodiments, the virus is an RNA virus (e.g., a double-stranded RNA (dsRNA) virus, a single-stranded RNA (ssRNA) virus (e.g., a positive-strand (sense) ssRNA virus or a negative-strand (antisense) ssRNA virus), or a ssRNA retrovirus) or a DNA virus (e.g., a dsDNA virus, ssDNA virus, or a dsDNA retrovirus) and is latent, e.g., within a cell. In some embodiments, the virus is a Group I, Group II, Group III, Group IV, Group V, Group VI, or Group VII class of virus, e.g., according to the Baltimore classification system, and is latent, e.g., within a cell.

In some embodiments, the virus is an RNA virus (e.g., an RNA virus described herein) and is latent, e.g., within a cell. In some embodiments, the virus is an ssRNA retrovirus (ssRNA RT virus), e.g., a Group VI virus, and is latent, e.g., within a cell. In some embodiments, the virus is the human immunodeficiency virus 1 (HIV)), or a subtype, species, or variant thereof, and is latent, e.g., within a cell.

In some embodiments, the methods of inducing expression of a PRR (e.g., STING) in a subject suffering from a viral infection disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof to a subject.

Treatment of Bacterial Infections

Recent studies have shown that PRRs (e.g., STING) play a critical role in host recognition of bacterial infections stemming from a variety of species (Dixit, E. and Kagan, J. C. *Adv Immunol* (2013) 117:99-125). In some cases, bacteria may secrete nucleic acids during the exponential growth phase (e.g., *Listeria monocytogenes*; Abdullah, Z. et al, *EMBO J* (2012) 31:4153-4164), which in turn are detected by PRRs such as RIG-I and thus promote the induction of further PRR expression. In other cases, such as for *Legionella pneumophila*, bacterial DNA enters into the cytosol over the course of infection and is transcribed into an RNA ligand for RIG-I (Chiu, Y. H. et al, *Cell* (2009) 138:576-591), thus triggering downstream PRR-mediated signaling events. PRR expression (e.g., STING expression) may further be induced upon recognition of RNA released during phagocytotic uptake of bacteria. Additionally, bacterial cell wall components such as peptidoglycans (e.g., muramyl dipeptide, i.e., MDP) may serve as ligands for activation and induction of PRRs, namely NOD2, and bacterial-derived nucleic acids such as cyclic dinucleotides (e.g., cyclic di-GMP) may bind to and activate PRRs, in particular STING.

In some embodiments, the expression of one or more PRRs may be induced through other means not explicitly recited herein.

In some embodiments, the methods of inducing expression of a PRR (e.g., STING) disclosed herein comprise administration of an effective amount of a compound of Formula (I) or a pharmaceutically acceptable salt thereof to a subject infected with a microbial infection, e.g., a bacterial infection.

In some embodiments, the bacterium is a Gram-negative bacterium or a Gram-positive bacterium. Exemplary bacteria include, but are not limited to, *Listeria* (e.g., *Listeria monocytogenes*), *Francisella* (e.g., *Francisella tularensis*), *Mycobacteria* (e.g., *Mycobacteria tuberculosis*), *Brucella* (e.g., *Brucella abortis*), *Streptococcus* (e.g., group B *Streptococcus*), *Legionella* (e.g., *Legionella pneumophila*), *Escherichia* (e.g., *Escherichia coli*), *Pseudomonas* (e.g., *Pseudomonas aeruginosa*), *Salmonella* (e.g., *Salmonella typhi*), *Shigella* (e.g., *Shigella flexneri*), *Campylobacter* (e.g., *Campylobacter jejuni*), *Clostridium* (e.g., *Clostrodium botulinum*), *Enterococcus* (e.g., *Enterococcus faecalis*), *Vibrio* (e.g., *Vibrio cholera*), *Yersinia* (e.g., *Yersinia pestis*), *Staphylococcus* (e.g., *Staphylococcus aureus*), or other genera, species, subtypes, or variants thereof.

In some embodiments, the methods of inducing expression of a PRR (e.g., STING) in a subject suffering from a bacterial infection disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof.

Treatment of Cancer

Many patients with advanced solid tumors show a spontaneous T cell-inflamed tumor microenvironment, which is predictive of prognosis and clinical response to immunotherapies. Recent findings suggest the STING pathway of cytosolic DNA sensing is an important innate immune sensing mechanism driving type I IFN production in the tumor context. Knowledge of this pathway is guiding the further development of novel immunotherapeutic strategies.

In early-stage colorectal cancer, the presence of activated CD8+ T cells within the tumor microenvironment is prognostic of a positive outcome. Patients with other solid tumor histology also appear to have a spontaneous T cell infiltrate that may have similar positive prognostic value. These include breast cancer, renal cell carcinoma, melanoma, ovarian cancer, and gastrointestinal tumors. It is believed that T cell infiltrate includes tumor antigen-specific T cells that have been activated spontaneously in response to the growing tumor, perhaps through immune surveillance mechanisms. This attempted host immune response, even if it does not eliminate the tumor completely, is thought to delay tumor progression and thus yield improved clinical outcome. Furthermore, the innate immune mechanisms can lead to adaptive T cell response against tumor antigens even in the absence of exogenous infection. In this regard, human cancer gene expression profiling studies reveal an association between a type I IFN signature, T cell infiltration, and clinical outcome. Thus, innate immune sensing pathways that trigger type I IFN production might represent crucial intermediate mechanistic step. In gene expression profiling of melanoma, two major subsets of tumor microenvironment have been found that represent either the presence or absence of a transcriptional profile indicative of T cell infiltrate. In fact, CD8+ T cells, macrophages, as well as of some B cells and plasma cells in these lesions in melanoma metastases is similar to the phenotype described in early-stage colon cancer and other tumors in which activated T cells have been associated with favorable prognosis. CD8+ T cells were required for the up-regulation of all immune factors within the tumor micro-environment. Studies indicate that IFN production is necessary for optimal T cell priming against tumor antigens. There are many PRRs that trigger IFN-β production by host DCs in response to a growing tumor in vivo including STING. STING is an adapter protein that is activated by cyclic dinucleotides generated by cyclic GMP-AMP synthase (cGAS), which in turn is directly activated by cytosolic DNA. In the presence of these cyclic dinucleotides and/or DNA, STING is translocated from the endoplasmic reticulum to various perinuclear components; for example, palmitoylation of STING at the Golgi has been shown to be essential for STING activation (Mukai, K. et al (2016) *Nat Commun* doi: 10.1038/ncomms11932).

Activated STING forms aggregates, activates TBK1, which in turn phosphorylates interferon regulatory factor 3 (IRF3) that directly contributes to type I IFN gene transcription. This pathway has been implicated in the sensing of DNA viruses, and also in selected autoimmune models. Moreover, activating mutations of STING have recently been identified in human patients with a vasculitis/pulmonary inflammation syndrome that is characterized by increased type I IFN production. Mechanistic studies using mouse transplantable tumor models revealed that STING-knockout mice, and IRF3-knockout mice showed defective spontaneous T cell priming against tumor antigens in vivo, and rejection of immunogenic tumors was ablated. Similarly, tumor-derived DNA was found within the cytosol of a major population of tumor-infiltrating DCs, and this was associated with STING pathway activation and IFN-β production. Therefore, the host STING pathway appears to be an important innate immune sensing pathway that detects the presence of a tumor and to drive DC activation and subsequent T cell priming against tumor-associated antigens in vivo. A functional role for the STING pathway in vivo has also been reported in other mouse-tumor systems. An inducible glioma model was shown to result in induction of a type I IFN gene signature as part of the host response. This induction was substantially reduced in STING-knockout mice, and tumors grew more aggressively, leading to shorter mouse survival. Exogenous delivery of cyclic dinucleotides as STING agonists exerted a therapeutic effect in vivo. A crucial role for host type I IFNs and the host STING pathway was also confirmed in the B16.OVA and EL4.OVA models in response to cryo-ablation. Interestingly, the mechanisms involved paralleled what was observed in the Bm12 mouse model of lupus because host STING was also required for maximal production of anti-DNA antibodies.

Thus, the antitumor immune response triggered in part by tumor DNA has overlap with the mechanisms involved in autoimmunity driven by extracellular DNA. A role for STING also has been explored in an inducible colon cancer model. It seems likely that the ability of a cancer in an individual patient to support STING pathway activation is linked to the spontaneous generation of a T cell-inflamed tumor microenvironment. Because this phenotype is associated with improved prognosis of early-stage cancer patients, and also with clinical response to immunotherapies in the metastatic setting, failed STING activation may therefore represent an early functional block, and thus itself may have prognostic/predictive value as a biomarker. Second, strategies that activate or mimic the output of the host STING pathway should have immunotherapeutic potential in the clinic. In as much as non-T cell-inflamed tumors appear to lack evidence of a type I IFN transcriptional signature, strategies to promote robust innate signaling via APCs in the tumor microenvironment might facilitate improved cross-priming of tumor antigen-specific CD8+ T cells, and also augment chemokine production for subsequent oncolytic activity.

Recognition of nucleic acid ligands by a PRRs such as cGAS, RIG-I and/STING stimulates the production of type I interferons (e.g., IFN-α or IFN-β), thus triggering a series of downstream signaling events that may lead to apoptosis in susceptible cells. In recent years, a connection between the induction of PRR expression and a number of cancers has been discovered. For example, RIG-I expression has been shown to be significantly downregulated in hepatocellular carcinoma, and patients exhibiting low RIG-I expression in tumors had shorter survival and poorer responses to IFN-α therapy (Hou, J. et al, *Cancer Cell* (2014) 25:49-63). As such, it has been suggested that the level of RIG-I expression may be useful as a biomarker for prediction of prognosis and response to immunotherapy. In other cases, induction of RIG-I expression has been shown to induce immunogenic cell death of pancreatic cancer cells, prostate cancer cells, breast cancer cells, skin cancer cells, and lung cancer cells (Duewell, P. et al, *Cell Death Differ* (2014) 21:1825-1837; Besch, R. et al, *J Clin Invest* (2009) 119: 2399-2411; Kaneda, Y. *Oncoimmunology* (2013) 2:e23566; Li, X. Y. et al, *Mol Cell Oncol* (2014) 1:e968016), highlighting a new approach in immune-mediated cancer treatment.

STING is recognized as the key adapter protein in the cGAS-STING-IFN cascade, although it is also reported to be a sensor for DNA. A role for STING in the stimulation of innate immunity in response to cancer has also been identified. Recent studies have revealed the presence of tumor-derived DNA in the cytosol of certain antigen-presenting cells, such as tumor-infiltrating dendritic cells, likely generated through tumor cell stress or cell death. This tumor-derived DNA is known to activate cGAS which causes the production of cyclic nucleotides that have been shown to activate STING, resulting in production of associated type 1 interferons (Woo, S. R. et al, *Immunity* (2014) 41:830-842). Stimulation of STING and resulting downstream signaling pathways also likely contributes to effector T cell recruitment into the inflamed tumor microenvironment (Woo, S. R. *Trends in Immunol* (2015) 36:250-256). STING activation in the tumor microenvironment can induce adaptive immune response leading to anti-tumor activity. Hence, in those tumors that are STING-deficient, the described herein can still have anti-tumor activity through activation of antigen-presenting cells and dendritic cells, (APCs and DCs) and induction of adaptive immune response.

In some embodiments, the methods of inducing expression of a PRR (e.g., a PRR described herein) comprise administration of an effective amount of a compound of Formula (I) or a pharmaceutically acceptable salt thereof to a subject suffering from cancer. In some embodiments, the methods of inducing expression of STING disclosed herein comprise administration of a compound of Formula (I) or a pharmaceutically acceptable salt thereof to a subject suffering from cancer. In some embodiments, the methods of inducing expression of RIG-I disclosed herein comprise administration of a compound of Formula (I) or a pharmaceutically acceptable salt thereof to a subject suffering from cancer. In some embodiments, the methods of inducing expression of NOD2 disclosed herein comprise administration of a compound of Formula (I) or a pharmaceutically acceptable salt thereof to a subject suffering from cancer. In some embodiments, the cancer is selected from a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the cancer comprises a solid tumor (e.g., a carcinoma, a sarcoma, or a lymphoma). In some embodiments, the cancer is a hepatocellular carcinoma or other cancer of the liver. In some embodiments, the cancer is a leukemia or other cancer of the blood. In some embodiments, the cancer comprises breast cancer, renal cell carcinoma, colon cancer, melanoma, ovarian cancer, head and neck squamous cell carcinoma, pancreatic cancer, prostate cancer, lung cancer, brain cancer, thyroid cancer, renal cancer, testis cancer, stomach cancer, urothelial cancer, skin cancer, cervical cancer, endometrial cancer, liver cancer, lung cancer, lymphoma or gastrointestinal stromal cancer and solid tumors. In some embodiments, the cancer cells (e.g., tumor cells) comprise specific cancer-associated antigens that induce a T-cell-mediated anti-tumor response.

In some embodiments, the methods of inducing expression of a PRR (e.g., STING, RIG-I, MDA5, LGP2) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRRs e.g., STING) occurs within about 5 minutes of administration of a compound of Formula (I) or a pharmaceutically acceptable salt thereof. In some embodiments, induction of expression of a PRRs (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof. It is recognized that activation of STING by compounds may lead to induction of expression of other PRRs such as RIG-I, MDA5, NOD2 etc. which may further amplify IFN production in the tumor microenvironment and prime T-cells for enhanced anti-tumor activity.

In some embodiments, the methods of inducing expression of a PRR (e.g., STING) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt or stereoisomer thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof.

Pharmaceutical Compositions

While a compound of the present disclosure (e.g., a compound of Formula (I)) may be administered alone, it is preferable to administer said compound as a pharmaceutical composition or formulation, where the compounds are combined with one or more pharmaceutically acceptable diluents, excipients or carriers. The compounds according to the disclosure may be formulated for administration in any convenient way for use in human or veterinary medicine. In certain embodiments, the compounds included in the pharmaceutical preparation may be active itself, or may be a prodrug, e.g., capable of being converted to an active compound in a physiological setting. Regardless of the route of administration selected, the compounds of the present disclosure, which may be used in a suitable hydrated form, and/or the pharmaceutical compositions of the present disclosure, are formulated into a pharmaceutically acceptable dosage form such as described below or by other conventional methods known to those of skill in the art.

The amount and concentration of compounds of the present disclosure (e.g., a compound of Formula (I)) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Thus, another aspect of the present disclosure provides pharmaceutically acceptable compositions comprising a therapeutically effective amount or prophylactically effective amount of a compound described herein (e.g., a compound of Formula (I)), formulated together with one or more pharmaceutically acceptable carriers (additives) and/or diluents. As described in detail below, the pharmaceutical compositions of the present disclosure may be specially formulated for administration in solid or liquid form, including those adapted for oral, intratumoral, parenteral administration, for example, by subcutaneous, intramuscular, intraperitoneal, or intravenous injection as, for example, a sterile solution or suspension. However, in certain embodiments the subject compounds may be simply dissolved or suspended in sterile water. In certain embodiments, the pharmaceutical preparation is non-pyrogenic, i.e., does not elevate the body temperature of a patient.

The phrases "systemic administration," "administered systemically," "peripheral administration" and "administered peripherally" as used herein mean the administration of the compound other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, stabilizing agent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ascorbic acid; (17) pyrogen-free water; (18) isotonic saline; (19) Ringer's solution; (20) ethyl alcohol; (21) phosphate buffer solutions; (22) cyclodextrins such as Captisol®; and (23) other non-toxic compatible substances such as antioxidants and antimicrobial agents employed in pharmaceutical formulations.

As set out above, certain embodiments of the compounds described herein may contain a basic functional group, such as an amine, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

In other cases, the compounds of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the compound of the present disclosure (e.g., a compound of Formula (I). These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutically acceptable carriers, as well as wetting agents, emulsifiers, lubricants, coloring agents, release agents, coating agents, sweetening, flavoring agents, perfuming agents, preservatives, antioxidants, and other additional components may be present in an amount between about 0.001% and 99% of the composition described herein. For example, said pharmaceutically acceptable carriers, as well as wetting agents, emulsifiers, lubricants, coloring agents, release agents, coating agents, sweetening, flavoring agents, perfuming agents, preservatives, antioxidants, and other additional components may be present from about 0.005%, about 0.01%, about 0.05%, about 0.1%, about 0.25%, about 0.5%, about 0.75%, about 1%, about 1.5%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 85%, about 90%, about 95%, or about 99% of the composition described herein.

Pharmaceutical compositions of the present disclosure may be in a form suitable for oral administration, e.g., a liquid or solid oral dosage form. In some embodiments, the liquid dosage form comprises a suspension, a solution, a linctus, an emulsion, a drink, an elixir, or a syrup. In some embodiments, the solid dosage form comprises a capsule, tablet, powder, dragée, or powder. The pharmaceutical composition may be in unit dosage forms suitable for single administration of precise dosages. Pharmaceutical compositions may comprise, in addition to the compound described herein (e.g., a compound of Formula (I)) or a pharmaceutically acceptable salt thereof, a pharmaceutically acceptable carrier, and may optionally further comprise one or more pharmaceutically acceptable excipients, such as, for example, stabilizers (e.g., a binder, e.g., polymer, e.g., a precipitation inhibitor, diluents, binders, and lubricants.

In some embodiments, the composition described herein comprises a liquid dosage form for oral administration, e.g., a solution or suspension. In other embodiments, the composition described herein comprises a solid dosage form for oral administration capable of being directly compressed into a tablet. In addition, said tablet may include other medicinal or pharmaceutical agents, carriers, and or adjuvants. Exemplary pharmaceutical compositions include compressed tablets (e.g., directly compressed tablets), e.g., comprising a compound of the present disclosure (e.g., a compound of Formula (I)) or a pharmaceutically acceptable salt thereof.

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, preferably from about 5 percent to about 70 percent, most preferably from about 10 percent to about 30 percent. Pharmaceutical compositions of this disclosure suitable for parenteral administration comprise compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a compound of the present disclosure (e.g., a compound of Formula (I)), it may be desirable to slow the absorption of the drug from subcutaneous, intraperitoneal, or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered form of the compound of the present disclosure is accomplished by dissolving or suspending compound in an oil vehicle.

In some embodiments, it may be advantageous to administer the compound of the present disclosure (e.g., a compound of Formula (I)) in a sustained fashion. It will be appreciated that any formulation that provides a sustained absorption profile may be used. In certain embodiments, sustained absorption may be achieved by combining a compound of the present disclosure with other pharmaceutically acceptable ingredients, diluents, or carriers that slow its release properties into systemic circulation.

Routes of Administration

The compounds and compositions used in the methods described herein may be administered to a subject in a variety of forms depending on the selected route of administration, as will be understood by those skilled in the art. Exemplary routes of administration of the compositions used in the methods described herein include topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time. In certain embodiments of the disclosure, a composition described herein comprising a compound of Formula (I) is administered orally. In other embodiments of the disclosure, a composition described herein comprising a compound of Formula (I) is administered parenterally (e.g., intraperitoneally). It is recognized that for treatment of solid tumors, direct injection of the compounds into the tumor may also be carried out (e.g., intratumoral administration). It is recognized that for treatment of solid tumors, direct injection of the compounds into the tumor may also be carried out (e.g., intratumoral administration).

For intravenous, intraperitoneal, or intrathecal delivery or direct injection (e.g., intratumoral), the composition must be sterile and fluid to the extent that the composition is deliverable by syringe. In addition to water, the carrier can be an isotonic buffered saline solution, ethanol, polyol (for example, glycerol, propylene glycol, and liquid polyethelyne glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved. For example, for local effects, the composition can be formulated for topical administration and applied directly where its action is desired. For systemic, long term effects, the composition can be formulated for enteral administration and given via the digestive tract. For systemic, immediate and/or short term effects, the composition can be formulated for parenteral administration and given by routes other than through the digestive tract.

Dosages

The compositions of the present disclosure are formulated into acceptable dosage forms by conventional methods known to those of skill in the art. Actual dosage levels of the active ingredients in the compositions of the present disclosure (e.g., a compound of Formula (I)) may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the substances of the disclosure employed in the composition at levels lower than that required in order to achieve the desired therapeutic effect and gradually increase the dosage until the desired effect is achieved. In general, a suitable daily dose of a composition of the disclosure will be that amount of the substance which is the lowest dose effective to produce a therapeutic effect. Such an effective dose will generally depend upon the factors described above. Preferably, the effective daily dose of a therapeutic composition may be administered as two, three, four, five, six or more sub-doses administered separately at appropriate intervals throughout the day, optionally, in unit dosage forms.

Preferred therapeutic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject afflicted with the disorders described herein (e.g., HBV infection). Preferred prophylactic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject. The dose may also be titrated (e.g., the dose may be escalated gradually until signs of toxicity appear, such as headache, diarrhea, or nausea).

The frequency of treatment may also vary. The subject can be treated one or more times per day (e.g., once, twice, three, four or more times) or every so-many hours (e.g., about every 2, 4, 6, 8, 12, or 24 hours). The composition can be administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Patient Selection and Monitoring

The methods of the present disclosure described herein entail administration of a compound of Formula (I) or a pharmaceutically acceptable salt thereof to a subject to activate the PRR for IFNs, ISGs and cytokines production or additionally induce the expression of PRRs (e.g., RIG-I, STING etc.). In some embodiments, the subject is suffering from or is diagnosed with a condition, e.g., a proliferative disease, e.g., cancer. Accordingly, a patient and/or subject can be selected for treatment using a compound of Formula (I) or a pharmaceutically acceptable salt thereof by first evaluating the patient and/or subject to determine whether the subject is infected with a proliferative disease, e.g., cancer. A subject can be evaluated as infected with a proliferative disease (e.g., cancer) using methods known in the art. The subject can also be monitored, for example, subsequent to administration of a compound described herein (e.g., a compound of Formula (I) or a pharmaceutically acceptable salt thereof.

In some embodiments, the subject is a mammal. In some embodiments, the subject is a human. In some embodiments, the subject is an adult. In some embodiments, the subject has a proliferative disease, e.g., cancer. In some embodiments, the subject has a cancer of the of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the subject has a cancer comprising a solid tumor (e.g., a carcinoma, a sarcoma, or a lymphoma). In some embodiments, the subject has a hepatocellular carcinoma or other cancer of the liver. In some embodiments, the subject has a leukemia or other cancer of the blood. In some embodiments, the subject has a breast cancer, renal cell carcinoma, colon cancer, melanoma, ovarian cancer, head and neck squamous cell carcinoma, pancreatic cancer, prostate cancer, lung cancer, brain cancer, or gastrointestinal stromal cancer. In some embodiments, the subject has cancer cells (e.g., tumor cells) comprising specific cancer-associated antigens that induce a T-cell response.

In some embodiments, the subject is treatment naïve. In some embodiments, the subject has been previously treated for a proliferative disease (e.g., a cancer). In some embodiments, the subject has relapsed.

Combination Therapies

A compound described herein may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compound described herein can be administered first, and the additional agent can be administered second, or the order of administration can be reversed.

In some embodiments, the combination of a compound of Formula (I) or a pharmaceutically acceptable salt thereof and the additional agent has a synergistic or additive effect. In some embodiments, the term "additive" refers to an outcome wherein when two agents are used in combination, the combination of the agents acts in a manner equal to but not greater than the sum of the individual activity of each agent.

In some embodiments, the term "additive" refers to an outcome wherein when two agents are used in combination, the combination of the agents acts in a manner equal to but not greater than the sum of the individual activity of each agent. In some embodiments, the terms "synergy" or "synergistic" refer to an outcome wherein when two agents are used in combination, the combination of the agents acts so as to require a lower concentration of each individual agent than the concentration required to be efficacious in the absence of the other agent. In some embodiments, a synergistic effect results in a reduced in a reduced minimum inhibitory concentration of one or both agents, such that the effect is greater than the sum of the effects. A synergistic effect is greater than an additive effect. In some embodiments, the agents in the composition herein may exhibit a synergistic effect, wherein the activity at a particular concentration is greater than at least about 1.25, 1.5, 1.75, 2, 2.5, 3, 4, 5, 10, 12, 15, 20, 25, 50, or 100 times the activity of either agent alone.

For example, any of the methods described herein may further comprise the administration of a therapeutically effective amount of an additional agent. Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, the additional agent is an anti-cancer agent, e.g., an alkylating agent (e.g., cyclophosphamide).

In an embodiment, the additional agent is an immunooncology agent, for example, an agent that activate the immune system, e.g., making it able to recognize cancer cells and destroy them. Exemplary immonooncology compounds are compounds that inhibit the immune checkpoint blockade pathway. In an embodiment, the compound is an antibody such as a PD-1 or PD-L1 antibody or a co-stimulatory antibody. In some embodiments, the compound is an anti-CTLA4 antibody. In another embodiment, the agent is a cell based agent such as CAR-t therapy.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:
3H-BD Iyer-Beaucage reagent
Ac Acetyl
DCA dichloroacetic acid
DCC N,N'-dicyclohexylcarbodiimide
DCM dichloromethane
DMAP 4-dimethylaminopyridine
DMT Dimethoxytrityl
EtOAc Ethyl acetate
ETT 5-(ethylthio)-1H-tetrazole
h hours
IPA isopropyl alcohol
LCMS liquid chromatography-mass spectrometry
MeOH methanol
MSNT 1-Mesitylene-2-sulfonyl-3-nitro-1,2,4-triazole
PTSA p-Toluenesulfonic acid
Py Pyridine
r.t. room temperature
TBHP Tert-butyl hydroperoxide
TEA Triethylamine
THF tetrahydrofuran
TLC thin-layer chromatography Example 1. Synthesis of Exemplary Compounds of the Disclosure

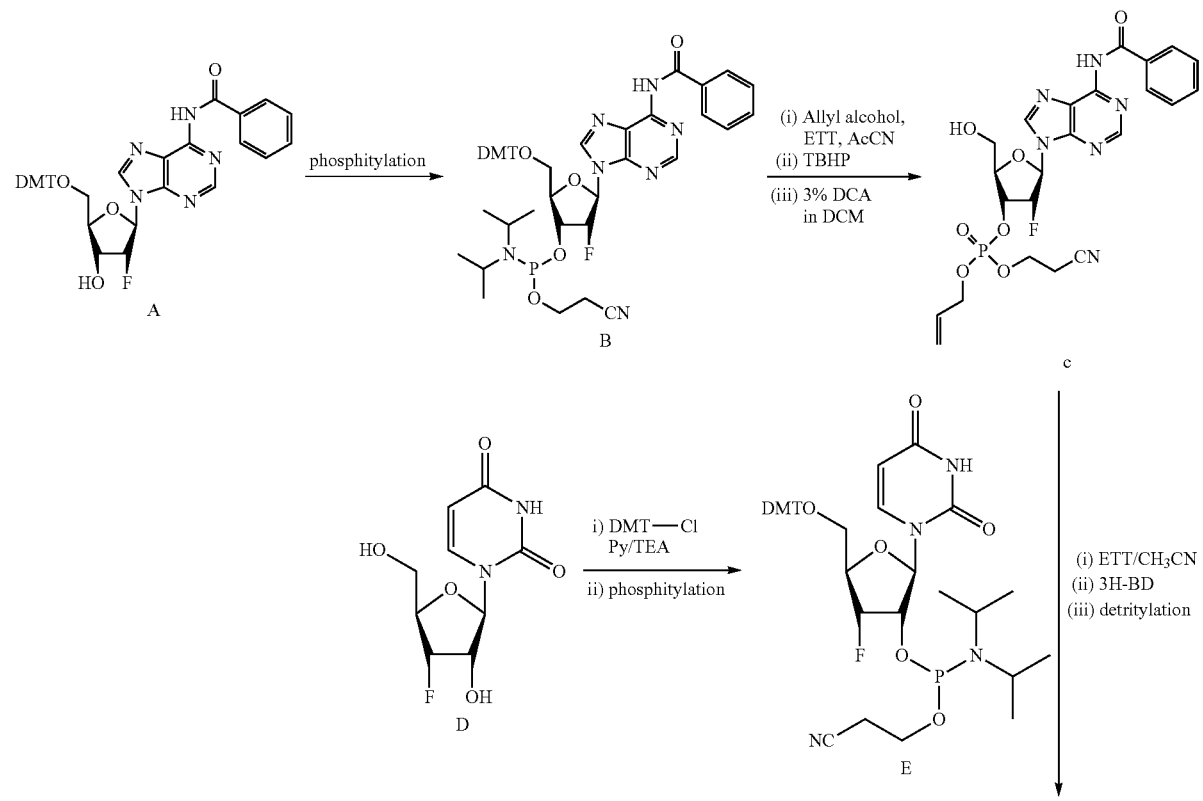

227

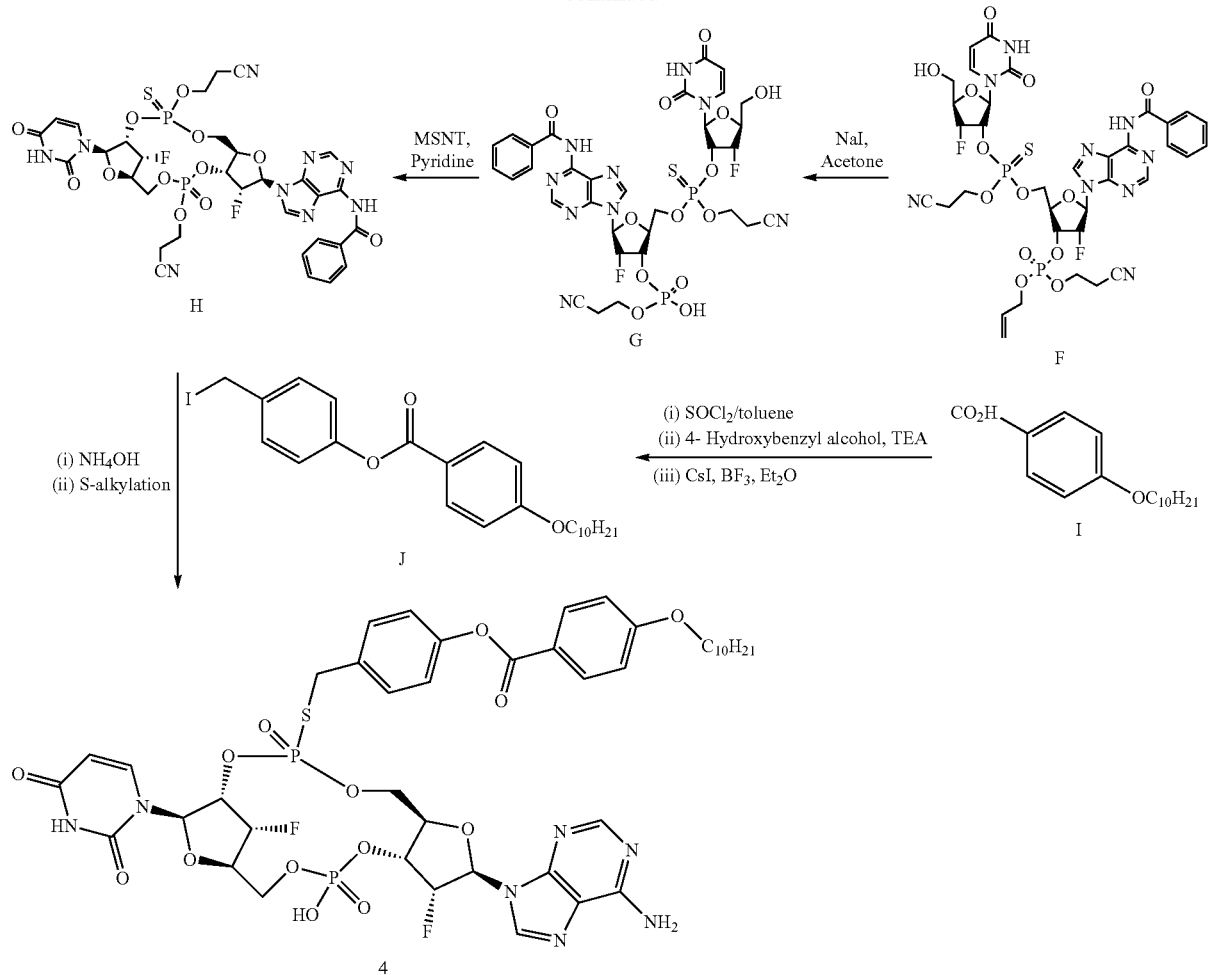

Synthesis of Allyl ((2R,3R,4R,5R)-5-(6-benzamido-9H-purin-9-yl)-4-fluoro-2-(hydroxymethyl)tetrahydrofuran-3-yl) (2-cyanoethyl) phosphate (C)

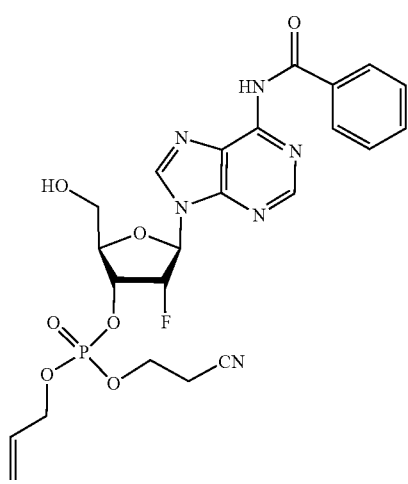

Step 1:

5'O-DMT-2'F-3'Phosphramidite-dA (15.0 g, 17.12 mmol) was co-evaporated with anhydrous acetonitrile (2×100 mL), and dried under high vacuum for 1 h. Argon was flushed over the residue in the flask. Acetonitrile (150 mL, anhydrous) was added to residue under argon. Allyl alcohol (Aldrich, 99%) (2.32 mL, 34.24 mmol) was added to the solution followed by ETT (2.22 g, 17.12 mmol) in acetonitrile (20 mL). The reaction mixture was stirred at room temperature under argon for 2.5 hours. TLC analysis (98:2 DCM:MeOH, multiple runs) showed completion of the reaction. It was then cooled in an ice water bath to 0-5 C. Tert-butyl hydroperoxide (TBHP, 5-6 M solution in nonane, 2.0 equivalents) was added to the reaction mixture dropwise at 0-5° C. (ice water bath). The mixture was allowed to warm to room temperature and stirred for an additional 30 minutes at room temperature. Excess TBHP was quenched by cooling the solution followed by the addition of saturated thiosulfate solution (10 mL). Reaction mixture was warmed up to room temperature and solvents were evaporated under reduced pressure to remove acetonitrile. The reaction mixture was partitioned between DCM (150 mL) and water (100 mL). The organic layer was separated and water layer was extracted with DCM (50 mL). The combined organic layers were dried over $Na_2SO_4$ and filtered to remove the $Na_2SO_4$ salt.

Step 2 Detritylation:

The solution of crude DMT-N-bz-3'-O-Allyl-2'-FdA obtained above (200 mL) in DCM was cooled in an ice-water bath. Para-Toluene Sulfonic Acid (PTSA) (10.0 g) was dissolved in MeOH (60 mL) and diluted with DCM (140 mL) to make 5% PTSA solution in DCM:MeOH (7:3, 200 mL) and added to DMT-N-bz-3'-O-Allyl-2'-FdA. This was stirred at 0-5 C for about 30 minutes and checked for reaction completion by TLC (95:5 DCM:MeOH, Rf=0.2). When DMT deprotection was completed, water (100 mL) was added and stirred for 15 min whilst the reaction was allowed to warm to room temperature. The mixture was transferred to a separatory funnel and the layers were separated. The aqueous layer was extracted with DCM (25 mL) and the combined organic layers were washed with aq. NaHCO$_3$ (5%, 2×100 mL). The organic layer was then washed with saturated brine (100 mL) and dried over Na$_2$SO$_4$. After filtering the salts, the solution was concentrated in vacuo to yield the crude product which was dried under high vacuum to yield a foamy solid. The crude product was dissolved in DCM (30 mL) and added to t-butyl methyl ether (180 mL) to yield a white precipitate, which was collected by filtration. After the first isolation, the product was triturated with t-butyl methyl ether (150 mL) and filtered to obtain a white powder, which was dried under high vacuum for overnight to get 9.3 g (99% yield) of pure product C as white solid.

Synthesis of allyl ((2R,3R,4R,5R)-5-(6-benzamido-9H-purin-9-yl)-2-((((2-cyanoethoxy)(((2R,3S,4R,5R)-2-(2,4-dioxo-3,4-dihydropyrimidin-1(2H)-yl)-4-fluoro-5-(hydroxymethyl)tetrahydrofuran-3-yl)oxy)phosphorothioyl)oxy)methyl)-4-fluorotetrahydrofuran-3-yl) (2-cyanoethyl) phosphate (F)

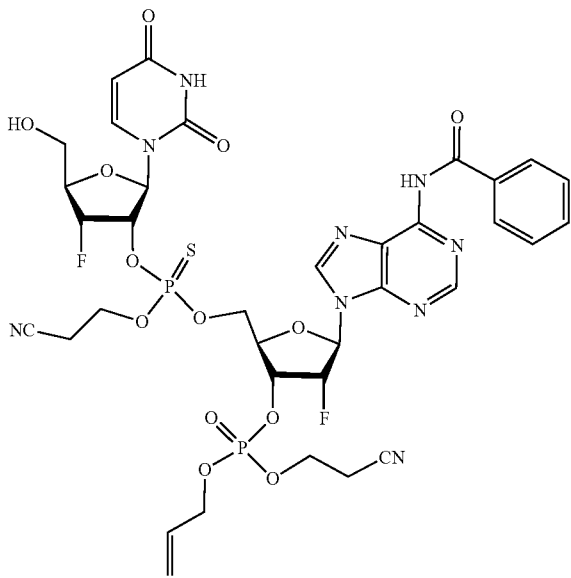

Step 1 Coupling Reaction for Synthesis of Phosphorothioate Dimer:

A mixture of C (1.09 g, 2.0 mmol) and E (1.5 g, 2.0 mmol) was co-evaporated with anhydrous acetonitrile (2×40 mL) and dried under high vacuum for 1 h. Argon was flushed over the round bottom flask and anhydrous acetonitrile (40 mL) was added to reaction mixture. ETT (260 mg, 2.0 mmol) in acetonitrile (2.0 mL) was added to the mixture of C and E, under argon. The mixture was stirred at room temperature under argon for 2 h. TLC analysis (95:5 DCM:MeOH, Rf=0.5) indicated reaction completion. Deoxygenated water was added to the reaction mixture (72 µL, 2 equivalents to E).

Step 2 Sulfurization:

In a silanized flask, Iyer-Beaucage reagent (3H-BD) (800 mg, 4.0 mmol) was dissolved in acetonitrile (10.0 mL). The reaction mixture of C and E from above was added to a solution of sulfurizing reagent (3H-BD) under argon and stirred at room temperature for 45 minutes to complete the sulfurization reaction. Methanol (10 mL) was added to reaction mixture and it was stirred for 30 min followed by concentration under reduced pressure until dryness. The dried residue was dissolved in DCM (50 mL) and washed with water (50 mL). The DCM layer was collected and dried over Na$_2$SO$_4$ and filtered.

Step 3 Detritylation:

The dried DCM solution (50 mL) was cooled to approximately 0° C. in a round bottom flask. PTSA (2.5 g) was dissolved in methanol (15 mL) and diluted with DCM (35 mL) to make 5% PTSA solution in DCM:MeOH (7:3, 50 mL) which was added to DCM reaction mixture solution and stirred for 15-20 min in an ice water bath. Reaction progress was monitored by TLC (95:5 DCM:MeOH, Rf=0.15). Water (50 mL) was added and mixed for another 15 minutes. The mixtures were transferred to separator funnel, the water layer was separated and the organic layer was collected. The water layer was extracted with DCM (25.0 mL). The combined organic layers were washed with 5% NaHCO$_3$ solution (2×50 mL) to ensure the pH of the aqueous layer was >7.0. The organic layers were then washed with saturated brine and dried over Na$_2$SO$_4$, filtered, and concentrated under reduced pressure to give crude product, which was dried under high vacuum. Crude product was purified by combiflash silica gel column chromatography using 0-5% MeOH in DCM to give 550 mg of the desired product F as off white solid.

Synthesis of (2S,3S,4S,5S)-5-(6-benzamido-9H-purin-9-yl)-2-((((2-cyanoethoxy)(((2S,3R,4S,5S)-2-(2,4-dioxo-3,4-dihydropyrimidin-1(2H)-yl)-4-fluoro-5-(hydroxymethyl)tetrahydrofuran-3-yl)oxy)phosphorothioyl)oxy)methyl)-4-fluorotetrahydrofuran-3-yl (2-cyanoethyl) hydrogen phosphate (G)

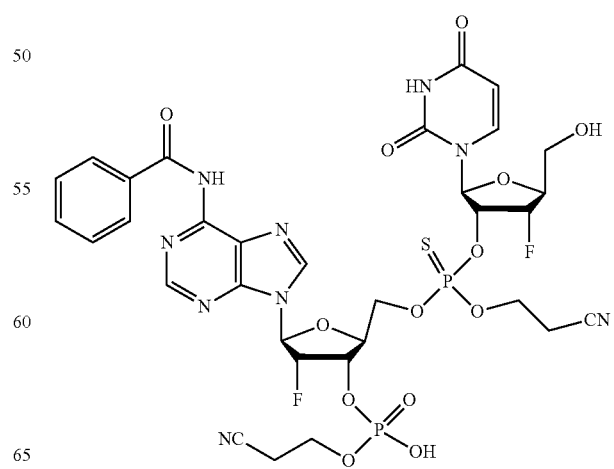

To a solution of 3'-Allyl protected dimer (500 mg, 0.565 mmol) in acetone (10 mL) was added sodium iodide (810 mg, 5.41 mmol) and the resulting solution was stirred at 60° C. for 1 h. TLC analysis (80:20 DCM:MeOH, Rf=0.15) showed completion of the reaction. The reaction mixture was cooled to room temperature. DCM (10 mL) was added to the suspension to precipitate of the product. Product was collected by centrifugation, which was triturate with DCM (25 mL) then centrifuged a second time to obtain the product. The product was dried under high vacuum to yield an off white solid. This solid was triturated with 20% MeOH in DCM:tButyl methyl ether (1:1, 25 mL) and collected by centrifugation, which was dried under high vacuum to get 500 mg of product as off white solid.

Synthesis of (H)

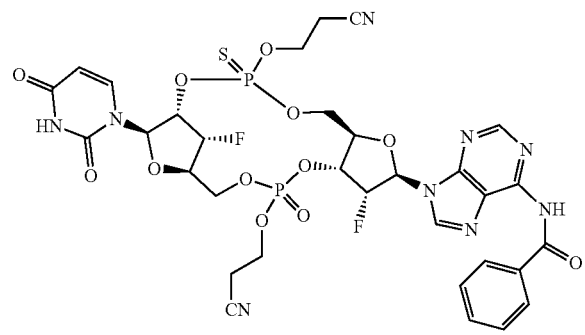 [SMILES: N#CCCOP1(=O)OC[C@H]2O[C@@H](n3ccc(=O)[nH]c3=O)[C@H](OP(=S)(OCCC#N)OC[C@H]3O[C@@H](n4cnc5c(NC(=O)c6ccccc6)ncnc54)[C@H](F)[C@@H]3O1)[C@@H]2F]

Dinucleotide G (500 mg, 0.565 mmol) was co-evaporated with anhydrous pyridine (2×20 mL), dried under high vacuum, flushed with argon (3 times) and dissolved in anhydrous pyridine (20 mL). 1-Mesitylene-2-sulfonyl-3-nitro-1,2,4-triazole (MSNT) (0.838 g, 2.82 mmol) was added to the solution of G at room temperature. The resulting mixture was stirred at room temperature for 1.5 h. Reaction progress was monitored by TLC analysis (90:10 DCM:MeOH) showed completion of the cyclization after 1.5 hours. Toluene (20 mL) was added to the reaction mixture. Solvents were evaporated under reduced pressure to give crude product. The resulting mixture was dissolved in 25% IPA in DCM (50 mL) and washed with water (50 mL). The aqueous layer was extracted with 25% IPA in DCM (50 mL), and the combined organic layers were washed with saturated aq. $NaHCO_3$ (10 mL) and brine (10 mL). Organic layers were dried over $Na_2SO_4$, filtered, and concentrated under reduced pressure to give crude product. Crude product was dissolved in 10% MeOH in DCM (5 mL) and precipitated by adding to t-butyl methyl ether (10 mL) (to remove colored impurities). The precipitate was collected by centrifugation. Product was triturated with DCM: t-butyl methyl ether (1:1, 15 mL) and product was collected by centrifugation to give light yellow product. Crude product was purified by combiflash silica gel column chromatography (gradient 0-10% MeOH in DCM) to yield 80 mg of product H as off white solid.

Synthesis of 4-(Iodomethyl)phenyl 4-(decyloxy)benzoate (I)

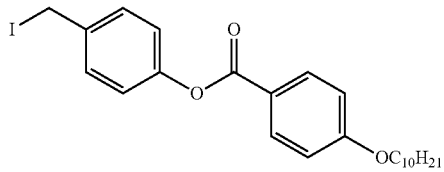

Step 1:

To a suspension of benzoic acid derivative (10 g, 0.054 mol) in a 250 mL single neck flask in toluene, thionyl chloride (7.8 mL) was added slowly and stirred at r.t. for 15 minutes followed by heating in an oil bath at 80-85° C. to obtain a clear solution that was maintained for ~3 h. The reaction mixture was cooled to RT and excess thionyl chloride was removed in vacuo. The toluene was concentrated using a rotavap at 40-45° C. It was then co-evaporated twice with ethyl acetate (25 mL). The residue was taken up in ethyl acetate (15 ml). 4-Hydroxybenzyl alcohol (4.5 g, 0.054 mol) was suspended in ethyl acetate (25 mL) and cooled in an ice bath. TEA (5.5 mL) was added with stirring followed by the addition of the ethyl acetate solution of acid chloride. A suspension forms and this was stirred overnight. The insoluble solids were removed by filtration and the filtrate was transferred to a separatory funnel. The filtrate was diluted with ethyl acetate (200 mL), washed with water (50 mL), and the organic layer washed with brine (50 mL). Concentration after drying gave the crude product, which was taken up in 200 mL of 4:1 Hexane (or Heptanes): EtOAc, and stirred for 2 h to precipitate the product. The precipitated product was filtered and the solid dried under high vacuum to yield 9.0 g (67% yield) of the desired product.

Step 2:

To a suspension of 4-hydroxyl benzyl alcohol coupled derivative (9.0 g, 0.026 mol) in a mixture of anhydrous acetonitrile (80 mL) and anhydrous dichloromethane (30 mL) in a 250 mL single neck flask, was added CsI (18.2 g, 0.078 mol) in one portion. To this, $BF_3.Et_2O$ (8.7 mL) was added slowly and stirred in the dark (covered with aluminum foil) under argon overnight at room temperature. The reaction was found to be complete by TLC Hex:EtOAc (7:3). The product was concentrated and the reaction mixture was worked up by adding water (50 mL) followed by extraction with DCM (200 mL) in a separatory funnel. The organic layer was washed with saturated sodium bicarbonate (25 mL), followed by washing with $NaHSO_3$ (5%, 30 mL). The organic layer was dried over anhydrous $Na_2SO_4$, filtered, concentrated to a film and later dried in high vacuum for two days to give 9.6 g (85% yield) the desired product I.

Synthesis of Example 4

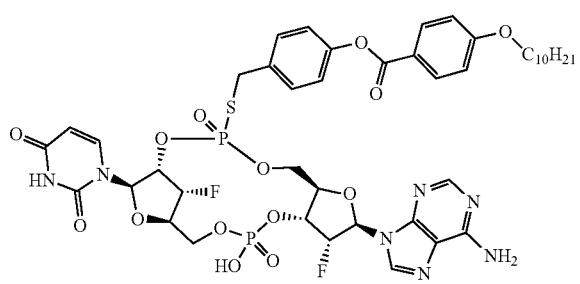

Step 1 Deprotection of Cyclic Phosphoromonothio Diphosphate:

Fully protected cyclic phosphoro monothio diphosphate (70 mg) was dissolved in a mixture of conc. NH$_4$OH (2.0 mL) and DCM (5.0 mL) stirred at room temperature overnight. LC-MS analysis showed completion of the reaction. Reaction mixture was transferred to separatory funnel and the DCM layer was removed. The aqueous layer was evaporated under reduced pressure to remove ammonia and was then washed with ethyl acetate (3×5 mL) to remove benzamide byproduct completely. The product was isolated from the aqueous layer by lyophilization to yield 60 mg of as white solid.

Step 2:

Cyclic phosphoromonothio diphosphate (50 mg, 0.072 mmol) was dissolved in water (500 uL). A solution of I (53 mg, 0.108 mmol) in a mixture of THF:Acetone (1:1, 3.5 mL) was added to the reaction mixture. The solution was stirred at room temperature for two days. Solvents were removed under reduced pressure. The crude product was re-dissolved in THF:acetone (1:1, 5.0 mL) and precipitated by adding to diethyl ether (10 mL) to remove unreacted iodo-compound. The precipitate was collected by centrifugation to yield product as an off white solid. This was re-dissolved in IPA:DCM (1:1, 20 mL) and mixed with water (20 mL), which was formed as a single-phase solution. Saturated sodium chloride (5 mL) was added to achieve separation of the two phases. The organic layer was collected (lower layer) and aqueous layer was re-extracted with IPA:DCM (1:1, 2×10 mL). The combined organic layers were dried over Na$_2$SO$_4$, filtered, and concentrated under reduced pressure to yield the product as off white solid. The product was re-dissolved in 5% acetonitrile in water (2.0 mL) and lyophilized to obtain 76 mg of product 4 as off white solid.

Example 2. In Vitro Induction of IRF and NF-κβ in THP1 Cells

TABLE 2

EC$_{50}$ values for exemplary compounds of the disclosure. "A" represents an EC$_{50}$ of less than 50 nM; "B" an EC$_{50}$ of between 50 nM and 500 nM; "C" an EC$_{50}$ of between 500 nM and 1 μM; "D" an EC$_{50}$ of between 1 μM and 2 μM; "E" an EC$_{50}$ of greater than 2 μM.

| Compound No. | IRF EC$_{50}$ (nM) | NF-κβ EC$_{50}$ (nM) |
|---|---|---|
| 1 | E | E |
| 2 | A | D |
| 3 | A | E |
| 4 | A | A |

Example 3: Evaluation of Induction of IRF and NF-KB

THP1 dual cells grown in complete media were treated with various concentrations of a compound of the present disclosure or DMSO control. Dual cells carry both secreted embryonic alkaline phosphatase (SEAP) reporter gene under the control of an IFN-β minimal promoter fused to five copies of the NF-kB consensus transcriptional response element to measure NF-kB activity and Lucia reporter gene under the control of an ISG54 minimal promoter to measure IRF activity. After 20 h incubation, IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. Any negative values were given base value 1 for plotting data in log scale for accurate demonstration of dose response. EC$_{50}$ values were generated by curve fit in Xlfit.

Cells grown in complete media were treated with various concentrations of a compound of the disclosure or DMSO control. Dual cells carry both secreted embryonic alkaline phosphatase (SEAP) reporter gene under the control of an IFN-β minimal promoter fused to five copies of the NF-kB consensus transcriptional response element to measure NF-kB activity and Lucia reporter gene under the control of an ISG54 minimal promoter to measure IRF activity. After 20 h incubation, IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. EC$_{50}$ values are generated by curve fit in Xlfit.

Example 4: Study to Determine the Efficacy of Compound 4 in a CT26 Murine Colon Carcinoma Model Using Female BALB/c Mice Mice Female BALB/c mice (BALB/c AnNcr1, Charles River) were eight weeks old on Day 1 of the study and had a body weight range of 15.1 to 19.7 g. The animals were fed ad libitum water (reverse osmosis, 1 ppm Cl) and a NIH 31 Modified and Irradiated Lab Diet consisting of 18.0% crude protein, 5.0% crude fat, and 5.0% crude fiber.

Tumor Cell Culture

CT26 murine colon carcinoma cells were grown in RPMI-1640 medium containing 10% fetal bovine serum, 2 mM glutamine, 100 units/mL penicillin G sodium, 100 μg/mL streptomycin sulfate, and 25 μg/mL gentamicin. The cells were cultured in tissue culture flasks in a humidified incubator at 37° C., in an atmosphere of 5% CO$_2$ and 95% air.

In Vivo Implantation and Tumor Growth

On the day of implantation, cultured CT26 cells were harvested during log phase growth and resuspended in phosphate buffered saline, pH 7.4 (PBS) at a concentration of $3 \times 10^6$ cells/mL. Each mouse was injected subcutaneously in the right flank with $3 \times 10^5$ tumor cells (0.1 mL cell suspension) and tumors were monitored as their volumes approached the target range of 80 to 120 mm$^3$. Eleven days after tumor cell implantation, on Day 1 of the study, animals were sorted into three groups (n=8/group) with individual tumor volumes of 63 to 126 mm$^3$, and a group mean tumor volume of 105 mm$^3$. Tumors were measured with a caliper twice weekly for the duration of the study. Tumor size was calculated using the formula:

$$\text{Tumor Volume}(\text{mm}^3) = \frac{w^2 \times l}{2}$$

wherein w is width and l is length, in mm, of a tumor. Tumor weight may be estimated with the assumption that 1 mg is equivalent to 1 mm³ of tumor volume.

Test Articles

Compound 4 was dissolved by adding the appropriate volume of sterile saline (vehicle) into each tube, vortexing, incubating at 37° C. for 2-5 minutes, followed by sonication, if needed. Preparations of Compound 4 resulted in the appropriate 0.2 and 0.6 mg/mL dosing solutions which provided 1 and 3 mg/kg doses in a dosing volume of 5 mL/kg, adjusted to the body weight of the animal. A fresh vial was prepared on each day of dosing.

Treatment

Figure 20:
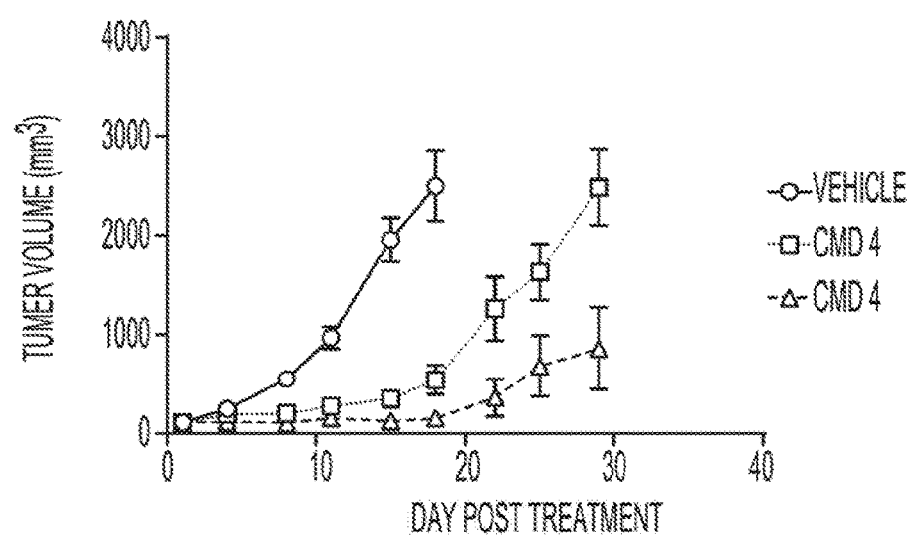
FIG. 20 depicts compound 4 administered intravenously at 1 mg/kg and 3 mg/kg to mice in a CT26 colon cancer model. Tumor growth was slowed in the compound 4 group(s) compared to the vehicle.
Figure 21:
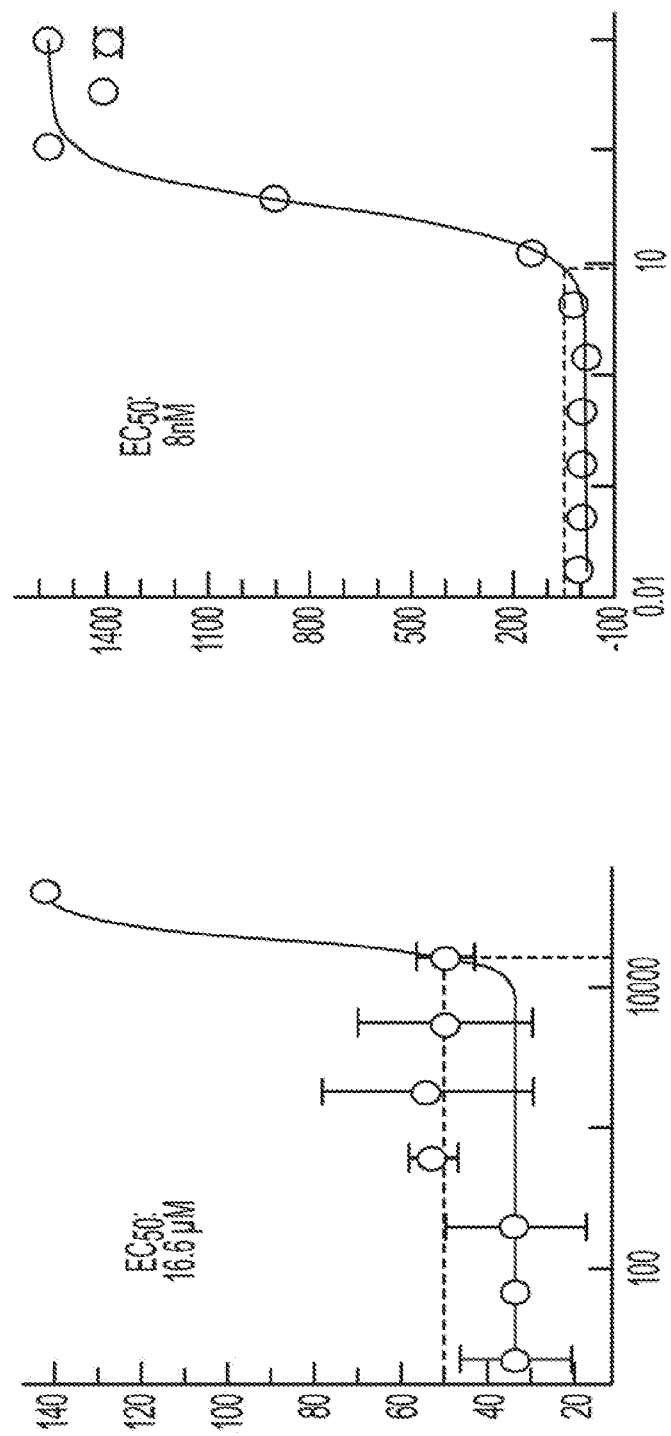
FIG. 21 depicts cells stably expressing both or either one of the reporters to measure IRF and NF-kB activity were treated with a range of concentrations of compound 1 or DMSO control for 20 hours. IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit. Compound 1 did not induce IRF activity or NF-κβ in STING KO cells. Compound 1 possess STING dependent activity.
Figure 22:
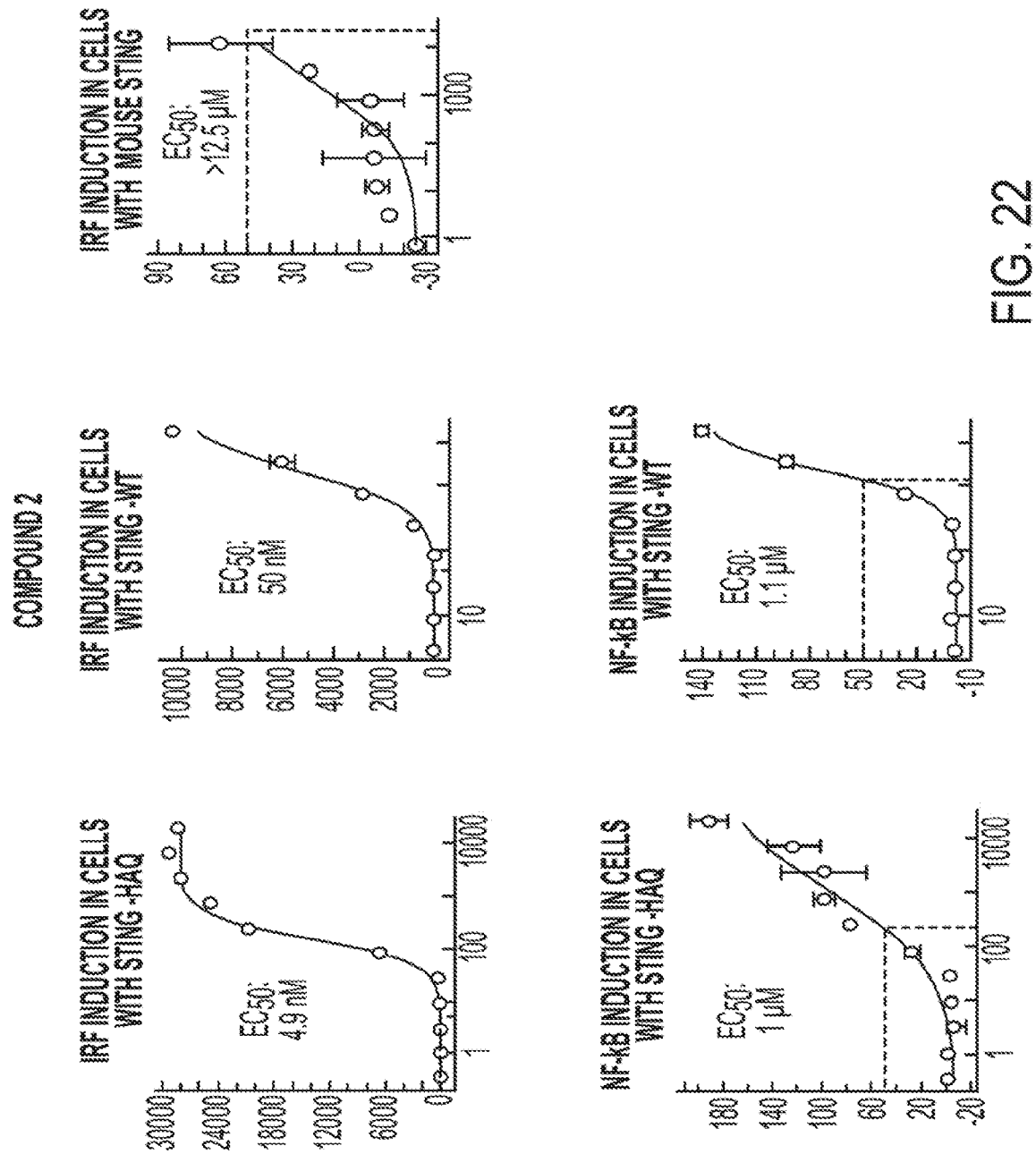
FIG. 22 depicts cells stably expressing both or either one of the reporters to measure IRF and NF-kB activity were treated with a range of concentrations of compound 2 or DMSO control for 20 hours. IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit. Compound 2 did not induce IRF activity or NF-κβ in STING KO cells. Compound 2 possess activity against wild type STING, R71H-G230A-R293Q (HAQ) variants of hSTING and wt-mSTING.
Figure 23:
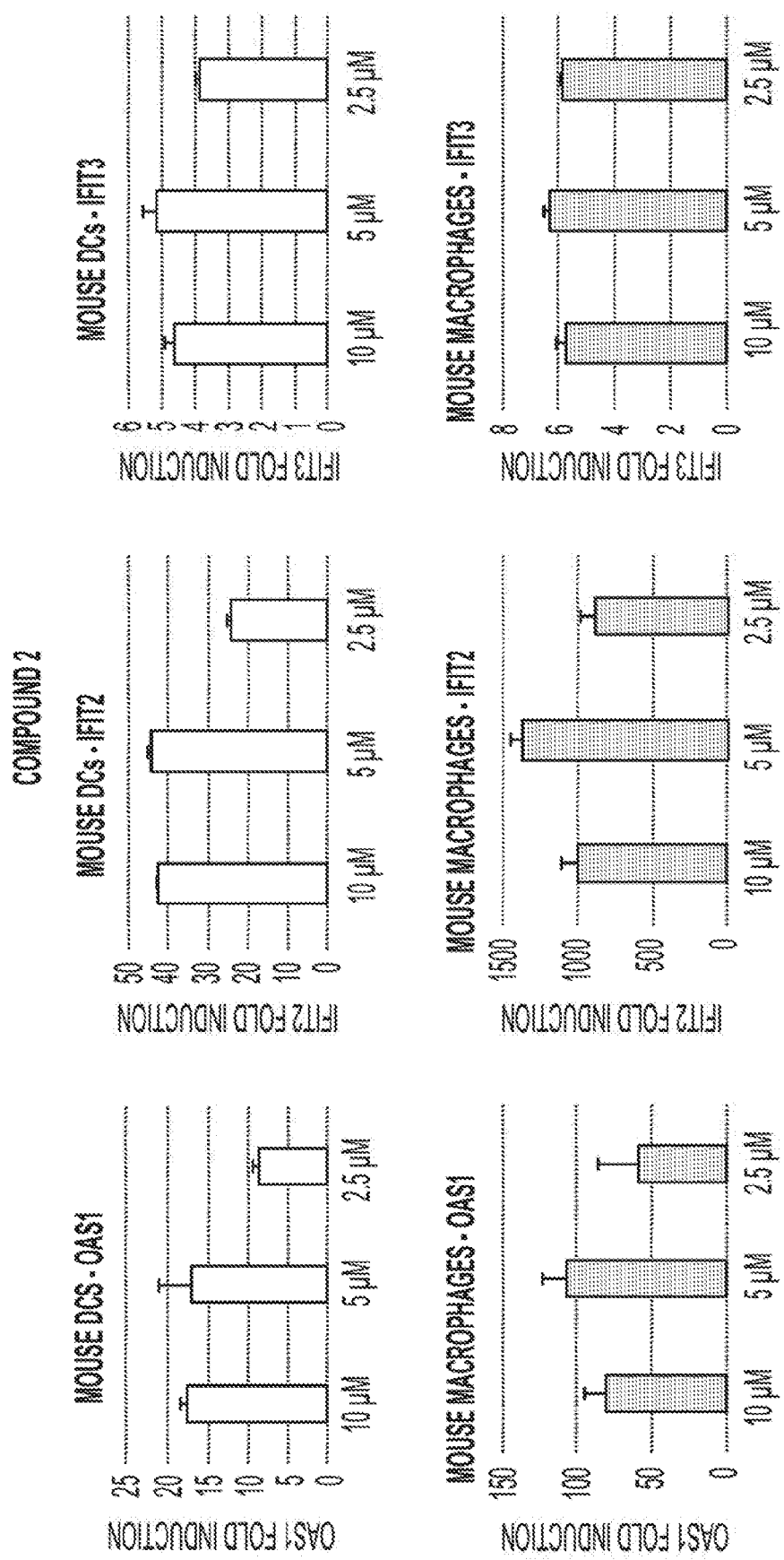
FIG. 23 depicts cryopreserved mouse bone marrow derived dendritic cells (DCs) and macrophages treated with a range of concentrations of compound 2 or DMSO control for 20 hours. Cell pellets were harvested to collect total RNA. The gene expression levels of ISGs were measured by Taqman Assays. Compound 2 induces ISG expression in mouse bone marrow derived DCs and macrophages.
Figure 24:
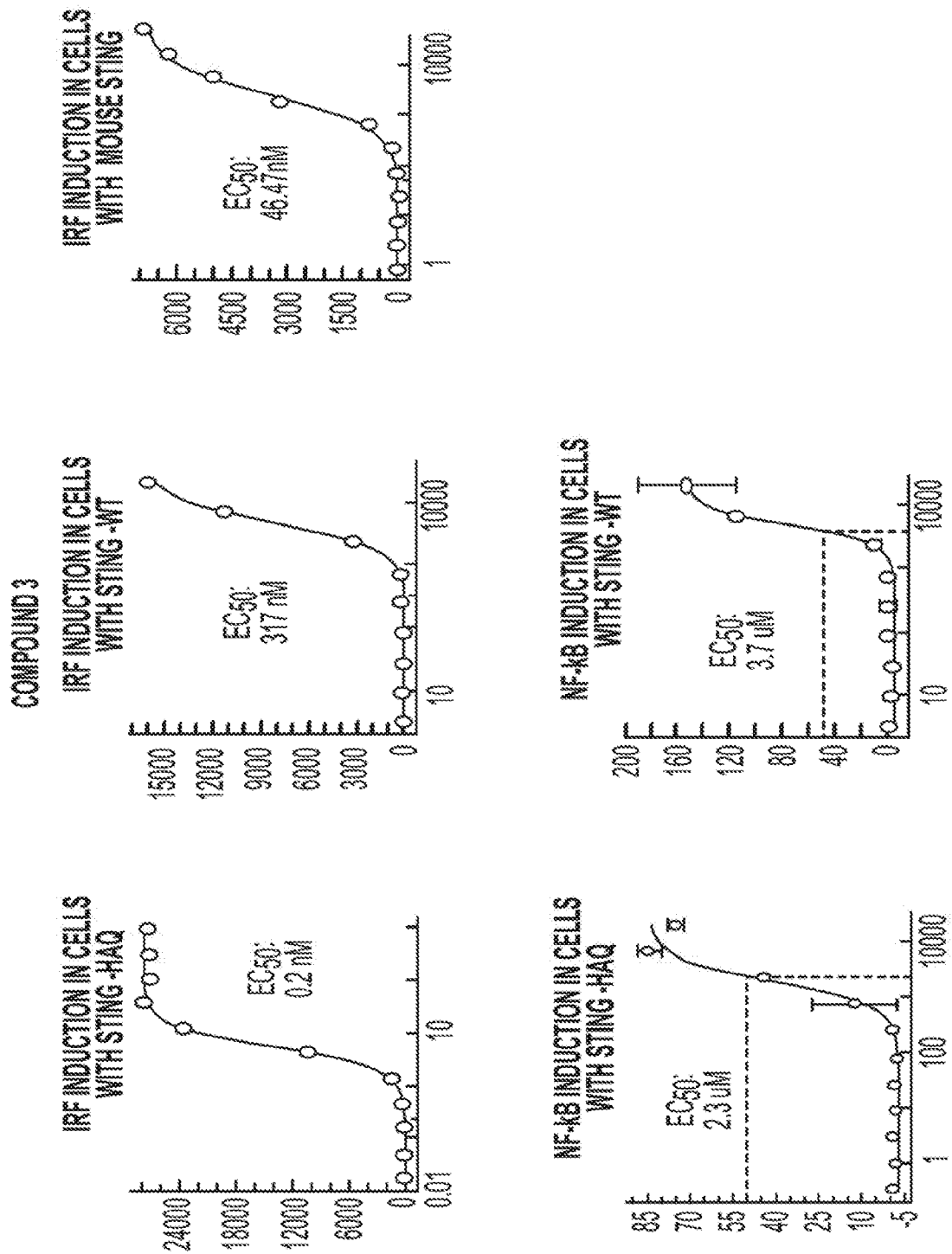
FIG. 24 depicts cells stably expressing both or either one of the reporters to measure IRF and NF-kB activity were treated with a range of concentrations of compound 3 or DMSO control for 20 hours. IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit. Compound did not induce IRF activity or NF-κβ in STING KO cells. Compound 3 possess activity against wild type STING, STING-HAQ and wt-mSTING.
Figure 25:
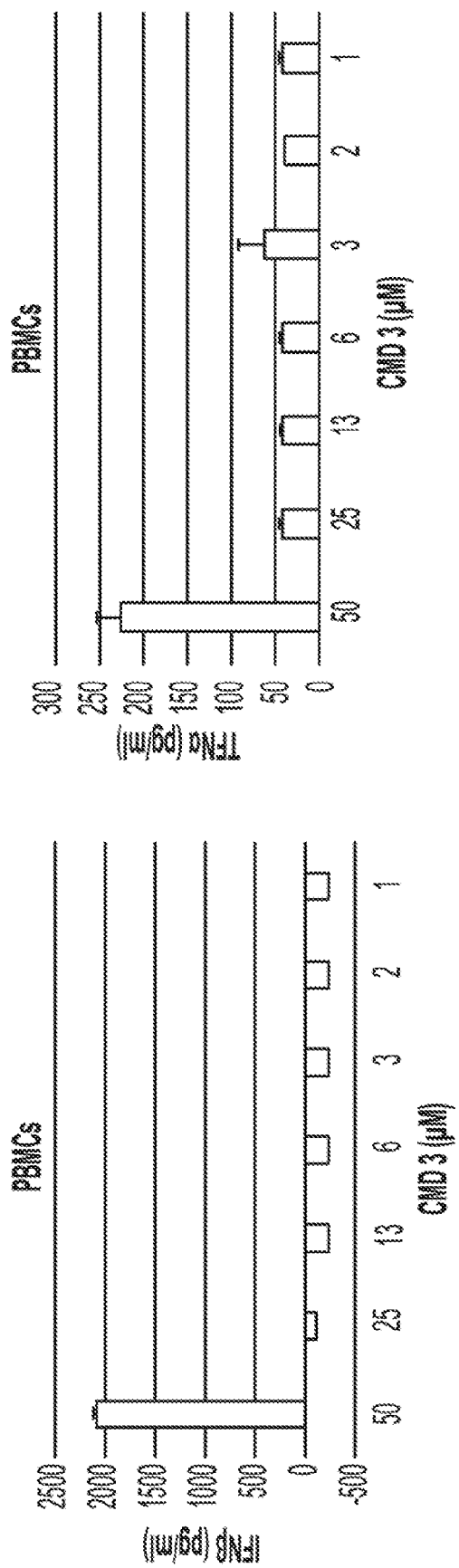
FIG. 25 depicts freshly isolated peripheral blood mononuclear cells (PBMCs) treated with a range of concentrations of compound 3 or DMSO control for 20 hours. Supernatants were collected to measure IFNb and TNFa secretion by Verikine-Human IFN beta Serum ELISA kit and Human TNF Alpha ELISA kit respectively. The amount of cytokine releases into supernatant was calculated by a standard curve. Compound 3 induces IFNβ and TNFα secretion in PBMCs after treatment.
Figure 26:
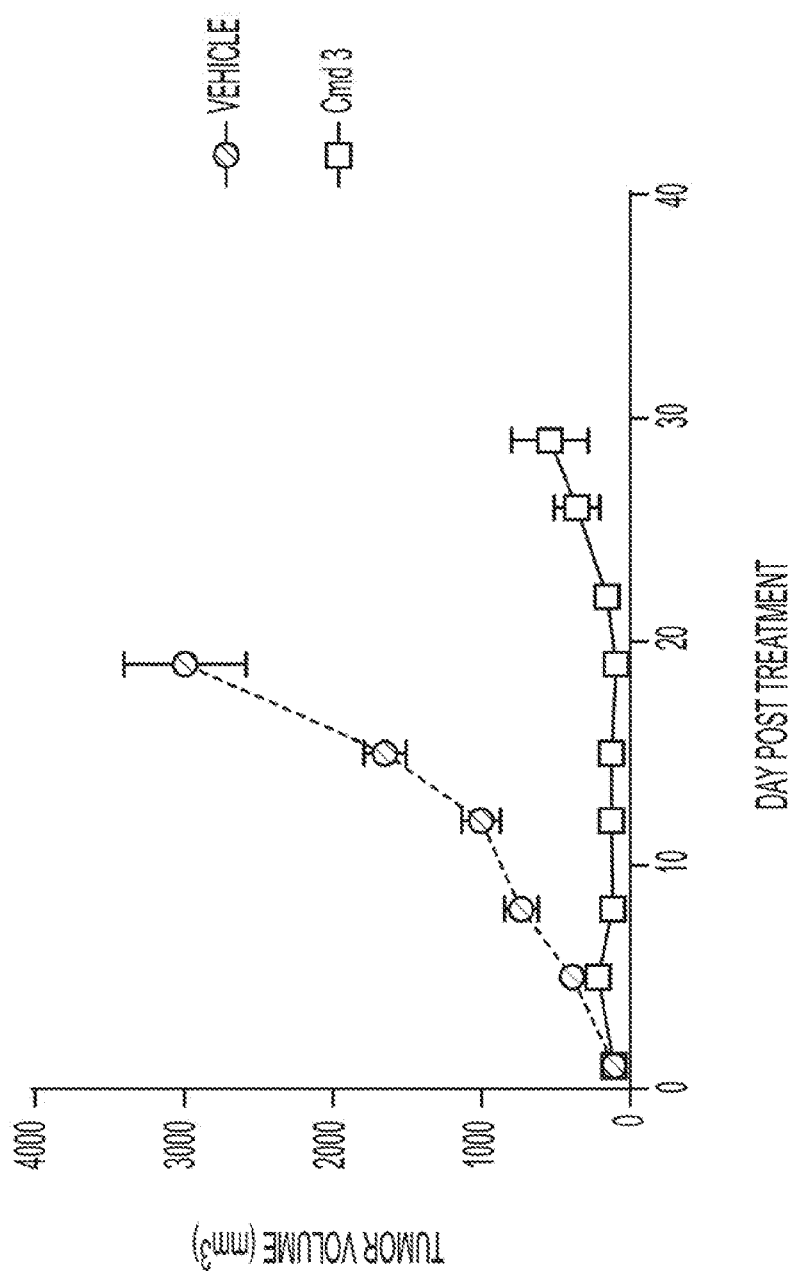
FIG. 26 depicts compound 3 administered intravenously at 3 mg/kg to mice in a CT26 colon cancer model. Tumor growth was slowed in the compound 3 group when compared to the vehicle.
Figure 27:
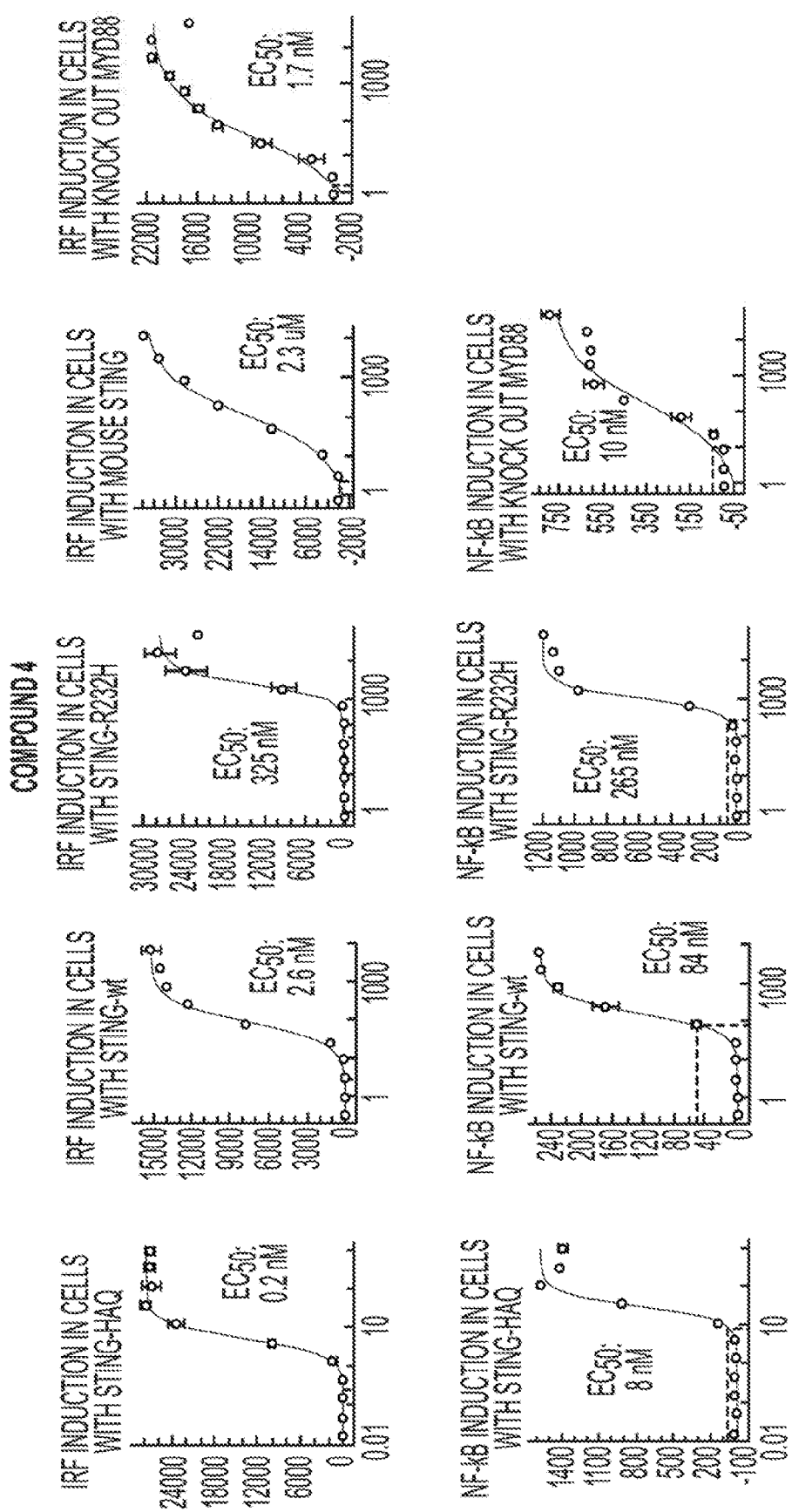
FIG. 27 depicts cells stably expressing both or either one of the reporters to measure IRF and NF-kB activity were treated with a range of concentrations of compound 4 or DMSO control for 20 hours. IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit. Compound 4 did not induce IRF activity or NF-κβ in STING KO cells. Compound 4 possess activity against wild type STING, R71H-G230A-R293Q (HAQ), R232H variants of hSTING, MYD88 knock out cells and wt-mSTING.
Figure 28:
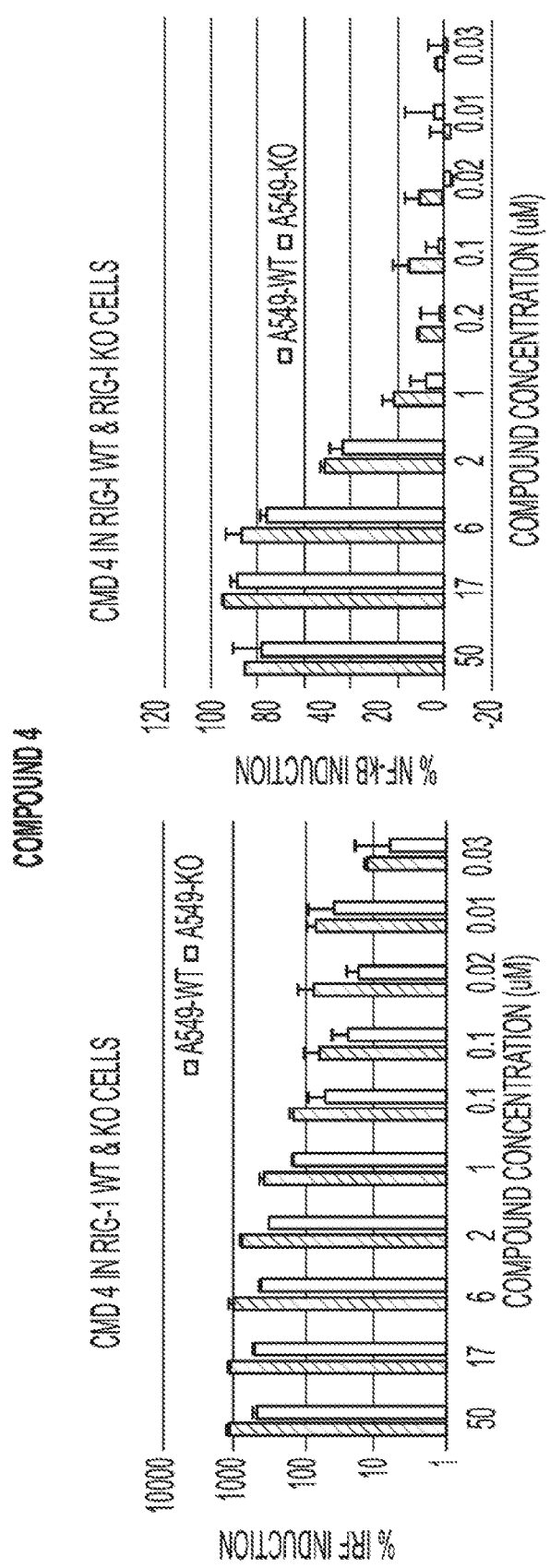
FIG. 28 depicts cells stably expressing both or either one of the reporters to measure IRF and NF-kB activity were treated with a range of concentrations of compound 4 or DMSO control for 20 hours. IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit. RIG-I is not implicated in the mechanism of action of compound 4.
Figure 29:
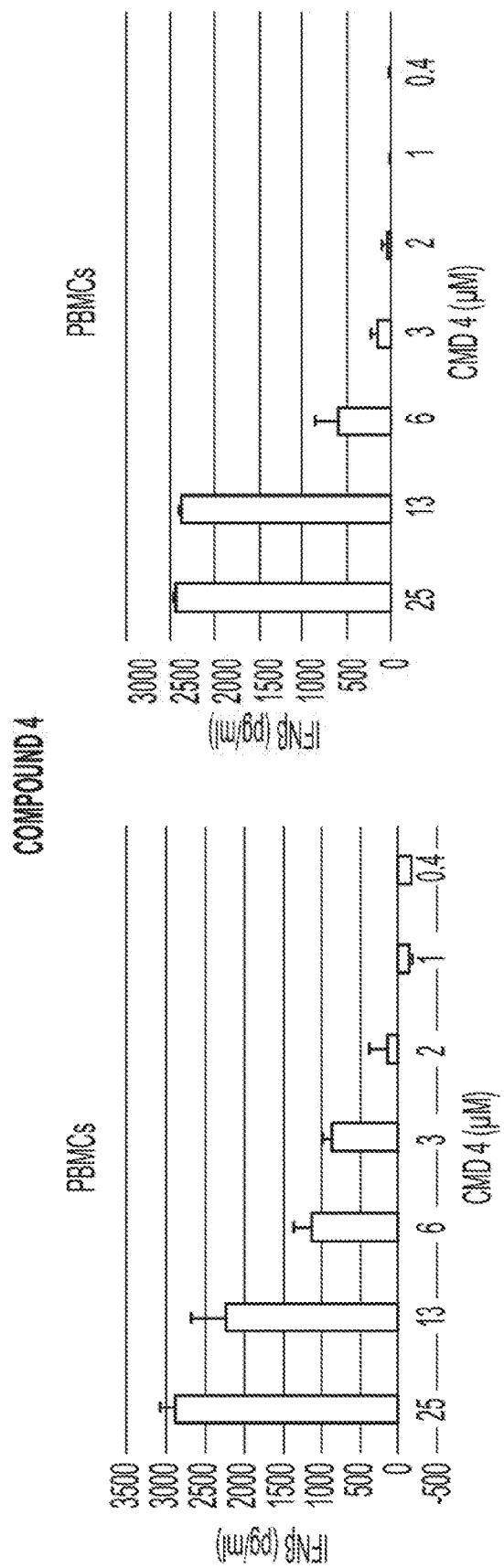
FIG. 29 depicts freshly isolated PBMCs that were treated with a range of concentrations of compound 4 or DMSO control for 20 hours. Supernatants were collected to measure IFNb and TNFa secretion by Verikine-Human IFN beta Serum ELISA kit and Human TNF Alpha ELISA kit respectively. The amount of cytokine releases into supernatant was calculated by a standard curve. Compound 4 induces IFNβ and TNFα secretion in PBMCs after treatment.
Figure 30:
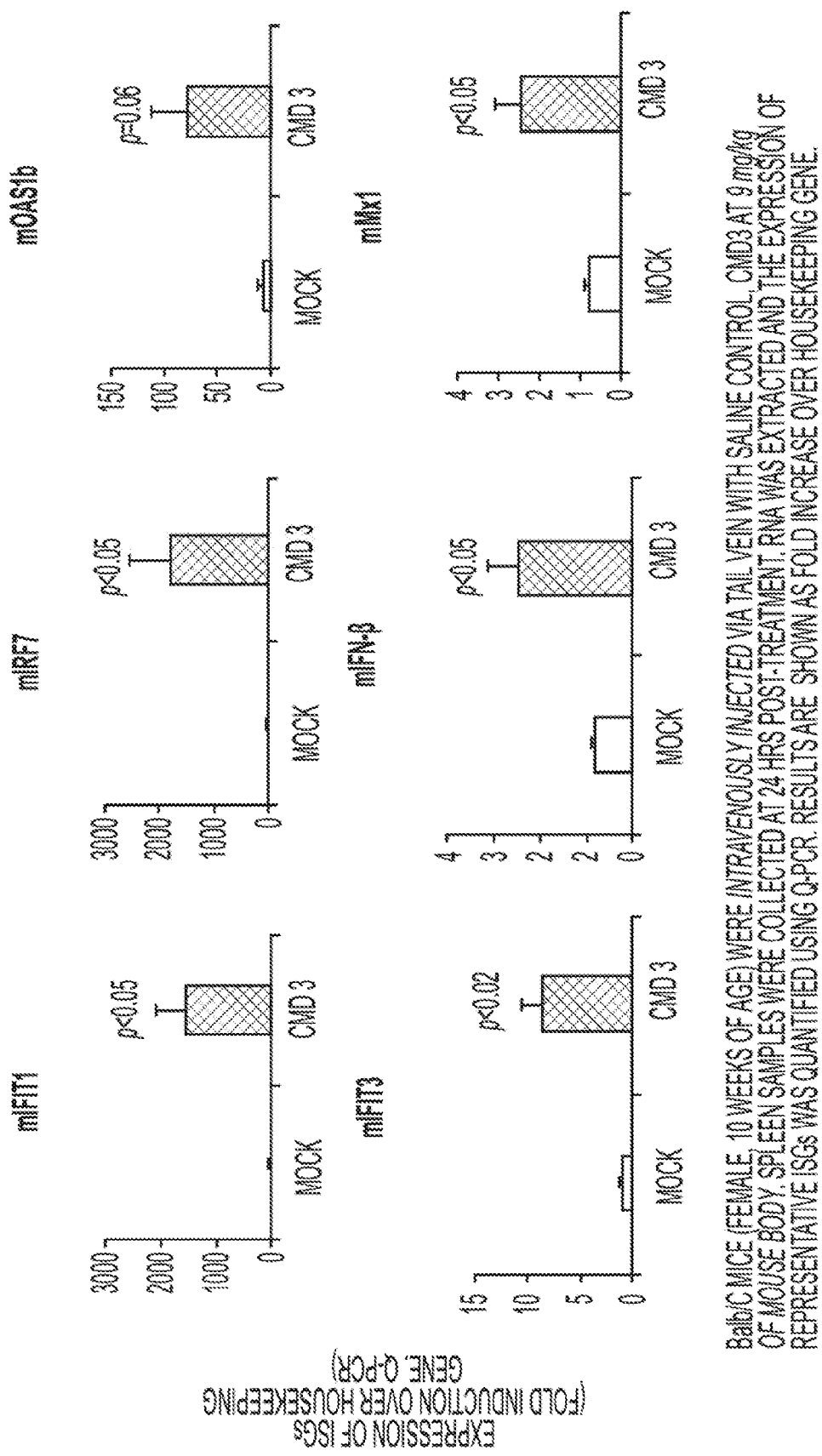
FIG. 30 depicts that compound 3 administered intravenously (9 mg/kg) strongly induced upregulation of ISGs/type I IFN response in normal Balb/C mice.
Figure 31A:
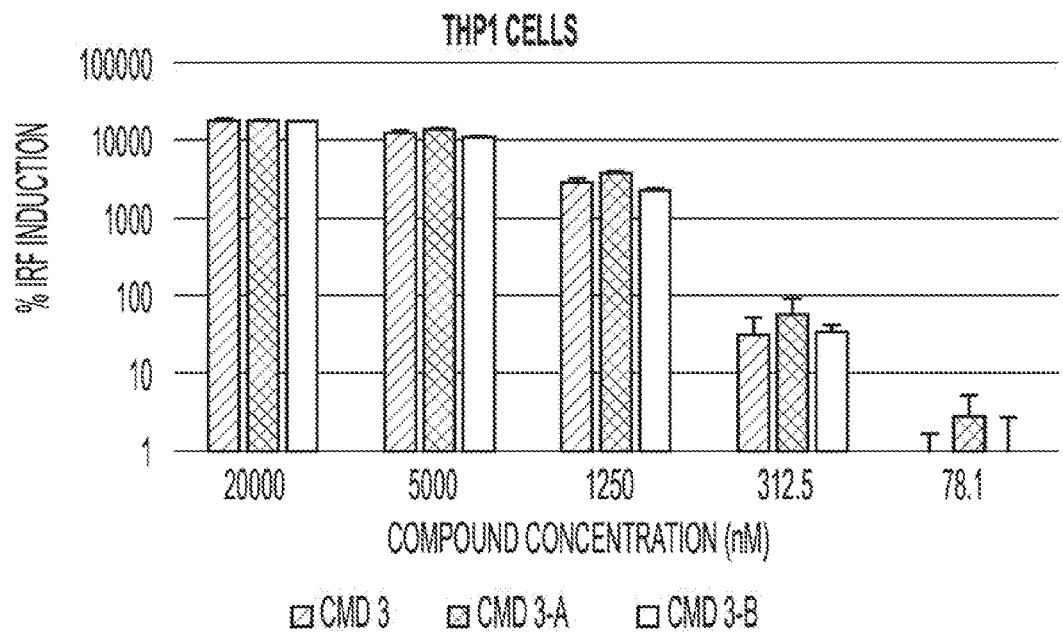
FIG. 31A depicts cells treated with various concentrations of compound 3 and two of its diastereomers (3A and 3B), or DMSO control for 20 hours. Cells stably expressed one or both of the reporters used to measure IRF activity. IRF activity was assessed using QUANTI-luc to measure levels of Lucia. % induction was calculated from fold change in luminescence/absorbance compared to DMSO treated sample.
Figure 31B:
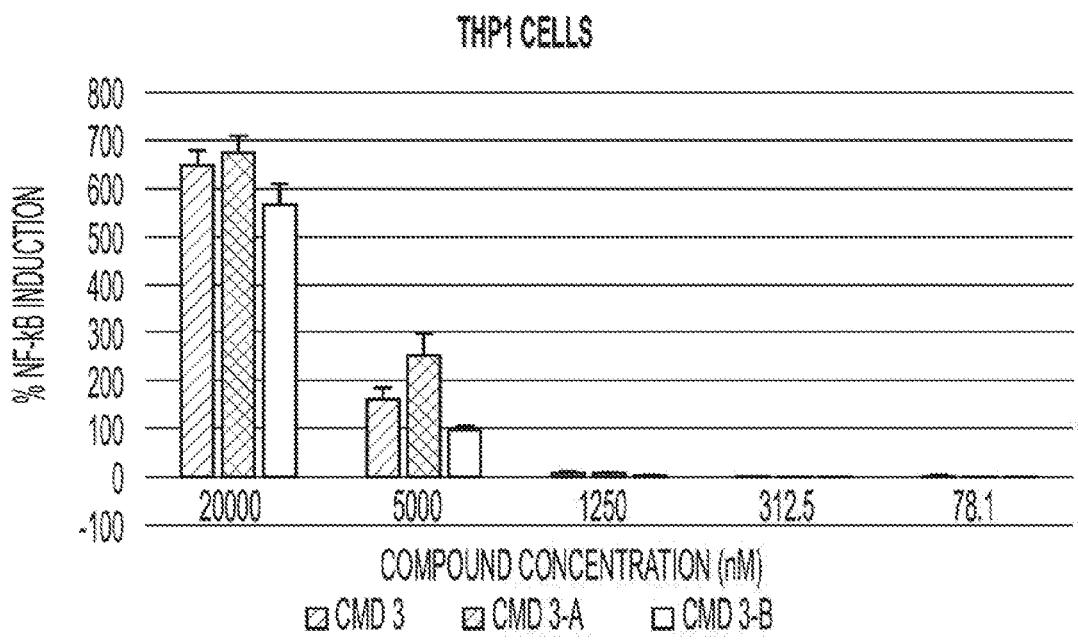
FIG. 31B depicts cells treated with various concentrations of compound 3 and two of its diastereomers (3-A and 3-B), or DMSO control for 20 hours. Cells stably expressed one or both of the reporters used to measure NF-kB activity. NF-kB activity was determined by measure SEAP levels at 620-655 nm. % induction was calculated from fold change in luminescence/absorbance compared to DMSO treated sample.
Figure 31C:
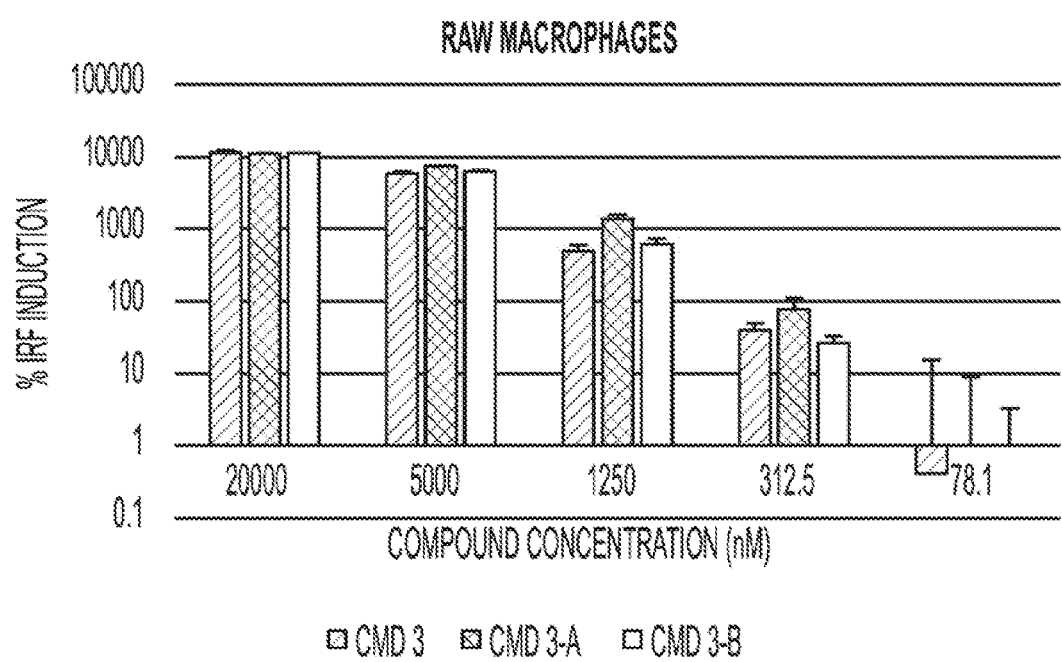
FIG. 31C depicts cells treated with various concentrations of compound 3 and two of its diastereomers (3-A and 3-B), or DMSO control for 20 hours. Cells stably expressed one or both of the reporters used to measure NF-kB activity. IRF activity was assessed using QUANTI-luc to measure levels of Lucia. % induction was calculated from fold change in luminescence/absorbance compared to DMSO treated sample.
Figure 32:
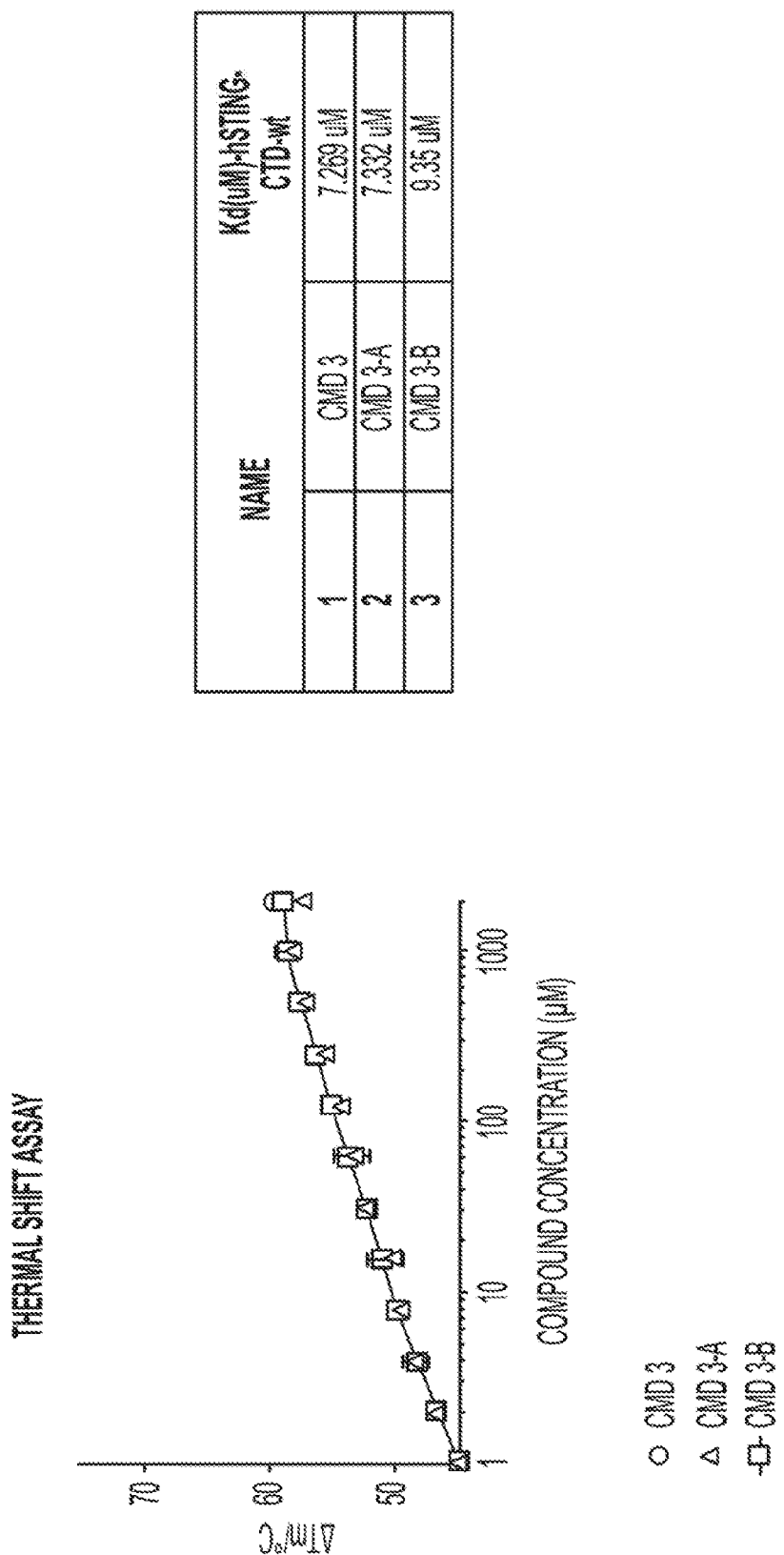
FIG. 32 depicts compound 3 and its diastereomers (3-A and 3-B) bind to STING with high affinity. Thermal shift assay was conducted with 0.1 mg/mL of STING CTD with various dilutions compound 3 and two of its diastereomers (3-A and 3-B) from 2 mM to 0.05 uM in 10 mM HEPES (pH 7.5), 140 mM NaCl and a 5× dilution of SYPRO Orange dye (Invitrogen). Fluorescence as a function of temperature was recorded using a Real Time PCR machine (Thermo Fisher). The temperature gradient was performed in the range of 25-80° C. with a ramp of 0.2° C. over the course of 60 minutes. Data was analyzed with the Thermal Shift Software (Thermo Fisher) and DSF analysis. The Derivative model was used to fit the fluorescence data to obtain the midpoint temperature for the thermal protein unfolding transition (Tm) using the curve-fitting software Prism.
Figure 33:
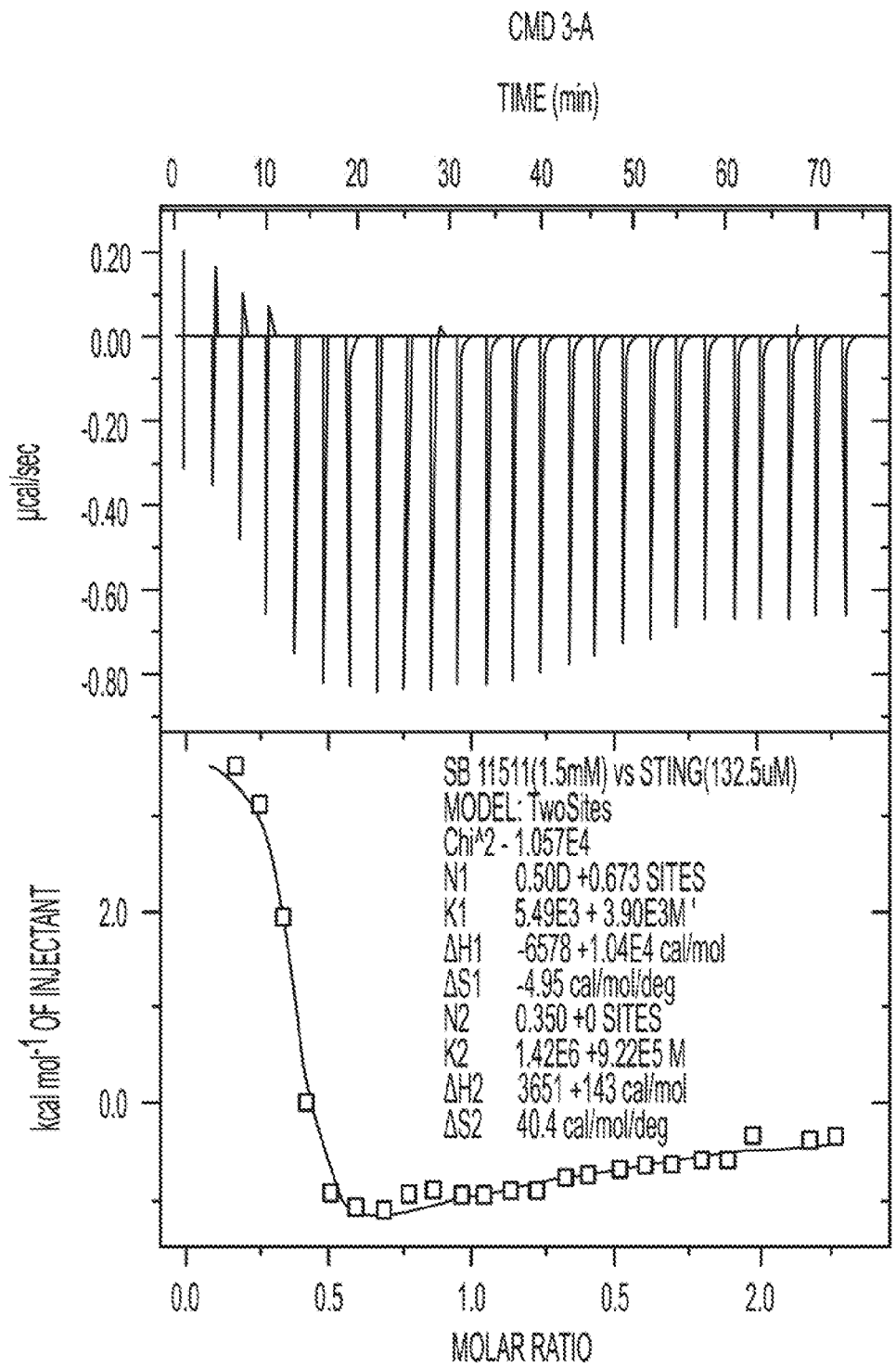
FIG. 33 depicts compound 3 and its diastereomers (3-A and 3-B) bind to STING with high affinity. Isothermal Calorimetry was carried out on a MicroCal Itc200 at 25° C. 1.5 mM. compound 3 and two of its diastereomers (3-A and 3-B) were titrated against 132.5 µM human wtSTING-CTD (with SUMO tag). After buffer subtraction, the resulting binding curve was fit using either two binding sites (3-A) or one binding site (3-B).
Figure 33:
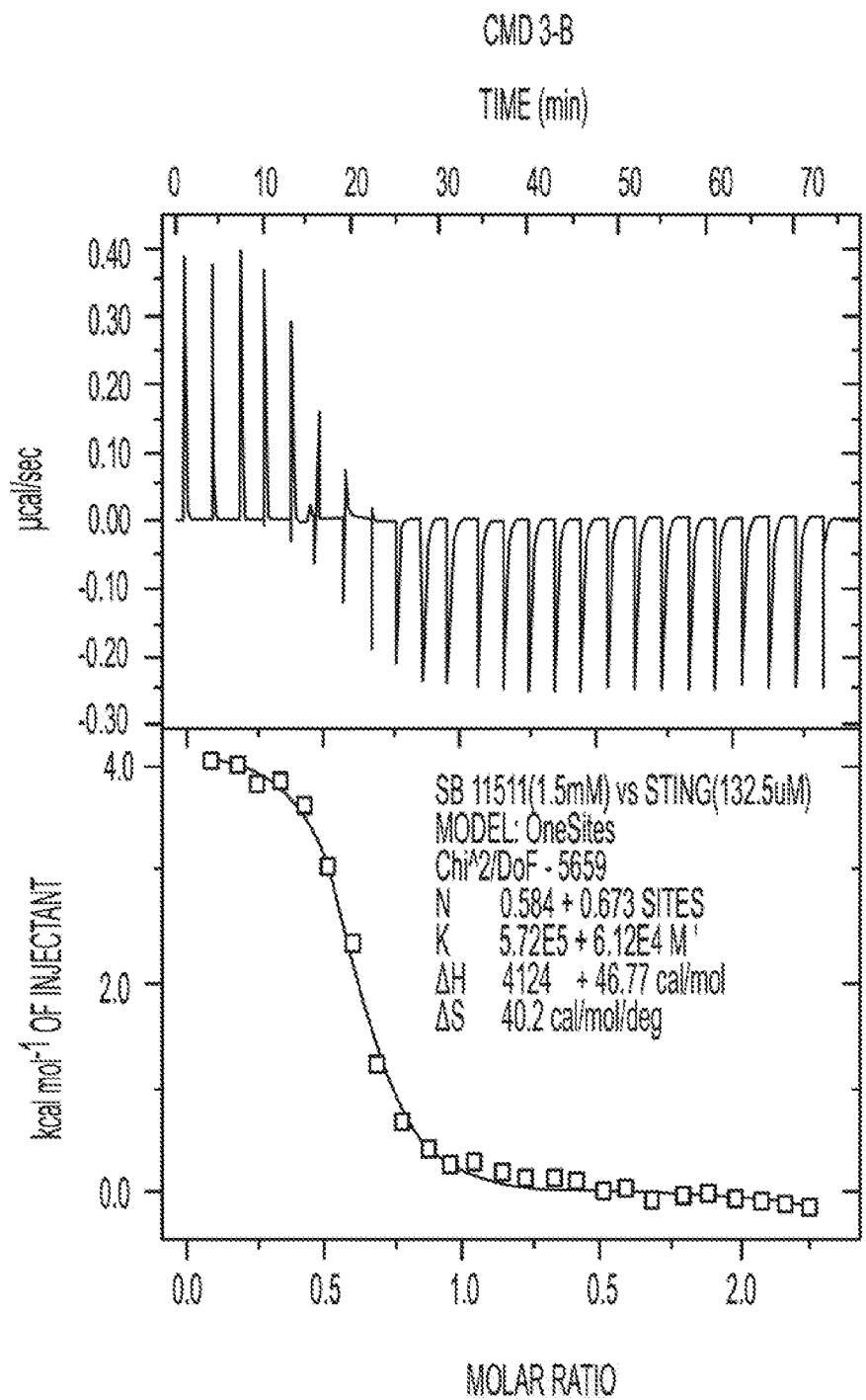
Figure 34A:
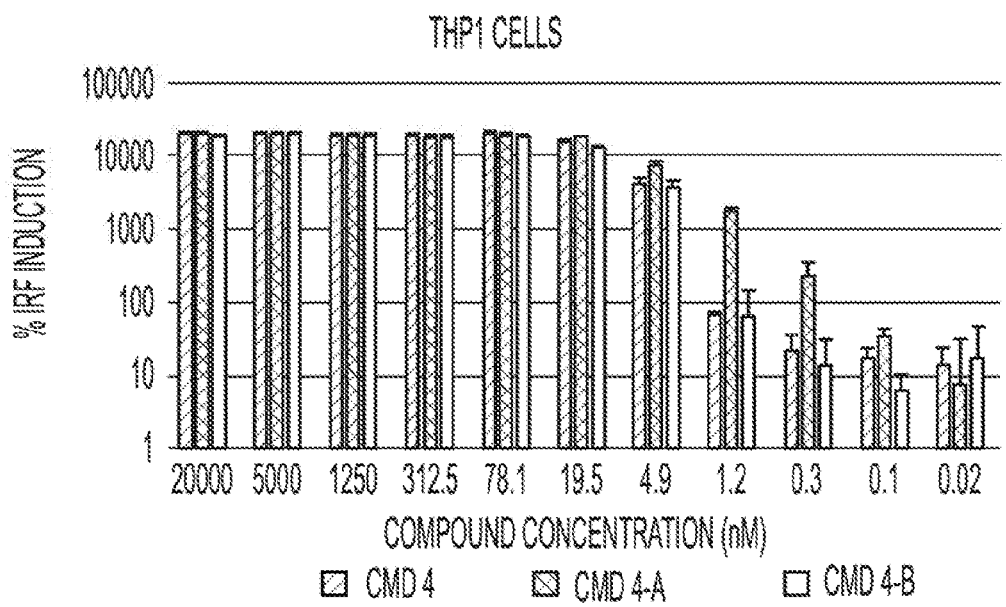
FIG. 34A depicts compound 4 and its diastereomers (4-A and 4-B) are efficacious in inducing IRF signaling. Cells were treated with various concentrations of compound 3 and two of its diastereomers (4-A and 4-B), or DMSO control for 20 hours. Cells stably expressed one or both of the reporters used to measure IRF activity. IRF activity was assessed using QUANTI-luc to measure levels of Lucia. % induction was calculated from fold change in luminescence/absorbance compared to DMSO treated sample.
Figure 34B:
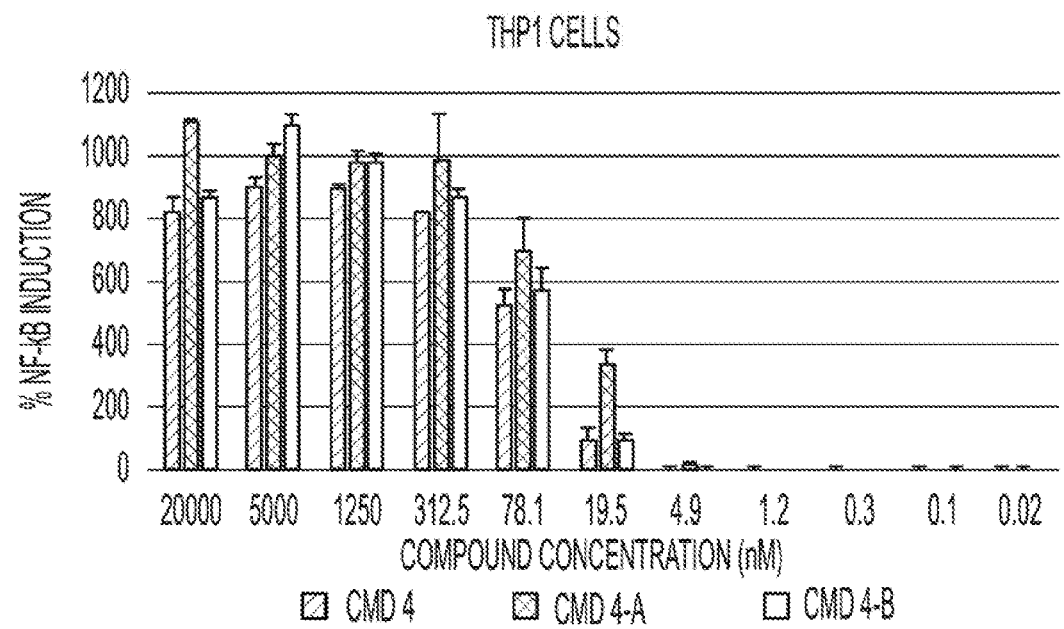
FIG. 34B depicts compound 4 and its diastereomers (4-A and 4-B) are efficacious in inducing NF-kB signaling. Cells were treated with various concentrations of compound 4 and two of its diastereomers (4-A and 4-B), or DMSO control for 20 hours. Cells stably expressed one or both of the reporters used to measure NF-kB activity. NF-kB activity was determined by measure SEAP levels at 620-655 nm. % induction was calculated from fold change in luminescence/absorbance compared to DMSO treated sample.
Figure 34C:
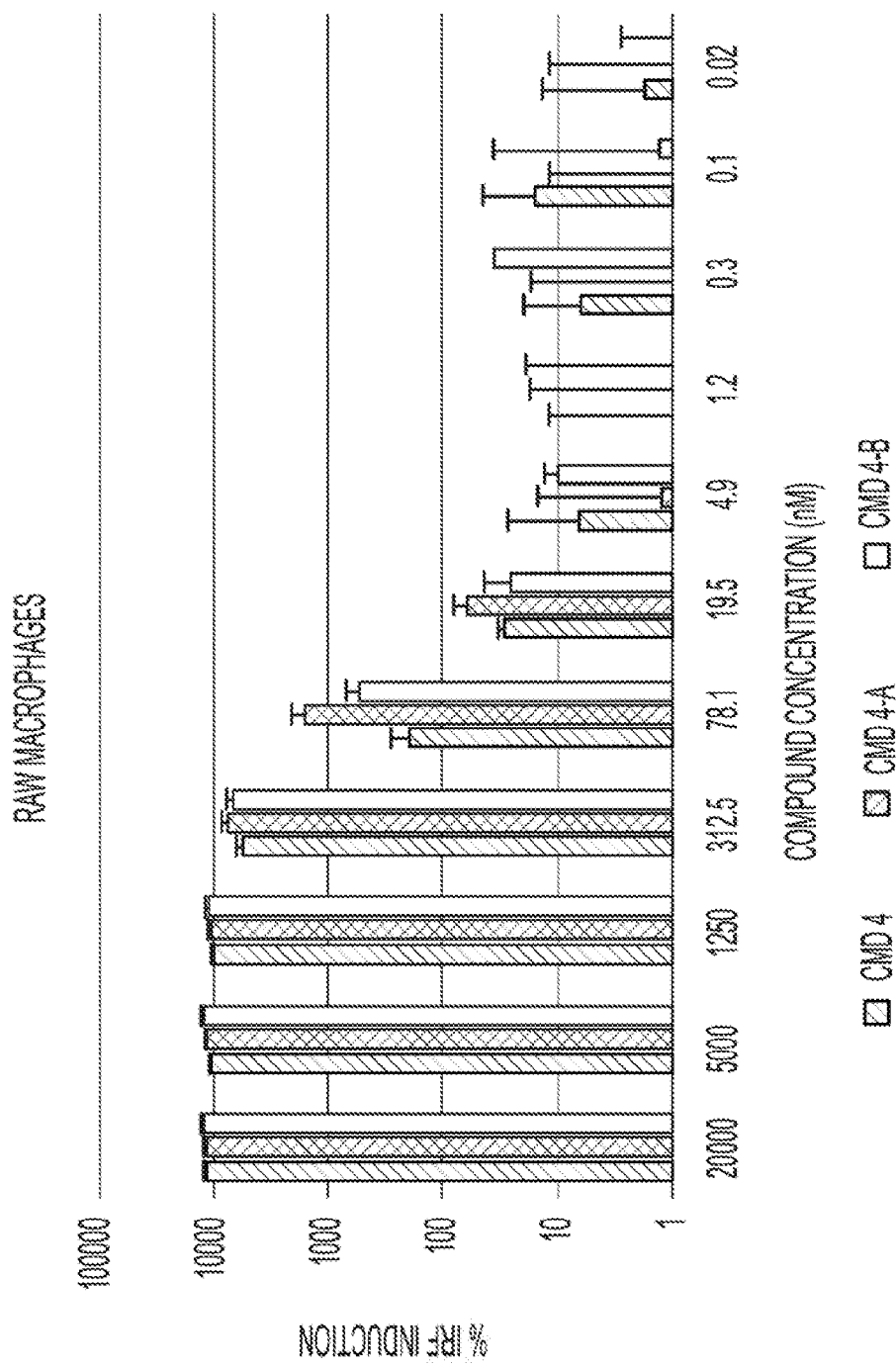
FIG. 34C depicts compound 4 and its diastereomers (4-A and 4-B) are efficacious in inducing IRF signaling. Cells were treated with various concentrations of compound 4 and two of its diastereomers (4-A and 4-B), or DMSO control for 20 hours. Cells stably expressed one or both of the reporters used to measure IRF activity. IRF activity was assessed using QUANTI-luc to measure levels of Lucia. % induction was calculated from fold change in luminescence/absorbance compared to DMSO treated sample.

On Day 1 of the study, three groups of BALB/c mice (n=8) began dosing according to the protocol in FIG. 20. Compound 4 and vehicle were administered intravenously (i.v.). Group 1 received vehicle on Days 1, 5, 9, and 14. Groups 2 and 3 received CMD 4 at 1 and 3 mg/kg, respectively, on Days 1, 5, 9, and 14.

Tumor Growth Delay Endpoint

The study endpoint was a tumor volume of 2000 mm³ or Day 30, whichever came first. The study ended on Day 29. The study protocol specified a tumor growth delay assay based on the median time-to-endpoint (TTE) in a treated group versus the control group. Tumors were measured using calipers twice per week, and each animal was euthanized for tumor progression (TP) when its tumor reached the 2000 mm³ volume endpoint. The TTE for each mouse was calculated with the following equation:

$$TTE = \frac{\log_{10}(\text{endpoint volume}) - b}{m}$$

where b is the intercept and m is the slope of the line obtained by linear regression of a log-transformed tumor growth data set. The data set is comprised of the first observation that exceeded the study endpoint volume and the three consecutive observations that immediately preceded the attainment of the endpoint volume. Any animal that did not reach endpoint was euthanized at the end of the study and assigned a TTE value equal to the last day of the study (Day 29). In instances in which the log-transformed calculated TTE preceded the day prior to reaching endpoint or exceeded the day of reaching tumor volume endpoint, a linear interpolation was performed to approximate TTE.

On Day 29, MTV (n) was defined as the median tumor volume of the number of animals, n, that survived to the last day and whose tumors had not reached the volume endpoint. Any animal determined to have died from treatment-related (TR) causes was to be assigned a TTE value equal to the day of death. Any animal that died from non-treatment-related (NTR) causes was to be excluded from the analysis. Treatment outcome was evaluated from tumor growth delay (TGD), which was defined as the increase in the median TTE for a treatment group compared to the control group:

TGD=T−C expressed in days, or as a percentage of the median TTE of the control group:

$$\% \; TGD = \frac{T - C}{C} \times 100$$

wherein T is the median TTE for a treatment group and C is the median TTE for the control group.

Tumor Growth Inhibition (TGI) Analysis

The study endpoint was defined as a mean tumor volume of 2000 mm³ in the control group (sum of both flank tumors) or 30 days, whichever came first. The study reached TGI endpoint on Day 18. Treatment efficacy was determined using data from the final day that all control animals remained on study (Day 18). The MTV (n), the median tumor volume for the number of animals, n, on the final day, was determined for each group. Percent tumor growth inhibition (% TGI) was defined as the difference between the MTV of the designated control group (Group 1) and the MTV of the drug-treated group, expressed as a percentage of the MTV of the control group:

$$\% \; TGI = \left( \frac{MTV_{control} - MTV_{drug-treated}}{MTV_{control}} \right) \times 100 = [1 - (MTV_{drug-treated} / MTV_{control})] \times 100$$

The data set for TGI analysis includes all animals in a group, except those euthanized for sample collection (ES) and those that die due to treatment-related (TR) or non-treatment-related (NTR) causes.

Criteria for Regression Responses

Treatment efficacy was also determined from the number of regression responses. Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm³ for one or more of these three measurements. In a CR response, the tumor volume is less than 13.5 mm³ for three consecutive measurements during the course of the study. Animals were scored only once during the study for a PR or CR event and only as CR if both PR and CR criteria were satisfied. Any animal with a CR response on the last day of the study is additionally classified as a tumor-free-survivor (TFS).

Toxicity

Animals were weighed daily for the first five days of the study and twice weekly thereafter. The mice were observed frequently for health and overt signs of any adverse treatment related (TR) side effects, and noteworthy clinical observations were recorded. Individual body weight loss was monitored per protocol, and any animal with weight loss exceeding 30% for one measurement, or exceeding 25% for three measurements, was to be euthanized for health as a TR death. If group mean body weight recovered, dosing may resume in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity is considered above the maximum tolerated dose (MTD). A death was to be classified as TR if it was attributable to treatment side effects as evidenced by clinical signs and/or necropsy, or may also be classified as TR if due to unknown causes during the dosing period or within 14 days of the last dose. A death was classified as NTR if there was evidence that the death was related to the tumor model, rather than treatment-related. NTR deaths are further categorized as NTRa (due to accident or human error), NTRm (due to necropsy-confirmed tumor dissemination by invasion or metastasis), and NTRu (due to unknown causes).

Study Design

TABLE 2

Protocol Design for the CT26 Study

| Group | n | Agent | mg/kg | Route | Schedule |
|---|---|---|---|---|---|
| 1 | 8 | vehicle | — | iv | Days 1, 5, 9, 14 |
| 2 | 8 | CMD 4 | 1 | iv | Days 1, 5, 9, 14 |
| 3 | 8 | CMD 4 | 3 | iv | Days 1, 5, 9, 14 |

Table 1 displays the study design as of Day 1 of the study. Vehicle is saline.

EQUIVALENTS

The disclosures of each and every patent, patent application, and publication cited herein are hereby incorporated by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

What is claimed is:

1. A compound of Formula (I):

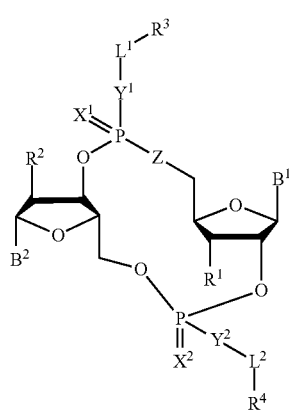

Formula (I)

or a pharmaceutically acceptable salt or stereoisomer thereof, wherein:

Z is either S or O;

$B^1$ is a purinyl nucleobase and $B^2$ is a pyrimidinyl nucleobase; or $B^2$ is a purinyl nucleobase and $B^1$ is a pyrimidinyl nucleobase;

each of $X^1$ and $X^2$ is independently O or S;

each of $Y^1$ and $Y^2$ is independently O, S, or $NR^5$;

each of $L^1$ and $L^2$ is independently absent, $C_1$-$C_6$ alkyl or $C_1$-$C_6$ heteroalkyl, wherein each alkyl and heteroalkyl is optionally substituted with $R^6$;

each of $R^1$ and $R^2$ is independently hydrogen, halo, —CN, $C_1$-$C_{20}$ alkyl, or $OR^7$;

each of $R^3$ and $R^4$ is independently hydrogen, $C_1$-$C_{20}$ alkyl, $C_1$-$C_{20}$ heteroalkyl, $OC(O)OC_1$-$C_{20}$ alkyl, cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or $C_1$-$C_{20}$ alkyl;

$R^6$ is halo, —CN, $C_1$-$C_{20}$ alkyl, $OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, $C_1$-$C_{20}$ alkyl, cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently $C_1$-$C_{20}$ alkyl, $C_1$-$C_{20}$ heteroalkyl, $C(O)$—$C_1$-$C_{20}$ alkyl, $OC(O)$—$C_1$-$C_{20}$ alkyl, $C(O)O$—$C_1$-$C_{20}$ alkyl, $OC(O)O$—$C_1$-$C_{20}$ alkyl, $C(O)N(R^5)$—$C_1$-$C_{20}$ alkyl, $N(R^5)C(O)$—$C_1$-$C_{20}$ alkyl, $OC(O)N(R^5)$—$C_1$-$C_{20}$ alkyl, O-aryl, O-heteroaryl, C(O)-aryl, C(O)-heteroaryl, OC(O)-aryl, C(O)O-aryl, OC(O)-heteroaryl, C(O)O-heteroaryl, C(O)O-aryl, C(O)O-heteroaryl, $C(O)N(R^5)$-aryl, $C(O)N(R^5)$-heteroaryl, $N(R^5)C(O)$-aryl, $N(R^5)_2C(O)$-aryl, or $N(R^5)C(O)$-heteroaryl, $S(O)_2N(R^5)$-aryl, wherein each alkyl, heteroalkyl, aryl, and heteroaryl is optionally substituted by one or more $R^9$; and each $R^9$ is independently $C_1$-$C_{20}$ alkyl, O—$C_1$-$C_{20}$ alkyl, $C_1$-$C_{20}$ heteroalkyl, halo, —CN, OH, oxo, aryl, heteroaryl, O-aryl, or O-heteroaryl.

2. The compound of claim 1, wherein the compound is a compound of Formula (I-a), (I-b), (I-c), or (I-d):

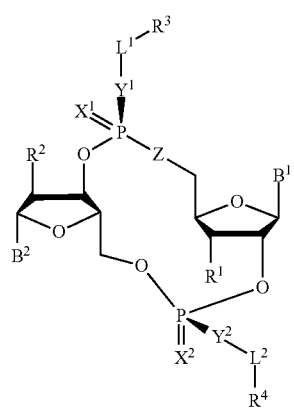

Formula (I-a)

Formula (I-b)

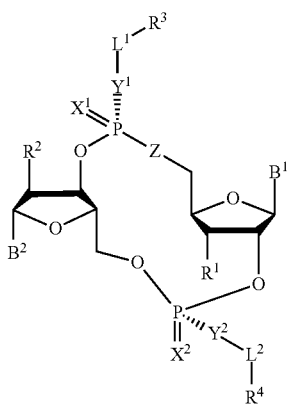

Formula (I-c)

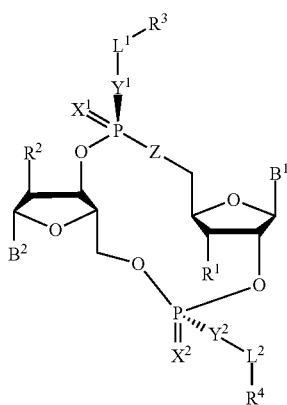

Formula (I-d)

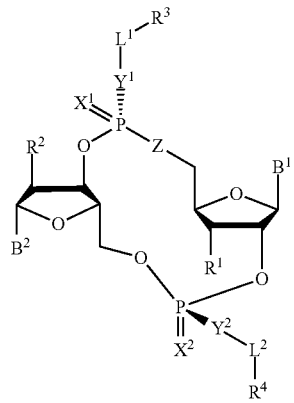

or a pharmaceutically acceptable salt thereof.

3. The compound of claim 1, wherein Z is O.

4. The compound of claim 1, wherein Z is S.

5. The compound of claim 1, wherein $B^2$ is adeninyl and $B^1$ is uracilyl.

6. The compound of claim 1, wherein $B^1$ is adeninyl or guaninyl and $B^2$ is cytosinyl, thyminyl, or uracilyl; or $B^2$ is adeninyl or guaninyl and $B^1$ is cytosinyl, thyminyl, or uracilyl.

7. The compound of claim 1, wherein $B^1$ is adeninyl and $B^2$ is uracilyl.

8. The compound of claim 1, wherein each of $R^1$ and $R^2$ is independently hydrogen, halo, or $OR^7$.

9. The compound of claim 1, wherein each of $R^1$ and $R^2$ is independently halo.

10. The compound of claim 1, wherein each of $X^1$ and $X^2$ is independently O.

11. The compound of claim 1, wherein each of $Y^1$ and $Y^2$ is independently O or S.

12. The compound of claim 1, wherein one of $Y^1$ or $Y^2$ is O and the other of $Y^1$ or $Y^2$ is S.

13. The compound of claim 1, wherein each of $L^1$ and $L^2$ is independently $C_1$-$C_6$ alkyl.

14. The compound of claim 1, wherein each of $R^3$ and $R^4$ is independently hydrogen, aryl, or heteroaryl, wherein aryl and heteroaryl is optionally substituted with 1-5 $R^8$.

15. The compound of claim 1, wherein $R^3$ is aryl or heteroaryl, each of which is optionally substituted with 1-5 $R^8$, and $R^4$ is hydrogen.

16. The compound of claim 1, wherein $R^3$ is phenyl substituted with 1 $R^8$ and $R^4$ is hydrogen.

17. The compound of claim 1, wherein each of $R^3$ and $R^4$ is independently phenyl substituted with 1 $R^8$.

18. The compound of claim 1, wherein each of $Y^1$ and $Y^2$ is O and each of $R^3$ and $R^4$ is independently hydrogen.

19. The compound of claim 1, wherein $Y^2$ is O and $R^4$ is hydrogen.

20. The compound of claim 1, wherein $Y^1$ is S and $R^3$ is substituted with 1 $R^8$.

21. The compound of claim 1, wherein $R^8$ is C(O)-aryl optionally substituted by 1-5 $R^9$.

22. The compound of claim 21, wherein $R^9$ is O—$C_1$-$C_{12}$ alkyl.

23. The compound of claim 1, wherein $R^8$ is OC(O)-aryl optionally substituted by 1-5 $R^9$.

24. The compound of claim 1, wherein the compound is selected from the following table:
| Compound No. | Structure |
|---|---|
| 1 | 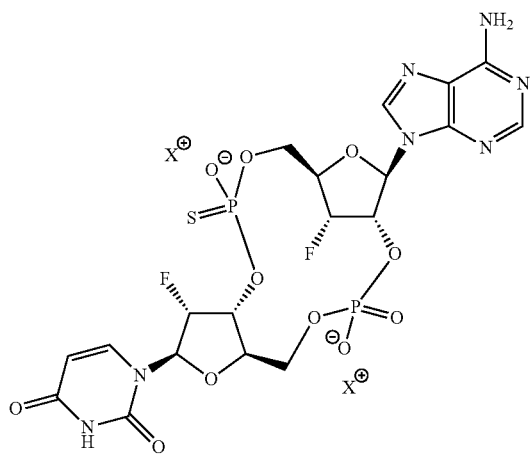 |
| 2 | 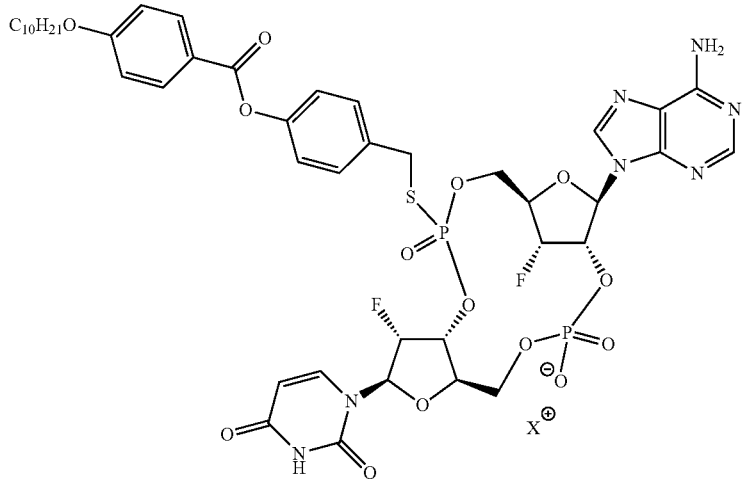 |
| 3 | 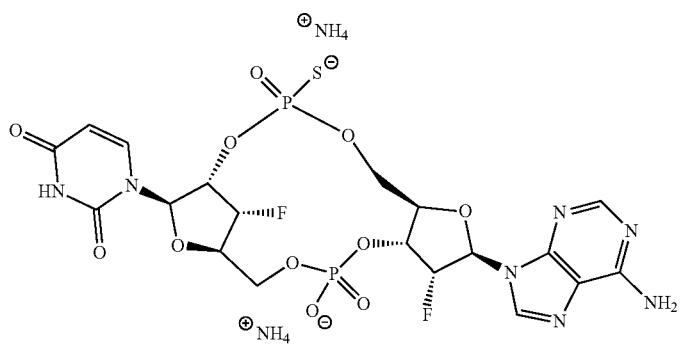 [SMILES: [NH4+] ; Nc1ncnc2c1ncn2[C@@H]1O[C@@H]2COP(=O)([S-])O[C@@H]3[C@H](F)[C@@H](COP(=O)([O-])O[C@H]2[C@H]1F)O[C@H]3n1ccc(=O)[nH]c1=O ; [NH4+]] |

-continued
| Compound No. | Structure |
|---|---|
| 4 | 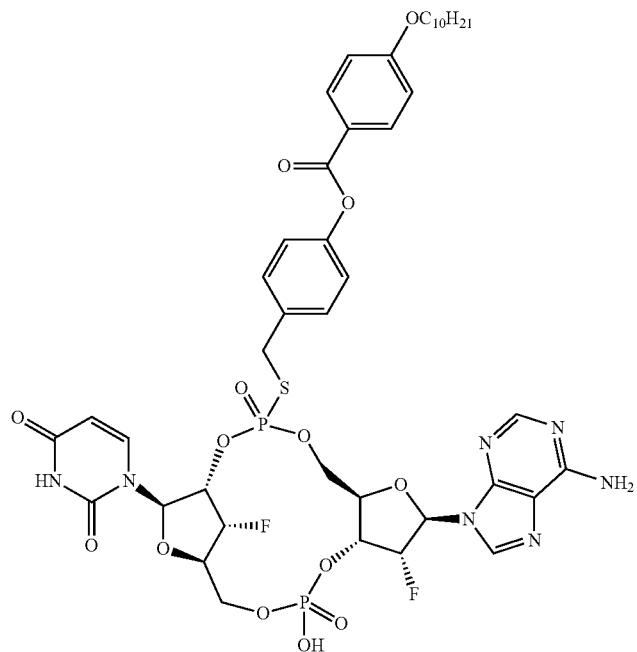 |
| 5 | 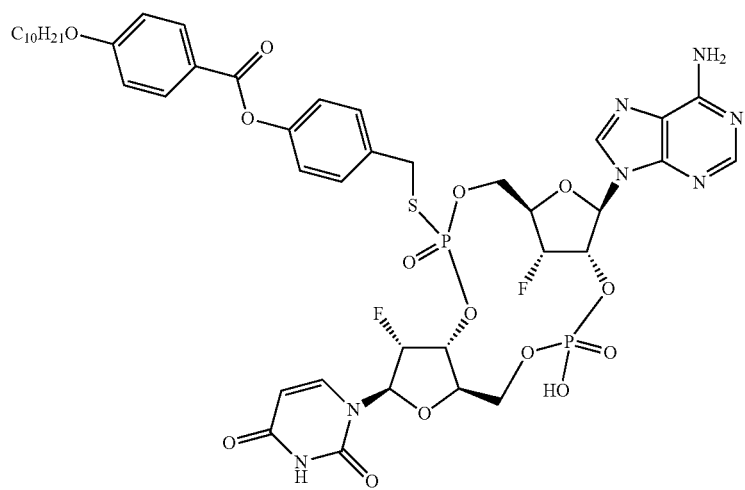 |

| Compound No. | Structure |
|---|---|
| 6 | 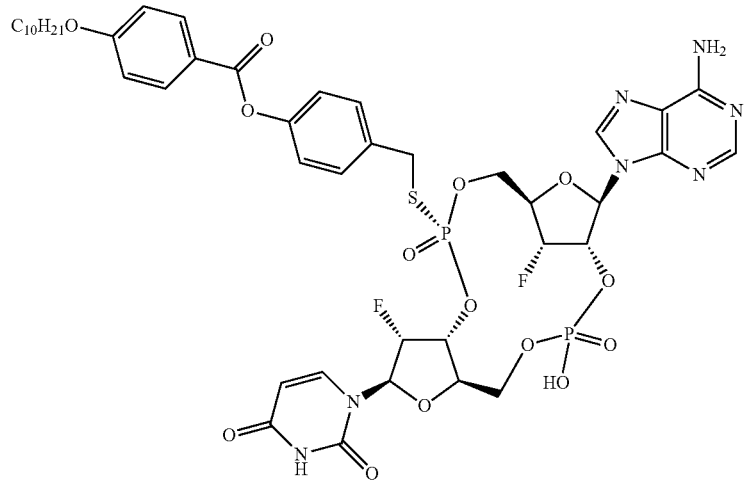 |
| 7 | 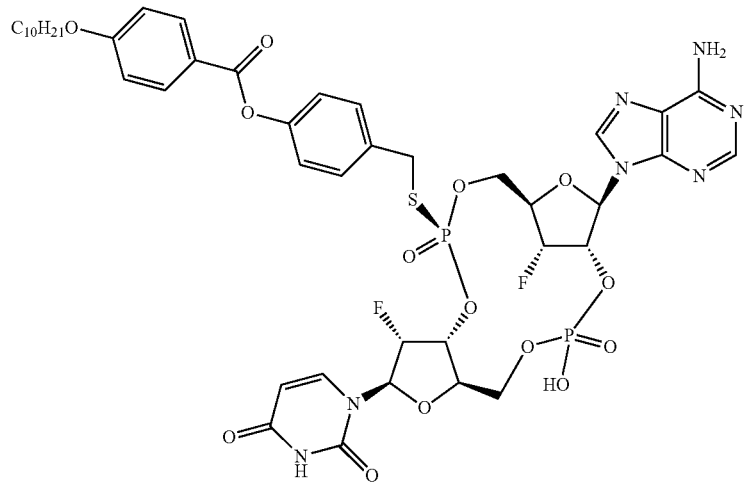 |
| 8 | 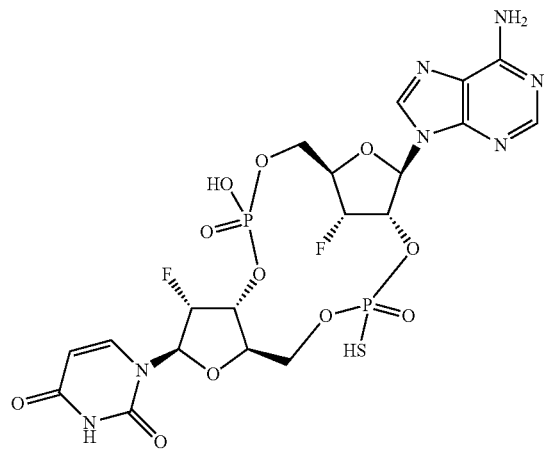 [SMILES: Nc1ncnc2c1ncn2[C@@H]1O[C@@H]2COP(=O)(O)O[C@H]3[C@@H](F)[C@H](n4ccc(=O)[nH]c4=O)O[C@@H]3COP(=O)(S)O[C@@H]1[C@@H]2F] |

-continued
| Compound No. | Structure |
|---|---|
| 9 | 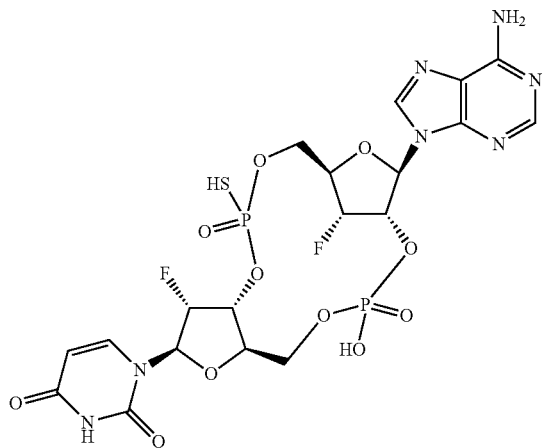 [SMILES: Nc1ncnc2c1ncn2[C@@H]1O[C@@H]2COP(=O)(S)O[C@H]3[C@@H](F)[C@H](n4ccc(=O)[nH]c4=O)O[C@@H]3COP(=O)(O)O[C@@H]1[C@@H]2F] |
| 10 | 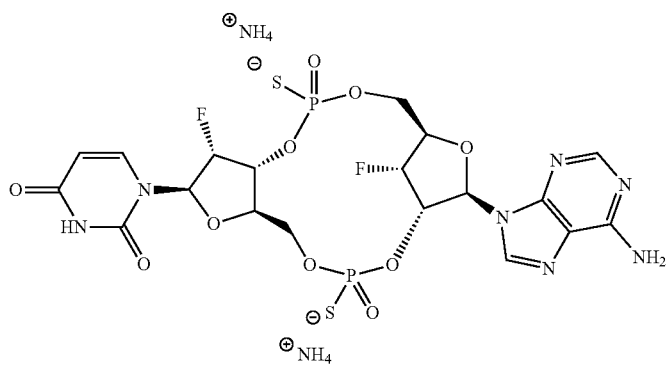 |
| 11 | 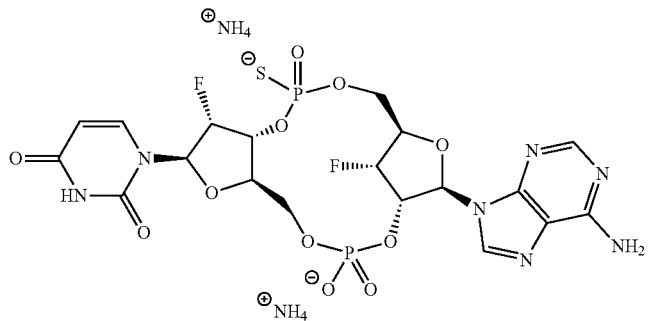 [SMILES: [NH4+] ; Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([O-])O[C@@H]1[C@@H]2F ; [NH4+]] |
| 12 | 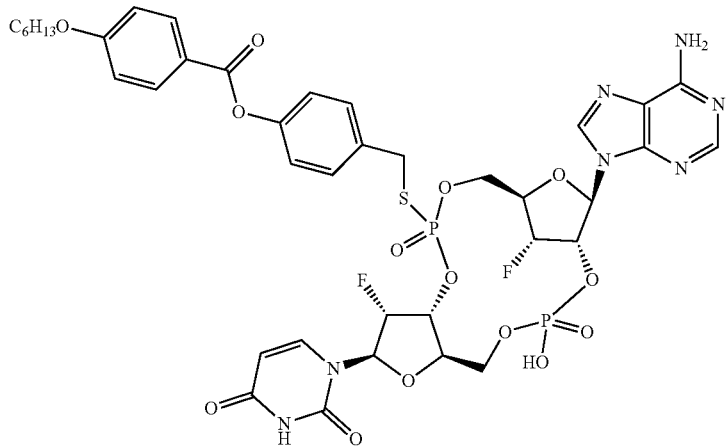 |

| Compound No. | Structure |
|---|---|
| 13 | 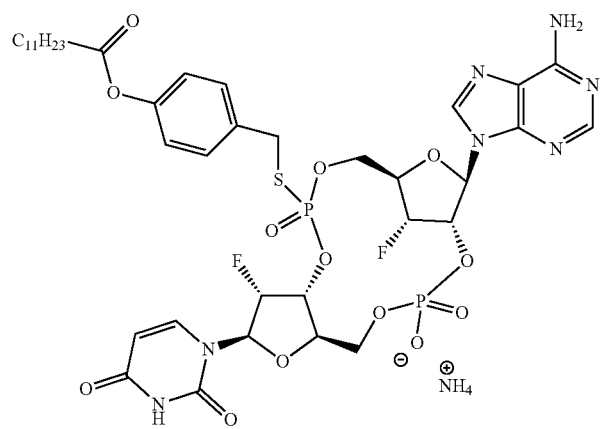 |
| 14 | 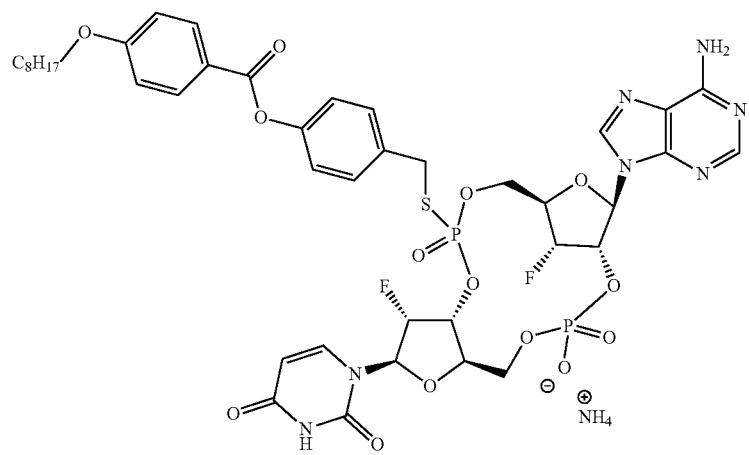 |
| 15 | 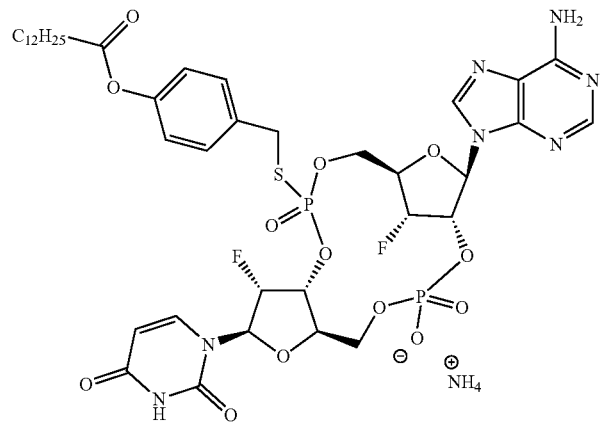 |

| Compound No. | Structure |
|---|---|
| 16 | 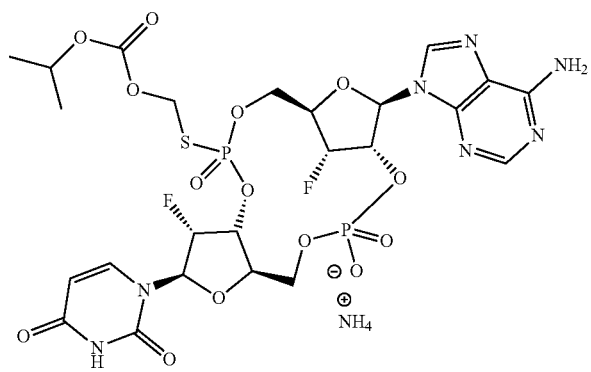 |
| 17 | 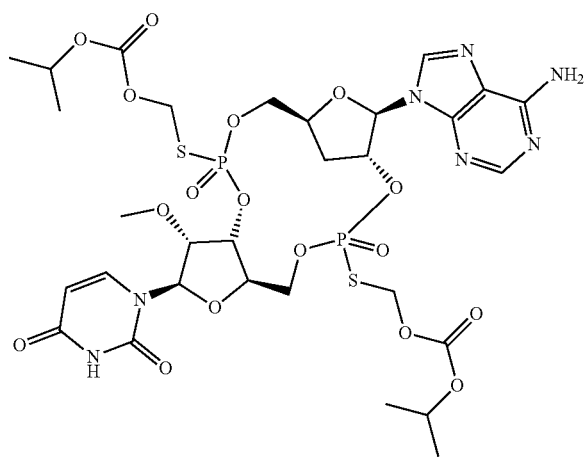 |
| 18 | 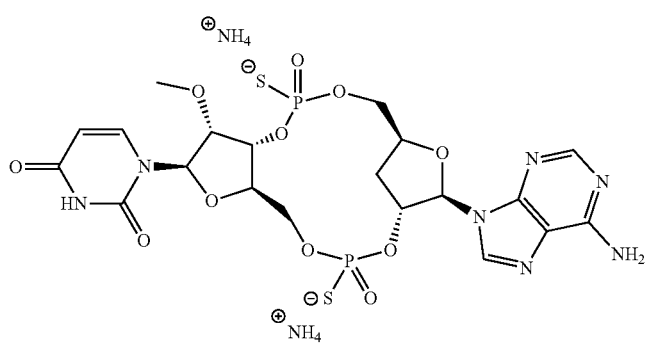 [SMILES: [NH4+] ; CO[C@@H]1[C@@H]2OP(=O)([S-])OC[C@@H]3C[C@@H](OP(=O)([S-])OC[C@H]2O[C@H]1n1ccc(=O)[nH]c1=O)[C@H](n1cnc2c(N)ncnc21)O3 ; [NH4+]] |
| 19 | 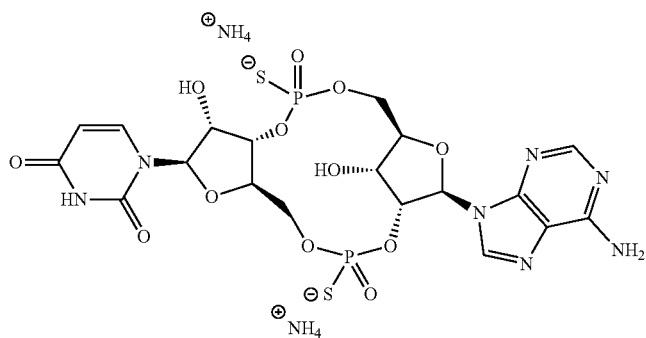 [SMILES: [NH4+] ; Nc1ncnc2c1ncn2[C@@H]1O[C@@H]2COP(=O)([S-])O[C@H]3[C@@H](O)[C@H](n4ccc(=O)[nH]c4=O)O[C@@H]3COP(=O)([S-])O[C@@H]1[C@@H]2O ; [NH4+]] |

-continued
| Compound No. | Structure |
|---|---|
| 20 | 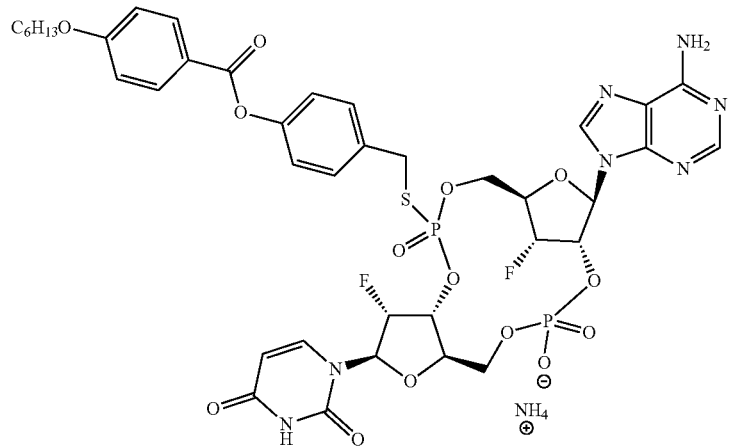 |
| 21 | 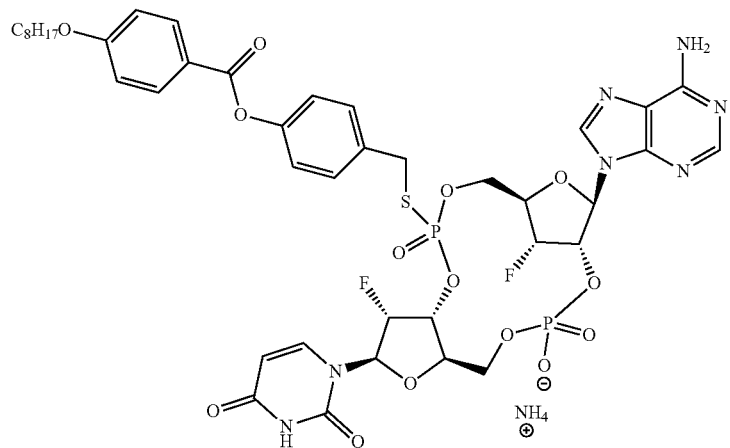 |
| 22 | 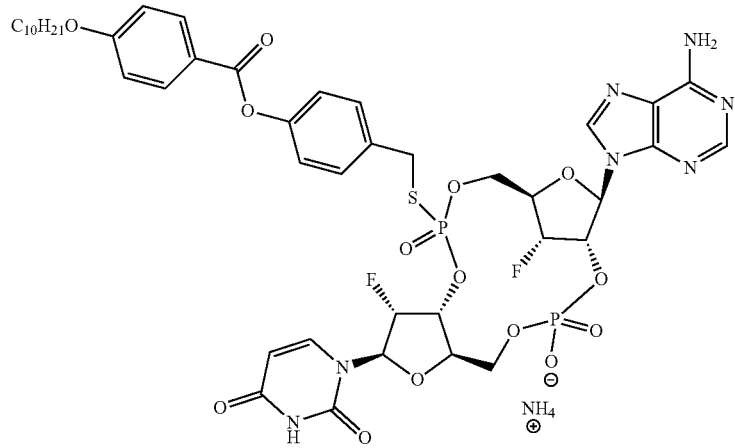 |

-continued
| Compound No. | Structure |
|---|---|
| 23 | 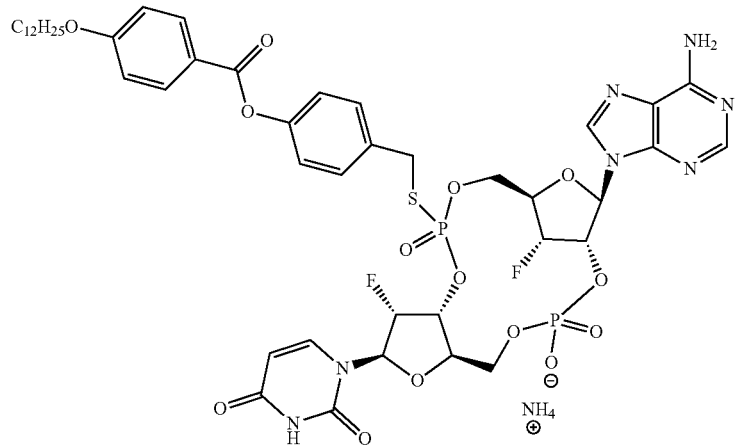 |
| 24 | 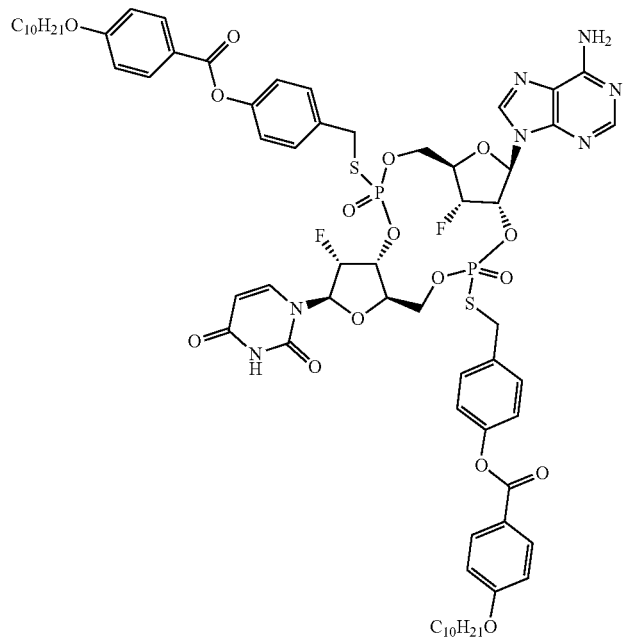 |
| 25 | 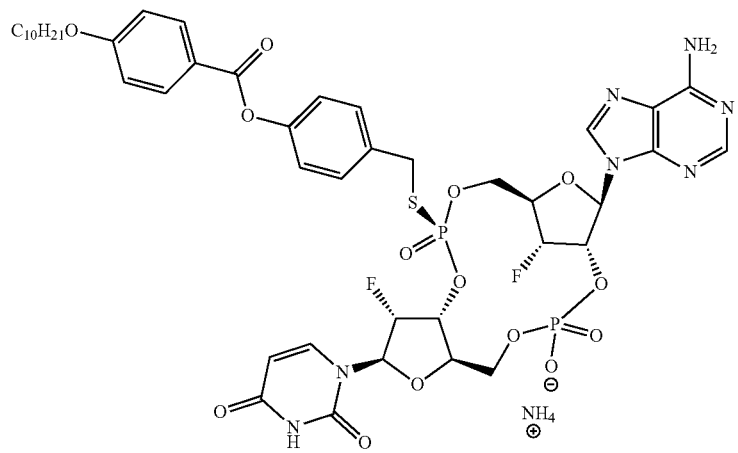 |

| Compound No. | Structure |
|---|---|
| 26 | 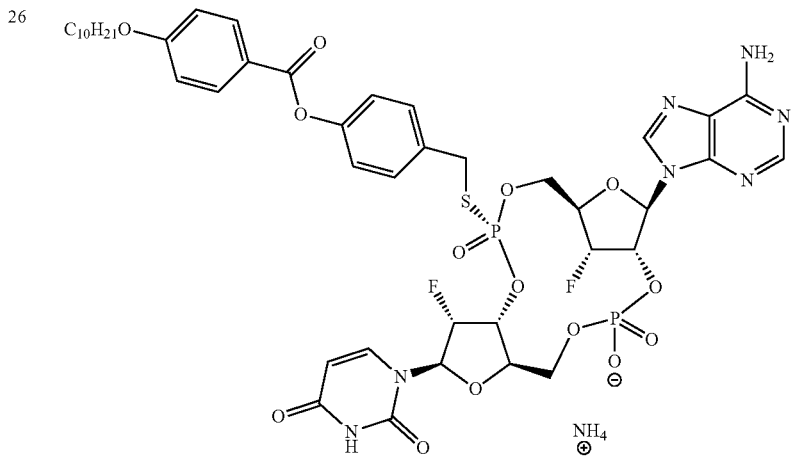 |
| 27 | 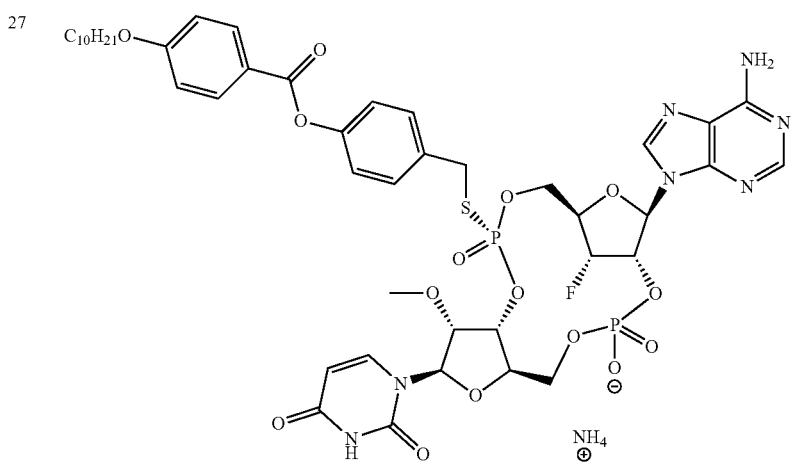 |
| 28 | 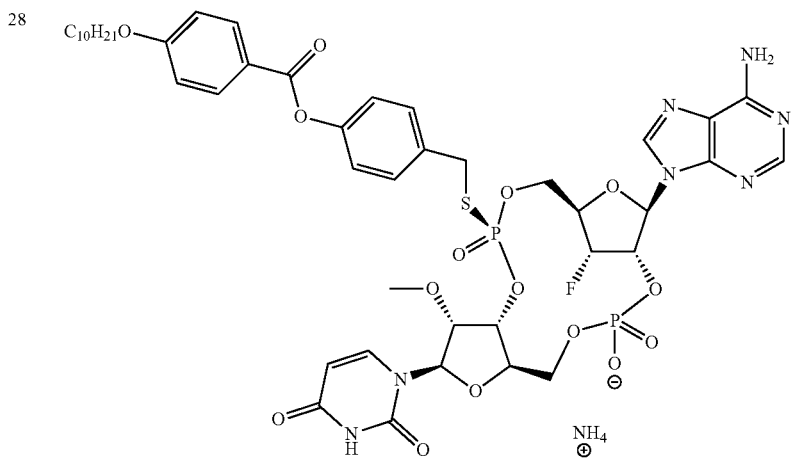 |

| Compound No. | Structure |
|---|---|
| 29 | 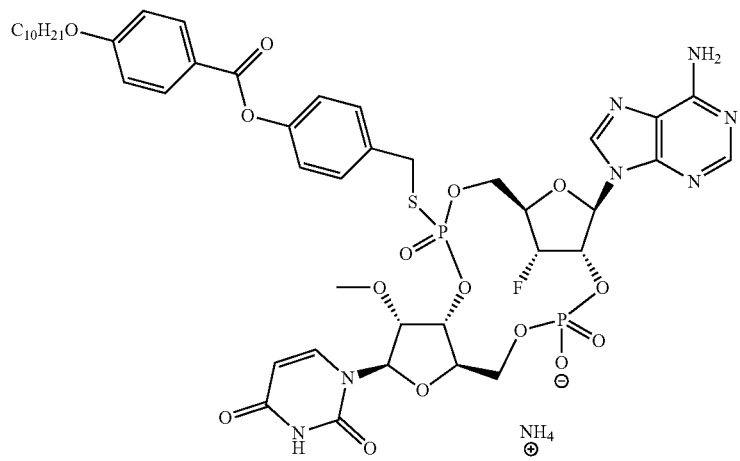 |
| 30 | 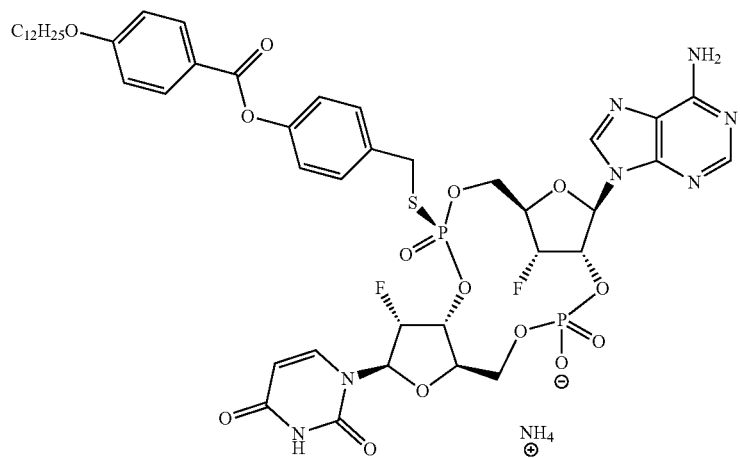 |
| 31 | 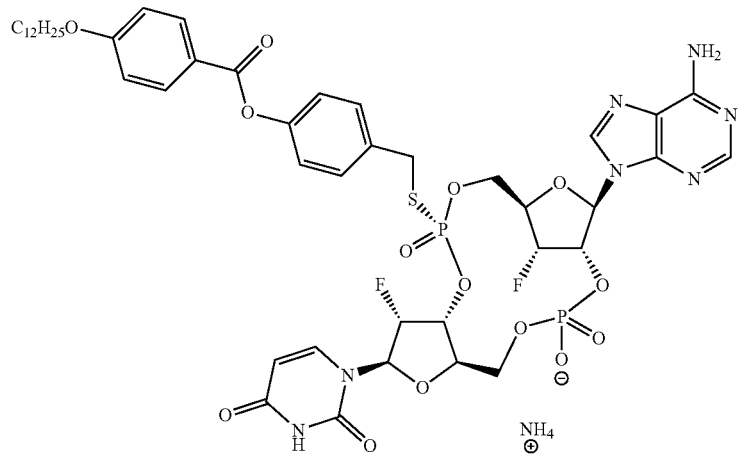 |

| Compound No. | Structure |
|---|---|
| 33 | 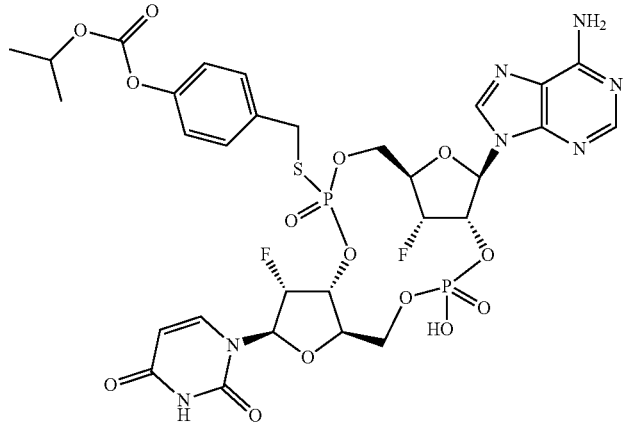 [SMILES: CC(C)OC(=O)Oc1ccc(CSP2(=O)OC[C@H]3O[C@@H](n4cnc5c(N)ncnc54)[C@H](OP(=O)(O)OC[C@H]4O[C@@H](n5ccc(=O)[nH]c5=O)[C@H](F)[C@@H]4O2)[C@@H]3F)cc1] |
| 34 | 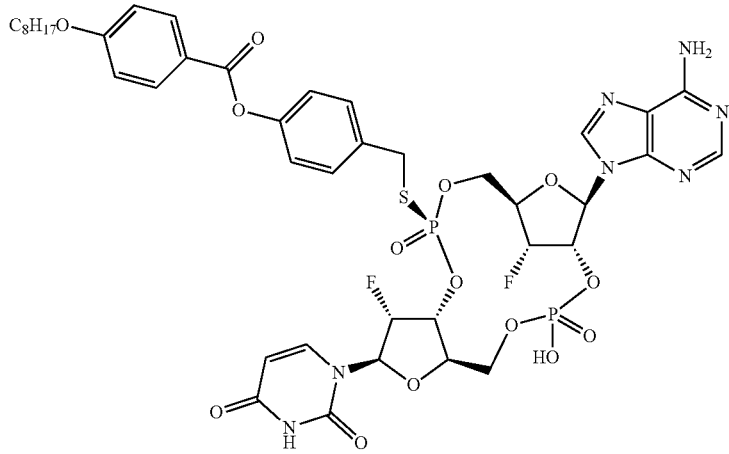 |
| 35 | 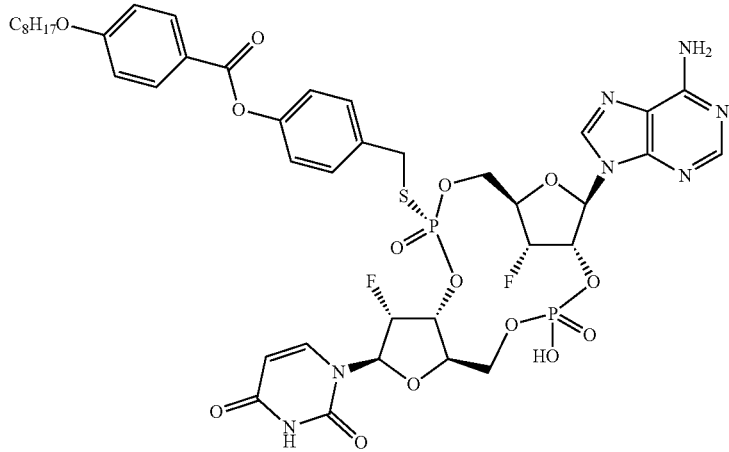 |

-continued

| Compound No. | Structure |
|---|---|
| 36 | (structure) |
| 37 | (structure) |
| 38 | (structure) |
| 39 | (structure) |

-continued
| Compound No. | Structure |
|---|---|
| 40 | 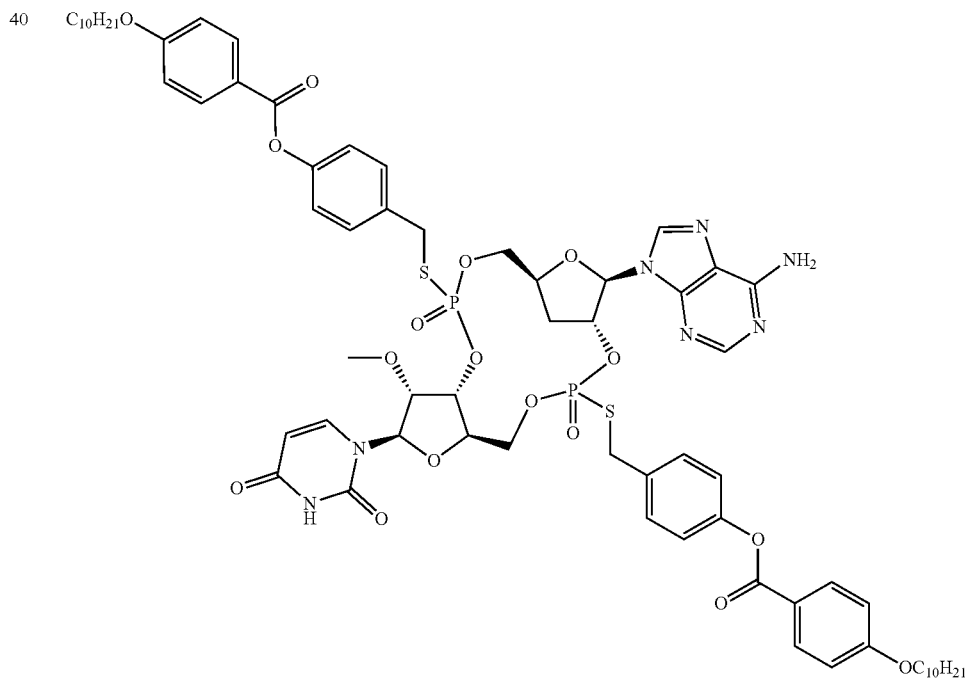 |
| 41 | 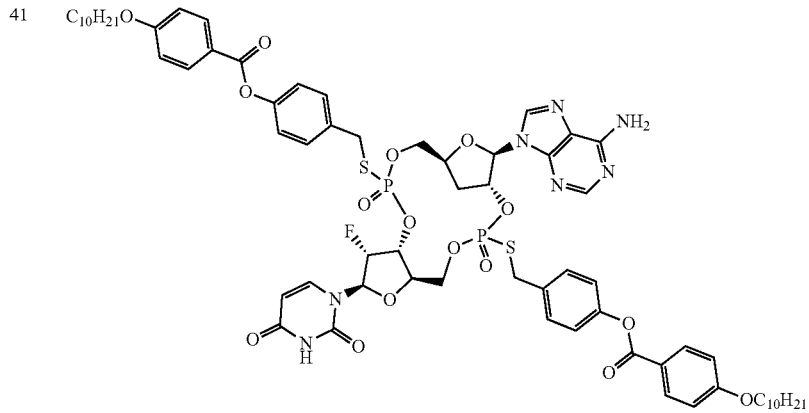 |
| 42 | 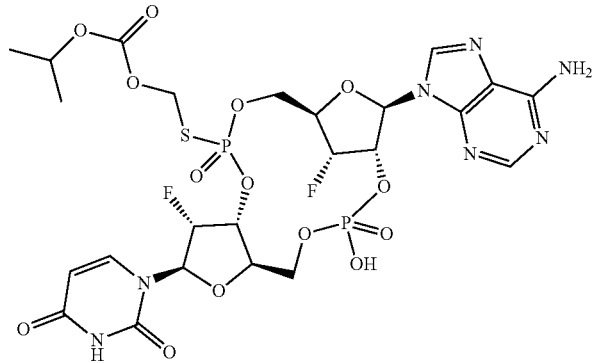 [SMILES: CC(C)OC(=O)OCSP1(=O)OC[C@H]2O[C@@H](n3cnc4c(N)ncnc43)[C@H](OP(=O)(O)OC[C@H]3O[C@@H](n4ccc(=O)[nH]c4=O)[C@H](F)[C@@H]3O1)[C@@H]2F] |

-continued
| Compound No. | Structure |
|---|---|
| 43 | 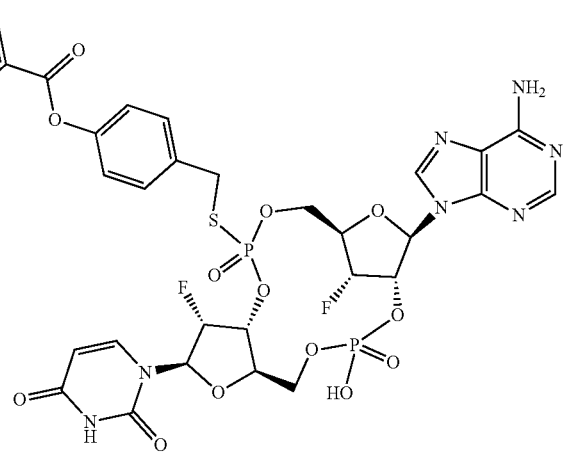 |
| 44 | 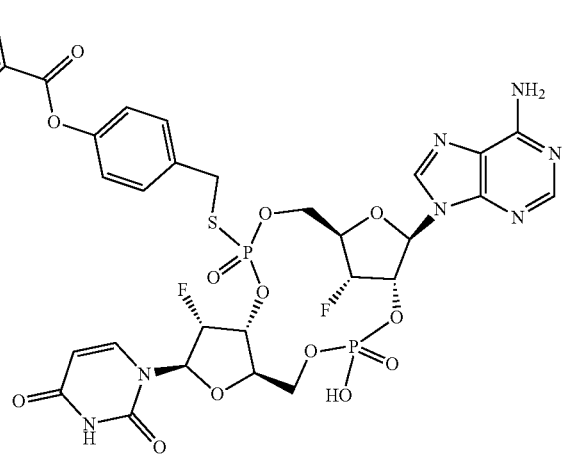 |
| 45 | 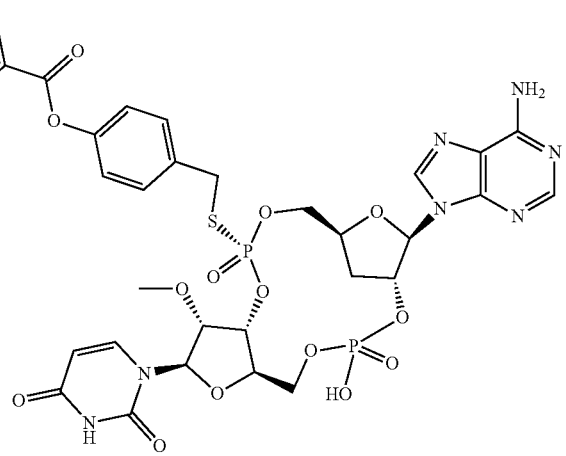 |

-continued
| Compound No. | Structure |
|---|---|
| 46 | 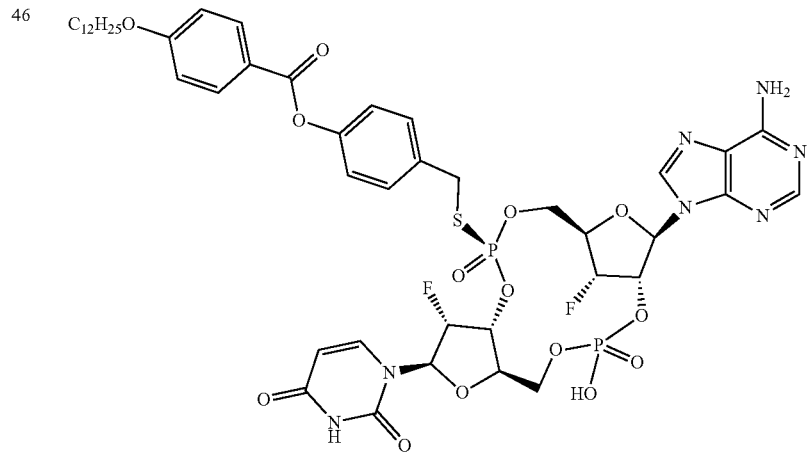 |
| 47 | 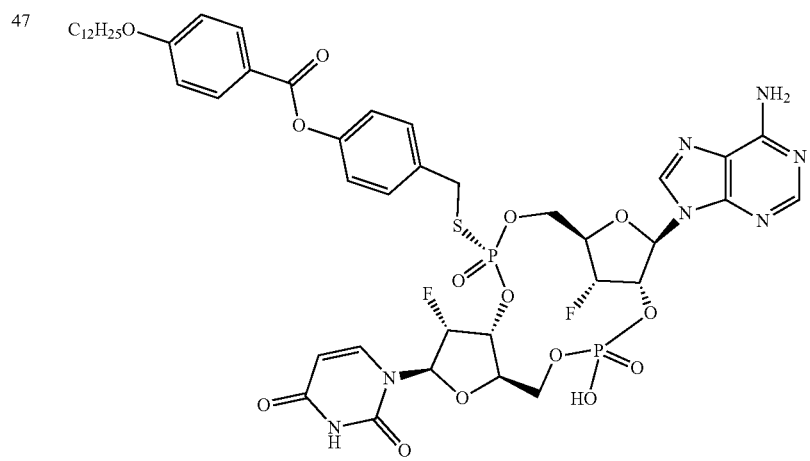 |
| 48 | 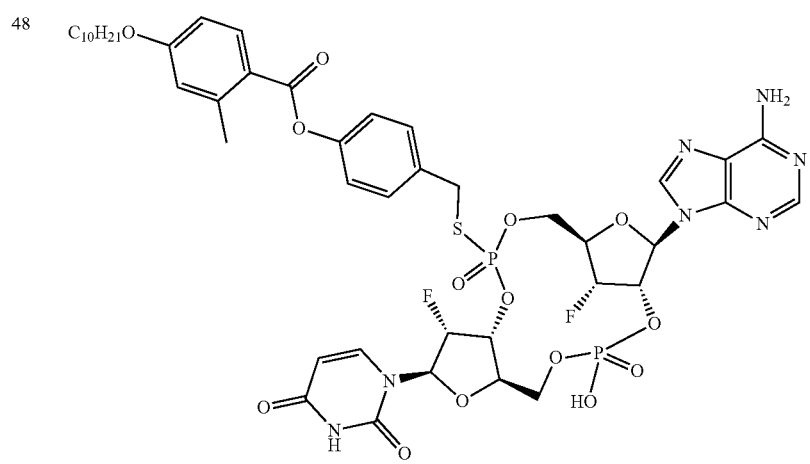 |

-continued
| Compound No. | Structure |
|---|---|
| 49 | 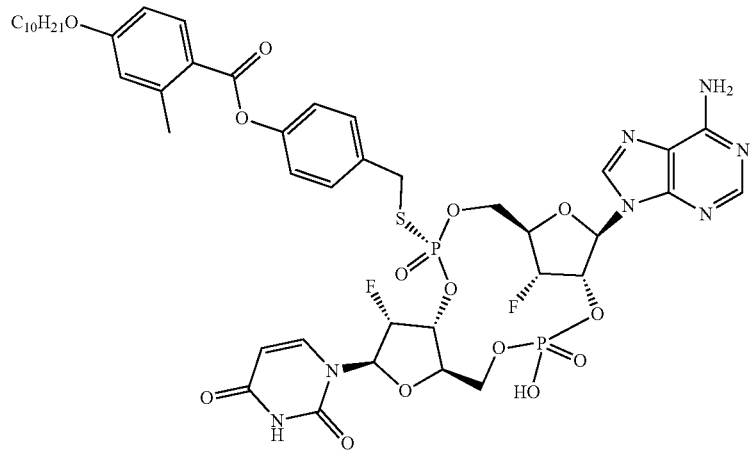 |
| 50 | 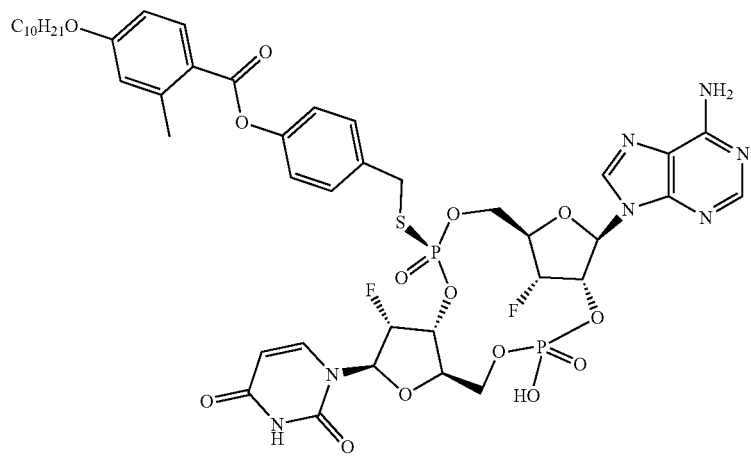 |
| 51 | 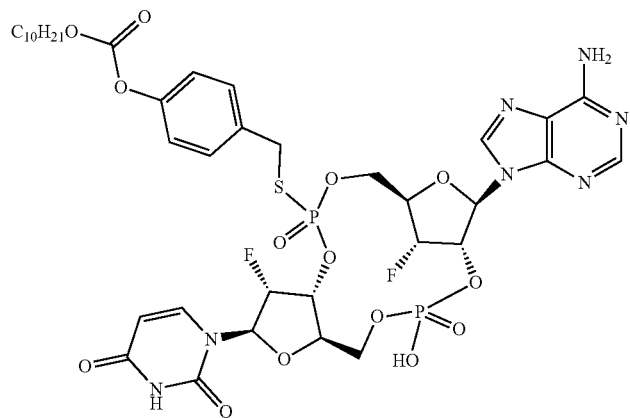 |

| Compound No. | Structure |
|---|---|
| 52 | 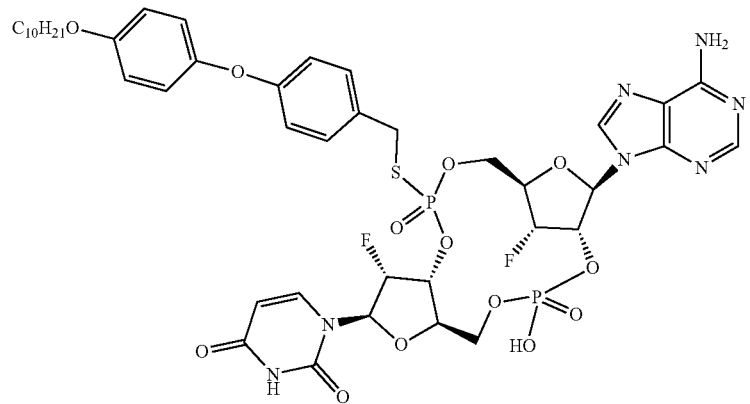 |
| 53 | 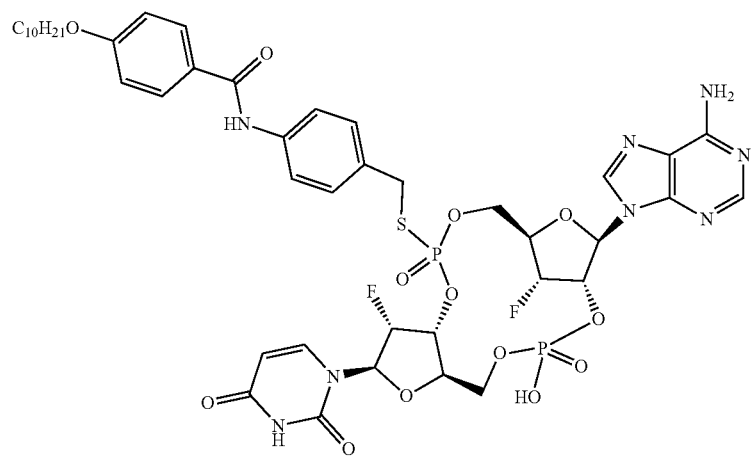 |
| 54 | 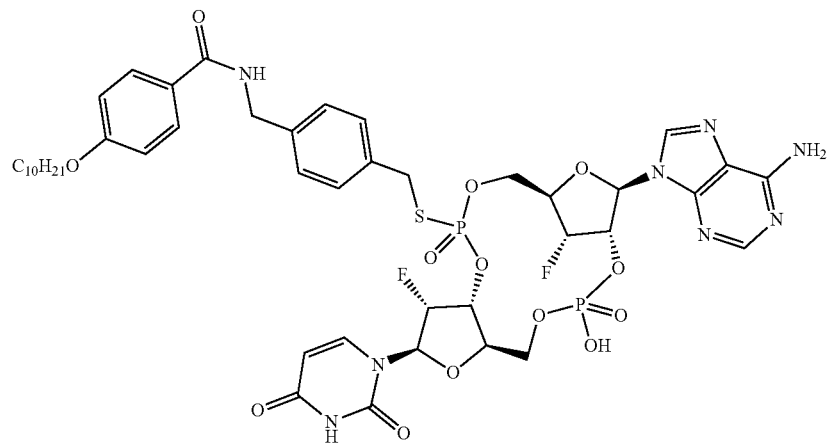 |

| Compound No. | Structure |
|---|---|
| 55 | 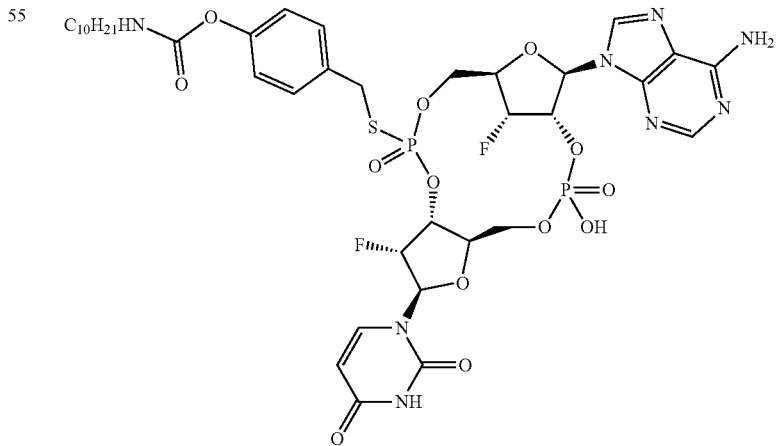 |
| 56 | 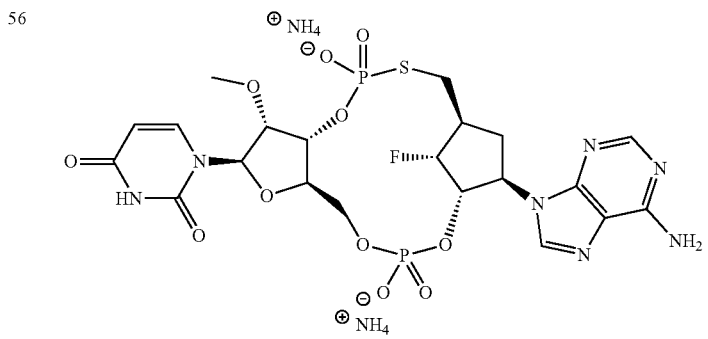 |
| 57 | 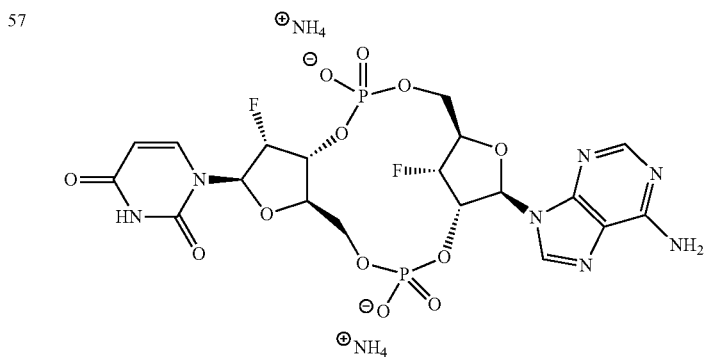 |
| 58 | 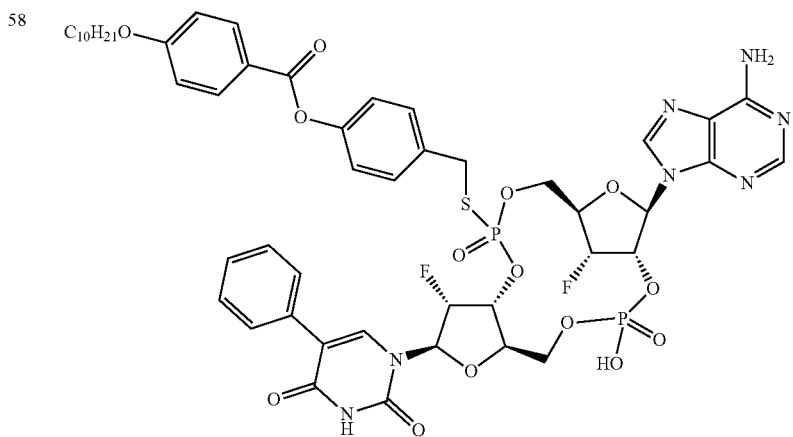 |

-continued
| Compound No. | Structure |
|---|---|
| 59 | 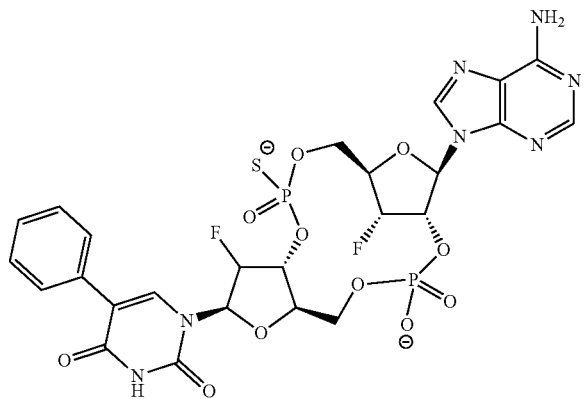 [SMILES: Nc1ncnc2c1ncn2[C@@H]1O[C@@H]2COP(=O)([S-])O[C@H]3C(F)[C@H](n4cc(-c5ccccc5)c(=O)[nH]c4=O)O[C@@H]3COP(=O)([O-])O[C@@H]1[C@@H]2F] |
| 60 | 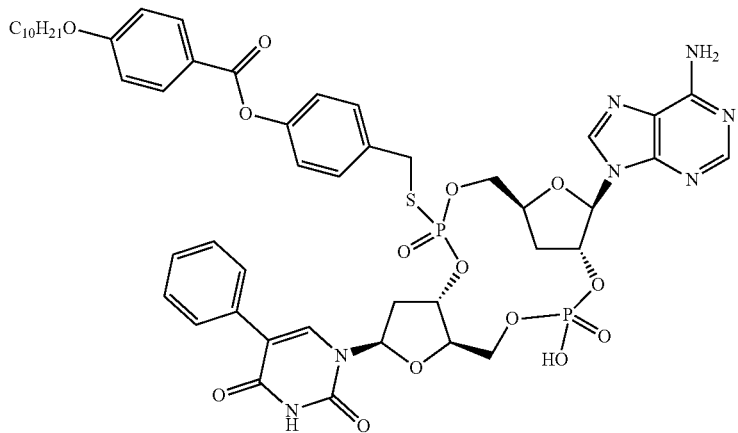 |
| 61 | 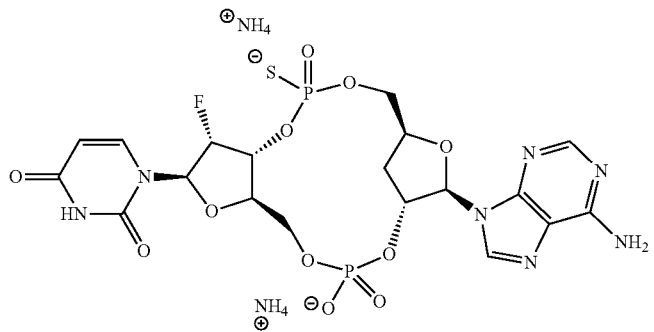 [SMILES: [NH4+] ; Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([O-])O[C@@H]1C2 ; [NH4+]] |

-continued
| Compound No. | Structure |
|---|---|
| 62 | 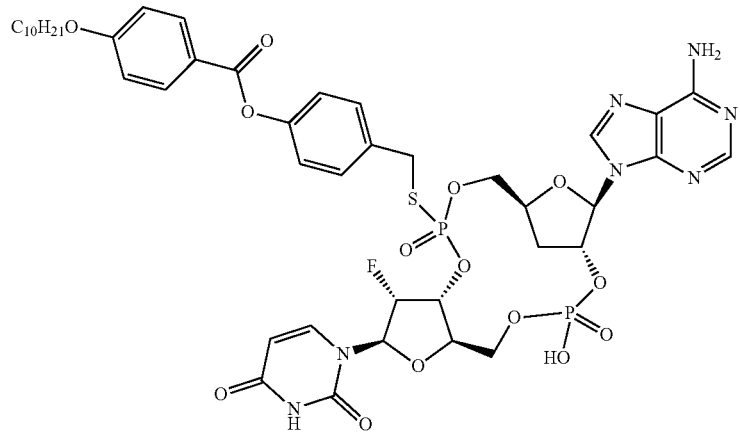 |
| 63 | 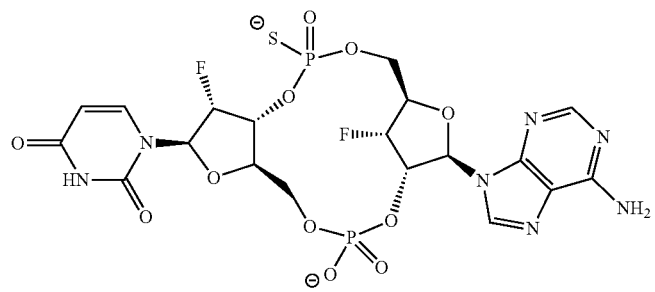 [SMILES: Nc1ncnc2c1ncn2[C@@H]1O[C@@H]2COP(=O)([S-])O[C@H]3[C@@H](F)[C@H](n4ccc(=O)[nH]c4=O)O[C@@H]3COP(=O)([O-])O[C@@H]1[C@@H]2F] |
| 64 | 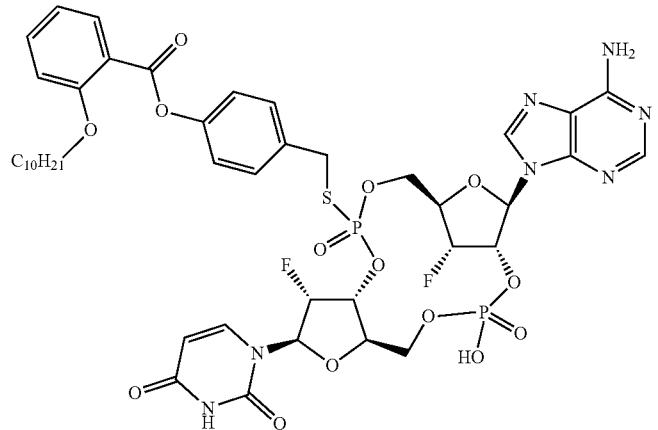 |

//
| Compound No. | Structure |
|---|---|
| 65 | 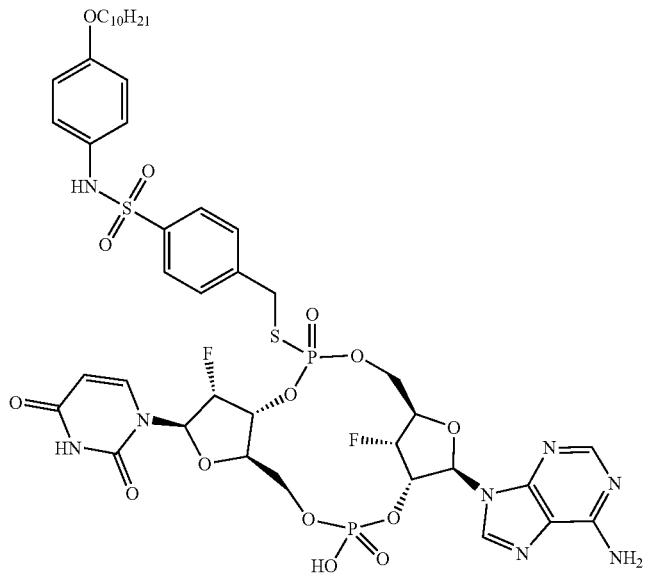 |
| 66 | 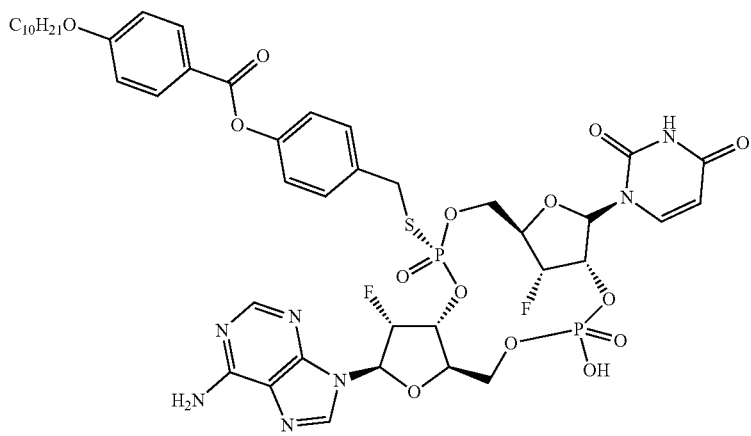 |
| 67 | 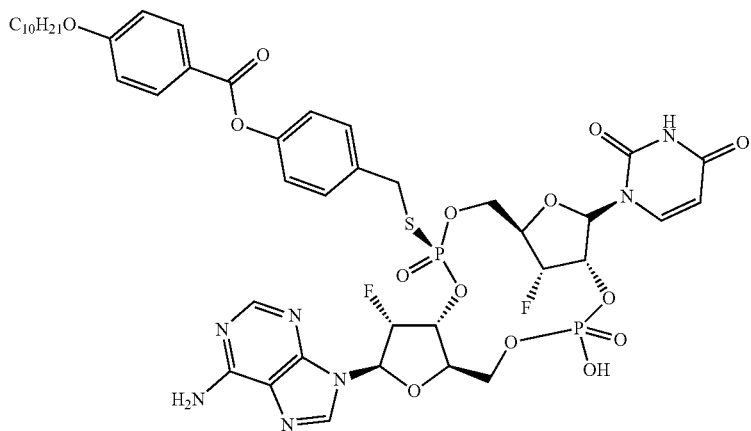 |

| Compound No. | Structure |
|---|---|
| 68 | 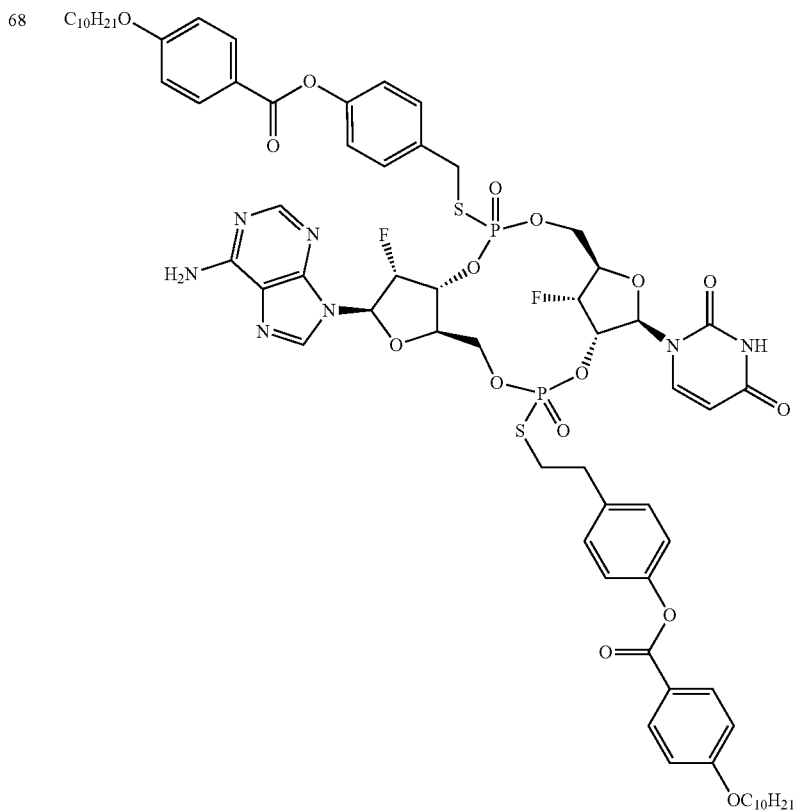 |
| 69 | 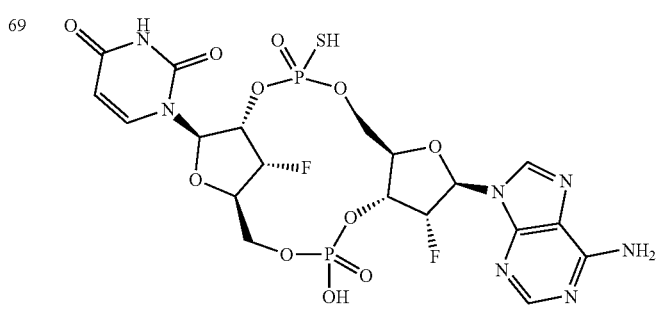 |
| 70 | 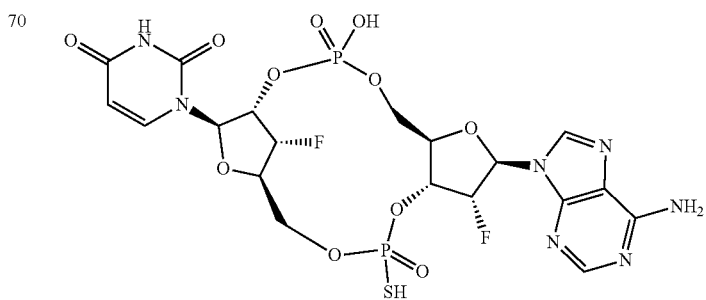 |

-continued
| Compound No. | Structure |
|---|---|
| 71 | 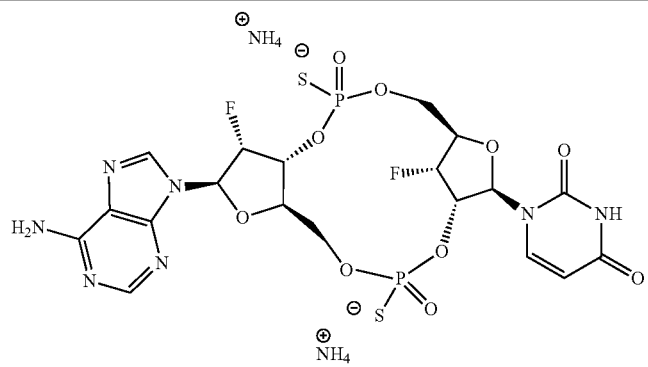 [SMILES: [NH4+] ; Nc1ncnc2c1ncn2[C@@H]1O[C@@H]2COP(=O)([S-])O[C@@H]3[C@H](F)[C@@H](COP(=O)([S-])O[C@H]2[C@H]1F)O[C@H]3n1ccc(=O)[nH]c1=O ; [NH4+]] |
| 72 | 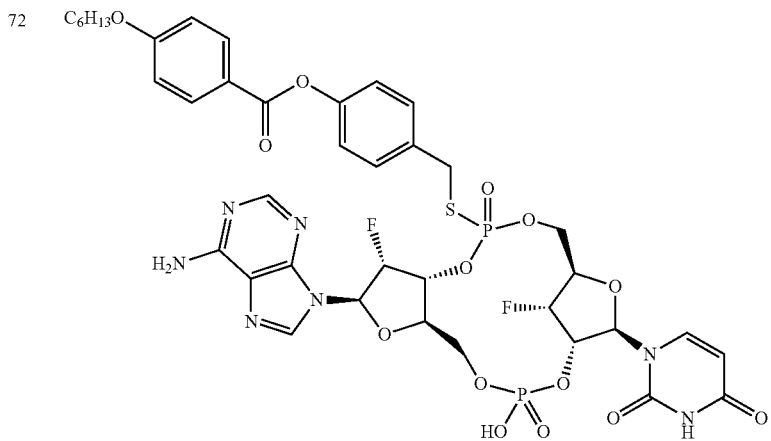 |
| 73 | 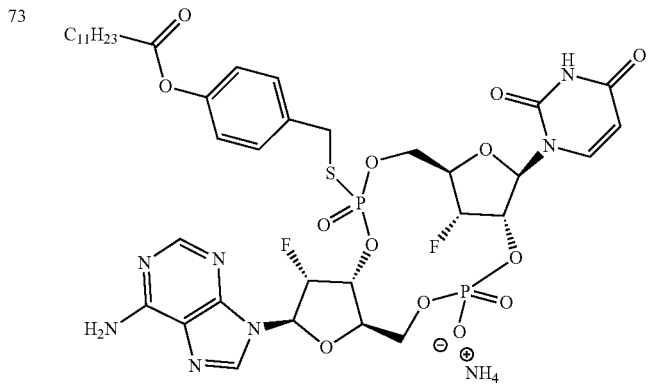 |
| 74 | 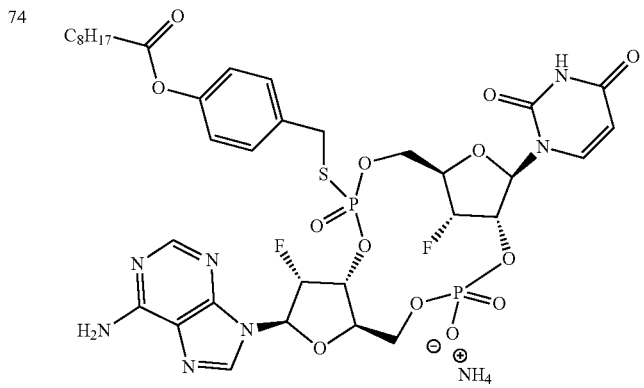 |

-continued
| Compound No. | Structure |
|---|---|
| 75 | 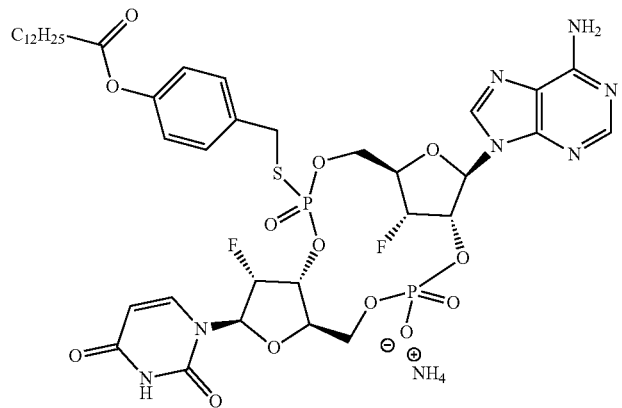 |
| 76 | 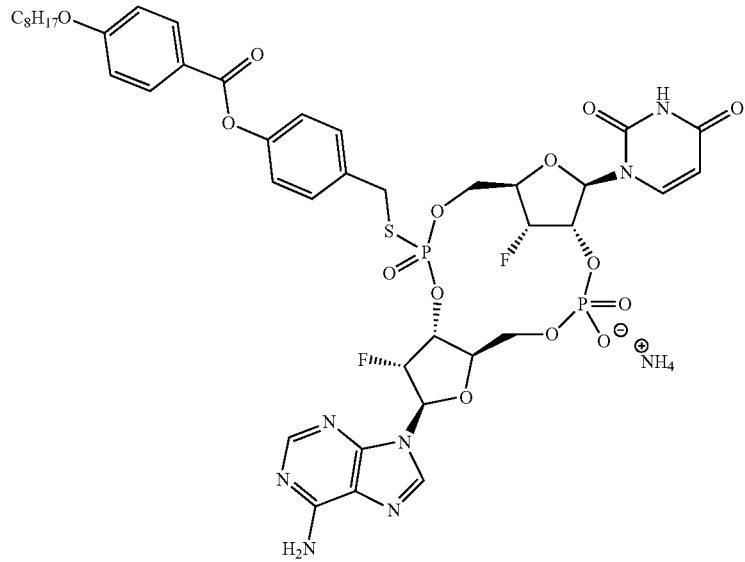 |
| 77 | 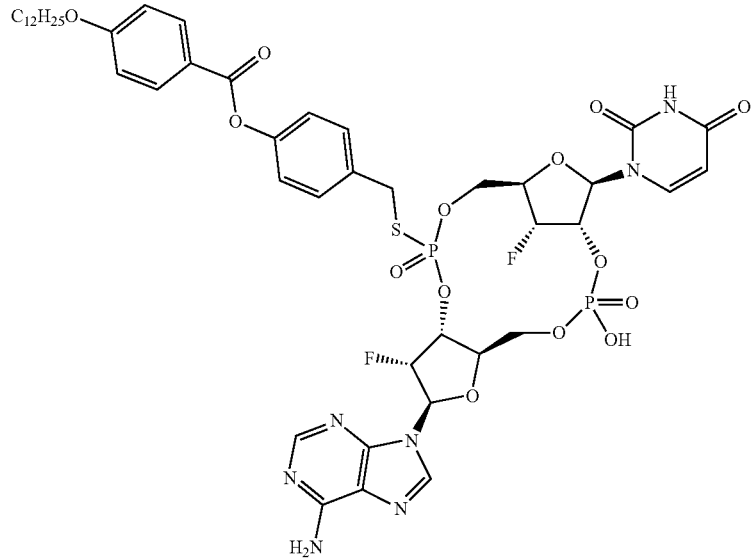 |

-continued
| Compound No. | Structure |
|---|---|
| 78 | 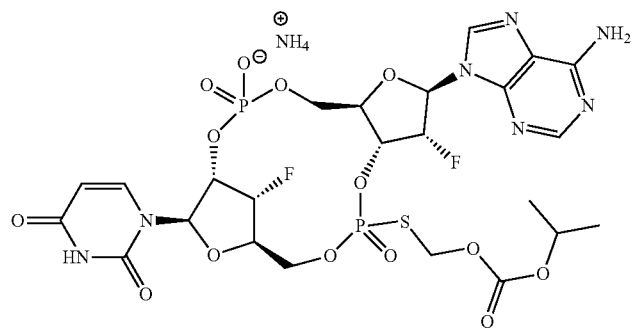 [SMILES: CC(C)OC(=O)OCSP1(=O)OC[C@H]2O[C@@H](n3ccc(=O)[nH]c3=O)[C@H](OP(=O)([O-])OC[C@H]3O[C@@H](n4cnc5c(N)ncnc54)[C@H](F)[C@@H]3O1)[C@@H]2F ; [NH4+]] |
| 79 | 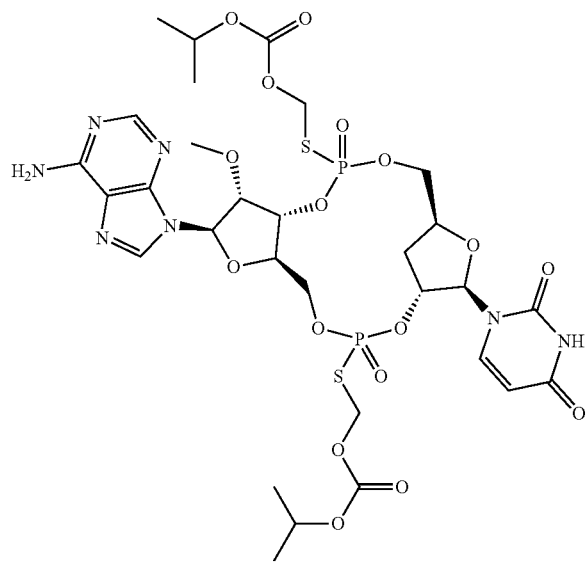 [SMILES: CO[C@@H]1[C@@H]2OP(=O)(SCOC(=O)OC(C)C)OC[C@@H]3C[C@@H](OP(=O)(SCOC(=O)OC(C)C)OC[C@H]2O[C@H]1n1cnc2c(N)ncnc21)[C@H](n1ccc(=O)[nH]c1=O)O3] |
| 80 | 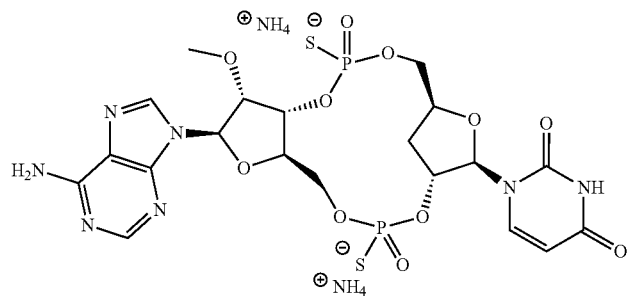 [SMILES: CO[C@@H]1[C@@H]2OP(=O)([S-])OC[C@@H]3C[C@@H](OP(=O)([S-])OC[C@H]2O[C@H]1n1cnc2c(N)ncnc21)[C@H](n1ccc(=O)[nH]c1=O)O3 ; [NH4+] ; [NH4+]] |
| 81 | 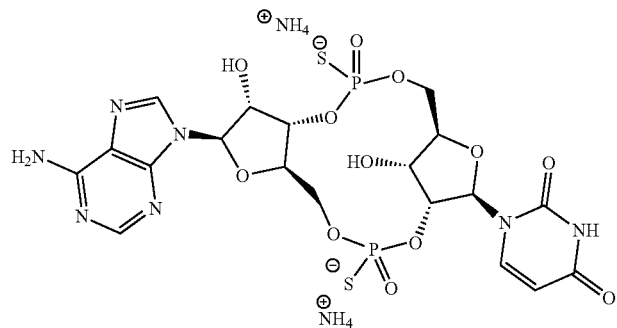 [SMILES: [NH4+] ; Nc1ncnc2c1ncn2[C@@H]1O[C@@H]2COP(=O)([S-])O[C@@H]3[C@H](O)[C@@H](COP(=O)([S-])O[C@H]2[C@H]1O)O[C@H]3n1ccc(=O)[nH]c1=O ; [NH4+]] |

| Compound No. | Structure |
|---|---|
| 82 | 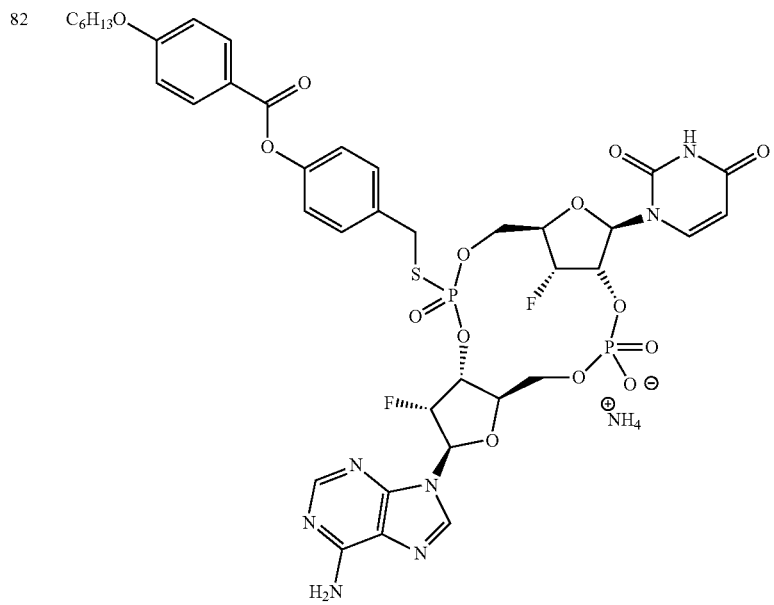 |
| 83 | 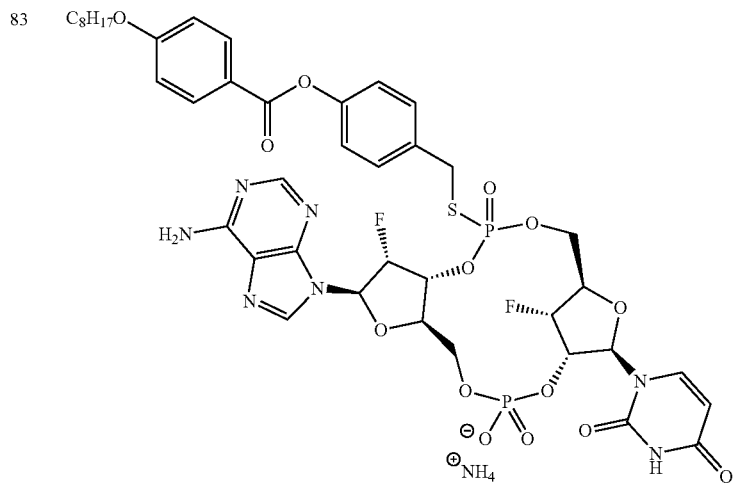 |

| Compound No. | Structure |
|---|---|
| 84 | 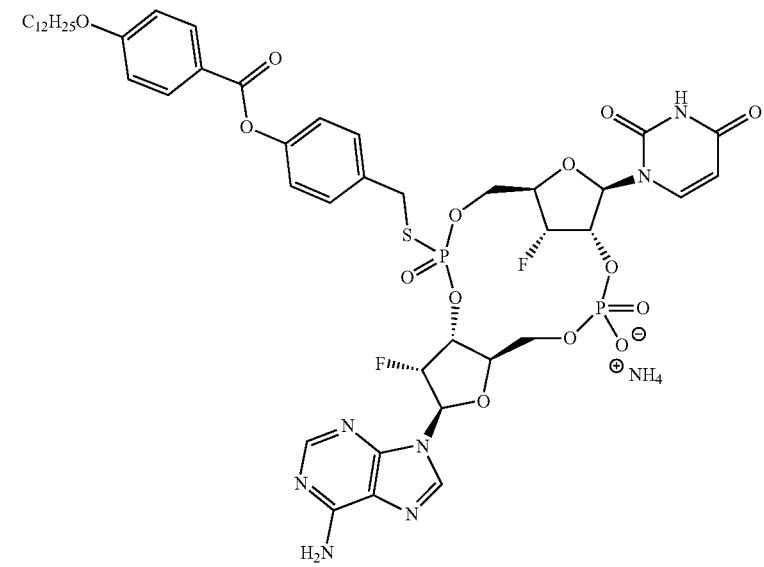 |
| 85 | 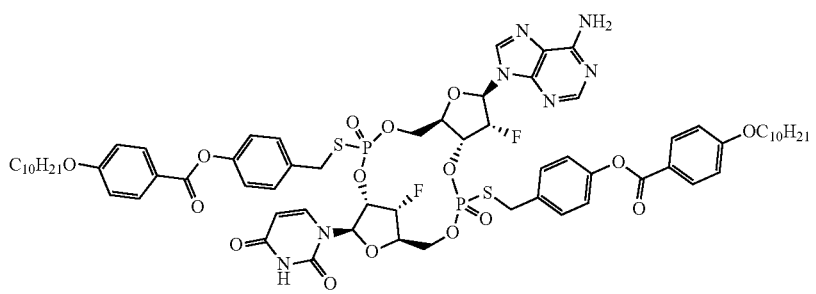 |
| 86 | 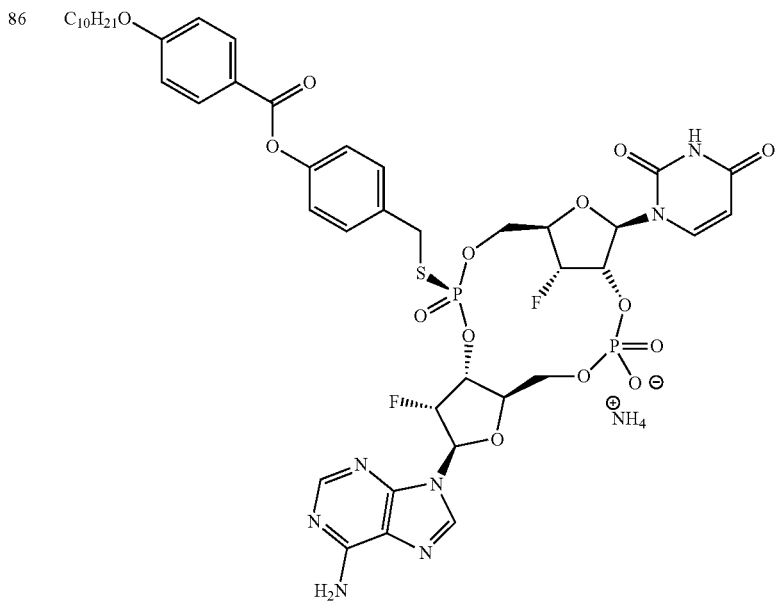 |

| Compound No. | Structure |
|---|---|
| 87 | 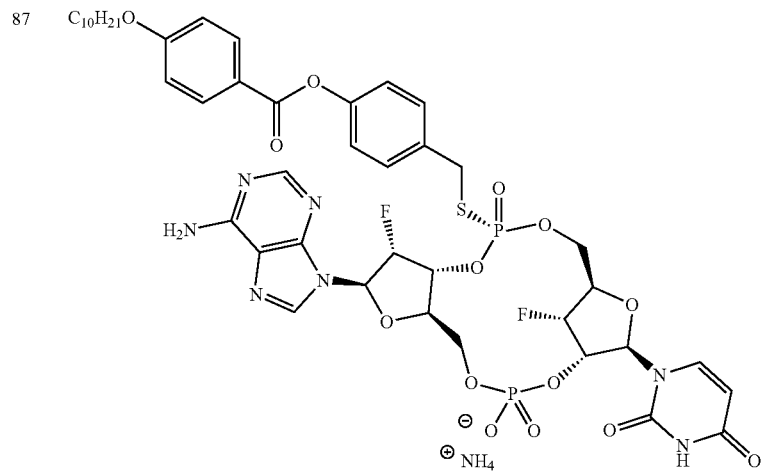 |
| 88 | 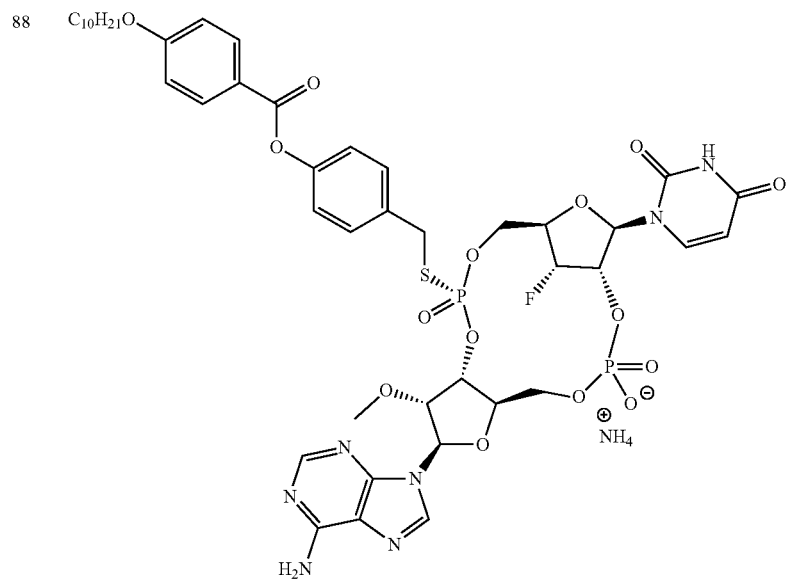 |
| 89 | 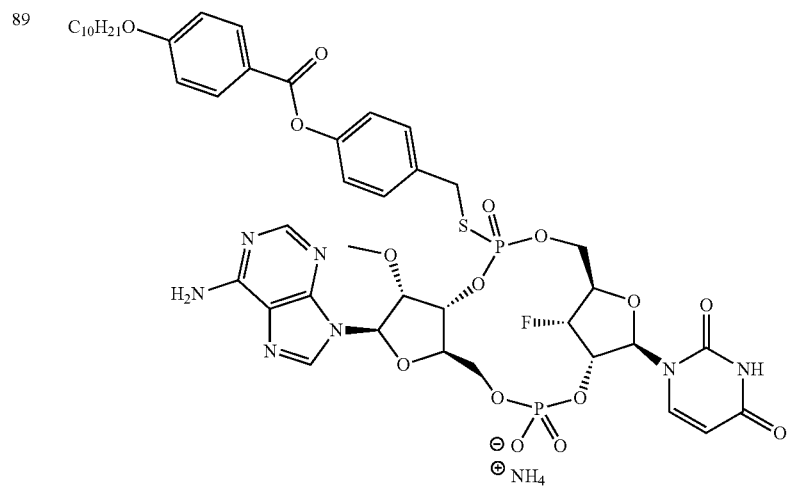 |

| Compound No. | Structure |
|---|---|
| 90 | 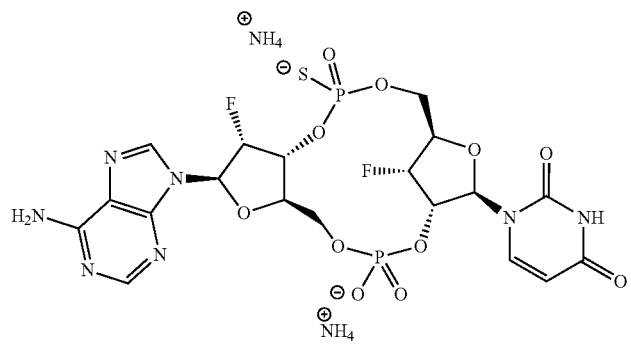 [SMILES: [NH4+] ; Nc1ncnc2c1ncn2[C@@H]1O[C@@H]2COP(=O)([O-])O[C@@H]3[C@H](F)[C@@H](COP(=O)([S-])O[C@H]2[C@H]1F)O[C@H]3n1ccc(=O)[nH]c1=O ; [NH4+]] |
| 91 | 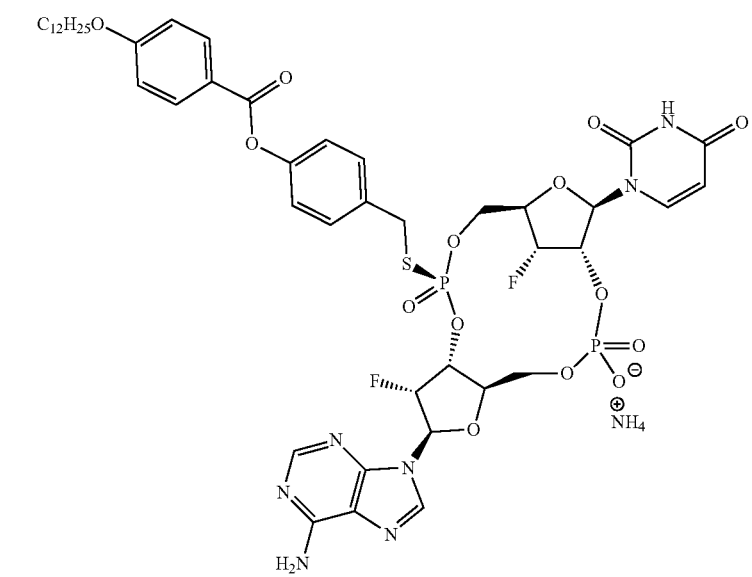 |
| 92 | 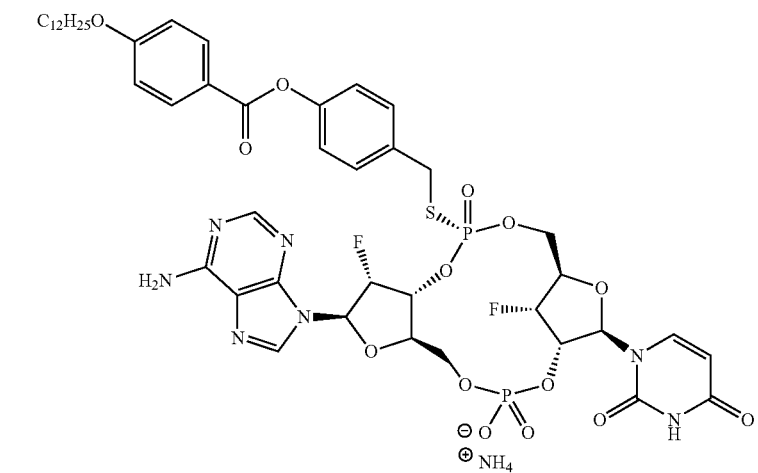 |

| Compound No. | Structure |
|---|---|
| 93 | 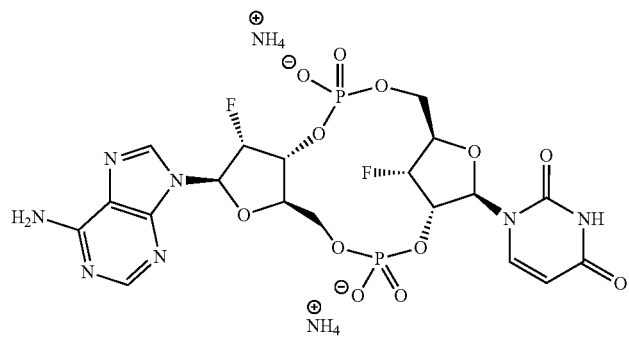 [SMILES: [NH4+] ; Nc1ncnc2c1ncn2[C@@H]1O[C@@H]2COP(=O)([O-])O[C@@H]3[C@H](F)[C@@H](COP(=O)([O-])O[C@H]2[C@H]1F)O[C@H]3n1ccc(=O)[nH]c1=O ; [NH4+]] |
| 94 | 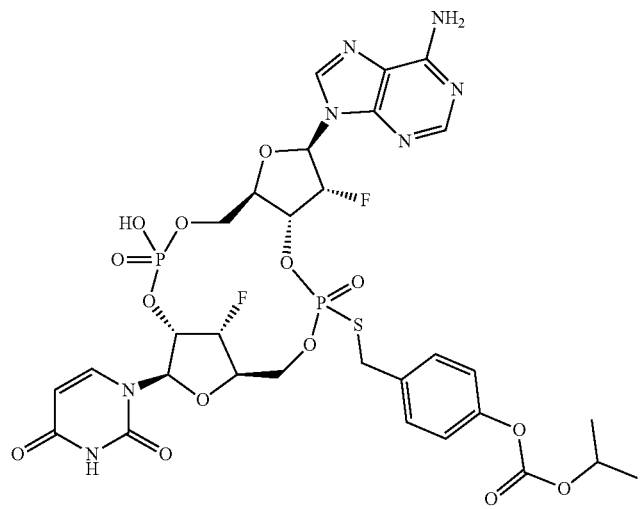 [SMILES: CC(C)OC(=O)Oc1ccc(CSP2(=O)OC[C@H]3O[C@@H](n4ccc(=O)[nH]c4=O)[C@H](OP(=O)(O)OC[C@H]4O[C@@H](n5cnc6c(N)ncnc65)[C@H](F)[C@@H]4O2)[C@@H]3F)cc1] |
| 95 | 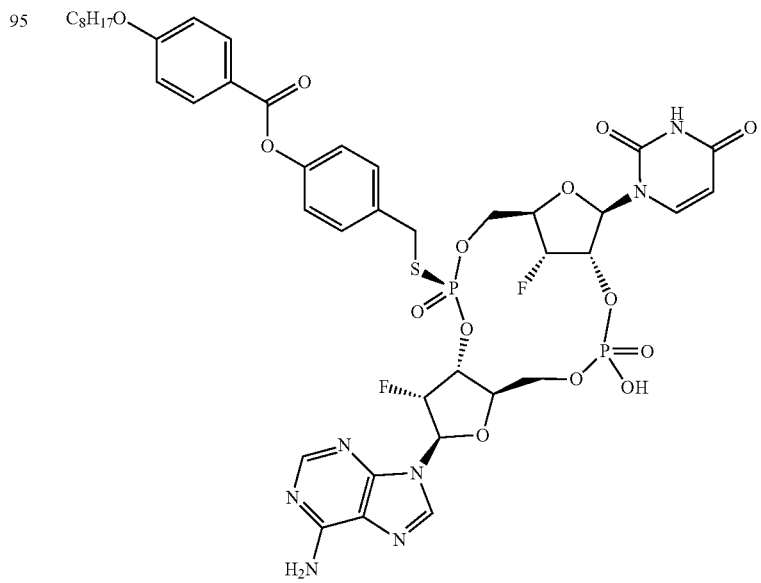 |

| Compound No. | Structure |
|---|---|
| 96 | 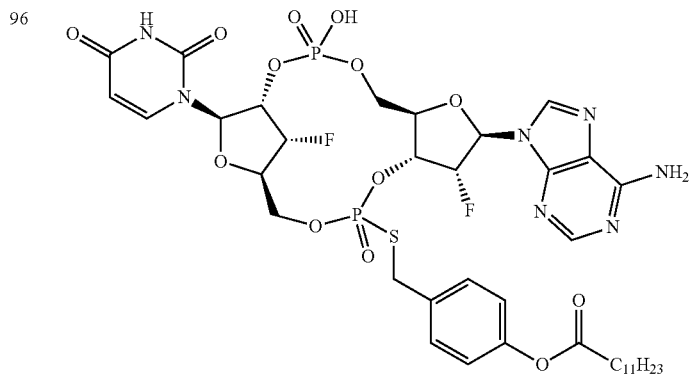 |
| 97 | 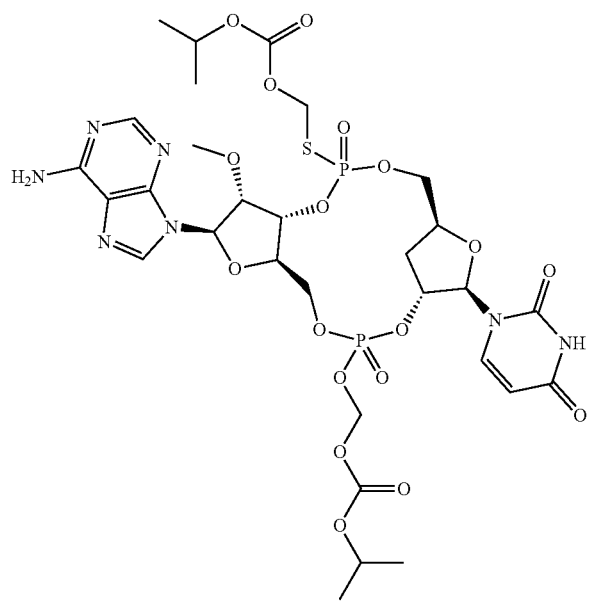 [SMILES: CO[C@@H]1[C@@H]2OP(=O)(SCOC(=O)OC(C)C)OC[C@@H]3C[C@@H](OP(=O)(OCOC(=O)OC(C)C)OC[C@H]2O[C@H]1n1cnc2c(N)ncnc21)[C@H](n1ccc(=O)[nH]c1=O)O3] |
| 98 | 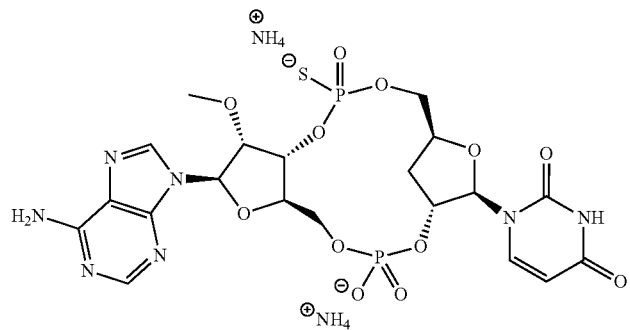 [SMILES: [NH4+] ; CO[C@@H]1[C@@H]2OP(=O)(S)OC[C@@H]3C[C@@H](OP(=O)([O-])OC[C@H]2O[C@H]1n1cnc2c(N)ncnc21)[C@H](n1ccc(=O)[nH]c1=O)O3 ; [NH4+]] |

| Compound No. | Structure |
|---|---|
| 99 | 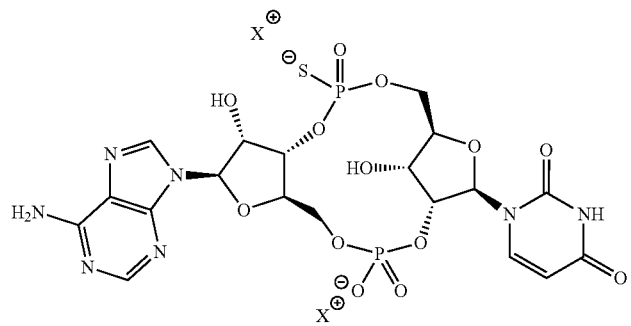 |
| 100 | 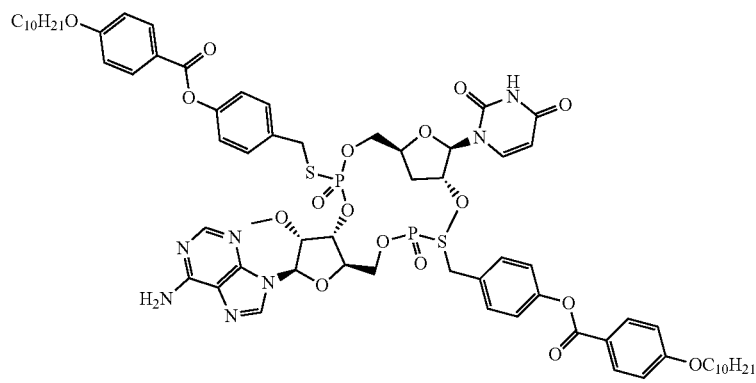 |
| 101 | 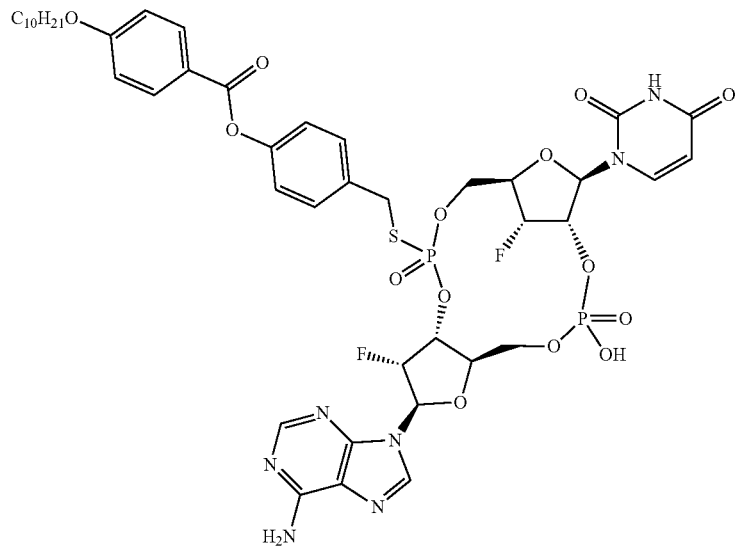 |

| Compound No. | Structure |
|---|---|
| 102 | 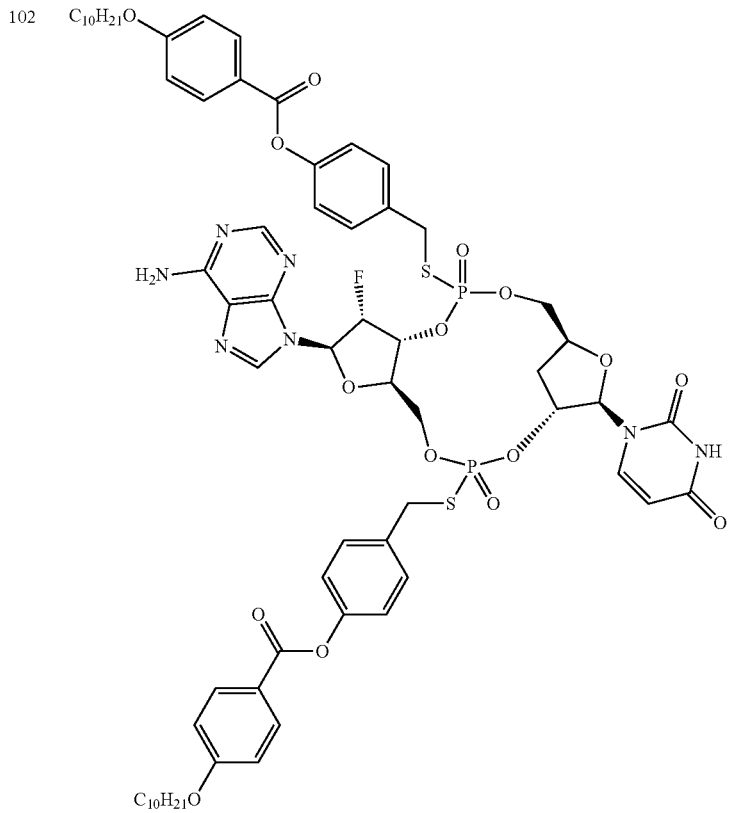 |
| 103 | 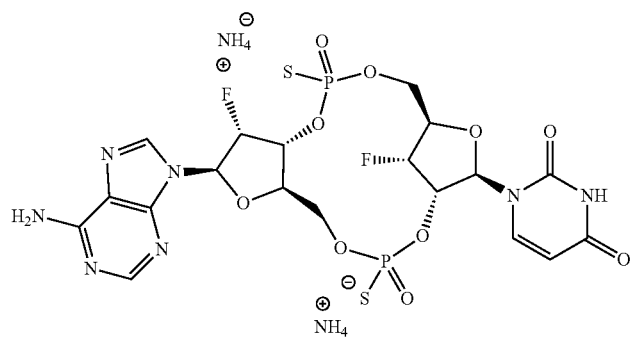 |
| 104 | 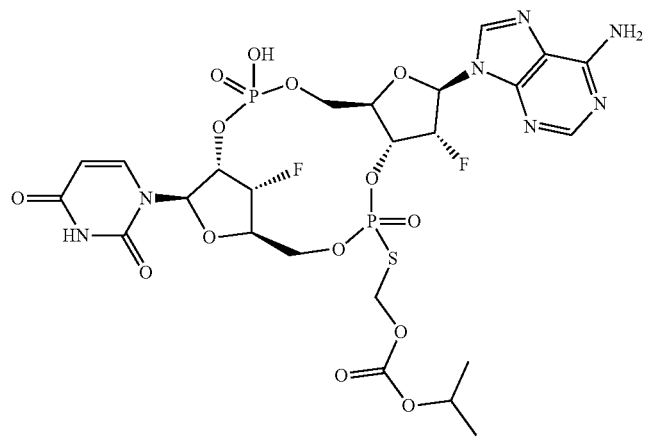 [SMILES: CC(C)OC(=O)OCSP1(=O)OC[C@H]2O[C@@H](n3ccc(=O)[nH]c3=O)[C@H](OP(=O)(O)OC[C@H]3O[C@@H](n4cnc5c(N)ncnc54)[C@H](F)[C@@H]3O1)[C@@H]2F] |

-continued
| Compound No. | Structure |
|---|---|
| 105 | 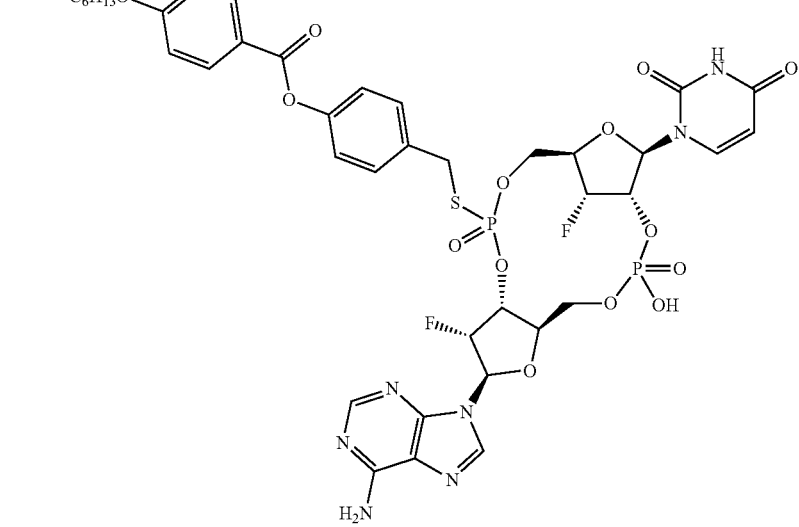 |
| 106 | 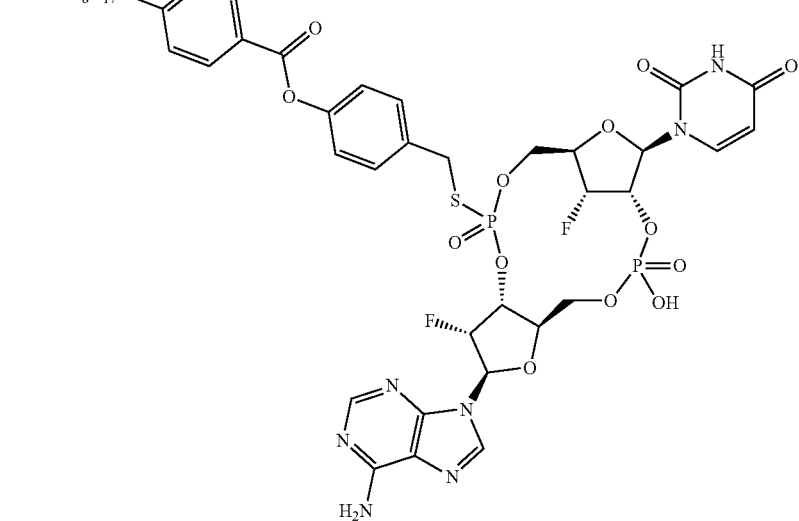 |

-continued
| Compound No. | Structure |
|---|---|
| 107 | C10H21O 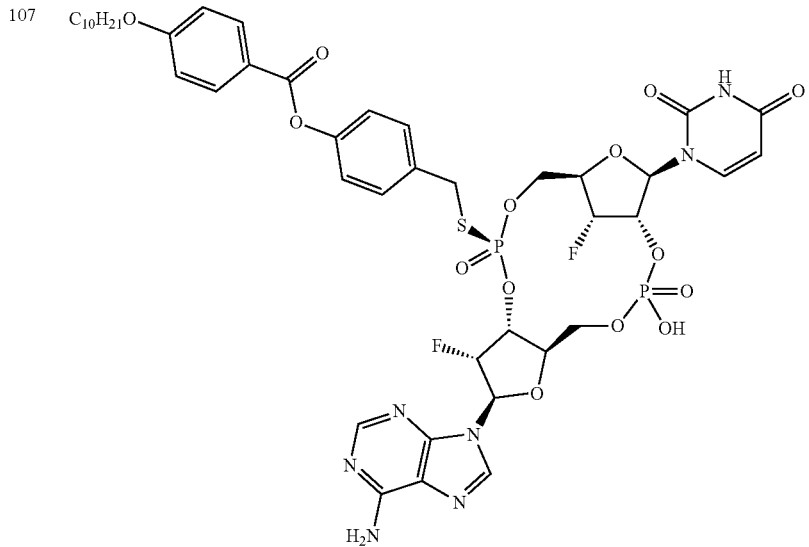 |
| 108 | C10H21O 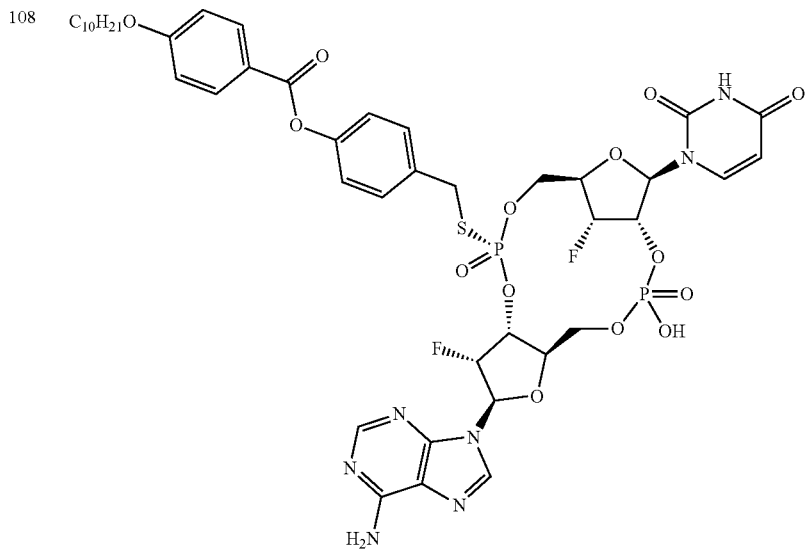 |
| 109 | C10H21O 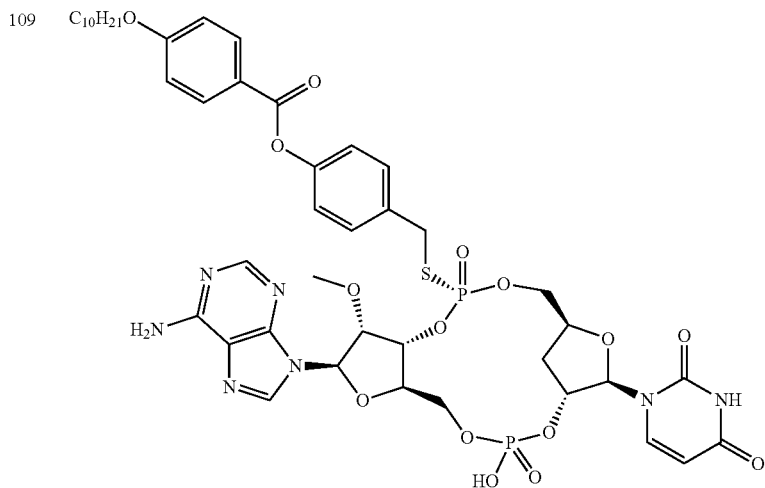 |

-continued
| Compound No. | Structure |
|---|---|
| 110 | 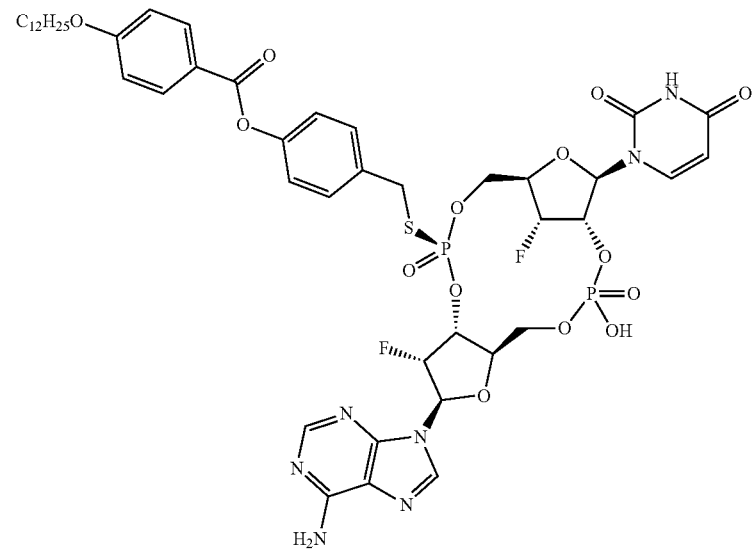 |
| 111 | 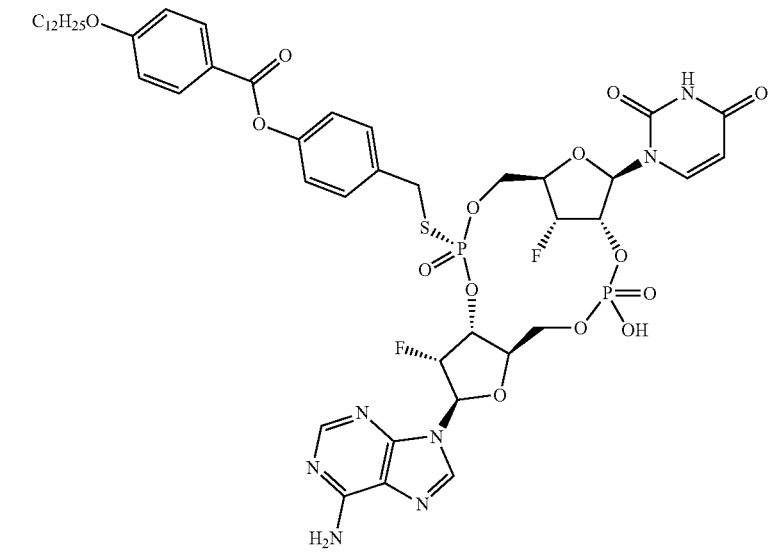 |

-continued
| Compound No. | Structure |
|---|---|
| 112 | 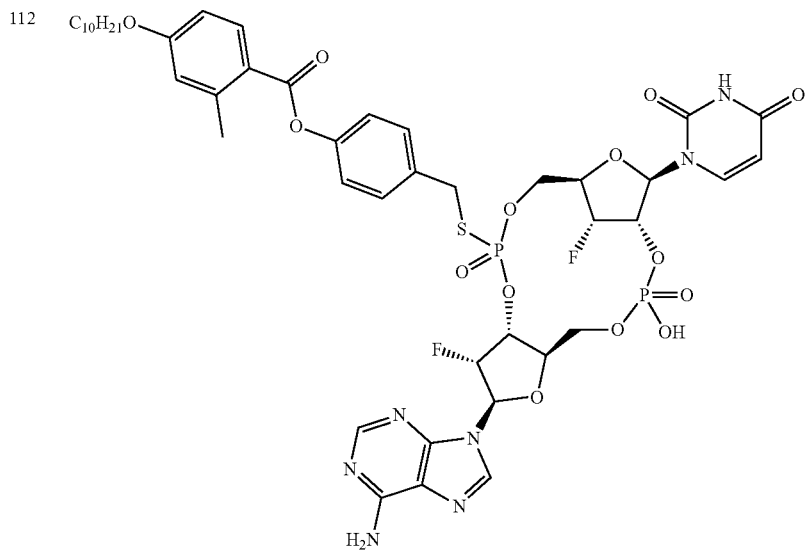 |
| 113 | 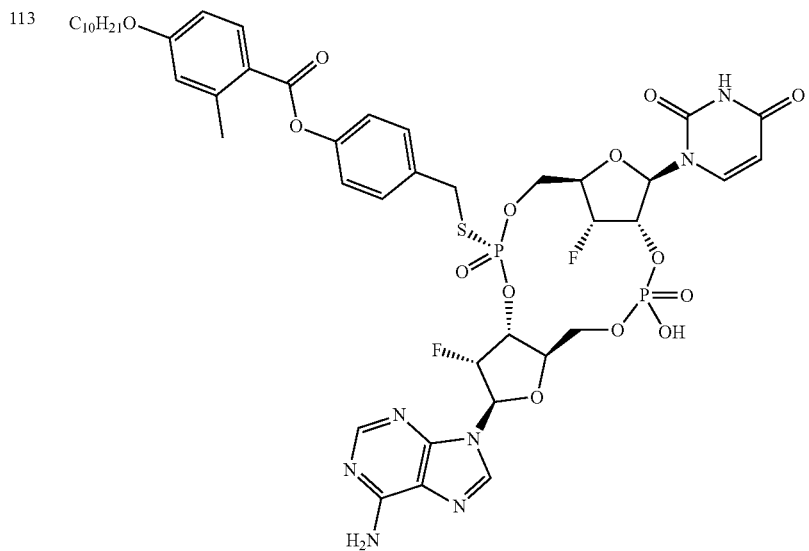 |

| Compound No. | Structure |
|---|---|
| 114 | 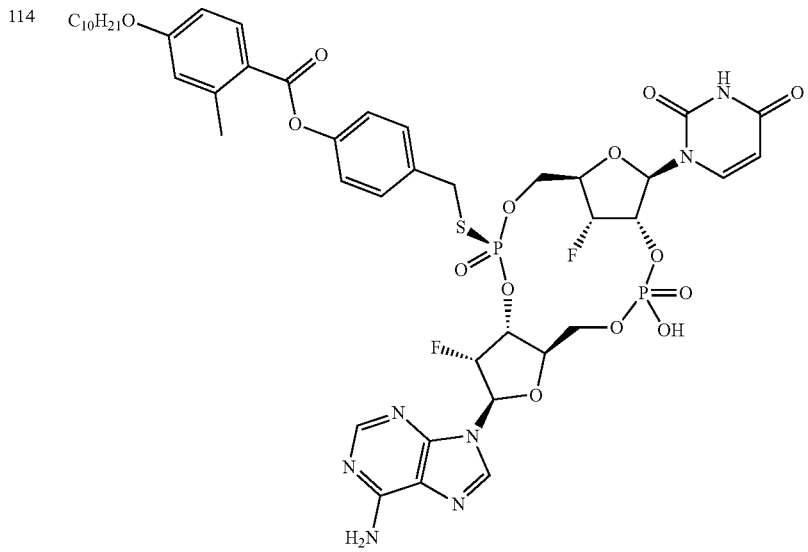 |
| 115 | 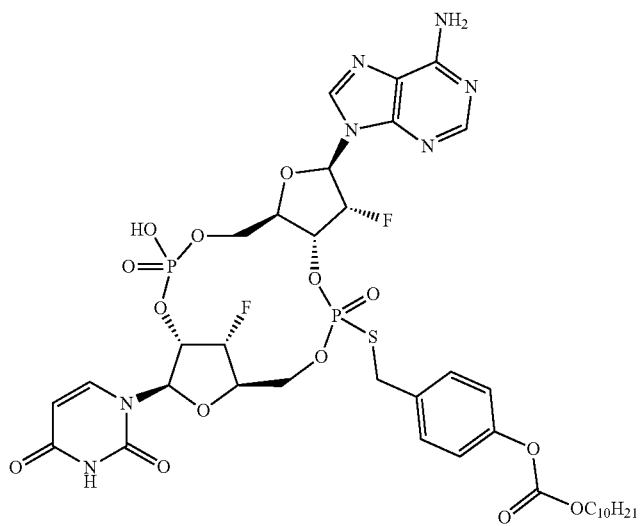 |
| 116 | 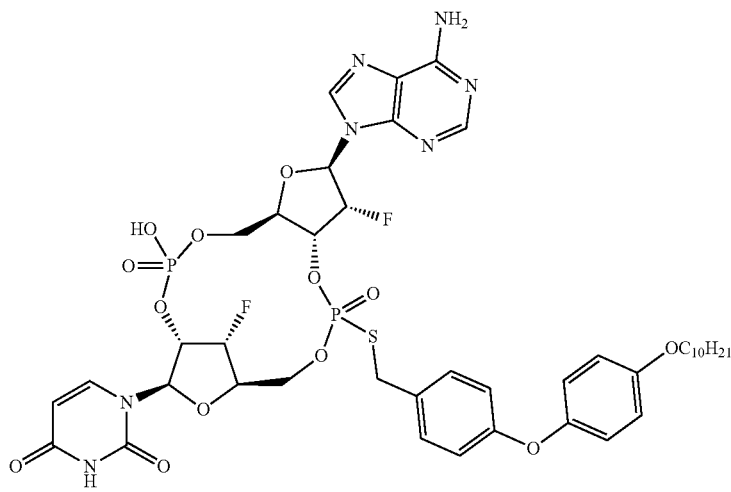 |

| Compound No. | Structure |
|---|---|
| 117 | 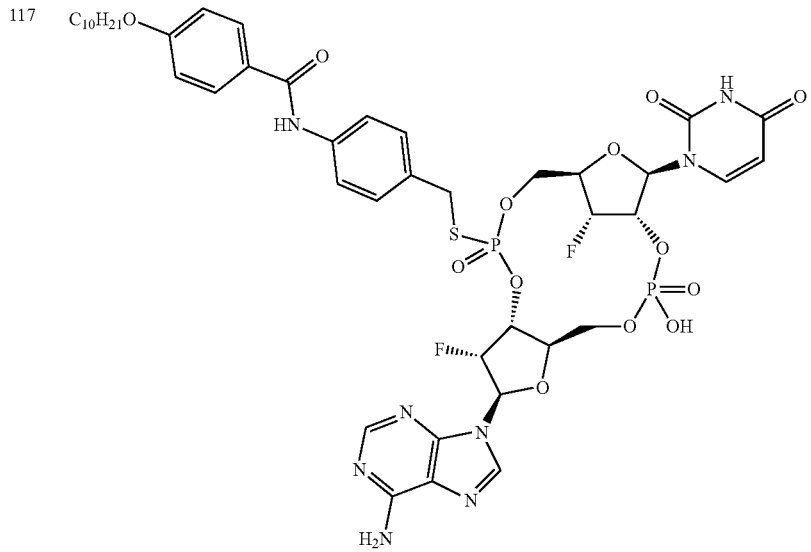 |
| 118 | 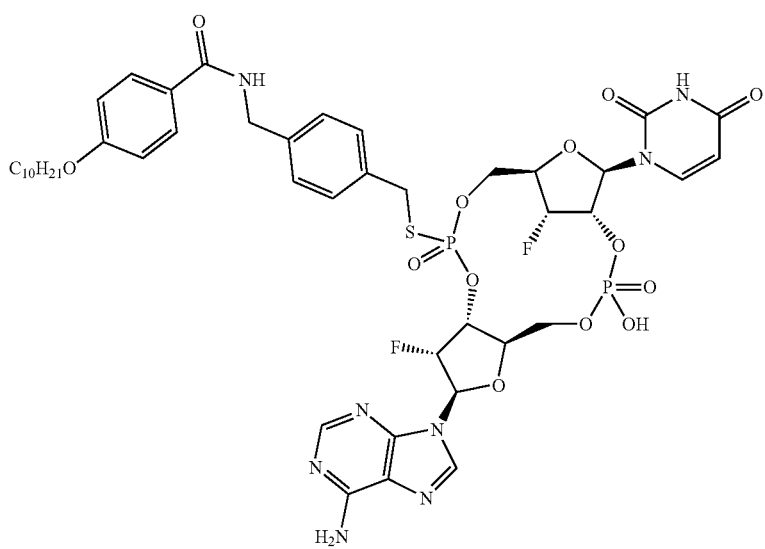 |
| 119 | 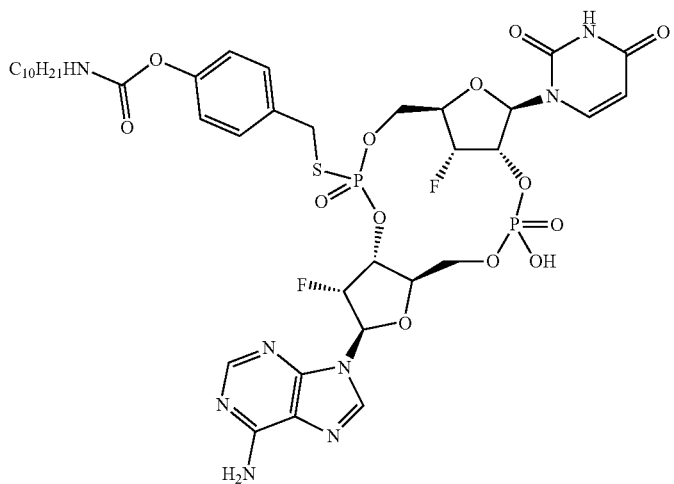 |

| Compound No. | Structure |
|---|---|
| 120 | 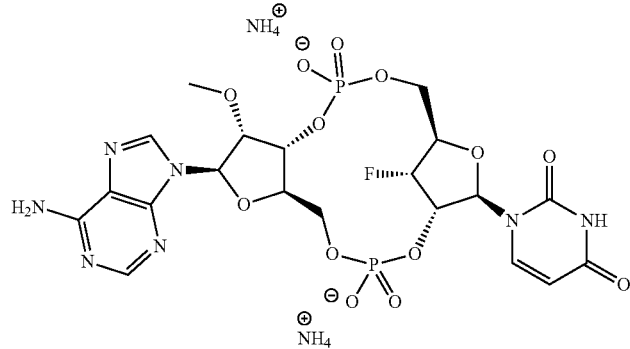 [SMILES: [NH4+] ; CO[C@@H]1[C@@H]2OP(=O)([O-])OC[C@H]3O[C@@H](n4ccc(=O)[nH]c4=O)[C@H](OP(=O)([O-])OC[C@H]2O[C@H]1n1cnc2c(N)ncnc21)[C@@H]3F ; [NH4+]] |
| 121 | 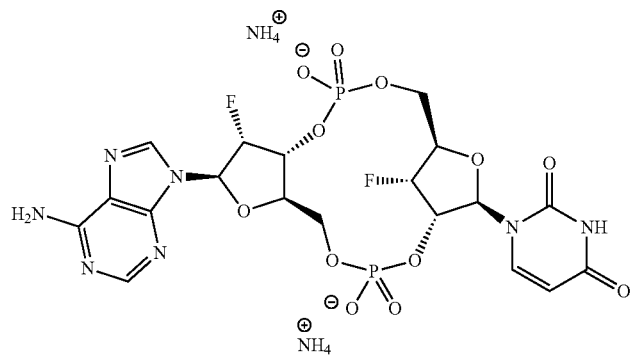 [SMILES: [NH4+] ; Nc1ncnc2c1ncn2[C@@H]1O[C@@H]2COP(=O)([O-])O[C@@H]3[C@H](F)[C@@H](COP(=O)([O-])O[C@H]2[C@H]1F)O[C@H]3n1ccc(=O)[nH]c1=O ; [NH4+]] |
| 122 | 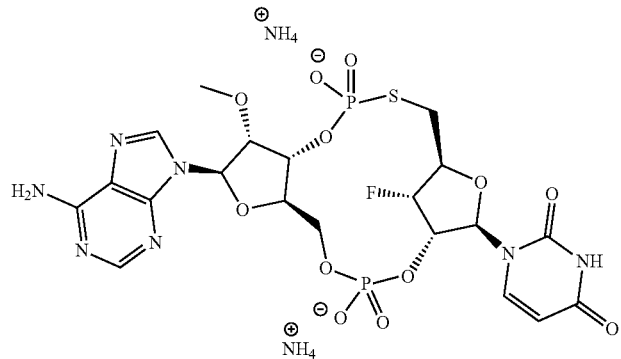 [SMILES: [NH4+] ; CO[C@@H]1[C@@H]2OP(=O)([O-])SC[C@H]3O[C@@H](n4ccc(=O)[nH]c4=O)[C@H](OP(=O)([O-])OC[C@H]2O[C@H]1n1cnc2c(N)ncnc21)[C@@H]3F ; [NH4+]] |

| Compound No. | Structure |
|---|---|
| 123 | 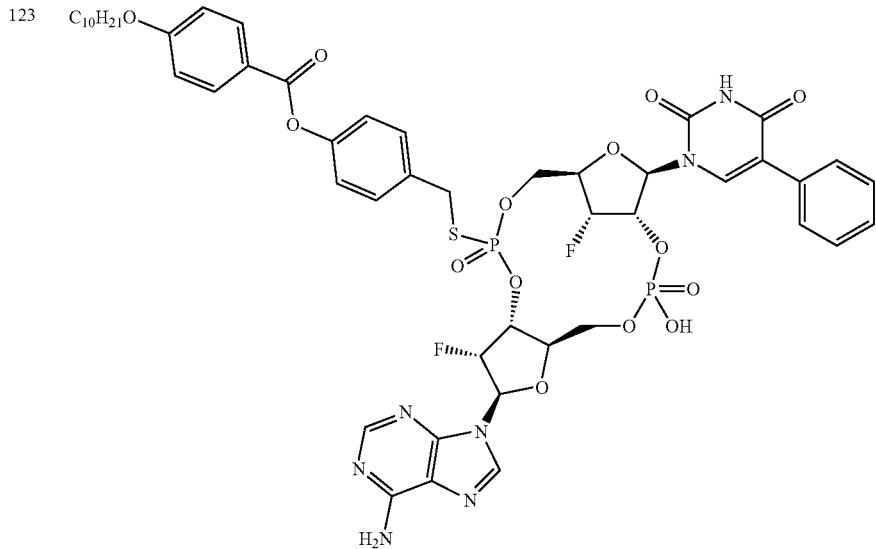 |
| 124 | 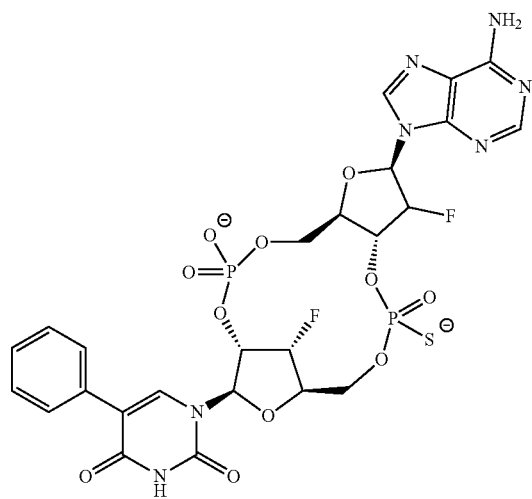 [SMILES: Nc1ncnc2c1ncn2[C@@H]1O[C@@H]2COP(=O)([O-])O[C@@H]3[C@H](F)[C@@H](COP(=O)([S-])O[C@H]2C1F)O[C@H]3n1cc(-c2ccccc2)c(=O)[nH]c1=O] |
| 125 | 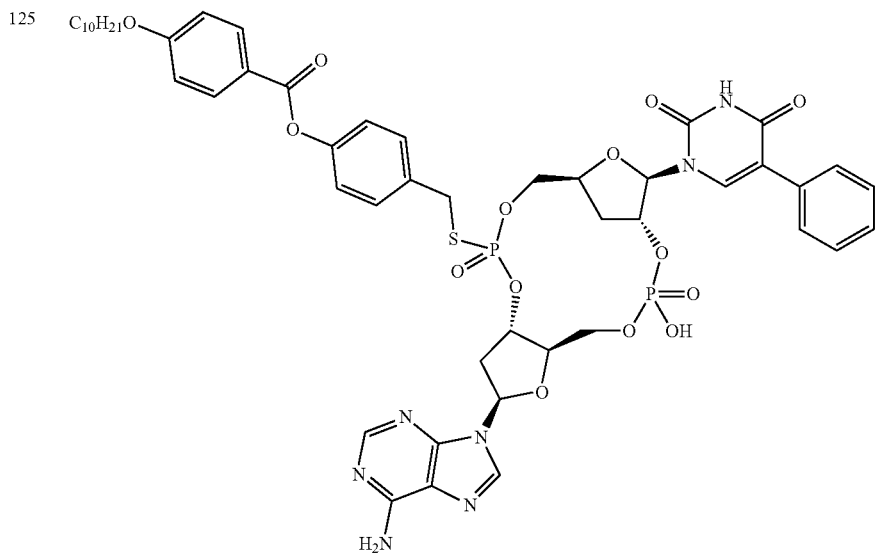 |

| Compound No. | Structure |
|---|---|
| 126 | 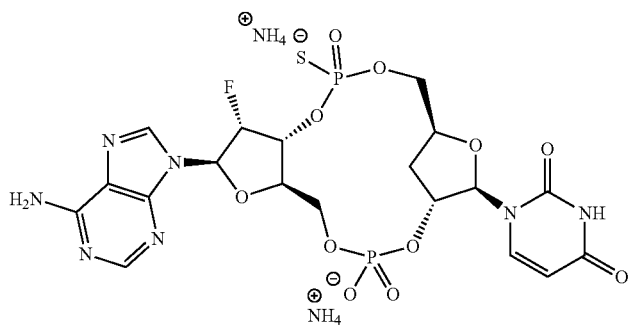 [SMILES: [NH4+] ; Nc1ncnc2c1ncn2[C@@H]1O[C@@H]2COP(=O)([O-])O[C@@H]3C[C@@H](COP(=O)([S-])O[C@H]2[C@H]1F)O[C@H]3n1ccc(=O)[nH]c1=O ; [NH4+]] |
| 127 | 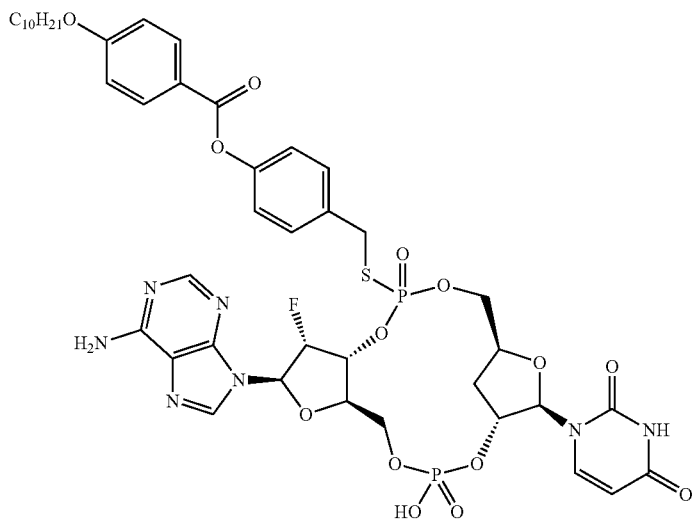 |
| 128 | 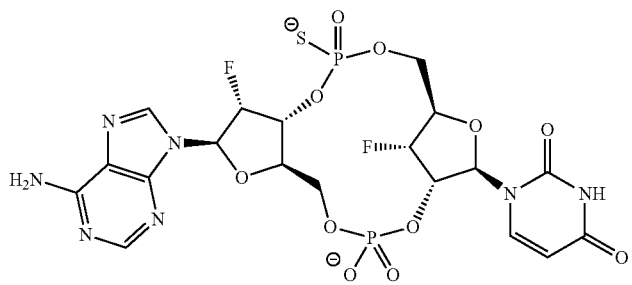 [SMILES: Nc1ncnc2c1ncn2[C@@H]1O[C@@H]2COP(=O)([O-])O[C@@H]3[C@H](F)[C@@H](COP(=O)(S)O[C@H]2[C@H]1F)O[C@H]3n1ccc(=O)[nH]c1=O] |

| Compound No. | Structure |
|---|---|
| 129 | 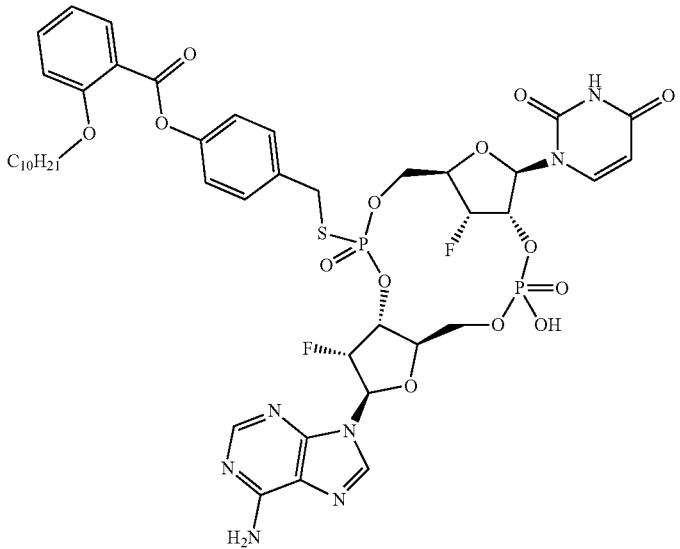 |
| 130 | 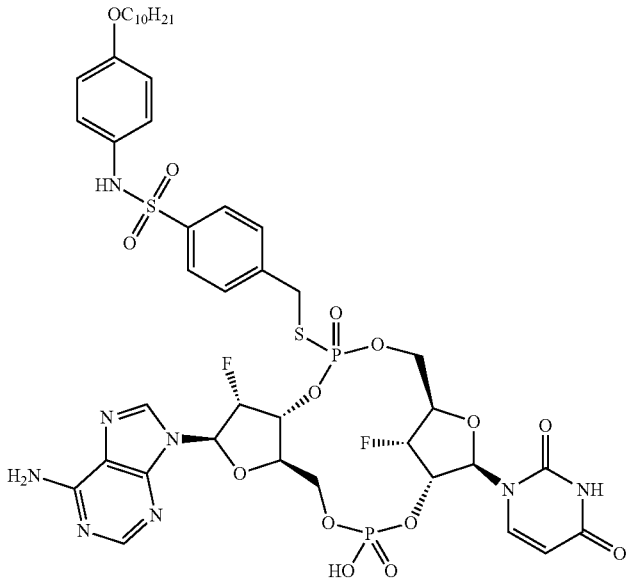 |

327
328
-continued
| Compound No. | Structure |
|---|---|
131 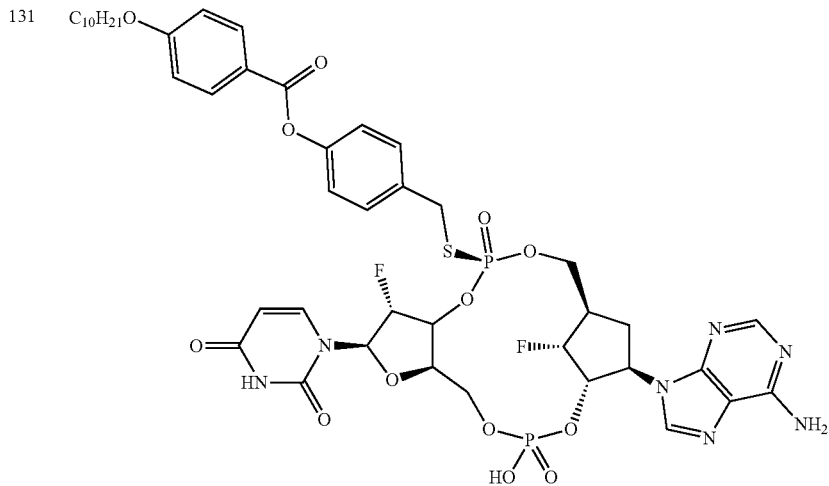
132 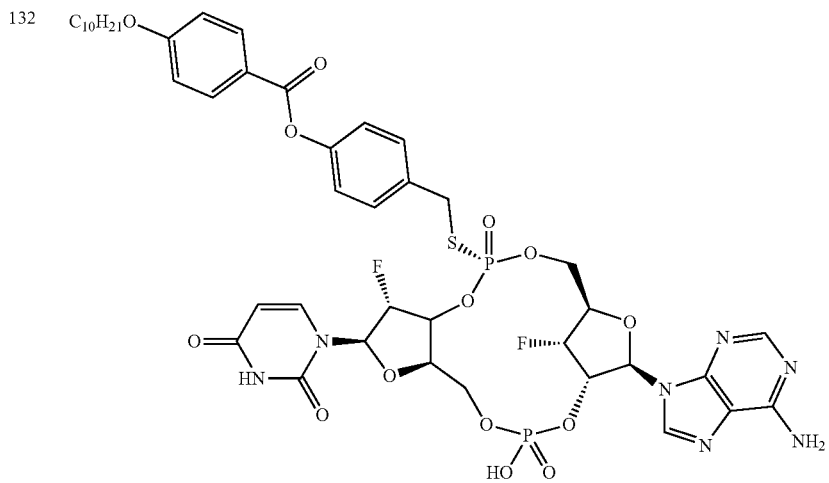
133 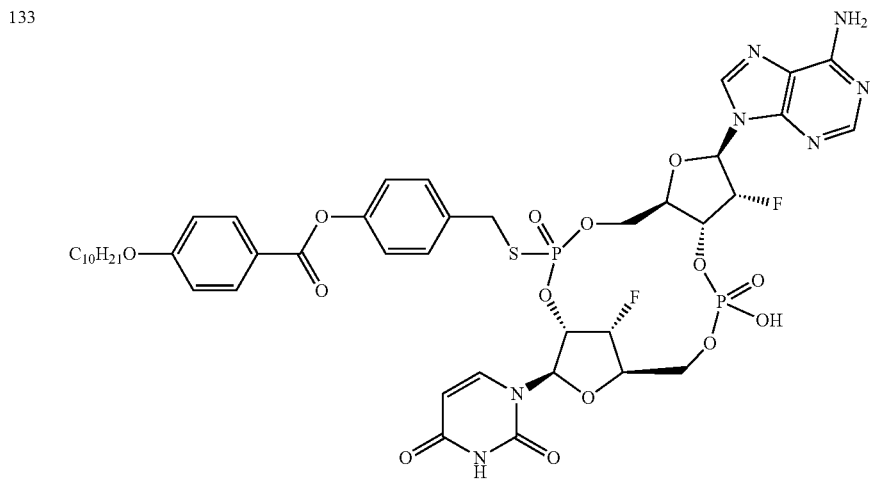

| Compound No. | Structure |
|---|---|
| 134 | 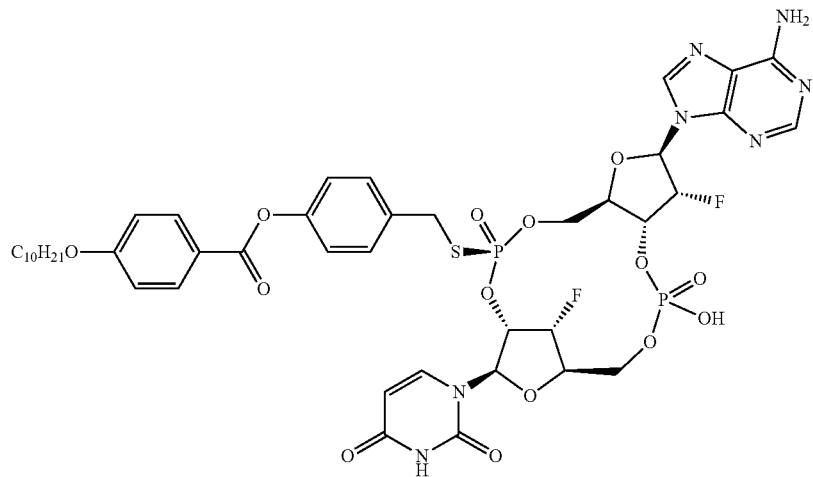 |
| 135 | 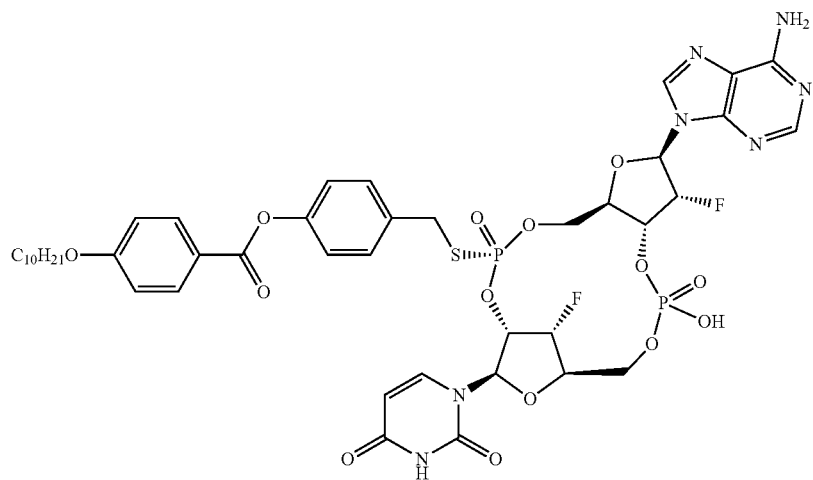 |
| 136 | 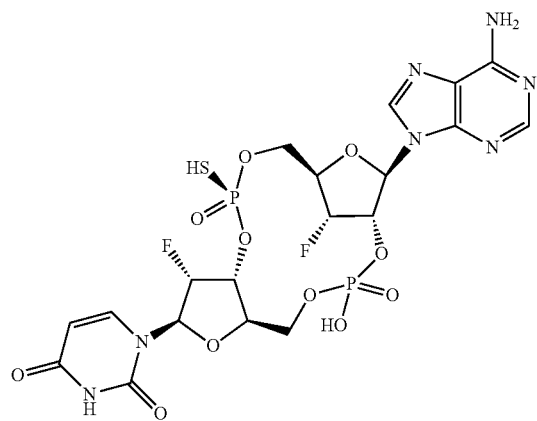 [SMILES: Nc1ncnc2c1ncn2[C@@H]1O[C@@H]2CO[P@](=O)(S)O[C@H]3[C@@H](F)[C@H](n4ccc(=O)[nH]c4=O)O[C@@H]3COP(=O)(O)O[C@@H]1[C@@H]2F] |

-continued
| Compound No. | Structure |
|---|---|
| 137 | 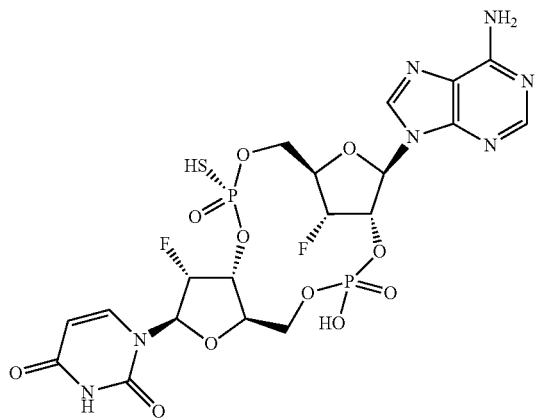 [SMILES: Nc1ncnc2c1ncn2[C@@H]1O[C@@H]2CO[P@@](=O)(S)O[C@H]3[C@@H](F)[C@H](n4ccc(=O)[nH]c4=O)O[C@@H]3COP(=O)(O)O[C@@H]1[C@@H]2F] |
| 138 | 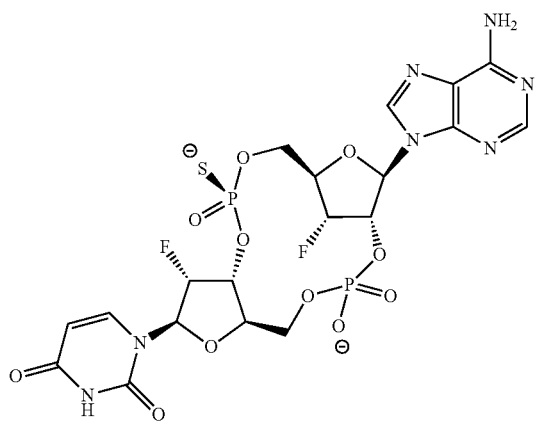 [SMILES: Nc1ncnc2c1ncn2[C@@H]1O[C@@H]2CO[P@](=O)([S-])O[C@H]3[C@@H](F)[C@H](n4ccc(=O)[nH]c4=O)O[C@@H]3COP(=O)([O-])O[C@@H]1[C@@H]2F] |
| 139 | 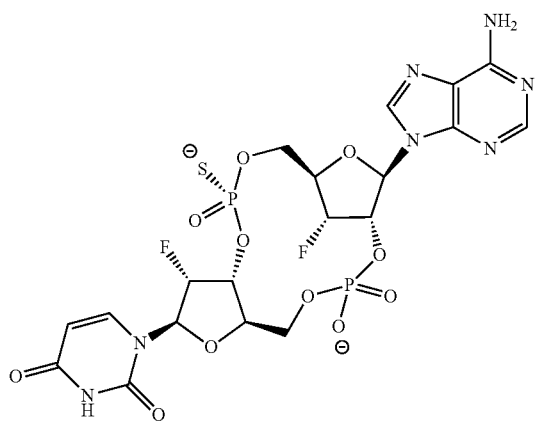 [SMILES: Nc1ncnc2c1ncn2[C@@H]1O[C@@H]2CO[P@@](=O)([S-])O[C@H]3[C@@H](F)[C@H](n4ccc(=O)[nH]c4=O)O[C@@H]3COP(=O)([O-])O[C@@H]1[C@@H]2F] |

| Compound No. | Structure |
|---|---|
| 140 | 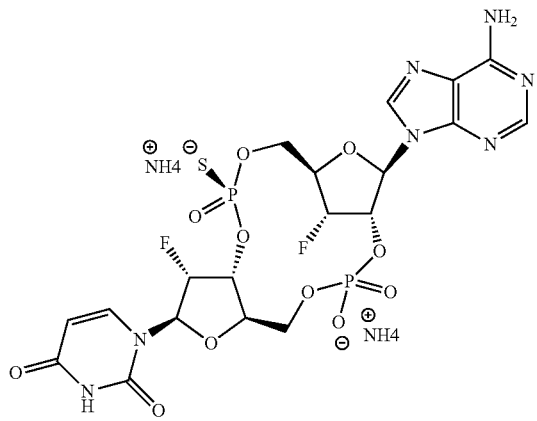 [SMILES: Nc1ncnc2c1ncn2[C@@H]1O[C@@H]2CO[P@](=O)([S-])O[C@H]3[C@@H](F)[C@H](n4ccc(=O)[nH]c4=O)O[C@@H]3COP(=O)([O-])O[C@@H]1[C@@H]2F ; [NH4+] ; [NH4+]] |
| 141 | 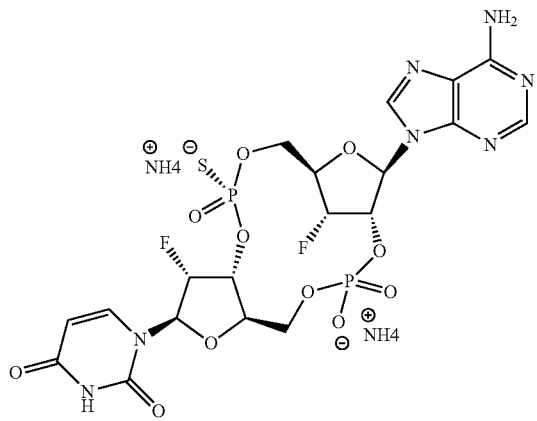 [SMILES: Nc1ncnc2c1ncn2[C@@H]1O[C@@H]2CO[P@@](=O)([S-])O[C@H]3[C@@H](F)[C@H](n4ccc(=O)[nH]c4=O)O[C@@H]3COP(=O)([O-])O[C@@H]1[C@@H]2F ; [NH4+] ; [NH4+]] |
| 142 | 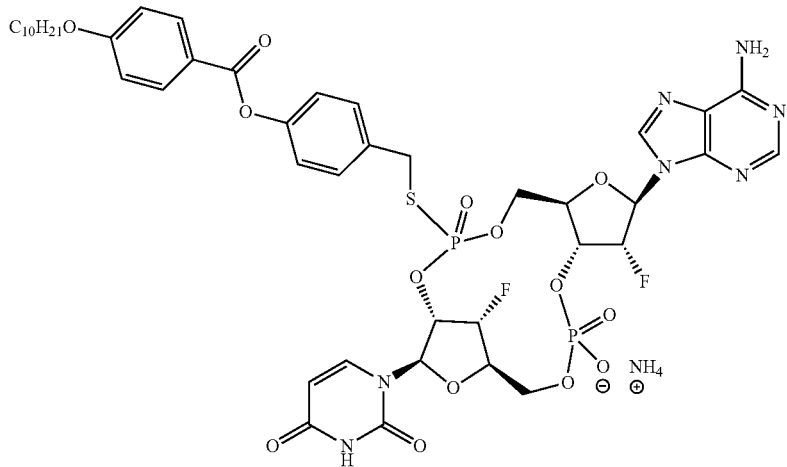 |

-continued
| Compound No. | Structure |
|---|---|
| 143 | 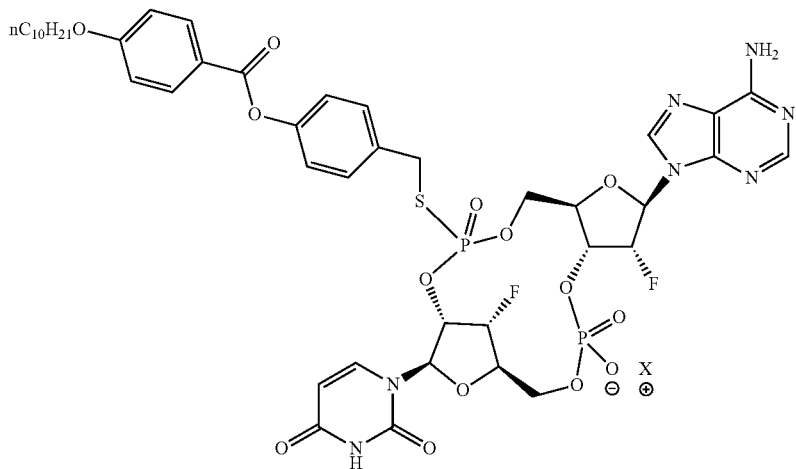 |
| 144 | 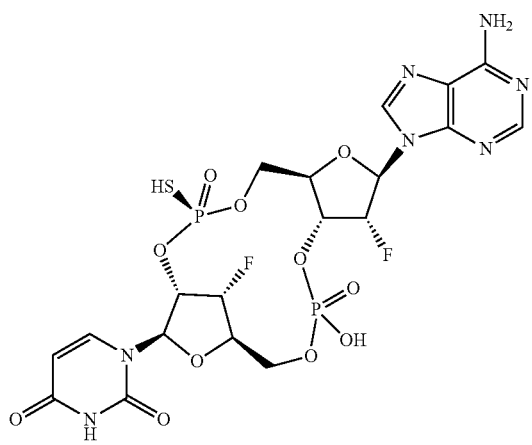 [SMILES: Nc1ncnc2c1ncn2[C@@H]1O[C@@H]2CO[P@](=O)(S)O[C@@H]3[C@H](F)[C@@H](COP(=O)(O)O[C@H]2[C@H]1F)O[C@H]3n1ccc(=O)[nH]c1=O] |
| 145 | 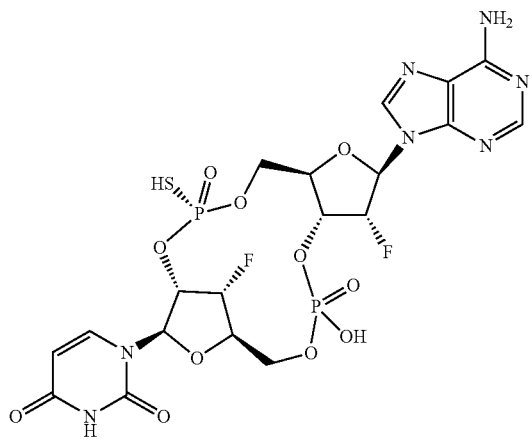 [SMILES: Nc1ncnc2c1ncn2[C@@H]1O[C@@H]2CO[P@@](=O)(S)O[C@@H]3[C@H](F)[C@@H](COP(=O)(O)O[C@H]2[C@H]1F)O[C@H]3n1ccc(=O)[nH]c1=O] |

| Compound No. | Structure |
|---|---|
| 146 | 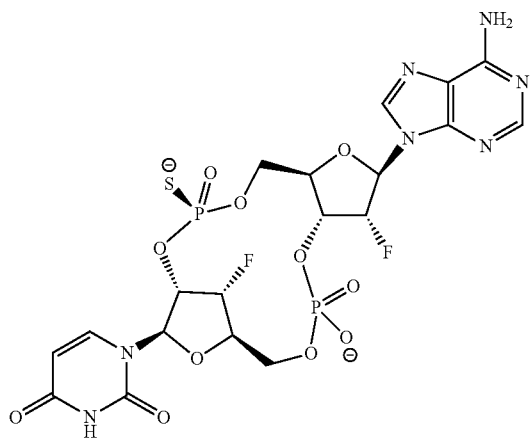 [SMILES: Nc1ncnc2c1ncn2[C@@H]1O[C@@H]2CO[P@](=O)([S-])O[C@@H]3[C@H](F)[C@@H](COP(=O)([O-])O[C@H]2[C@H]1F)O[C@H]3n1ccc(=O)[nH]c1=O] |
| 147 | 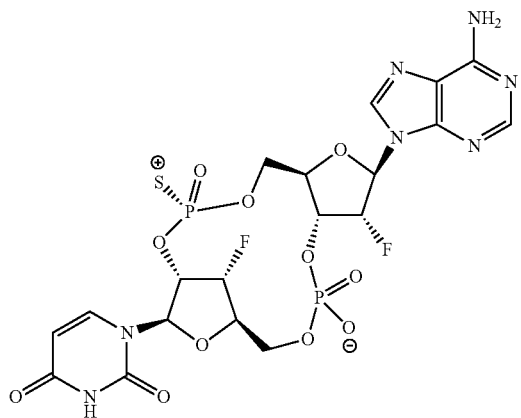 |
| 148 | 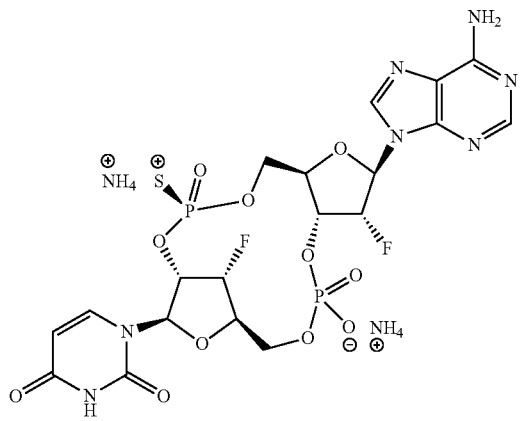 |

| Compound No. | Structure |
|---|---|
| 149 | 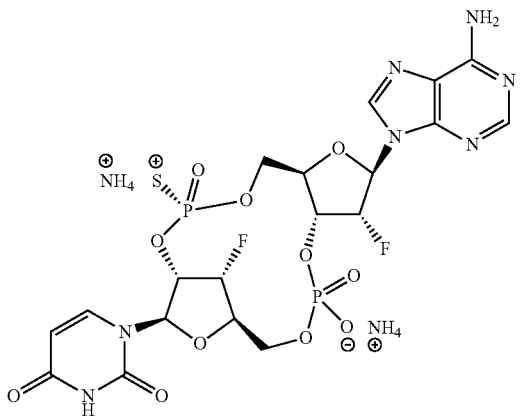 |
| 150 | 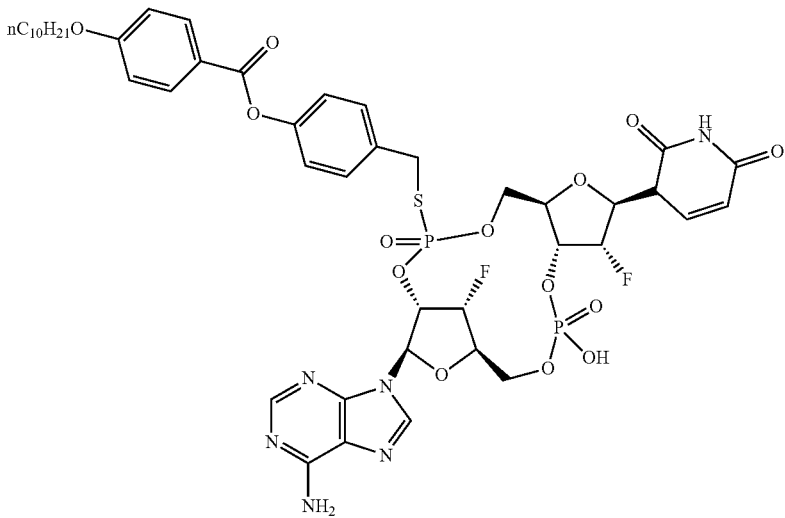 |
| 151 | 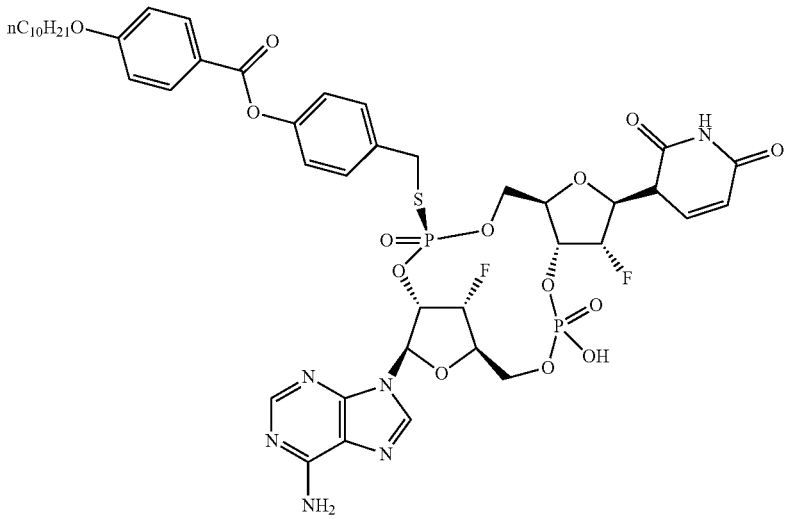 |

| Compound No. | Structure |
|---|---|
| 152 | 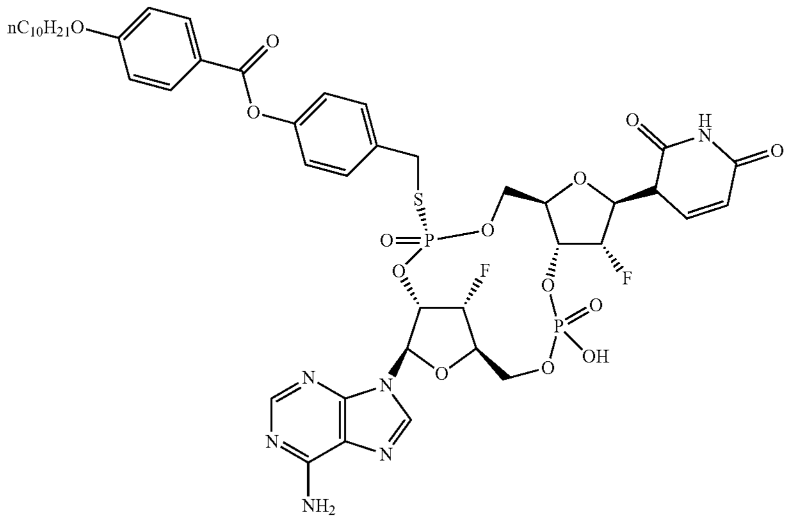 |
| 153 | 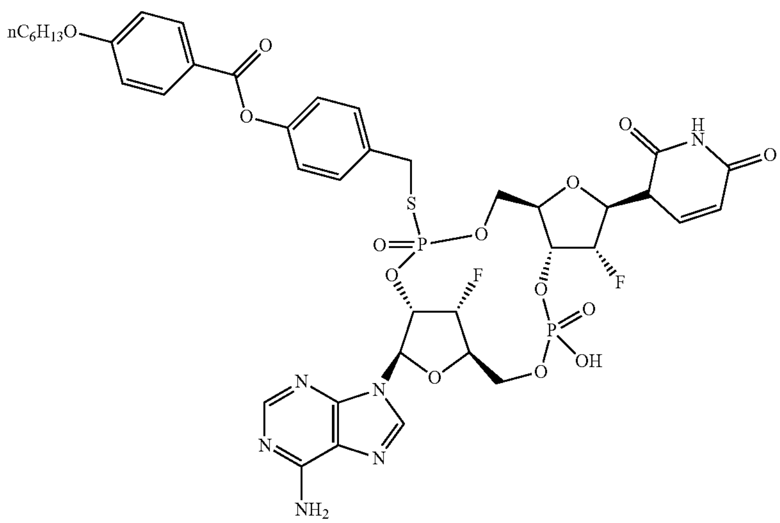 |
| 154 | 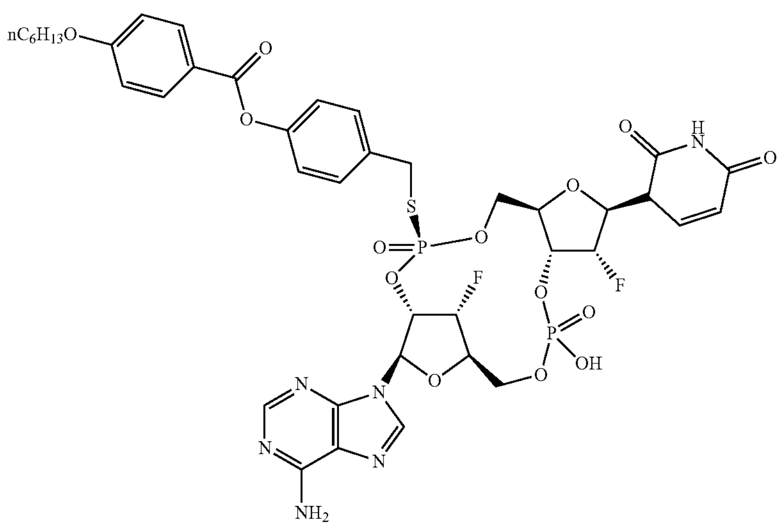 |

| Compound No. | Structure |
|---|---|
| 155 | nC₆H₁₃O— [structure] |
| 156 | nC₁₁H₂₃— [structure] |
| 157 | nC₈H₁₇O— [structure] |

| Compound No. | Structure |
|---|---|
| 158 | 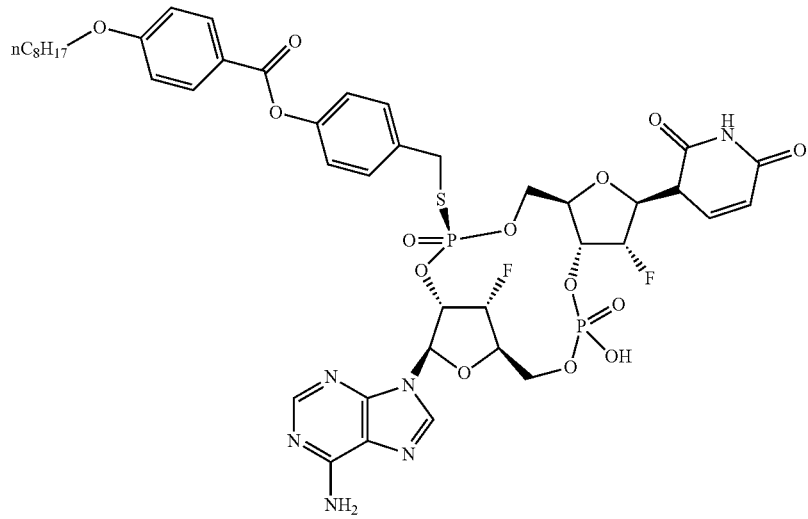 |
| 159 | 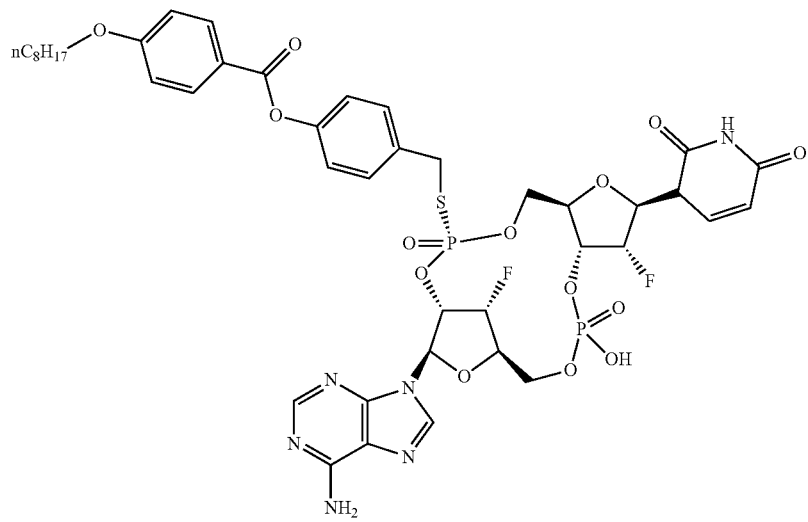 |
| 160 | 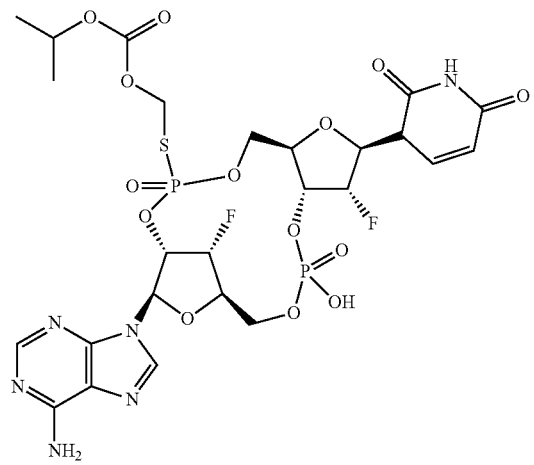 [SMILES: CC(C)OC(=O)OCSP1(=O)OC[C@H]2O[C@@H](C3C=CC(=O)NC3=O)[C@H](F)[C@@H]2OP(=O)(O)OC[C@H]2O[C@@H](n3cnc4c(N)ncnc43)[C@H](O1)[C@@H]2F] |

-continued
| Compound No. | Structure |
|---|---|
| 161 | 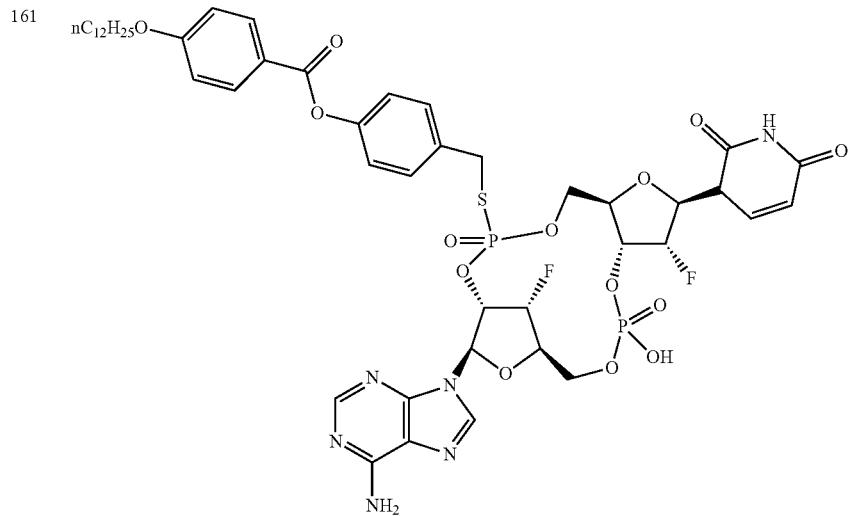 |
| 162 | 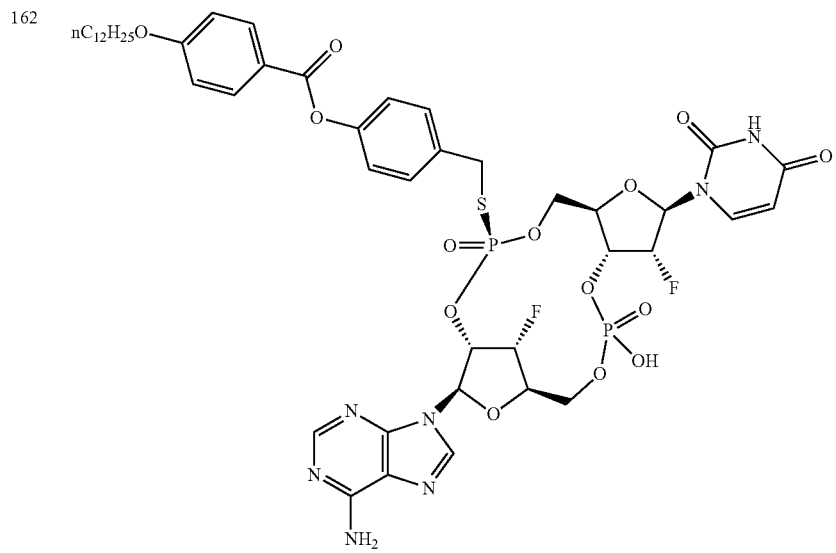 |

-continued
| Compound No. | Structure |
|---|---|
| 163 | 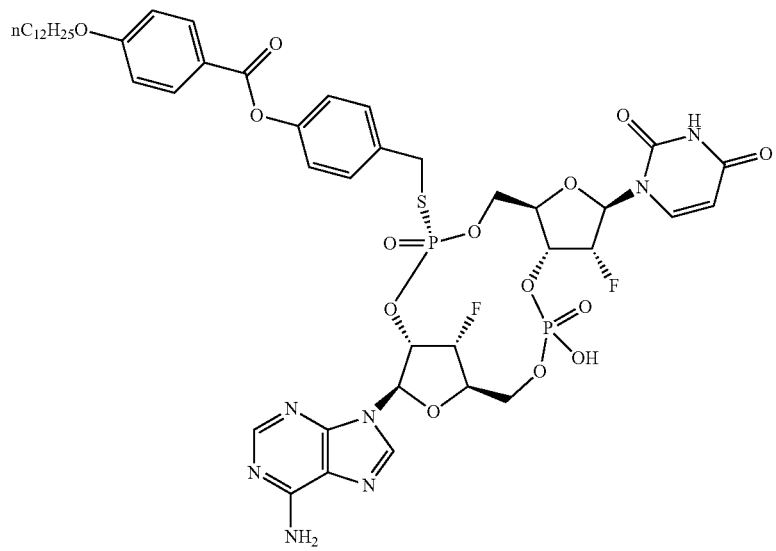 |
| 164 | 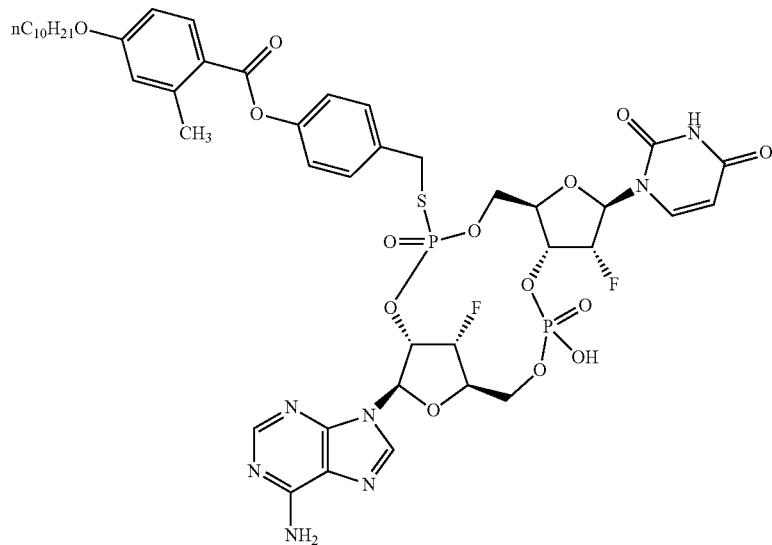 |

| Compound No. | Structure |
|---|---|
| 165 | 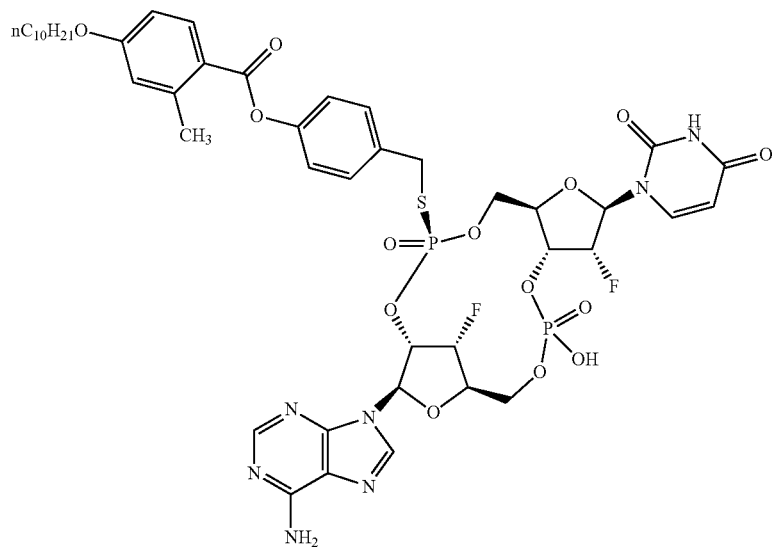 |
| 166 | 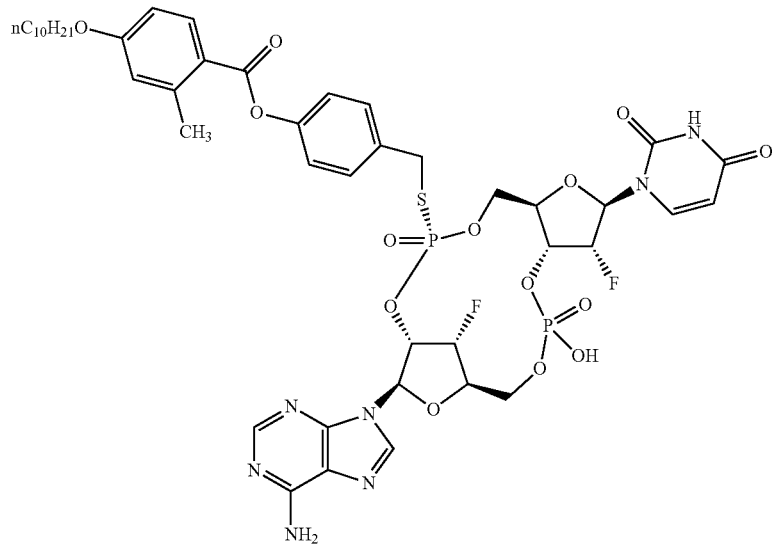 |

-continued
| Compound No. | Structure |
|---|---|
| 167 | 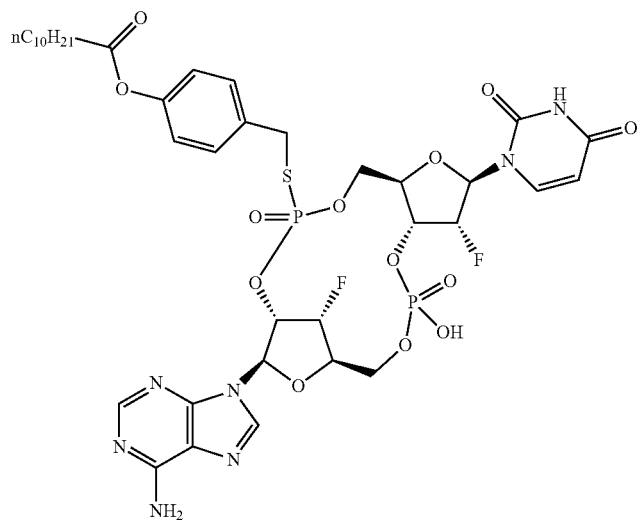 |
| 168 | 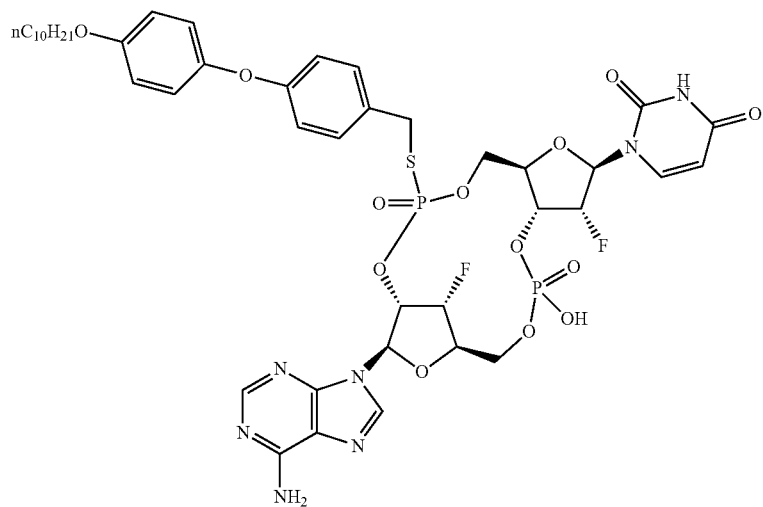 |
| 169 | 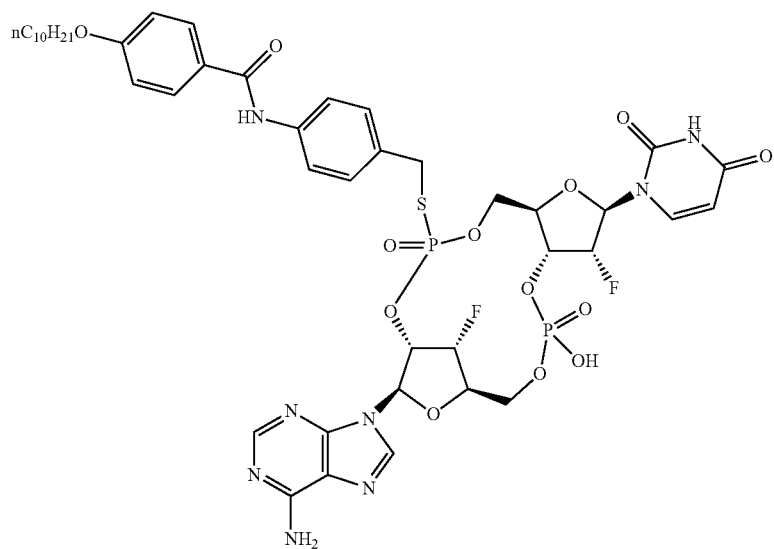 |

-continued

| Compound No. | Structure |
| --- | --- |
| 170 | 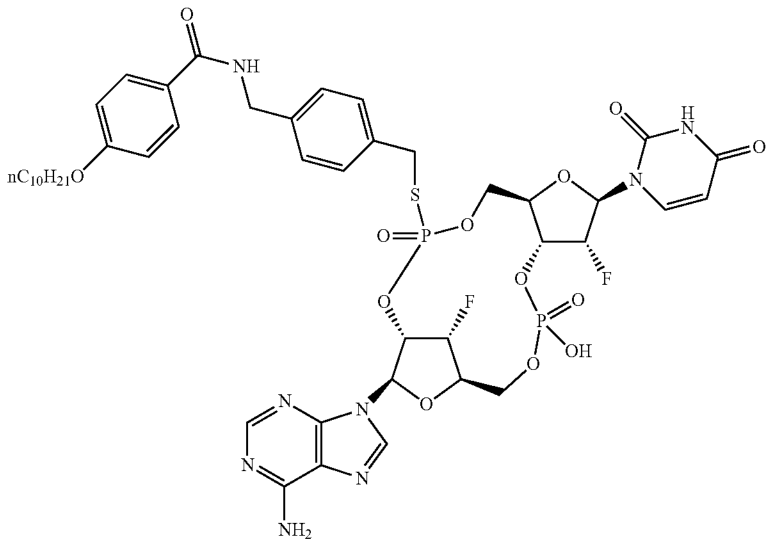 |
| 171 | 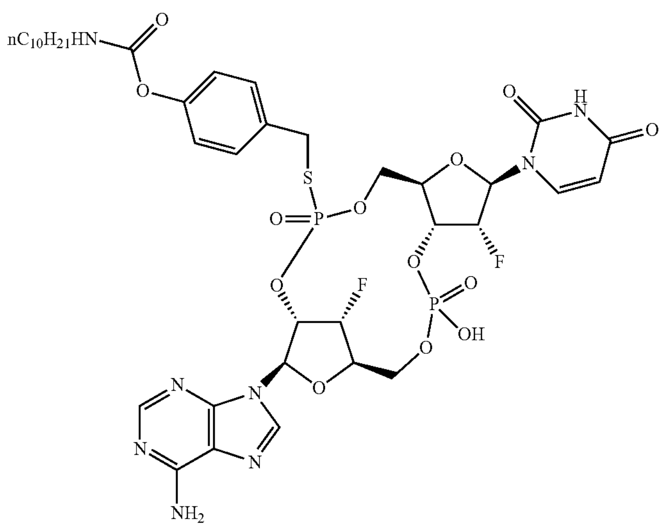 |
| 172 | 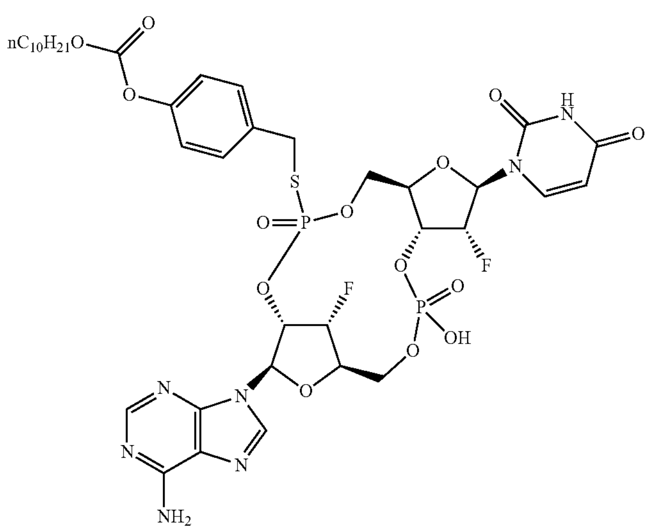 |

| Compound No. | Structure |
|---|---|
| 173 | 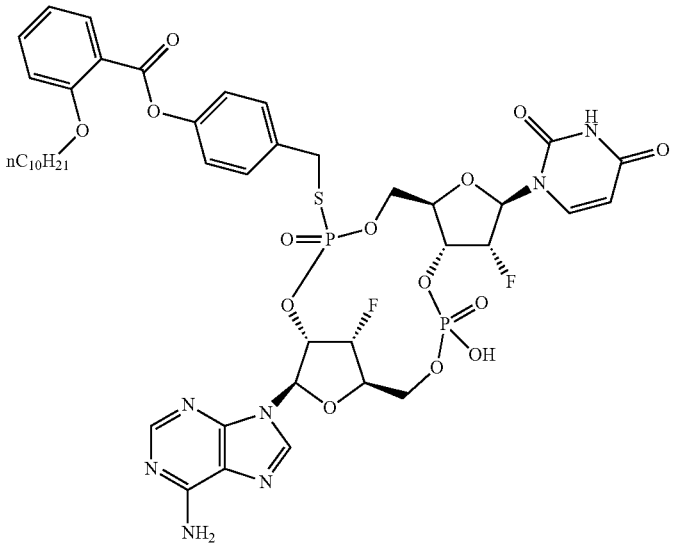 |
| 174 | 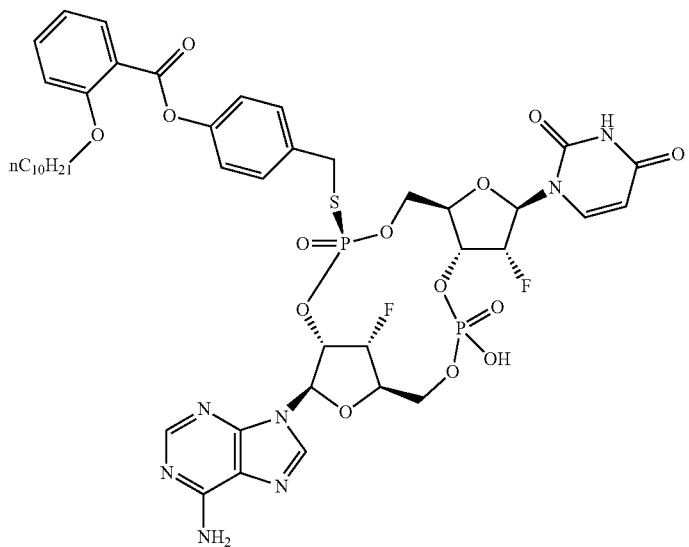 |

| Compound No. | Structure |
|---|---|
| 175 | 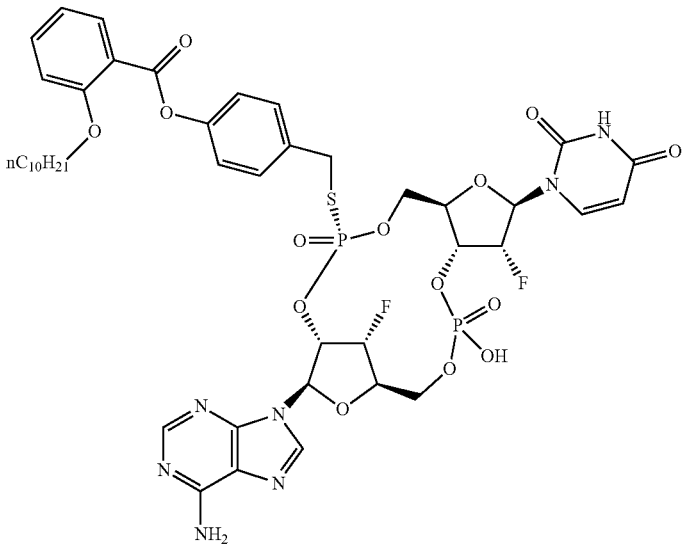 |
| 176 | 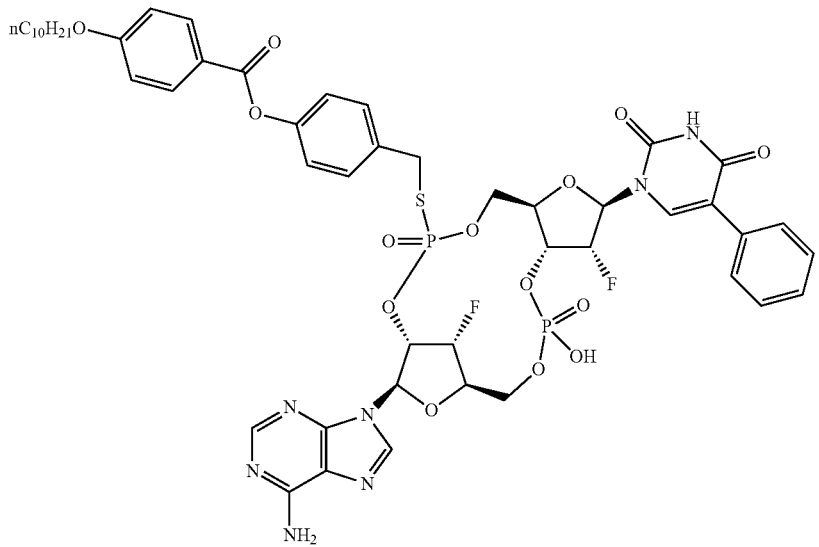 |

| Compound No. | Structure |
|---|---|
| 177 | 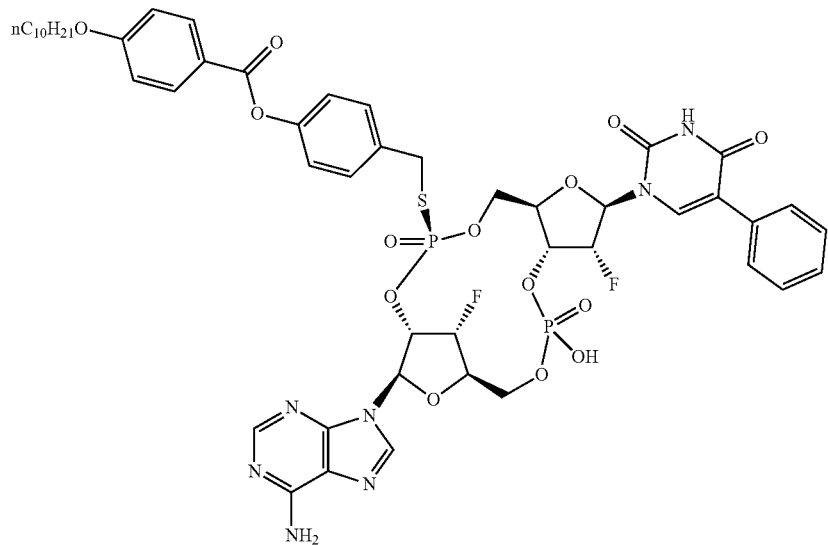 |
| 178 | 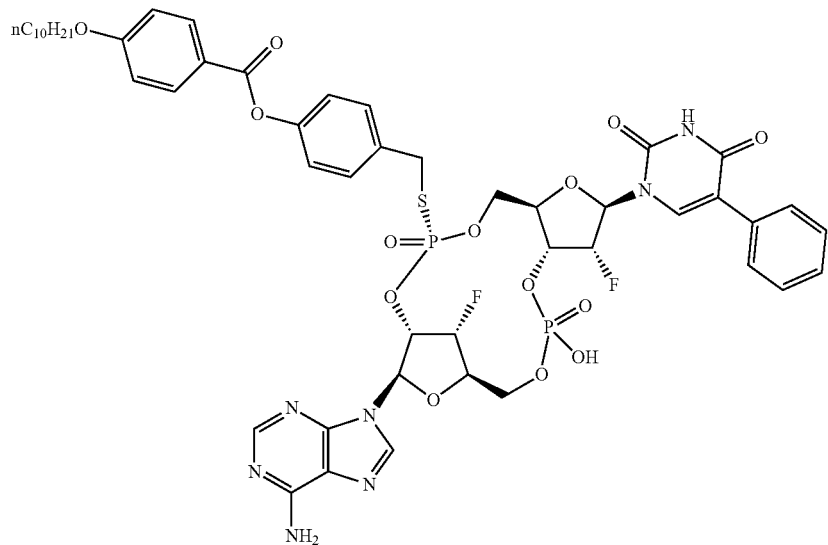 |

| Compound No. | Structure |
|---|---|
| 179 | 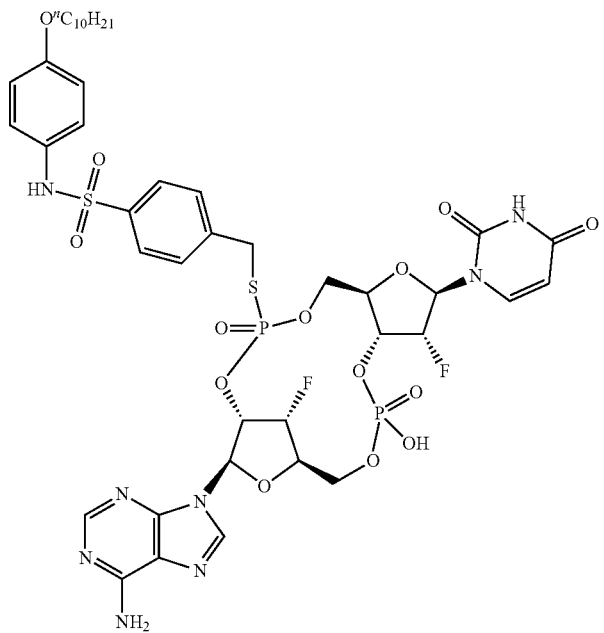 |
| 180 | 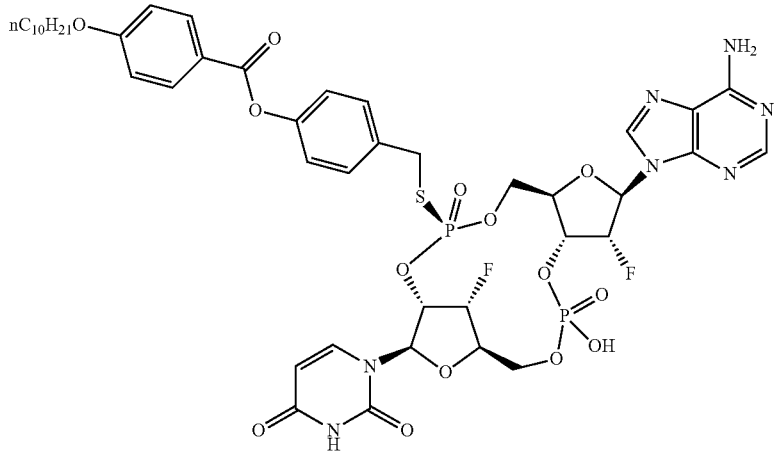 |
| 181 | 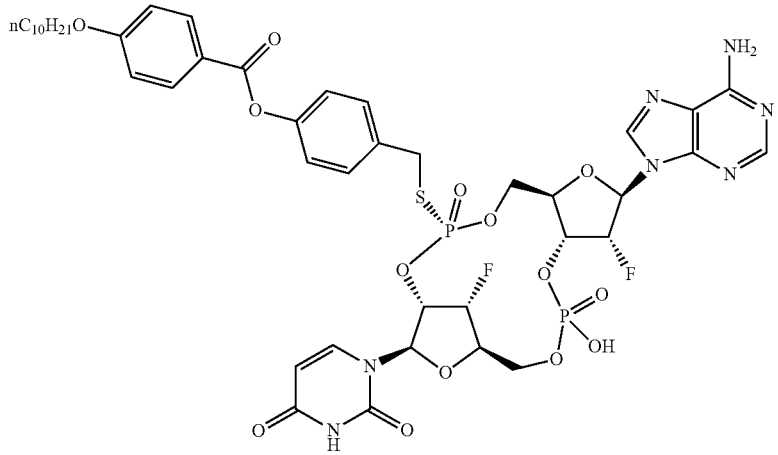 |

US 11,638,716 B2
-continued
| Compound No. | Structure |
|---|---|
| 182 | 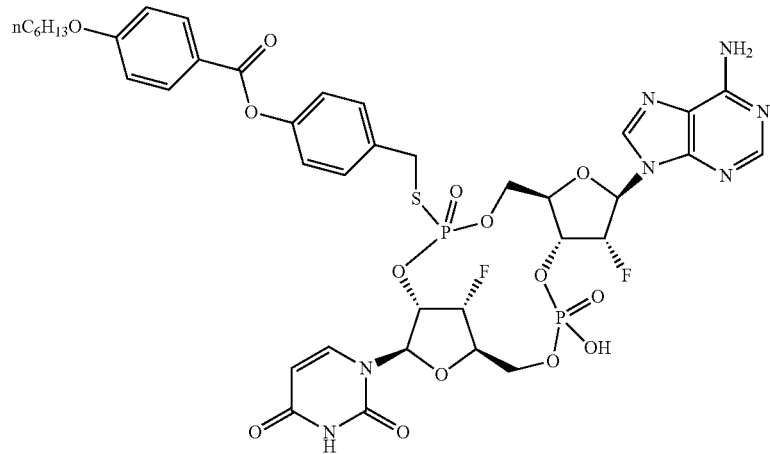 |
| 183 | 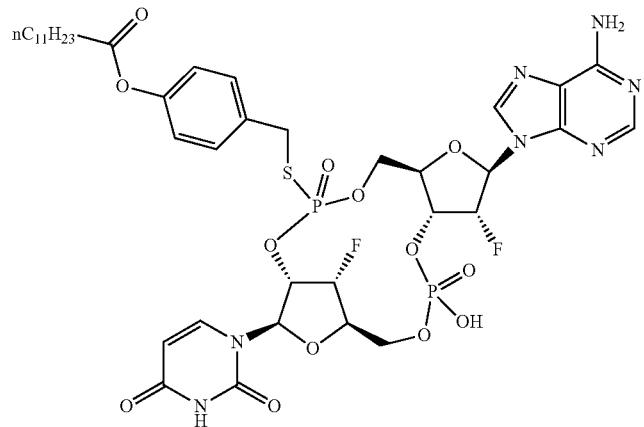 |
| 184 | 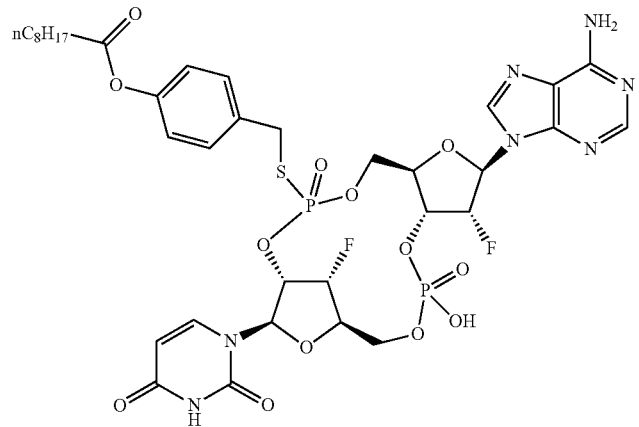 |

| Compound No. | Structure |
|---|---|
| 185 | 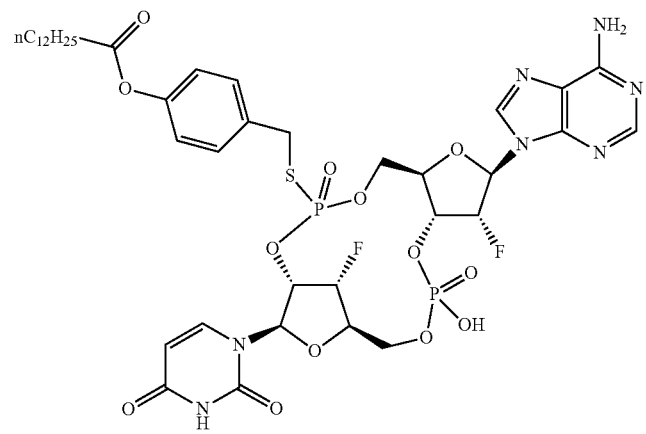 |
| 186 | 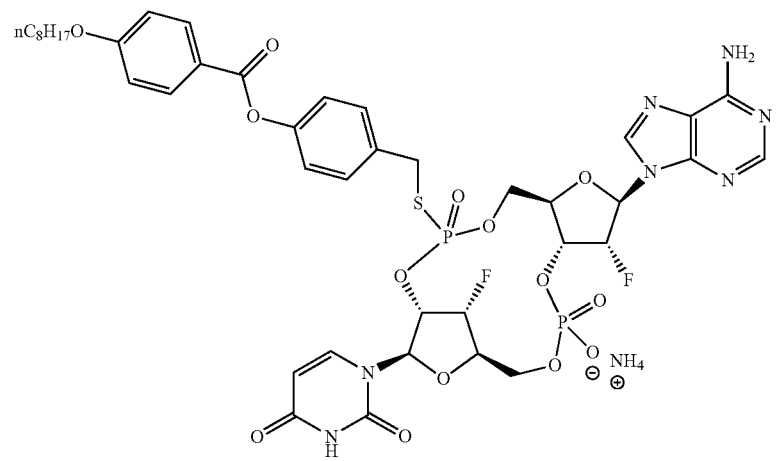 |
| 187 | 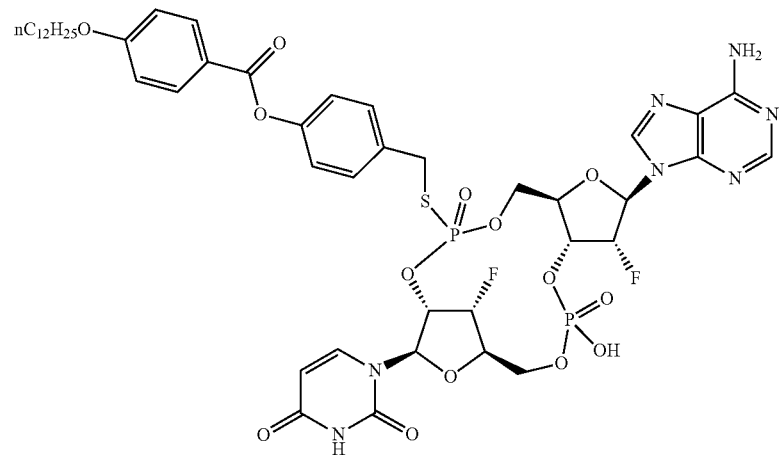 |

-continued
| Compound No. | Structure |
|---|---|
| 188 | 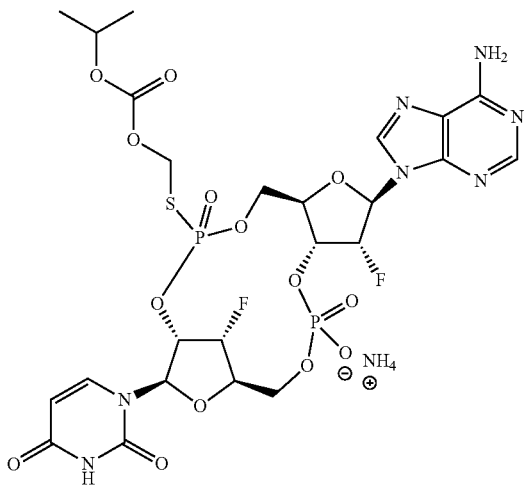 [SMILES: CC(C)OC(=O)OCSP1(=O)OC[C@H]2O[C@@H](n3cnc4c(N)ncnc43)[C@H](F)[C@@H]2OP(=O)([O-])OC[C@H]2O[C@@H](n3ccc(=O)[nH]c3=O)[C@H](O1)[C@@H]2F ; [NH4+]] |
| 189 | 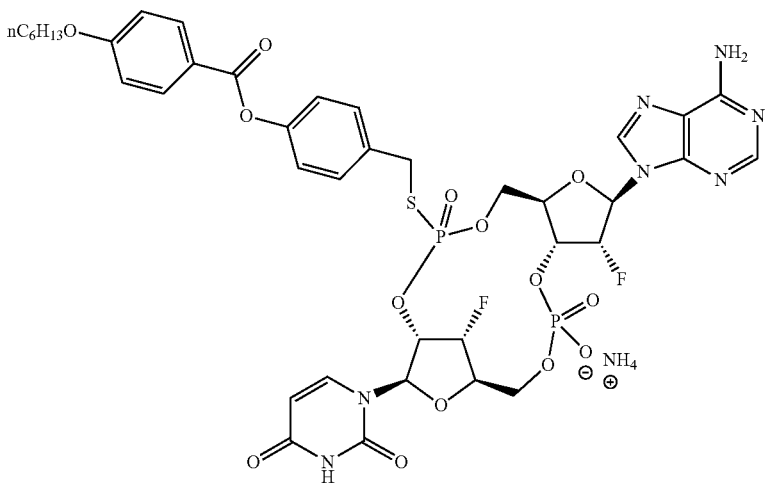 |
| 190 | 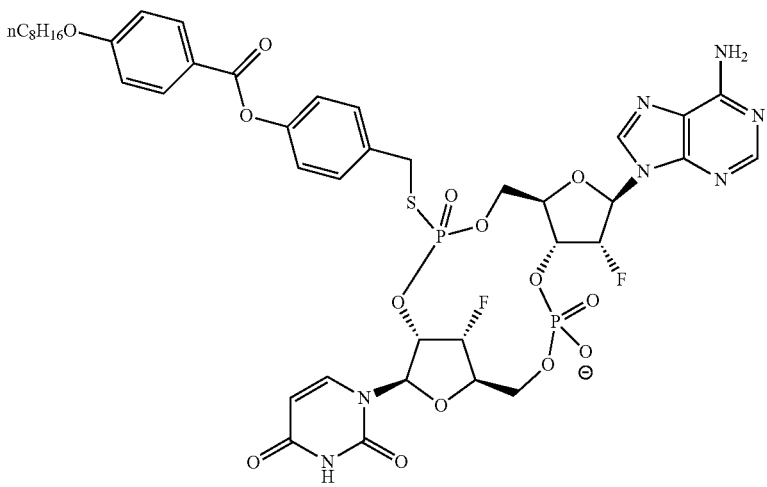 |

-continued
| Compound No. | Structure |
|---|---|
| 191 | 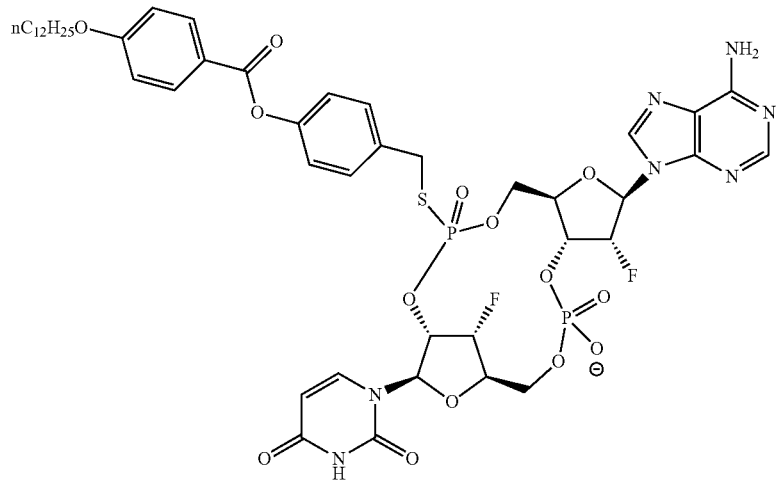 |
| 192 | 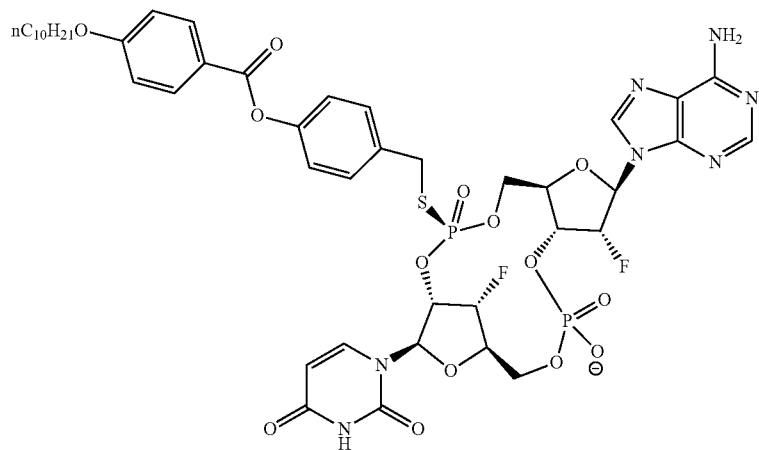 |
| 193 | 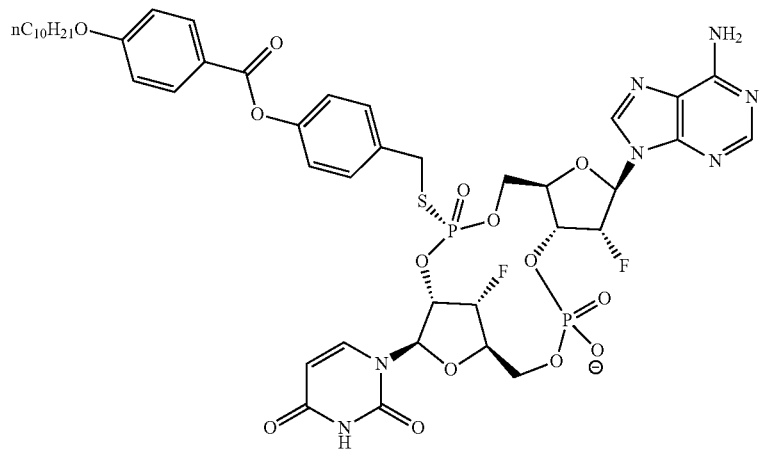 |

| Compound No. | Structure |
|---|---|
| 194 | 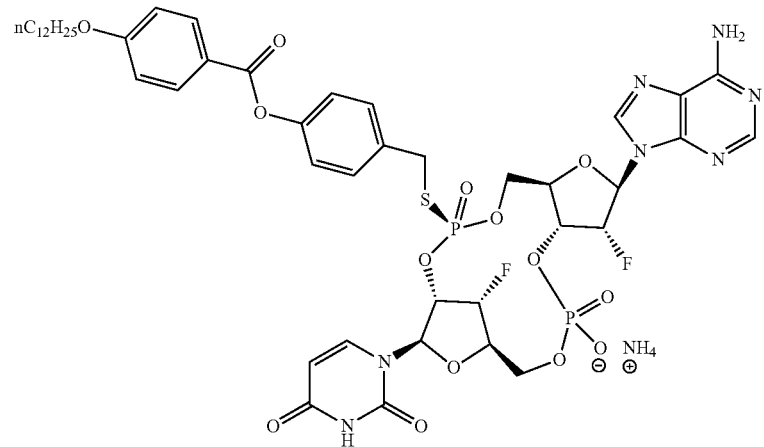 |
| 195 | 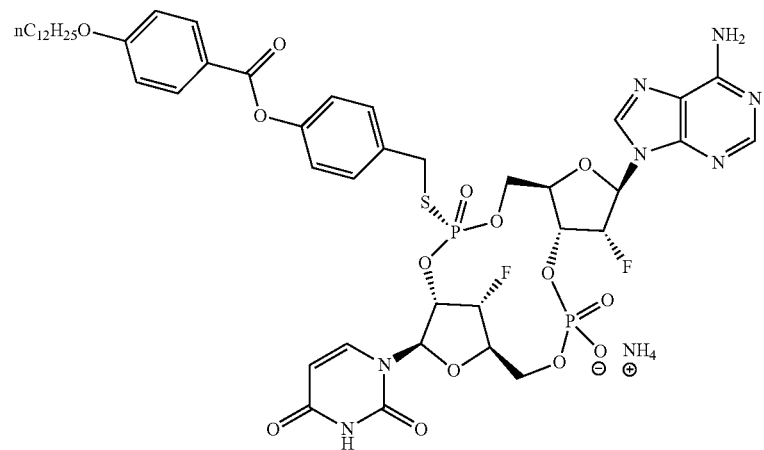 |
| 196 | 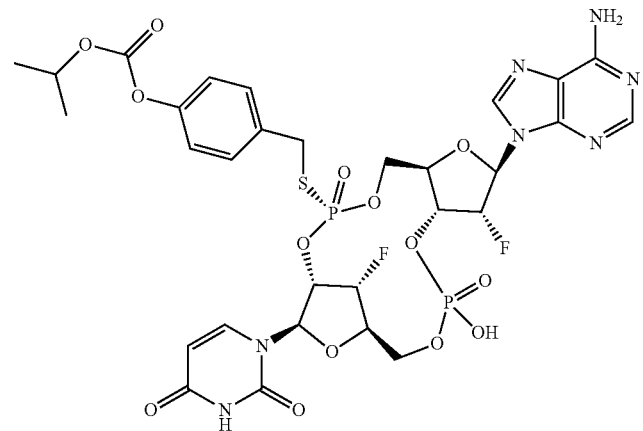 [SMILES: CC(C)OC(=O)Oc1ccc(CS[P@]2(=O)OC[C@H]3O[C@@H](n4cnc5c(N)ncnc54)[C@H](F)[C@@H]3OP(=O)(O)OC[C@H]3O[C@@H](n4ccc(=O)[nH]c4=O)[C@H](O2)[C@@H]3F)cc1] |

| Compound No. | Structure |
|---|---|
| 197 | 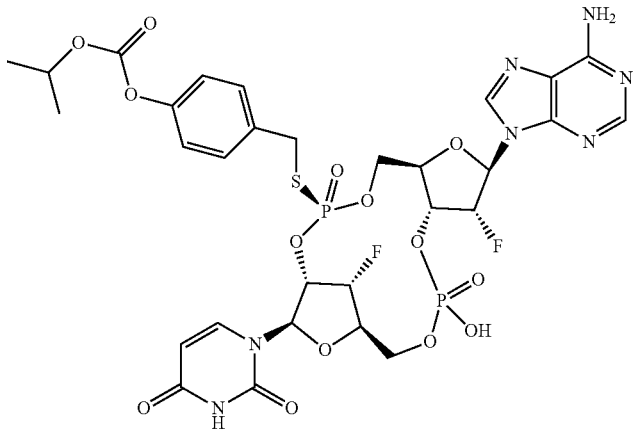 [SMILES: CC(C)OC(=O)Oc1ccc(CS[P@@]2(=O)OC[C@H]3O[C@@H](n4cnc5c(N)ncnc54)[C@H](F)[C@@H]3OP(=O)(O)OC[C@H]3O[C@@H](n4ccc(=O)[nH]c4=O)[C@H](O2)[C@@H]3F)cc1] |
| 198 | 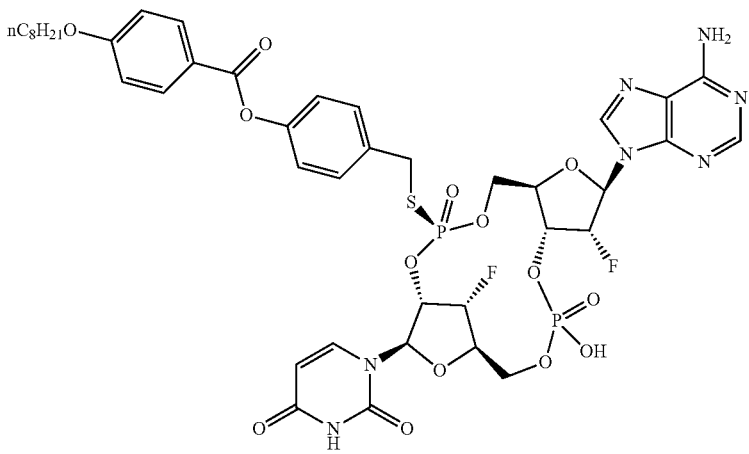 |
| 199 | 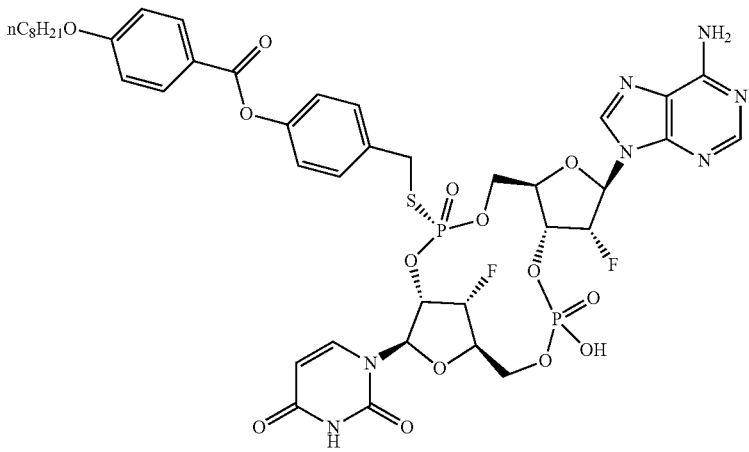 |

| Compound No. | Structure |
|---|---|
| 200 | 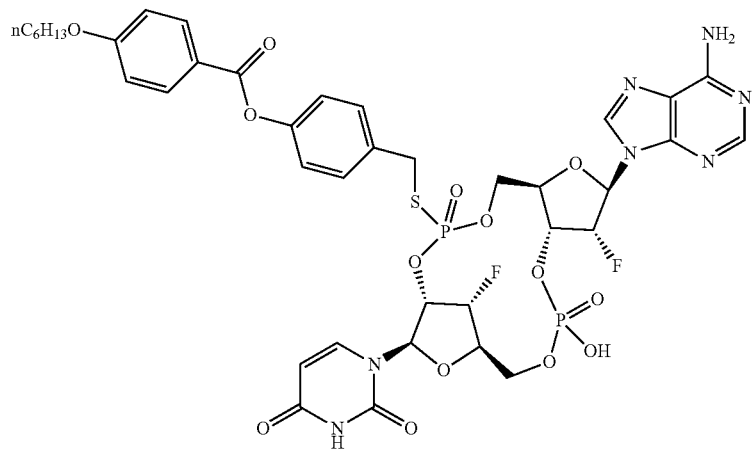 |
| 201 | 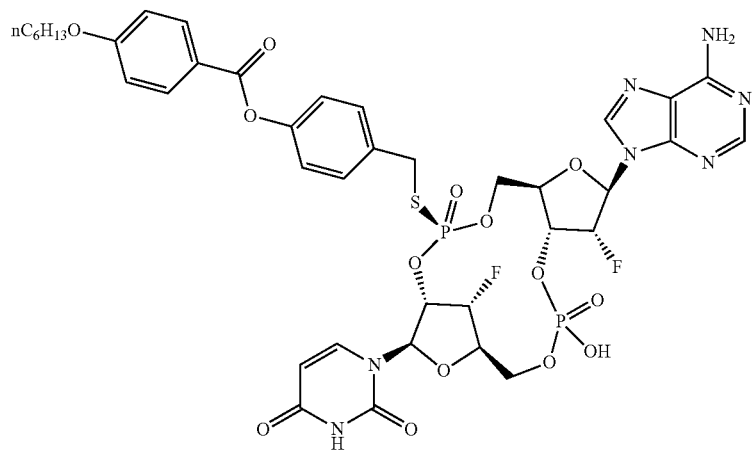 |
| 202 | 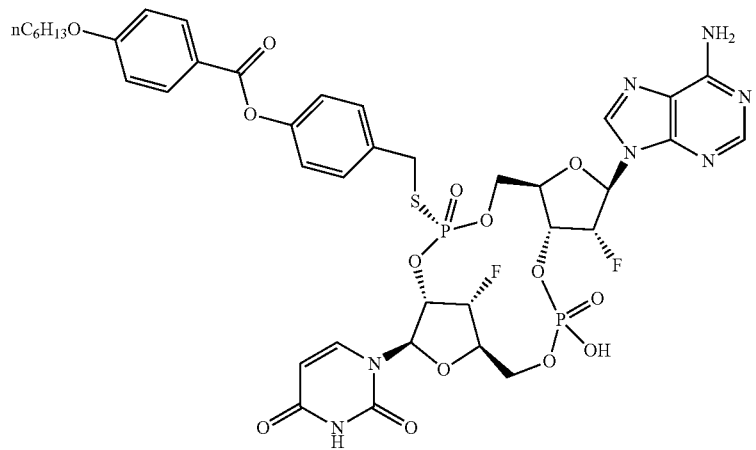 |

| Compound No. | Structure |
|---|---|
| 203 | 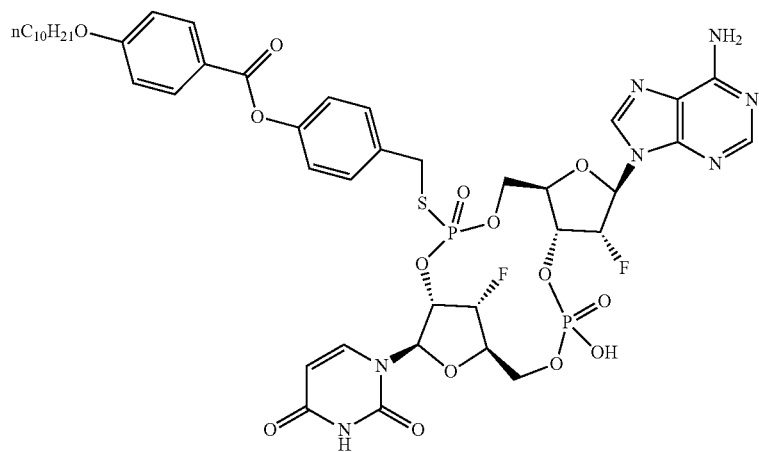 |
| 204 | 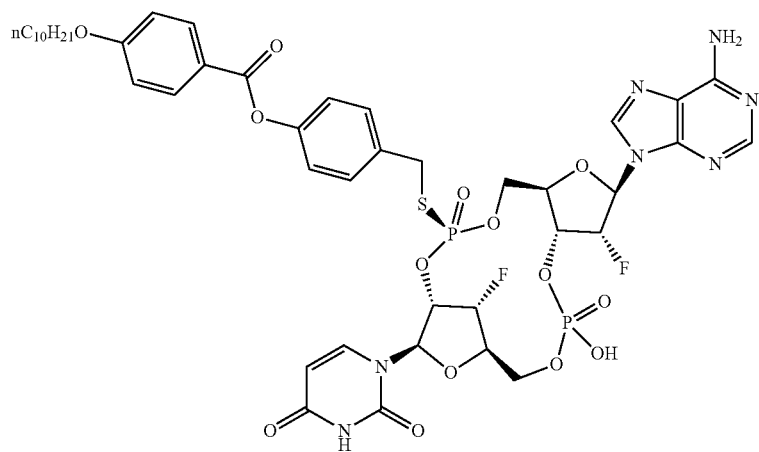 |
| 205 | 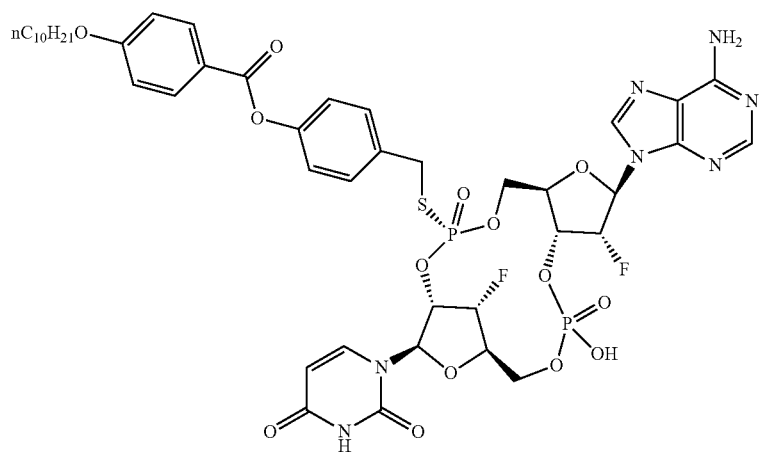 |

| Compound No. | Structure |
|---|---|
| 206 | 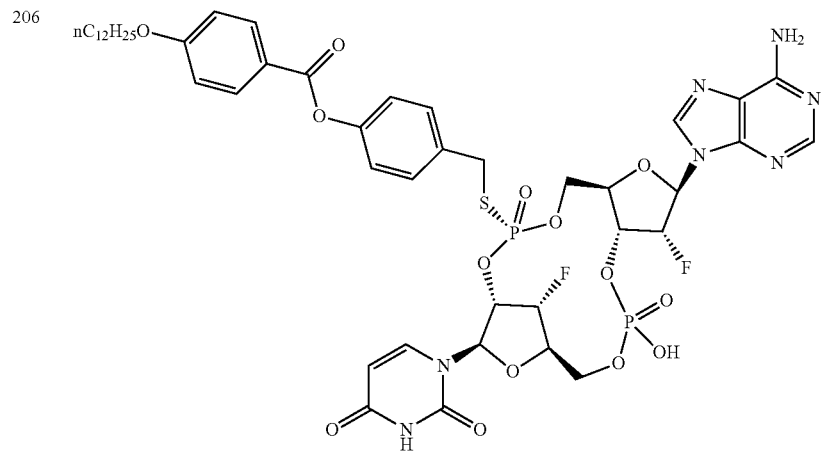 |
| 207 | 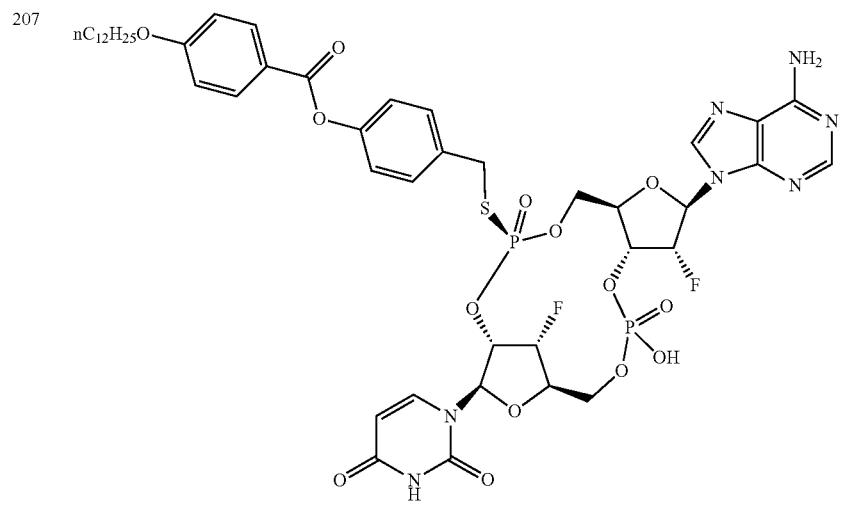 |
| 208 | 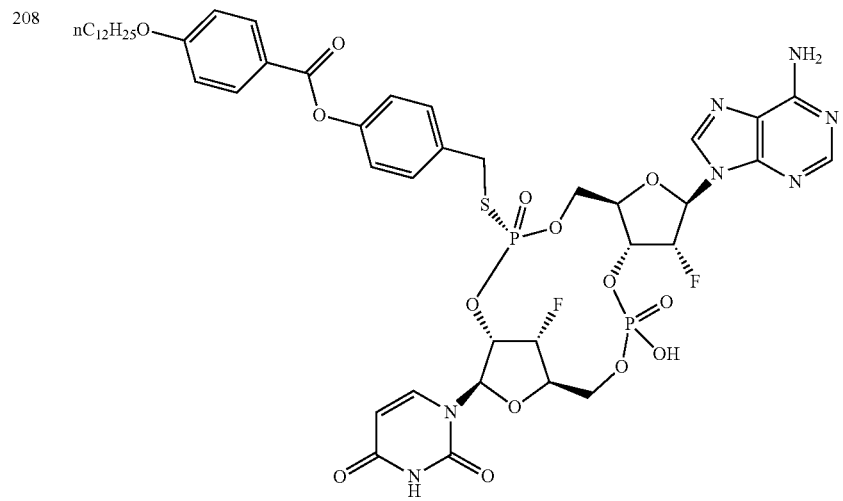 |

| Compound No. | Structure |
|---|---|
| 209 | 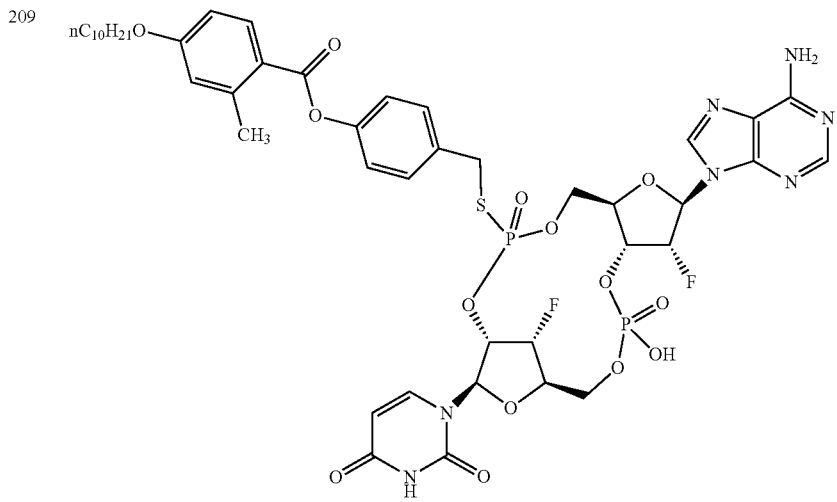 |
| 210 | 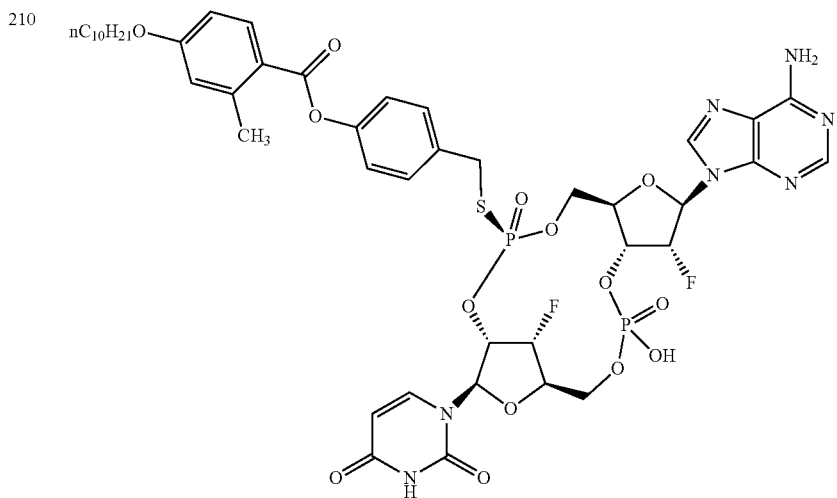 |
| 211 | 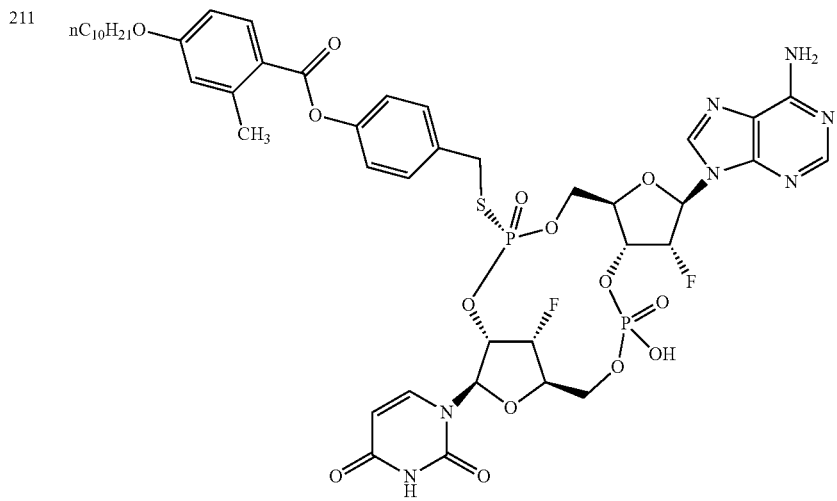 |

US 11,638,716 B2
385                                386
-continued
| Compound No. | Structure |
|---|---|
| 212 | 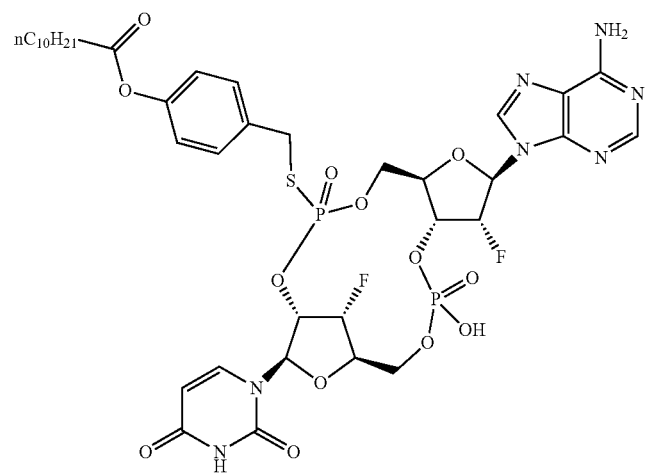 |
| 213 | 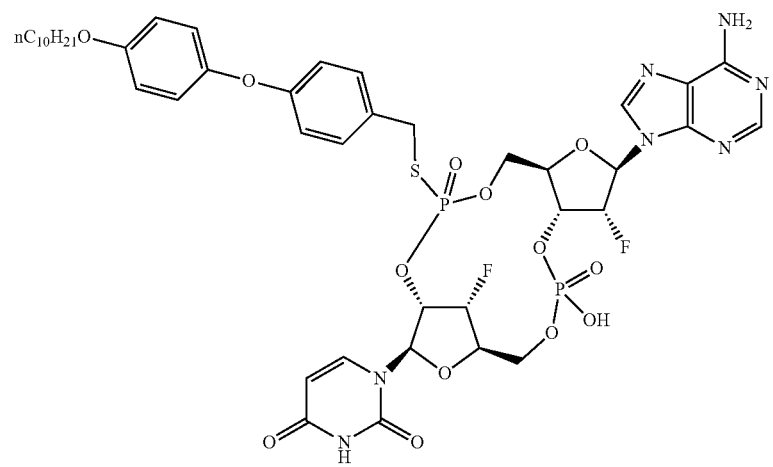 |
| 214 | 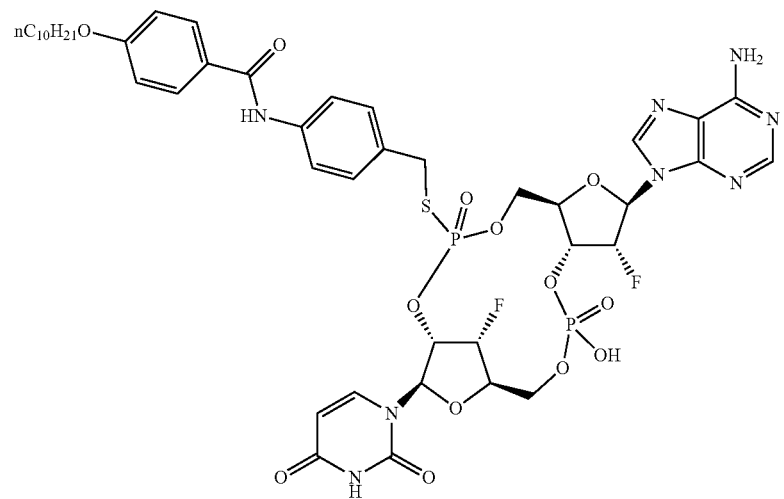 |

| Compound No. | Structure |
|---|---|
| 215 | 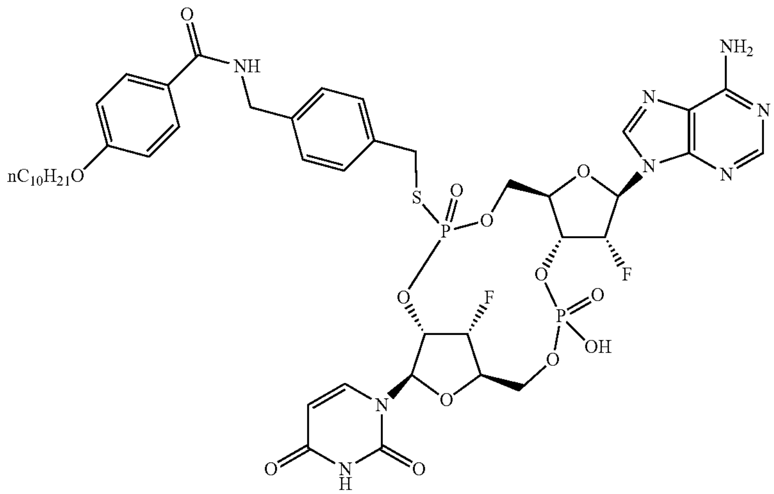 |
| 216 | 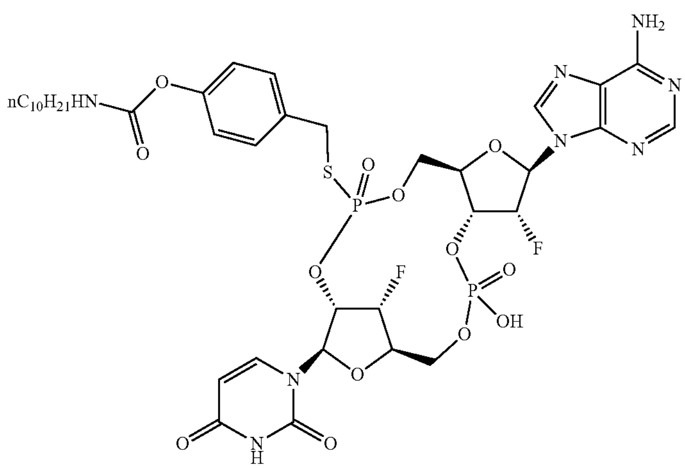 |
| 217 | 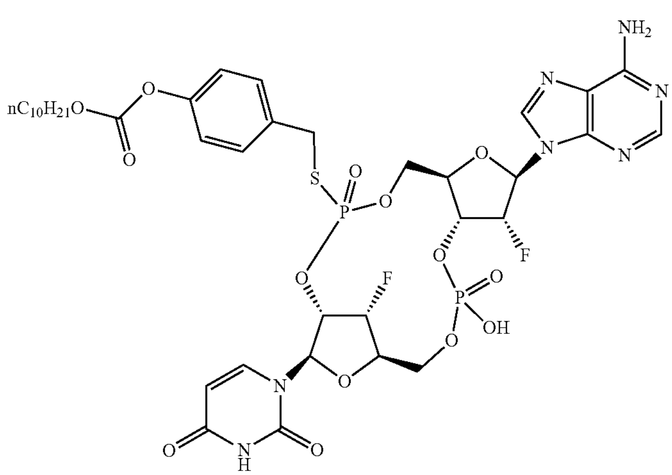 |

| Compound No. | Structure |
|---|---|
| 218 | 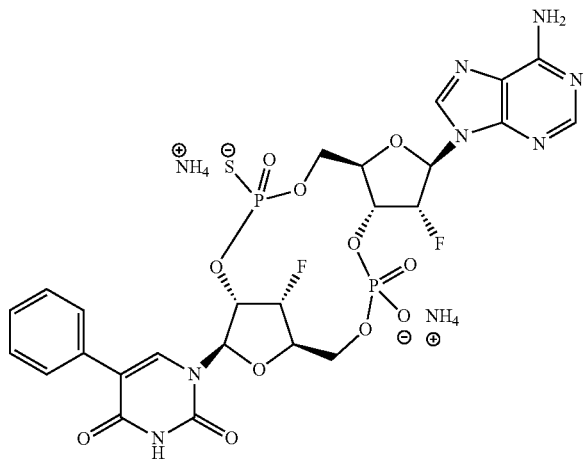 [SMILES: Nc1ncnc2c1ncn2[C@@H]1O[C@@H]2COP(=O)([S-])O[C@@H]3[C@H](F)[C@@H](COP(=O)([O-])O[C@H]2[C@H]1F)O[C@H]3n1cc(-c2ccccc2)c(=O)[nH]c1=O ; [NH4+] ; [NH4+]] |
| 219 | 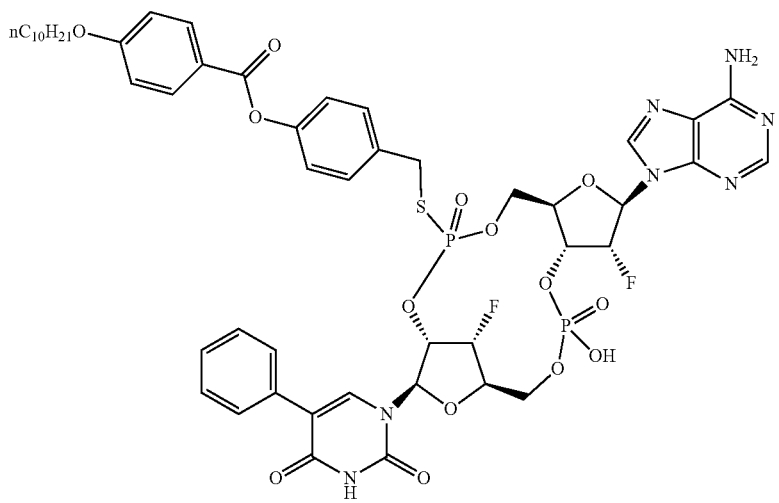 |
| 220 | 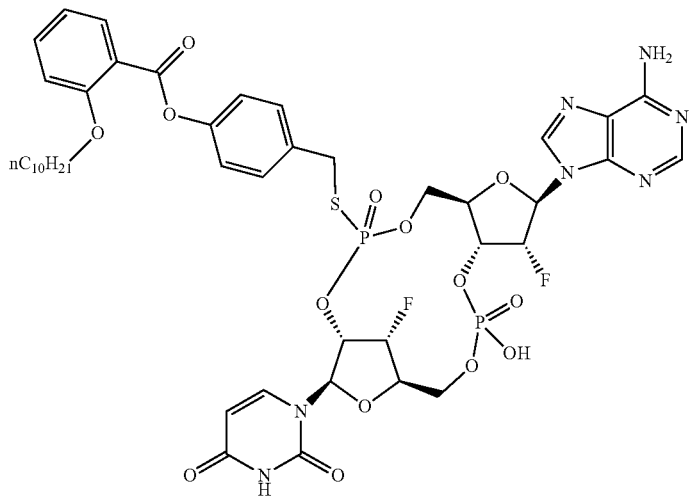 |

| Compound No. | Structure |
|---|---|
| 221 | 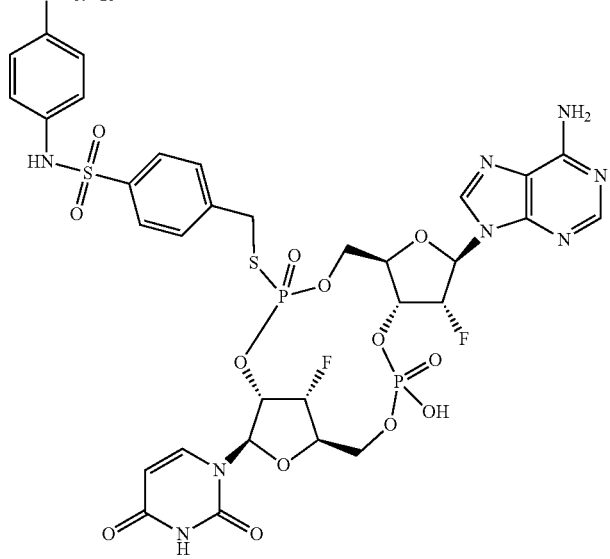 |
| 222 | 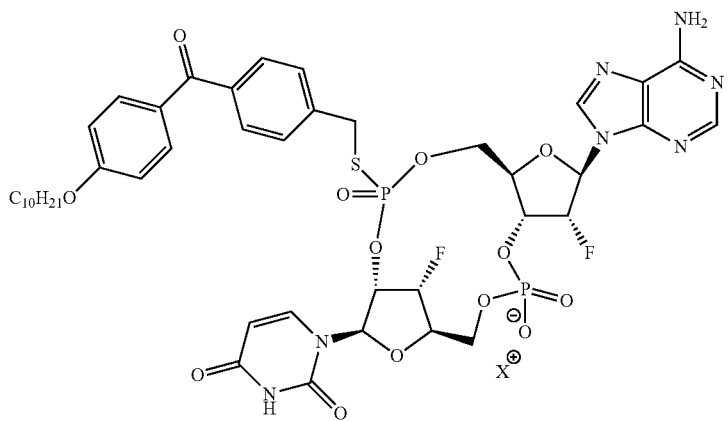 |
| 223 | 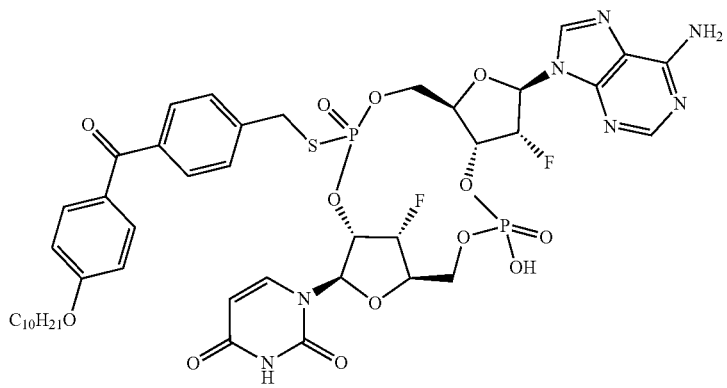 |

| Compound No. | Structure |
|---|---|
| 224 | 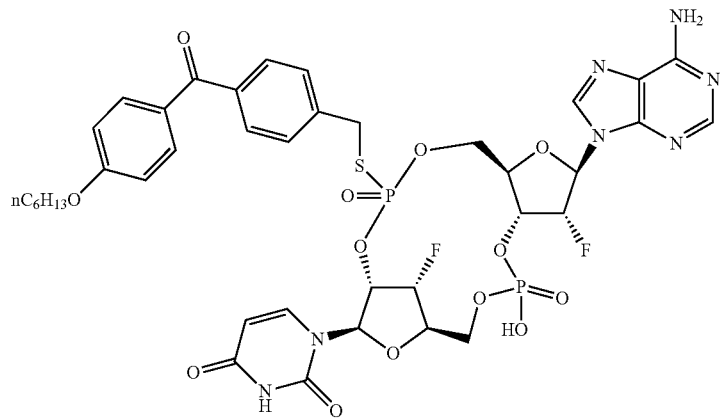 |
| 225 | 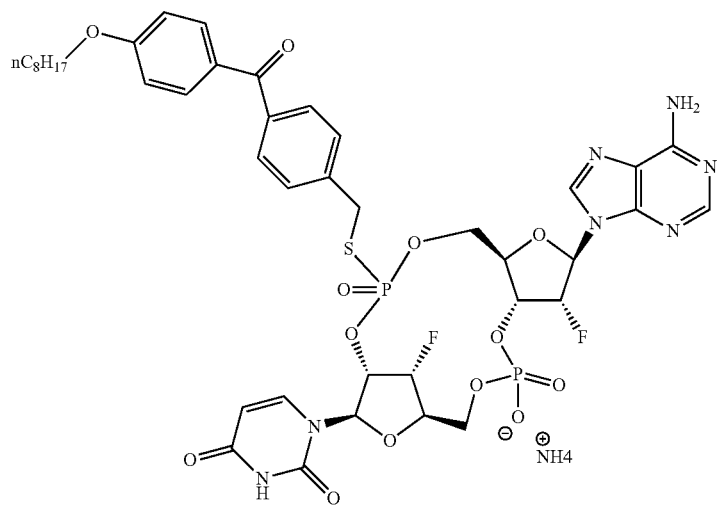 |
| 226 | 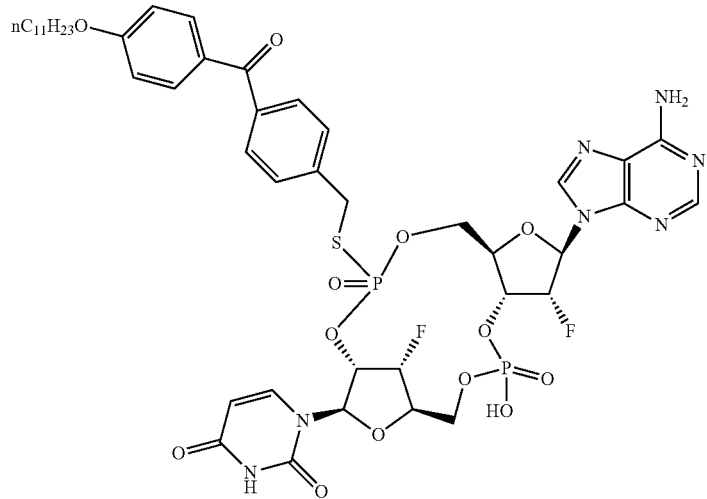 |

| Compound No. | Structure |
|---|---|
| 227 | 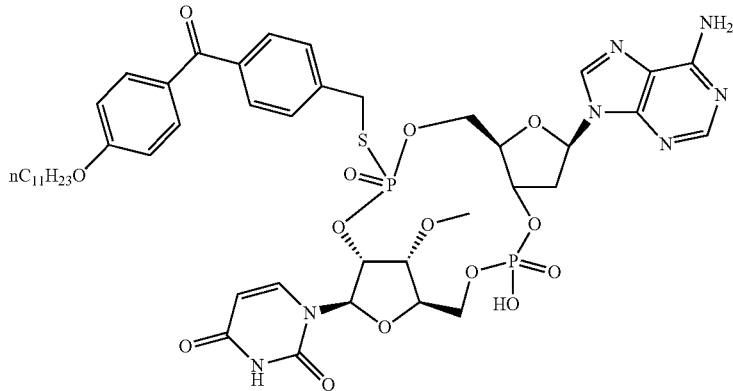 |
| 228 | 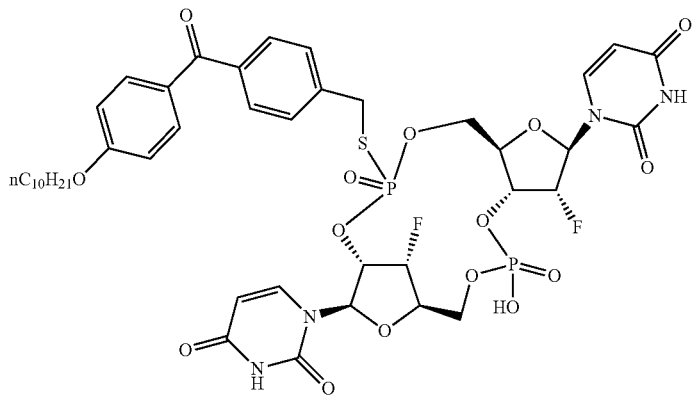 |
| 229 | 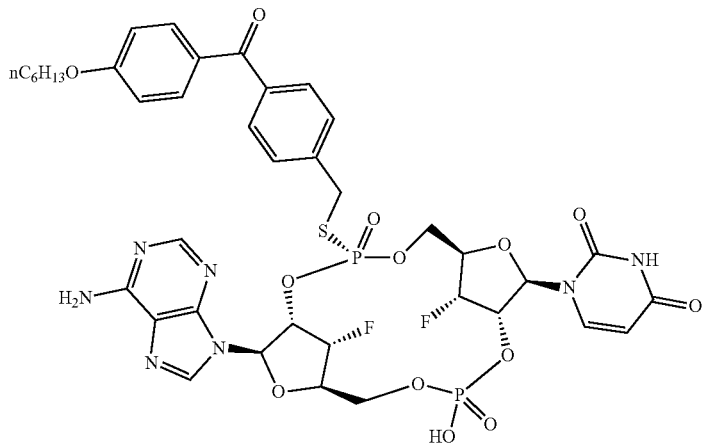 |

| Compound No. | Structure |
|---|---|
| 230 | 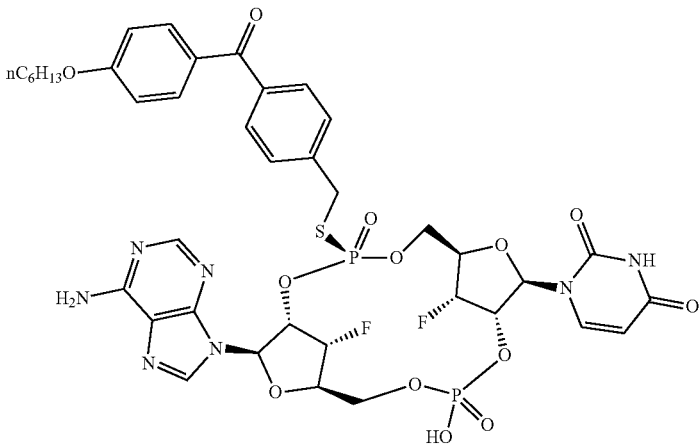 |
| 231 | 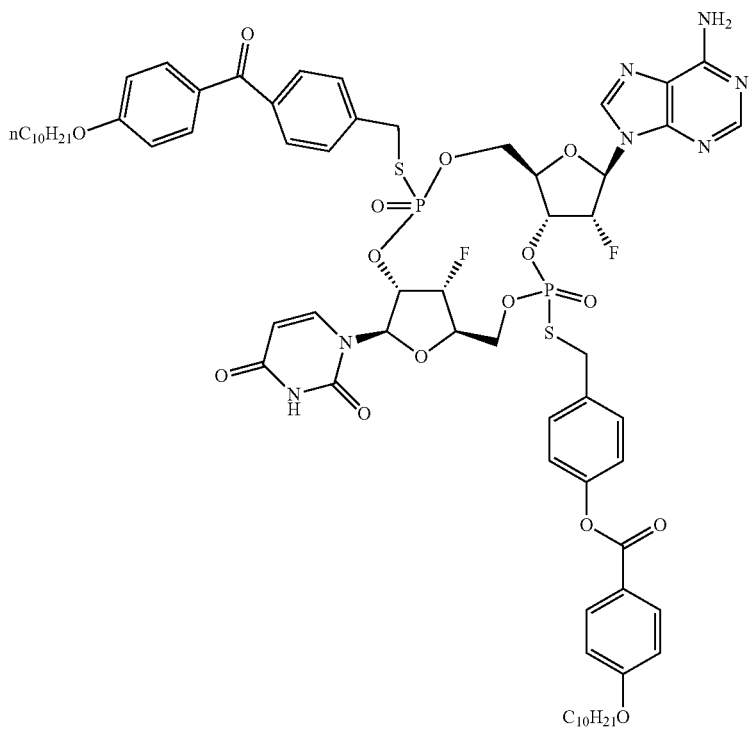 |

-continued
| Compound No. | Structure |
|---|---|
| 232 | 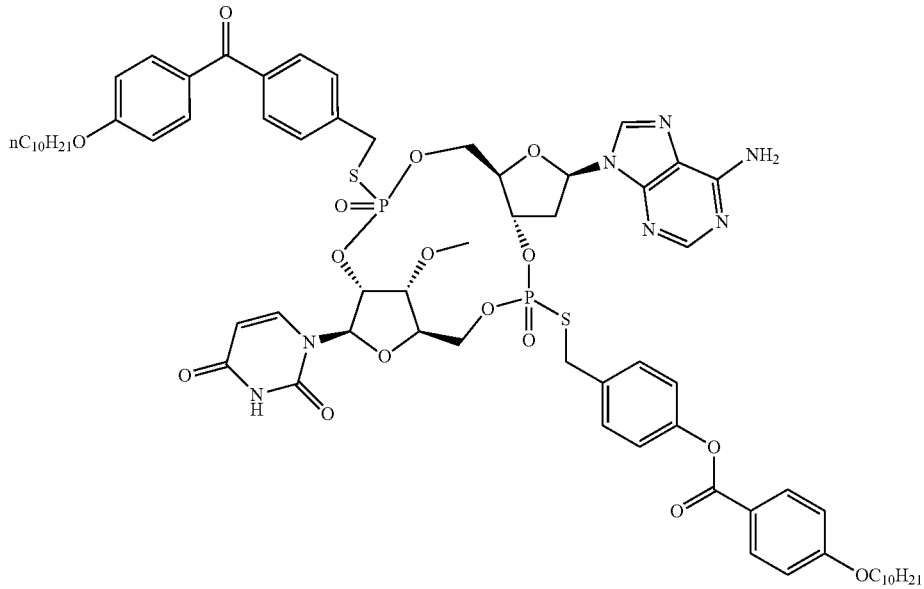 |
| 233 | 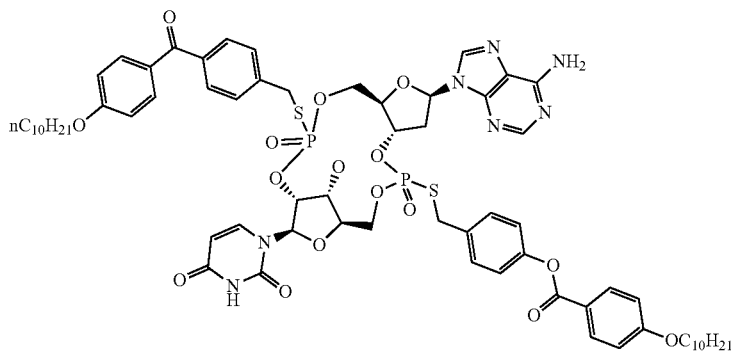 |
| 234 | 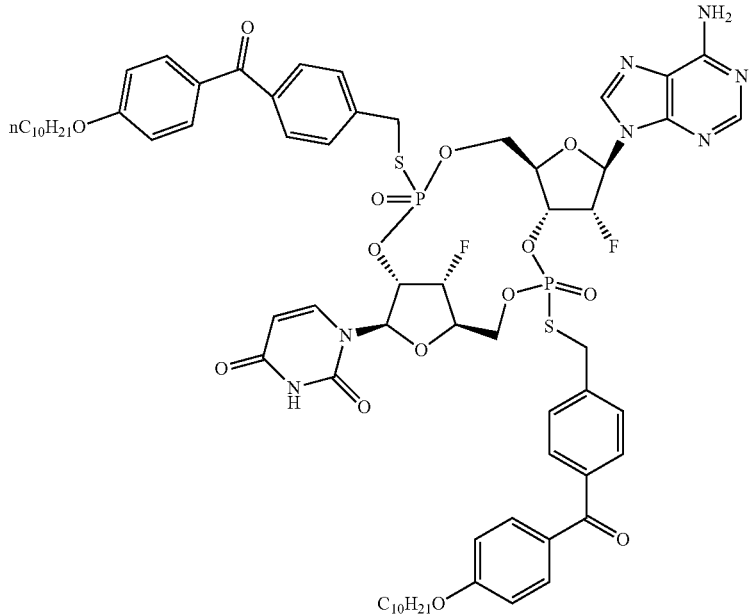 |

| Compound No. | Structure |
|---|---|
| 235 | 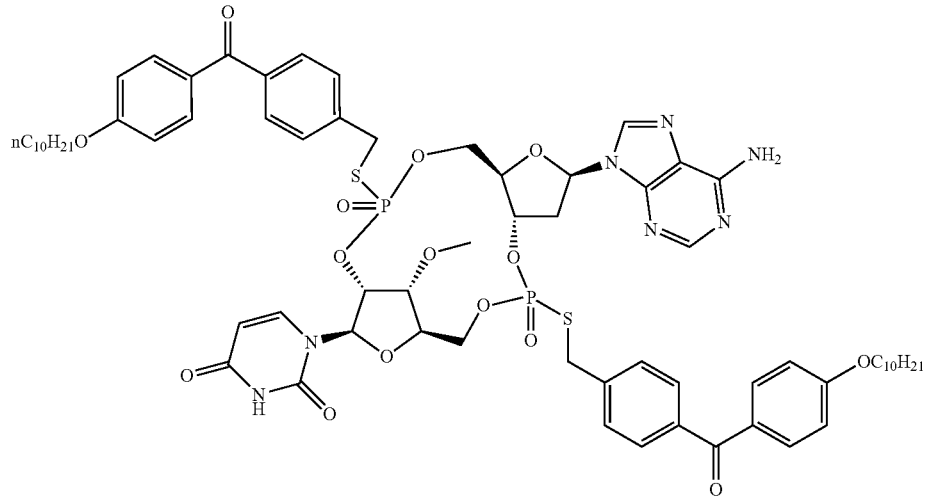 |
| 236 | 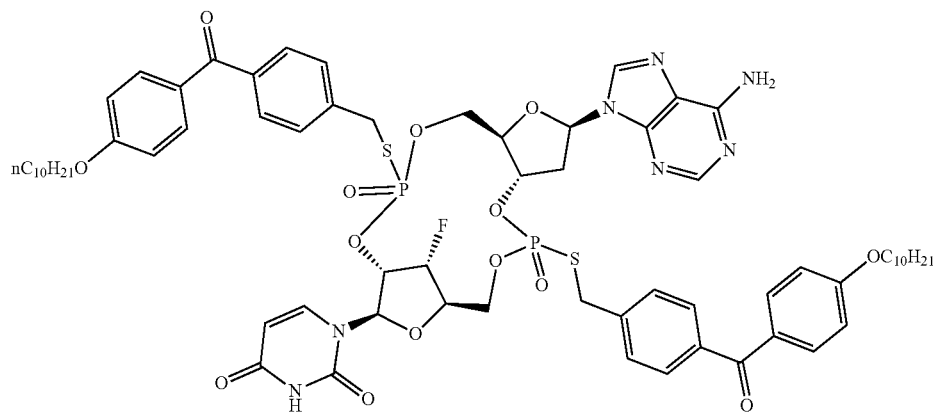 |
| 237 | 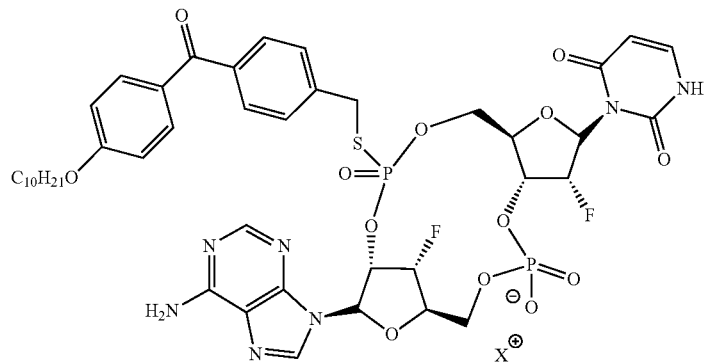 |

| Compound No. | Structure |
|---|---|
| 238 | 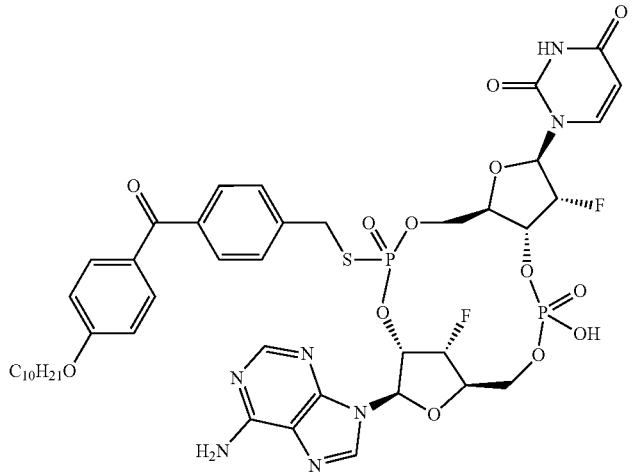 |
| 239 | 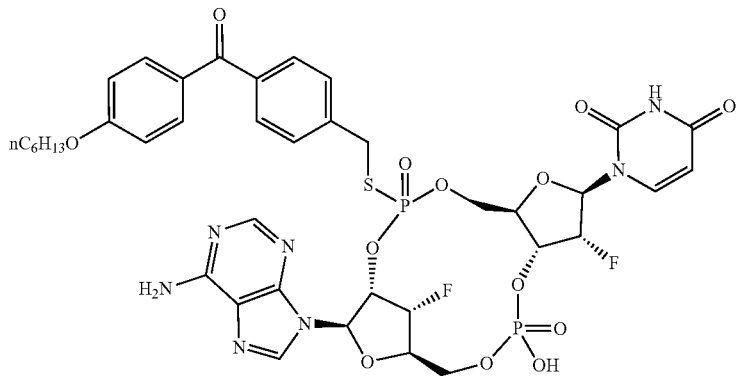 |
| 240 | 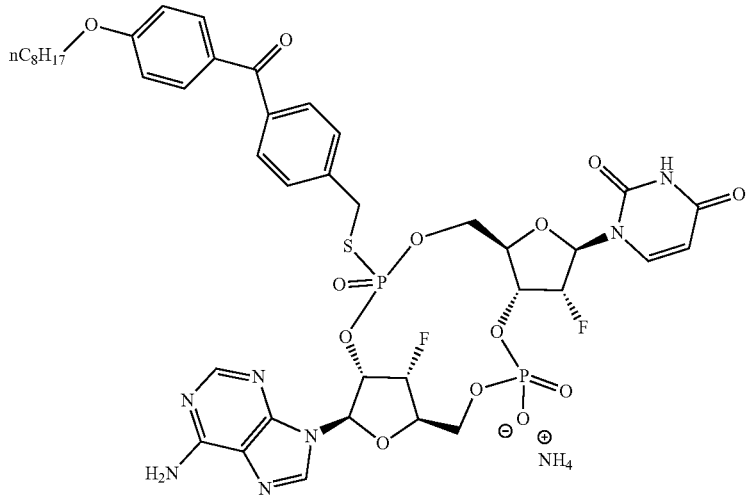 |

| Compound No. | Structure |
|---|---|
| 241 | 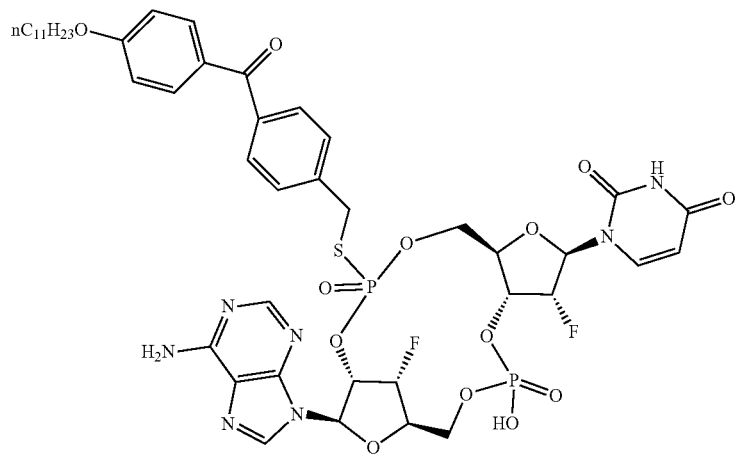 |
| 242 | 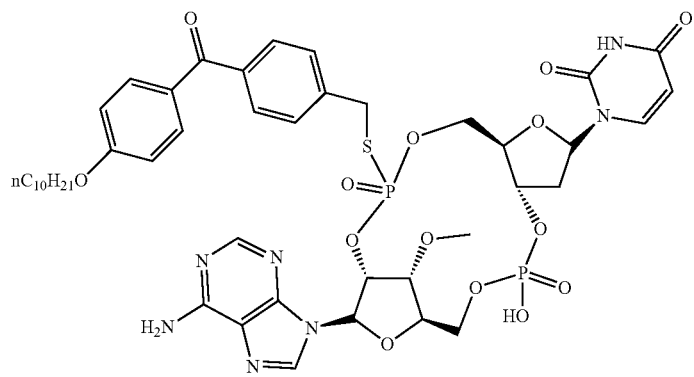 |
| 243 | 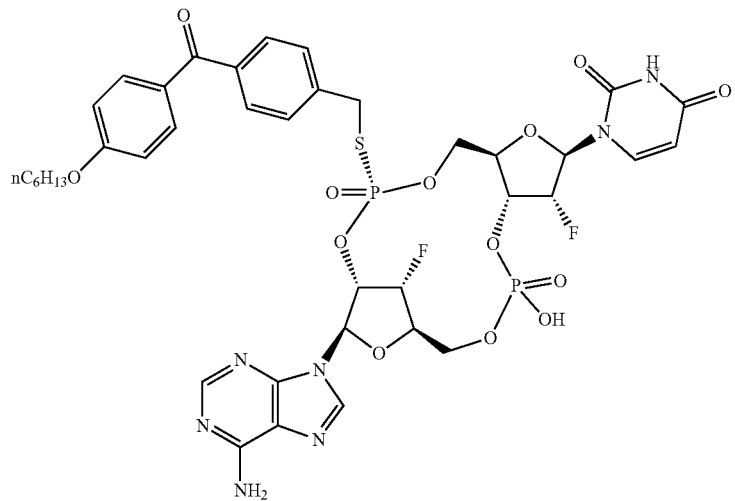 |

-continued
| Compound No. | Structure |
|---|---|
| 244 | 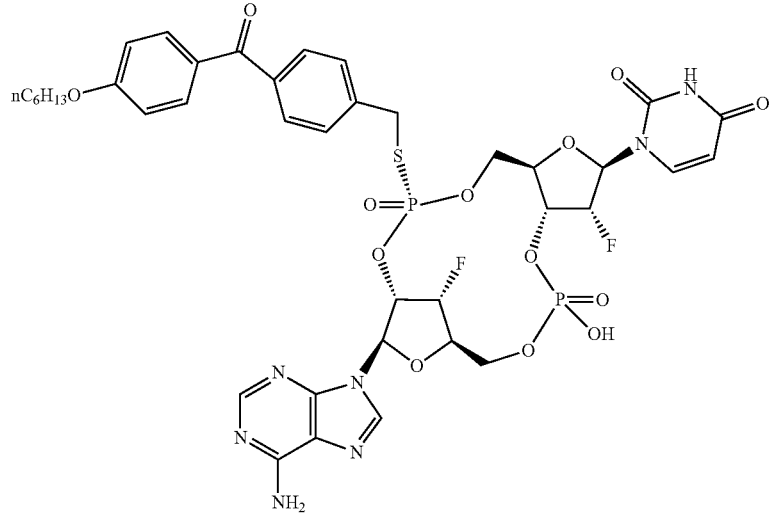 |
| 245 | 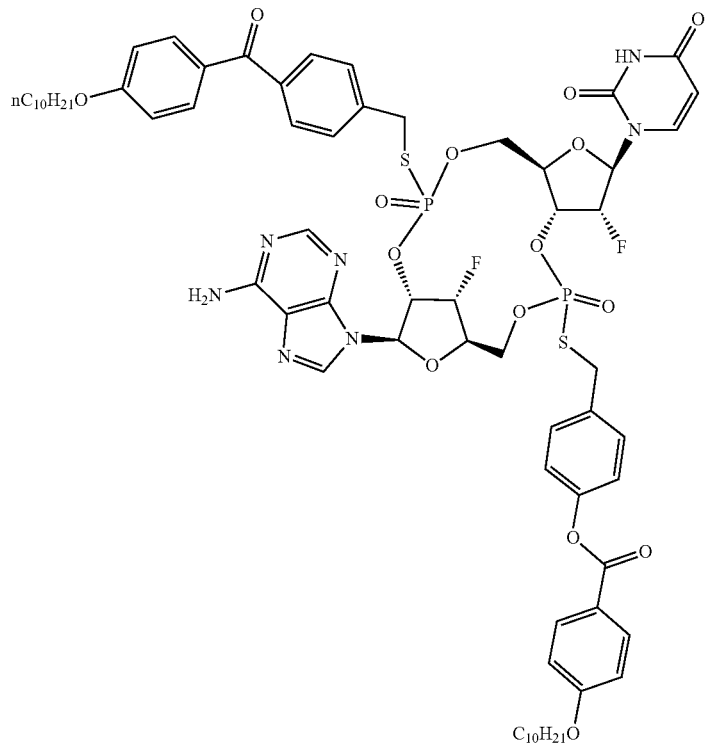 |

| Compound No. | Structure |
|---|---|
| 246 | 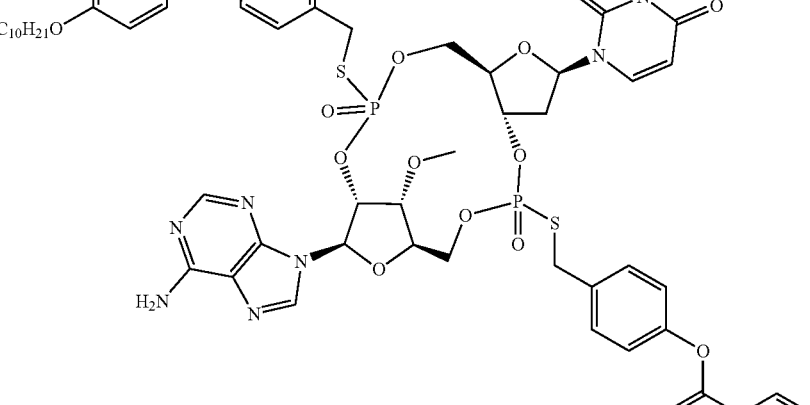 |
| 247 | 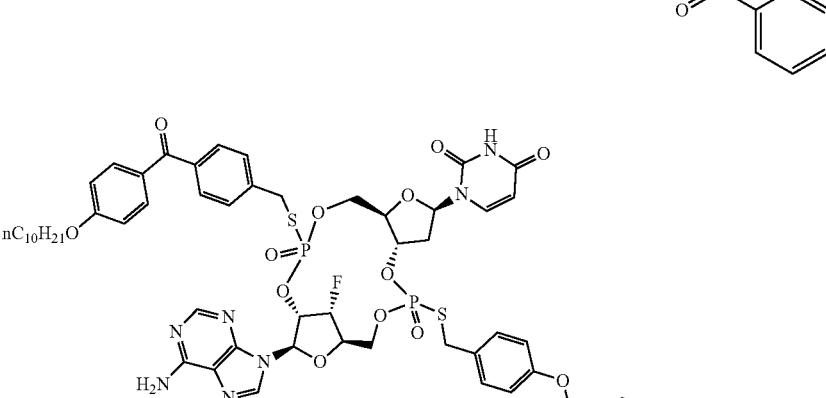 |
| 248 | 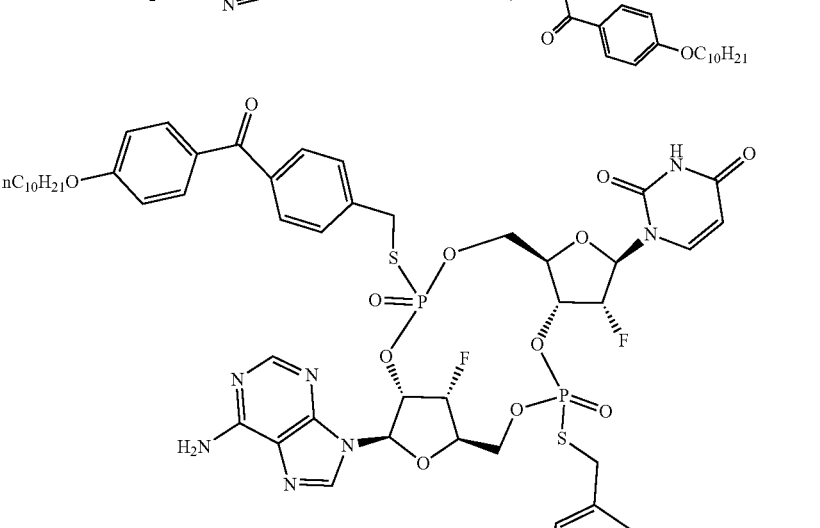 |

| Compound No. | Structure |
|---|---|
| 249 | 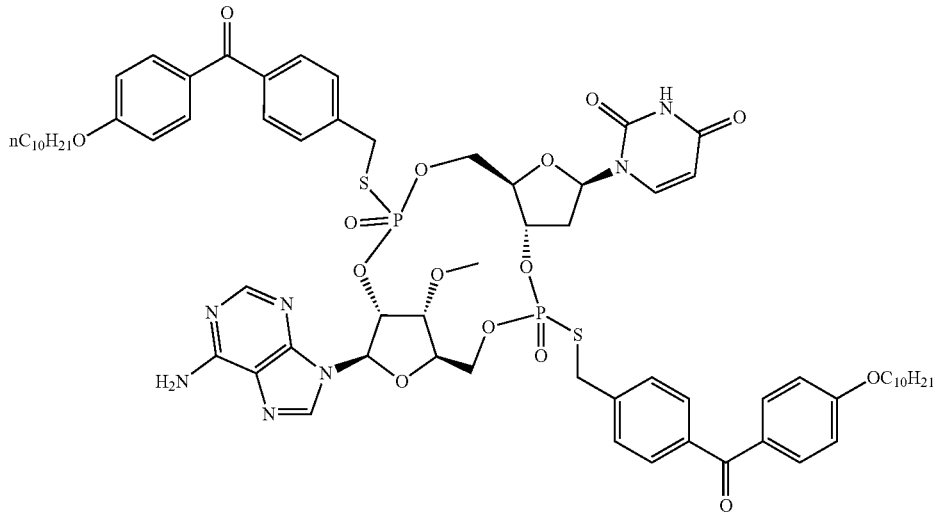 |
| 250 | 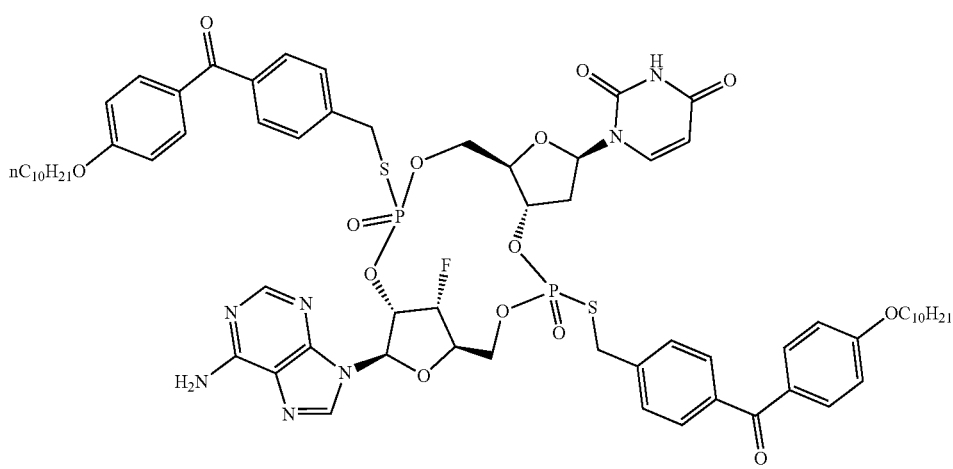 |
| 251 | 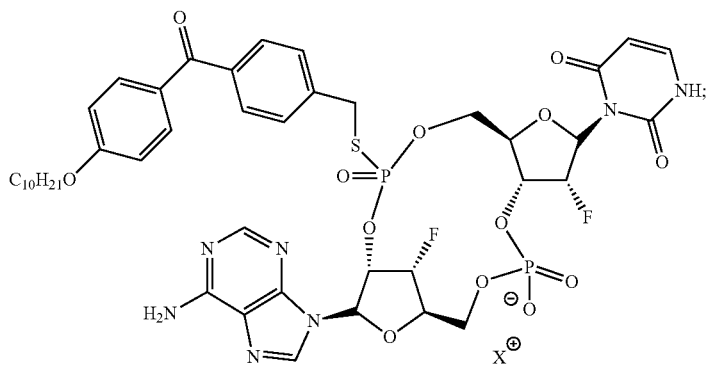 | or a pharmaceutically acceptable salt thereof.

25. A method of treating cancer in a subject, comprising administering to the subject a therapeutically effective amount of a compound of claim 1 or a pharmaceutically acceptable salt thereof.

26. The method of claim 25, wherein the cancer is a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body.

27. The method of claim 26, wherein the cancer is a cancer of the liver.

28. The method of claim 25, further comprising administering an effective amount of an additional agent.

29. The method of claim 28, wherein the additional agent comprises methotrexate, 5-fluorouracil, doxorubicin, vincristine, bleomycin, vinblastine, dacarbazine, toposide, cisplatin, epirubicin, or sorafenib tosylate.

30. A method of inducing the expression of a pattern recognition receptors (PRRs) for immune-modulation in a subject, comprising administering to the subject a therapeutically effective amount of a compound of claim 1 or a pharmaceutically acceptable salt thereof.

31. A method of inducing the expression of a pattern recognition receptors for immunomodulation and inducing a therapeutic response in a subject having cancer, comprising administering to the subject a therapeutically effective amount of a compound of claim 1 or a pharmaceutically acceptable salt thereof.

32. A method of inducing an immune response in a subject, comprising administering to the subject a therapeutically effective amount of a compound of claim 1 or a pharmaceutically acceptable salt thereof.

33. The method of claim 32, wherein the immune response comprises antitumoral immunity.

34. The method of claim 32, wherein the immune response comprises induction of a PRR.

35. A method of treating a microbial infection in a subject, comprising administering to the subject a therapeutically effective amount of a compound of claim 1 or a pharmaceutically acceptable salt thereof.

36. A method of inducing the expression of a pattern recognition receptor in a subject suffering from a microbial infection, comprising administering to the subject a therapeutically effective amount of a compound of claim 1 or a pharmaceutically acceptable salt thereof.

37. A method of treating a viral infection in a subject, comprising administering to the subject a therapeutically effective amount of a compound of claim 1 or a pharmaceutically acceptable salt thereof.

38. The method of claim 37, wherein the viral infection is Hepatitis C virus, Norovirus, Junin virus, Respiratory syncytial virus, or Dengue virus.

* * * * *